US009850183B2

(12) United States Patent
Reiley et al.

(10) Patent No.: US 9,850,183 B2
(45) Date of Patent: Dec. 26, 2017

(54) CONJUGATES DERIVED FROM NON-STEROIDAL ANTI-INFLAMMATORY DRUGS AND METHODS OF USE THEREOF IN IMAGING

(71) Applicant: Reiley Pharmaceuticals, Inc., San Jose, CA (US)

(72) Inventors: Mark A. Reiley, Washington, DC (US); B. Michael Silber, San Francisco, CA (US); Julio Medina, San Carlos, CA (US); Frank Kayser, San Francisco, CA (US); William D. Shrader, Belmont, CA (US)

(73) Assignee: Reiley Pharmaceuticals, Inc., San Jose, CA (US)

( * ) Notice: Subject to any disclaimer, the term of this patent is extended or adjusted under 35 U.S.C. 154(b) by 136 days.

(21) Appl. No.: 14/746,349

(22) Filed: Jun. 22, 2015

(65) Prior Publication Data

US 2015/0374858 A1    Dec. 31, 2015

Related U.S. Application Data

(60) Provisional application No. 62/018,397, filed on Jun. 27, 2014, provisional application No. 62/052,928, filed on Sep. 19, 2014, provisional application No. 62/109,544, filed on Jan. 29, 2015.

(51) Int. Cl.
| | | |
|---|---|---|
| *A61M 36/00* | (2006.01) | |
| *A61K 51/00* | (2006.01) | |
| *C07B 59/00* | (2006.01) | |
| *C07F 13/00* | (2006.01) | |
| *A61K 51/04* | (2006.01) | |

(52) U.S. Cl.
CPC ........ *C07B 59/004* (2013.01); *A61K 51/0402* (2013.01); *A61K 51/0478* (2013.01); *A61K 51/0487* (2013.01); *A61K 51/0497* (2013.01); *C07F 13/00* (2013.01); *C07F 13/005* (2013.01)

(58) Field of Classification Search
CPC .............. C07B 59/004; A61K 51/0402; A61K 51/0478
USPC ....................................................... 424/1.69
See application file for complete search history.

(56) References Cited

U.S. PATENT DOCUMENTS

| | | | |
|---|---|---|---|
| 5,245,018 A | | 9/1993 | Kondo et al. |
| 5,279,811 A | * | 1/1994 | Bergstein .............. A61K 51/04 424/1.65 |
| 6,045,773 A | | 4/2000 | Isakson et al. |
| 6,306,890 B1 | | 10/2001 | Kalgutkar et al. |
| 6,491,893 B1 | | 12/2002 | Babich |
| 6,692,724 B1 | | 2/2004 | Yang et al. |
| 7,736,624 B2 | | 6/2010 | Marnett et al. |
| 8,143,302 B2 | | 3/2012 | Marnett et al. |
| 8,865,130 B2 | | 10/2014 | Marnett et al. |
| 9,050,378 B2 | | 6/2015 | Yang et al. |
| 9,161,735 B2 | | 10/2015 | Bradford et al. |
| 2004/0097735 A1 | * | 5/2004 | Mahmood .......... A61K 51/0478 546/2 |
| 2005/0079133 A1 | | 4/2005 | Yang et al. |
| 2005/0129619 A1 | | 6/2005 | Yang et al. |
| 2005/0136001 A1 | | 6/2005 | McBride et al. |
| 2007/0148092 A1 | | 6/2007 | Biswal et al. |
| 2007/0231266 A1 | | 10/2007 | Low et al. |
| 2007/0292352 A1 | | 12/2007 | Marnett et al. |
| 2008/0241256 A1 | | 10/2008 | Kuhn |
| 2009/0180951 A1 | | 7/2009 | Zimmerman et al. |
| 2009/0252678 A1 | | 10/2009 | Marnett et al. |
| 2010/0111858 A1 | | 5/2010 | Howard et al. |
| 2010/0254910 A1 | | 10/2010 | Marnett et al. |
| 2011/0286923 A1 | | 11/2011 | Satchi-Fainaro et al. |
| 2012/0128588 A1 | * | 5/2012 | Takashima .............. A61K 51/04 424/1.81 |
| 2012/0276005 A1 | | 11/2012 | Yang et al. |

(Continued)

FOREIGN PATENT DOCUMENTS

| | | |
|---|---|---|
| CA | 2789869 A1 | 10/2010 |
| EP | 2463263 B1 | 4/2014 |

(Continued)

OTHER PUBLICATIONS

Abiraj et al., "Tetraamine-Derived Bifunctional Chelators for Technetium-99m Labelling: Synthesis, Bioconjugation and Evaluation as Targeted SPECT Imaging Probes for GRP-Receptor-Positive Tumours", Chem. Eur. J. 2010, vol. 16, 2010, pp. 2115-2124.

(Continued)

*Primary Examiner* — Michael G Hartley
*Assistant Examiner* — Sean R Donohue
(74) *Attorney, Agent, or Firm* — Morrison & Foerster LLP

(57) ABSTRACT

Conjugates derived from non-steroidal anti-inflammatory drugs (NSAIDs) and methods of use thereof are disclosed, useful for, inter alia, identifying and localizing the site of pathology and/or inflammation responsible for the sensation of pain in a patient; for identifying the sites of primary, secondary, benign, or malignant tumors; and for diagnosing infection or confirming or ruling out suspected infection. The NSAID-based conjugates contain an imaging moiety. The conjugates concentrate at sites of increased cyclooxygenase expression, thus revealing the sites of increased prostaglandin production, which is correlated with pain and inflammation, and correlated with tumor presence and/or location. Identifying areas of increased COX expressing can also aid in screening for infections.

12 Claims, 26 Drawing Sheets

(56) References Cited

U.S. PATENT DOCUMENTS

2013/0039853 A1  2/2013 Yang et al.
2013/0052138 A1  2/2013 Marnett et al.

FOREIGN PATENT DOCUMENTS

| WO | 95/09564 A1 | 4/1995 |
|---|---|---|
| WO | 00/41514 A2 | 7/2000 |
| WO | 01/40239 A2 | 6/2001 |
| WO | 01/83436 A2 | 11/2001 |
| WO | 03/086476 A1 | 10/2003 |
| WO | 03/092742 A1 | 11/2003 |
| WO | 03/101948 A2 | 12/2003 |
| WO | 2005/002293 A2 | 1/2005 |
| WO | 2006/050058 A2 | 5/2006 |
| WO | 2007/035906 A2 | 3/2007 |
| WO | 2008/045604 A2 | 4/2008 |
| WO | 2011/008985 A2 | 1/2011 |
| WO | 2011/016376 A1 | 2/2011 |
| WO | 2016/111834 A1 | 7/2016 |

OTHER PUBLICATIONS

Alberto et al., "First Application of fac-[99mTc(OH2)3(C0)3]+ in Bioorganometallic Chemistry: Design, Structure, and in Vitro Affinity of a 5-HT1A Receptor Ligand Labeled with 99mTc", J. Am. Chem. Soc., vol. 121, 1999, pp. 6076-6077.

Amo et al., "Two-Colour Screening in Combinatorial Chemistry: Prospecting for Enantioselectivity in a Library of Steroid-Based Receptors", Tetrahedron, vol. 65, 2009, pp. 6370-6381.

Baran et al., "Direct Coupling of Pyrroles with Carbonyl Compounds: Short Enantioselective Synthesis of (S)-Ketorolac", Angew. Chem. Int. Ed., vol. 44 2004, pp. 609-612.

Bernard et al., "Aqueous Synthesis of Derivatized Cyclopentadienyl Complexes of Technetium and Rhenium Directed toward Radiopharmaceutical Application", Inorganic Chemistry, vol. 42, No. 4, 2003, pp. 1014-1022.

Blobaum et al., "The 2'-Trifluoromethyl Analogue of Indomethacin Is a Potent and Selective COX-2 Inhibitor", ACS Med. Chem. Lett.vol. 4, 2013, pp. 486-490.

Boros et al., "Design, Synthesis, and Imaging of Small Amphiphilic Rhenium and 99mTechnetium Tricarbonyl Complexes", Bioconjugate Chem., vol. 20, 2009, pp. 1002-1009.

Chen et al., "Synthesis and Biological Evaluation of 99mTc, Re-Monoamine-Monoamide Conjugated to 2-(4-aminophenyl) benzothiazole as Potential Probes for b-Amyloid Plaques in the brain", Bioorganic & Medicinal Chemistry Letters vol. 18, 2008, pp. 1442-1445.

Chen et al., "Synthesis and biological evaluation of a novel 99mTc cyclopentadienyl tricarbonyl complex ([(Cp-R)99mTc(CO)3]) for sigma-2 receptor tumor imaging", Bioorganic & Medicinal Chemistry Letters vol. 22, 2012, pp. 6352-6357.

Cheng et al., "Technetium-99m Labeled Pyridyl Benzofuran Derivatives as Single Photon Emission Computed Tomography Imaging Probes for β-Amyloid Plaques in Alzheimer's Brains", J. Med. Chem., vol. 55, 2012, pp. 2279-2286.

Costa et al., "The Synthesis of Biologically Relevant Conjugates of Re(CO)3 Using Pyridine-2-Carboxyaldehyde", Organomet Chem. Jun. 15, 2013, vol. 734, 2013, 18 pages.

Eisenhut et al., "Melanoma Uptake of 99mTc Complexes Containing the N-(2-Diethylaminoethyl)benzamide Structural Element", J. Med. Chem. vol. 45, 2002, pp. 5802-5805.

Friebe et al., "[99mTc]Oxotechnetium(V) Complexes of Amine-Amide-Dithiol Chelates with Dialkylaminoalkyl Substituents as Potential Diagnostic Probes for Malignant Melanoma", J. Med. Chem. vol. 44, 2001, pp. 3132-3140.

Fritzberg et al., "Synthesis and Biological Evaluation of Technetium-99m MAG3 as a Hippuran Replacement", J Nucl Med. , vol. 27, 1986, pp. 111-116.

Guay et al., "Carrageenan-induced Paw Edema in Rat Elicits a Predominant Prostaglandin E2 (PGE2) Response in the Central Nervous System Associated with the Induction of Microsomal PGE2 Synthase-1*", The Journal of Biological Chemistry ,vol. 279, No. 23, Issue of Jun. 4, 2004, pp. 24866-24872.

Hansen et al., "Rhenium( V) Oxo Complexes Relevant to Technetium Renal Imaging Agents Derived from Mercaptoacetylglycylglycylglycylaminobenzoic Acid Isomers. Structural and Molecular Mechanics Studies", Inorg. Chem. ,vol. 31, 1992, pp. 2801-2808.

Harman et al., "Structural Basis of Enantioselective Inhibition of Cyclooxygenase-1 by S-?-Substituted Indomethacin Ethanolamides", The Journal of Biological Chemistry vol. 282, No. 38, 2007, pp. 28096-28105.

Hirano et al., "General Method for the 11C-Labeling of 2-Arylpropionic Acids and Their Esters: Construction of a PET Tracer Library for a Study of Biological Events Involved in COXs Expression", Chem. Eur. J., vol. 16, 2010, pp. 4250-4258.

Itoh, Kazuo, "99mTc-MAG3: Review of Pharmacokinetics, Clinical Application to Renal Diseases and Quantification of Renal Function", Annals of Nuclear Medicine, vol. 15, No. 3, 2001, pp. 179-190.

Kalgutkar et al., "Biochemically Based Design of Cyclooxygenase-2 (COX-2) Inhibitors: Facile Conversion of Nonsteroidal Antiinflammatory Drugs to Potent and Highly Selective COX-2 Inhibitors", PNAS, vol. 97, No. 2, Jan. 18, 2000, pp. 925-930.

Kalgutkar et al., "Ester and Amide Derivatives of the Nonsteroidal Antiinflammatory Drug, Indomethacin, as Selective Cyclooxygenase-2 Inhibitors", J. Med. Chem.vol. 43, 2000, pp. 2860-2870.

Kalgutkar et al., "Indolyl Esters and Amides Related to Indomethacin are Selective COX-2 Inhibitors", Bioorganic & Medicinal Chemistry, vol. 13, 2005, pp. 6810-6822.

Kocher, David C., "TechneScan MAG3™ Kit for the Preparation of Technetium Tc 99m Mertiatide Rx Only", Radioactive Decay Tables, vol. 108, 1981, 2 pages.

Kozak et al., "Enantiospecific, Selective Cyclooxygenase-2 Inhibitors", Bioorganic & Medicinal Chemistry Letters vol. 12, 2002, pp. 1315-1318.

Ktaifani et al., "Synthesis of 2-Methyl-2-Propoxypropyl Isocyanide and its Cu(I) Tetraflouroborate Complex", Chemical Papers, vol. 62, No. 3, 2008, pp. 329-333.

Laube et al., "Radiolabeled COX-2 Inhibitors for Non-Invasive Visualization of COX-2 Expression and Activity—A Critical Update", Molecules ,vol. 18, 2013, pp. 6311-6355.

Li et al., "Novel Cyclopentadienyl Tricarbonyl Complexes of 99mTc Mimicking Chalcone as Potential Single-Photon Emission Computed Tomography Imaging Probes for β-Amyloid Plaques in Brain", J. Med. Chem., vol. 56, 2013, pp. 471-482.

Meltzer et al., "A Technetium-99m SPECT Imaging Agent Which Targets the Dopamine Transporter in Primate Brain", J. Med. Chem. vol. 40, 1997, pp. 1835-1844.

Moth et al., "Stereoselective Binding of Indomethacin Ethanolamide Derivatives to Cyclooxygenase-1", J. Med. Chem., vol. 48, 2005, pp. 3613-3620.

Muchowski et al., "Synthesis and Antiinflammatory and Analgesic Activity of 5-Aroyl-1,2-dihydro-3H-pyrrolo[1,2-a ] pyrrole-1-carboxylic Acids and Related Compounds", J. Med. Chem., vol. 28, 1985, pp. 1037-1049.

Muller et al., "Organometallic 99mTc-technetium(I)- and Re-rhenium(I)-Folate Derivatives for Potential use in Nuclear Medicine", Journal of Organometallic Chemistry vol. 689, 2004, pp. 4712-4721.

Nantel et al., "Distribution and Regulation of Cyclooxygenase-2 in Carrageenan-Induced inflammation", British Journal of Pharmacology vol. 128, 1999, pp. 853-859.

Neil et al., "Preparation and Structural Characterization of Monoamine-Monoamide Bis( thiol) Oxo Complexes of Technetium(V) and Rhenium( V)", Inorganic Chemistry, vol. 33, 1994, pp. 319-323.

Ogawa et al., "Development of a Rhenium-186-Labeled MAG3-Conjugated Bisphosphonate for the Palliation of Metastatic Bone

(56) References Cited

OTHER PUBLICATIONS

Pain Based on the Concept of Bifunctional Radiopharmaceuticals", Bioconjugate Chem. vol. 16, 2005, pp. 751-757.

Ono et al., "99mTc/Re Complexes Based on Flavone and Aurone as SPECT Probes for Imaging Cerebral B-Amyloid Plaques", Bioorganic & Medicinal Chemistry Letters, vol. 20, 2010, pp. 5743-5748.

Ono et al., "Synthesis and Evaluation of Novel Chalcone Derivatives with 99mTc/Re Complexes as Potential Probes for Detection of β-Amyloid Plaques", ACS Chem. Neurosci., vol. 1, 2010, pp. 598-607.

Oya et al., "Small and Neutral TcvO Bat, Bisaminoethanethiol (N2S2) Complexes for Developing New Brain Imaging Agents", Nuclear Medicine & Biology, vol. 25, 1998, pp. 135-140.

Pacelli et al., "Imaging COX-2 Expression in Cancer Using PET/SPECT Radioligands: Current Status and Future Directions", J. Label Compd. Radiopharm , vol. 57, 2014, pp. 317-322.

International Search Report and Written Opinion received for PCT Patent Application No. PCT/US2015/036915, dated Sep. 15, 2015, 7 pages.

Seibert et al., "Pharmacological and Biochemical Demonstration of the Role of Cyclooxygenase 2 in Inflammation and Pain", Proc. Natl. Acad. Sci. USA vol. 91, 1994, pp. 12013-12017.

Shalini et al., "Mechanism of Anti-Inflammatory Effect of Tricin, a flavonoid Isolated from Njavara Rice Bran in LPS induced hPBMCs and Carrageenan induced Rats", Molecular Immunology, vol. 66, 2015, pp. 229-239.

Shen et al., "Non-Steroid Anti-Inflammatory Agents", Journal of the American Chemical Society, vol. 85, 1963, pp. 488-489.

Tietz et al., "Radiotracers for Molecular Imaging of Cyclooxygenase-2 (COX-2) Enzyme", Current Medicinal Chemistry, vol. 20, 2013, pp. 4350-4369.

Uddin et al., "Design, Synthesis, and Structure-Activity Relationship Studies of Fluorescent Inhibitors of Cycloxygenase-2 as Targeted Optical Imaging Agents", Bioconjugate Chem., vol. 24, 2013, pp. 712-723.

Uddin et al., "Fluorinated COX-2 Inhibitors as Agents in PET Imaging of Inflammation and Cancer", Cancer Prevention Research vol. 4, 2011, pp. 1536-1545.

Uddin et al., "Podophyllotoxin Analogues Active Versus Trypanosoma Brucei", Bioorganic & Medicinal Chemistry Letters, vol. 20, 2010, pp. 1787-1791.

Uddin et al., "Selective Visualization of Cyclooxygenase-2 in Inflammation and Cancer by Targeted Fluorescent Imaging Agents", Cancer Research, vol. 70, 2010, pp. 3618-3627.

Uddin et al., "Trifluoromethyl Fluorocoxib A Detects Cyclooxygenase-2 Expression in Inflammatory Tissues and Human Tumor Xenografts", ACS Medicinal Chemistry Letters, vol. 5, 2014, pp. 446-450.

Uehara et al., "Technetium-99m-Labeled Long Chain Fatty Acid Analogues Metabolized by â-Oxidation in the Heart", Journal of Medicinal Chemistry, vol. 50, 2007, pp. 543-549.

Vries et al., "Synthesis and in Vivo Evaluation of 18F-Desbromo-DuP-697 as a PET Tracer for Cyclooxygenase-2 Expression", The Journal of Nuclear Medicine, vol. 44, No. 10, 2003, pp. 1700-1706.

Wang et al., "Methods for MAG3 Conjugation and 99mTc Radiolabeling of Biomolecules", Nature Protocols, vol. 1, No. 3, 2006, pp. 1477-1480.

Wang et al., "Novel Cyclopentadienyl Tricarbonyl 99mTc Complexes Containing 1-Piperonylpiperazine Moiety: Potential Imaging Probes for Sigma-1 Receptors", Journal of Medicinal Chemistry, vol. 57, 2014, pp. 7113-7125.

Westerberg et al., "Synthesis of Novel Bifunctional Chelators and Their Use in Preparing Monoclonal Antibody Conjugates for Tumor Targeting", J. Med. Chem.,vol. 32, 1989, pp. 236-243.

Wyk et al., "Synthesis and 99mTc Labelling of MMI (MIBI) and its Ethyl Analogue EMI", Appl. Radial. Isot. vol. 42, No. 7, 1991, pp. 687-689.

Yamamoto et al., "11C-Labeled Analogs of Indomethacin Esters and Amides for Brain Cyclooxygenase-2 Imaging: Radiosynthesis, in Vitro Evaluation and in Vivo Characteristics in Mice", Chem. Pharm. Bull. vol. 59, No. 8, 2011, pp. 938-946.

International Preliminary Report on Patentability received for PCT Patent Application No. PCT/US2015/036915, dated Jan. 5, 2017, 6 pages.

\* cited by examiner

Rhenium complexes

Technetium complexes

260

261

262

263

264

265

CONJUGATES DERIVED FROM NON-STEROIDAL ANTI-INFLAMMATORY DRUGS AND METHODS OF USE THEREOF IN IMAGING

CROSS-REFERENCE TO RELATED APPLICATIONS

This patent application claims priority benefit of U.S. Provisional Patent Application No. 62/018,397, filed Jun. 27, 2014; of U.S. Provisional Patent Application No. 62/052,928, filed Sep. 19, 2014; and of U.S. Provisional Patent Application No. 62/109,544, filed Jan. 29, 2015. The entire contents of those applications are hereby incorporated by reference herein.

FIELD OF THE INVENTION

Conjugates derived from non-steroidal anti-inflammatory drugs (NSAIDs) and methods of use thereof are disclosed, useful for, inter alia, identifying and localizing the site of pathology and/or inflammation responsible for the sensation of pain in a patient, sites of infection, and identifying and localizing the sites of tumor pathology, including benign, malignant, primary, and secondary tumors.

BACKGROUND OF THE INVENTION

It is important in medicine to identify the site of pathology in order to properly screen for and/or treat a disease. Tumor screening for the presence of tumors (e.g. for breast cancer, cervical cancer, colon cancer, prostate cancer, etc.) is very common. Some of the difficulties with tumor screening are expense, patient's time, physician's time, and accuracy. Also, many of the screening tests are not particularly accurate. For example, testing for prostate cancer using serum acid phosphatase or prostate specific antigen (PSA) is non-specific, and elevation of the marker in healthy individuals can be cause for an unnecessary surgery, a prostate biopsy. An additional example is MRI screening for breast tumors, whose value has recently been questioned for both insensitivity and occasional misinterpretation. In addition, the presence or absence of sentinel (metastatic) nodes is critical for the optimal treatment of breast cancer. Low grade chondrosarcomas are notoriously difficult to read by the pathologist, and frequently have to be sent to multiple institutions for a diagnostic consensus. All of these examples suggest the need for improving detection for all benign, malignant, primary and secondary tumors. A rapid and non-invasive method of localizing tumors would aid immensely in diagnosing and treating the underlying cause. The growing tendency to understand tumors at the molecular level may also be guided by such improved non-invasive methods.

Localization of pain is another area where identifying the site of pathology is important for treatment; however, such localization is often not straightforward. The unpleasant sensation of pain serves as an indicator of a disease or pathological state. Pain often occurs at the site of pathology, and can be a helpful guide in determining diagnosis and appropriate treatment. However, in many cases, the area where a patient experiences pain may not be coincident with the area where the actual pathology has occurred. A classic example is sciatica, where pressure on the sciatic nerve due to a herniated disc in the lower spine can result in a sensation of pain in the leg, at a significant distance from the site of pathology. Another example is the difficulty in diagnosing pain in the chest or thorax, which can arise from multiple causes, such as cardiac ischemia, gastroesophageal reflux, or pulmonary embolism. In such cases, differential diagnosis requires a systematic process of elimination through tests and procedures until the cause and/or location of pathology is identified.

Screening for infectious diseases, particularly when a patient is still asymptomatic, also poses difficulties. Medicaments and methods for such screening would prove useful in limiting outbreaks of diseases; early treatment of infected individuals; and avoiding unnecessary treatment or isolation for individuals who are suspected of being infected, but who in actuality have not been infected, by a disease.

Because pathology is often accompanied by inflammation at the site of the pathology (which is not necessarily the site where pain is experienced), rapid and non-invasive methods of localizing inflammation in a patient experiencing pain would aid immensely in diagnosing and treating the underlying cause of the pain.

SUMMARY OF THE INVENTION

The current invention provides compounds and methods useful for identification of areas of pathology, including tumors and inflammation, and screening for infections and sites of infections, via non-invasive imaging. The compounds and methods can be used in both human and veterinary medicine.

In a first embodiment, the invention embraces conjugate comprising a non-steroidal anti-inflammatory drug (NSAID), a residue of a NSAID, or a derivative of a NSAID bonded or complexed to an imaging moiety which comprises a radioactive agent, wherein the radioactive agent is selected from the group consisting of a gamma-ray emitter, an X-ray emitter, and a beta emitter; or a pharmaceutically acceptable salt thereof. In this first embodiment, the imaging moiety can be optionally bonded to the non-steroidal anti-inflammatory drug (NSAID), residue of a NSAID, or derivative of a NSAID via a linker. In a second embodiment, the radioactive agent in the first embodiment can be $^{99m}$Tc, $^{52}$Mn, $^{186}$Re or $^{188}$Re. In a third embodiment, the imaging moiety of the first or second embodiment can further comprise a chelating group which bonds or complexes to the radioactive agent; and the imaging moiety can be optionally bonded to the non-steroidal anti-inflammatory drug (NSAID), residue of a NSAID, or derivative of a NSAID via a linker.

In a fourth embodiment, the imaging moiety comprising a chelating group bonded or complexed to the radioactive agent of the third embodiment is of the form:

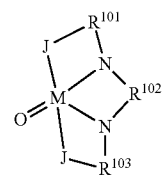

wherein M is selected from the group consisting of $^{99m}$Tc, $^{52}$Mn, $^{186}$Re or $^{188}$Re, wherein each J is independently selected from the group consisting of NH and S, $R^{101}$, $R^{102}$, and $R^{103}$ are independently selected from the group consisting of optionally substituted $C_2$-$C_4$ alkyl, and the NSAID, NSAID residue, or NSAID derivative is attached to the chelating group, either through a linker or directly, at a) any J, $R^{101}$, $R^{102}$, or $R^{103}$ atom where a hydrogen atom can be replaced with a bond to the linker (if present) or to the NSAID, NSAID residue, or NSAID derivative if no linker is present; or at b) the nitrogen atom in the —$R^{101}$—N—$R^{102}$— portion, forming a bond between that nitrogen and the linker (if present) or to the NSAID, NSAID residue, or NSAID derivative if no linker is present; or at c) the nitrogen atom in the —$R^{102}$—N—$R^{103}$— portion, forming a bond between that nitrogen and the linker (if present) or to the NSAID, NSAID residue, or NSAID derivative if no linker is present;

or the imaging moiety comprising a chelating group bonded or complexed to the radioactive agent of the third embodiment is of the form:

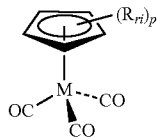

wherein $R_{(ri)}$ is —$CH_3$ or —$CH_2CH_3$ and p is an integer between 0 and 4 inclusive and the NSAID, NSAID residue, or NSAID derivative is attached to the chelating group either through a linker or directly if no linker is present, at any location on the cyclopentane ring which does not have a ($R_{ri}$) group.

In a fifth embodiment, in any of the first, second, third, or fourth embodiments, the NSAID, residue of an NSAID, or derivative of a NSAID and the imaging moiety are bonded or complexed via a linker, where the linker is selected from the group consisting of an optionally substituted $C_1$-$C_{10}$ hydrocarbylene group; an optionally substituted $C_2$-$C_{10}$ heterohydrocarbylene group; and a linker of the form -$L_E$-$R^4$-$L_F$-, where the linker -$L_E$-$R^4$-$L_F$- can be in either orientation with respect to the NSAID, residue of an NSAID, or derivative of a NSAID and the imaging moiety (that is, either $L_E$ or $L_F$ can be attached to the NSAID, residue of an NSAID, or derivative of a NSAID, and the other of $L_E$ or $L_F$ is attached to the imaging moiety). In this fifth embodiment, $L_E$ is absent or is selected from the group consisting of —NH—, —N($R^8$)—, and —C(=O)—, and $R^8$ is optionally substituted $C_1$-$C_4$ alkyl, $R^4$ is selected from the group consisting of optionally substituted $C_1$-$C_{10}$ hydrocarbylene, optionally substituted $C_2$-$C_{10}$ heterohydrocarbylene, $C_3$-$C_8$ cycloalkyl, $C_1$-$C_6$ alkyl-$C_3$-$C_8$ cycloalkyl, $C_3$-$C_8$ cycloalkyl-$C_1$-$C_6$ alkyl, $C_1$-$C_6$ alkyl-$C_3$-$C_8$ cycloalkyl-$C_1$-$C_6$ alkyl, $C_6$-$C_{10}$ aryl, $C_1$-$C_6$ alkyl-$C_6$-$C_{10}$ aryl, $C_6$-$C_{10}$ aryl-$C_1$-$C_6$ alkyl, and $C_1$-$C_6$ alkyl-$C_6$-$C_{10}$ aryl-$C_1$-$C_6$ alkyl, and $L_F$ is absent or is a functional group selected from the group consisting of —(C=O)—, —O—, —N($R^9$)—, —(C=O)N($R^9$)—, —N($R^9$)—(C=O)—, —(C=O)N(H)—, —N(H)—(C=O)— —N($R^9$)—(C=O)—($CH_2$)—, —($SO_2$)N($R^9$)—, —N($R^9$)—($SO_2$)—, —N($R^9$)(C=O)N($R^9$)—, —N($R^9$)—(C=O)—O—, —O—(C=O)N($R^9$)—, —(CH=CH)—, or a divalent cycloalkyl or heterocyclic group, where $R^9$ is selected from the group consisting of H and optionally substituted $C_1$-$C_4$ alkyl.

In a sixth embodiment, in any of the first, second, third, fourth, or fifth embodiments, the linker is selected from the group consisting of: —(NH)—($CH_2$)$_n$—, —(NR$_a$)—($CH_2$)$_n$—, —(NH)—($CH_2$)$_n$—(NH)—, —(NR$_a$)—($CH_2$)$_n$—(NR$_a$)—, —(NH)—($CH_2CH_2$)—($OCH_2CH_2$)$_m$—(NH)—, —(NR$_a$)—($CH_2CH_2$)—($OCH_2CH_2$)$_m$—(NR$_a$)—, —(NH)—($CH_2CH_2$)—((NH)$CH_2CH_2$)$_m$—(NH)—, —(NR$_a$)—($CH_2CH_2$)—((NH)$CH_2CH_2$)$_m$—(NR$_a$)—, (—$CH_2CH_2$—O—)$_n$, (—$CH_2CH(CH_3)$—O—)$_q$, where R$_a$ is ($C_1$-$C_4$ alkyl), n is an integer from 1 to 10 inclusive, m is an integer from 1 to 4 inclusive, and q is an integer from 1 to 3 inclusive, —NH—($CH_2$)$_2$—,
—NH—($CH_2$)$_3$—,
—NH—($CH_2$)$_4$—,
—NH—($CH_2$)$_5$—,
—NH—($CH_2$)$_6$—,
—NH—($CH_2$)$_7$—,
—NH—($CH_2$)$_8$—,
—NH—($CH_2$)$_2$—C(H)=C(H)—($CH_2$)$_2$—,
—NH—($CH_2$)$_2$—NH—,
—NH—($CH_2$)$_3$—NH—,
—NH—($CH_2$)$_4$—NH—,
—NH—($CH_2$)$_5$—NH—,
—NH—($CH_2$)$_6$—NH—,
—NH—($CH_2$)$_7$—NH—,
—NH—($CH_2$)$_8$—NH—,
—NH—($CH_2$)$_3$—C($CH_3$)$_2$—NH—,
—NH—($CH_2$)$_4$—C($CH_3$)$_2$—NH—,
—NH—($CH_2$)$_5$—C($CH_3$)$_2$—NH—,
—NH—($CH_2$)$_6$—C($CH_3$)$_2$—NH—,
—NH—($CH_2$)$_7$—C($CH_3$)$_2$—NH—,
—NH—($CH_2$)$_2$—C($CH_3$)$_2$—($CH_2$)$_2$—NH—,
—NH—($CH_2$)$_2$—C($CH_3$)$_2$—($CH_2$)$_2$—,
—NH—C($CH_3$)—($CH_2$)$_3$—,
—NH—C($CH_3$)—($CH_2$)$_4$—,
—NH—C($CH_3$)—($CH_2$)$_5$—,
—NH—C($CH_3$)—($CH_2$)$_6$—,
—NH—C($CH_3$)—($CH_2$)$_7$—,
—NH—CH(C$_3$)—($CH_2$)$_3$—,
—NH—CH(C$_3$)—($CH_2$)$_4$—,
—NH—CH(C$_3$)—($CH_2$)$_5$—,
—NH—CH(C$_3$)—($CH_2$)$_6$—,
—NH—CH(C$_3$)—($CH_2$)$_7$—,
—NH—($CH_2$)$_2$—C(H)=C(H)—($CH_2$)$_2$—NH—,
—NH—($CH_2$)$_2$—NH—(C=O)—,
—NH—($CH_2$)$_3$—NH—(C=O)—,
—NH—($CH_2$)$_4$—NH—(C=O)—,
—NH—($CH_2$)$_5$—NH—(C=O)—,
—NH—($CH_2$)$_6$—NH—(C=O)—,
—NH—($CH_2$)$_7$—NH—(C=O)—,
—NH—($CH_2$)$_8$—NH—(C=O)—,
—NH—($CH_2$)$_2$—C(H)=C(H)—($CH_2$)$_2$—NH—(C=O)—,
—NH—($CH_2$)$_2$—NH—(C=O)—($CH_2$)—,
—NH—($CH_2$)$_3$—NH—(C=O)—($CH_2$)—,
—NH—($CH_2$)$_4$—NH—(C=O)—($CH_2$)—,
—NH—($CH_2$)$_5$—NH—(C=O)—($CH_2$)—,
—NH—($CH_2$)$_6$—NH—(C=O)—($CH_2$)—,
—NH—($CH_2$)$_7$—NH—(C=O)—($CH_2$)—,
—NH—($CH_2$)$_8$—NH—(C=O)—($CH_2$)—,
—NH—($CH_2$)$_2$—C(H)=C(H)—($CH_2$)$_2$—NH—(C=O)—($CH_2$)—,
—C(=O)—($CH_2$)$_2$—,
—C(=O)—($CH_2$)$_3$—,
—C(=O)—($CH_2$)$_4$—,
—C(=O)—($CH_2$)$_5$—,
—C(=O)—($CH_2$)$_6$—,
—C(=O)—($CH_2$)$_7$—,
—C(=O)—($CH_2$)$_8$—,
—C(=O)—($CH_2$)$_2$—C(H)=C(H)—($CH_2$)$_2$—, —C(=O)—(CH$_2$)$_2$—NH—,
—C(=O)—(CH$_2$)$_3$—NH—,
—C(=O)—(CH$_2$)$_4$—NH—,
—C(=O)—(CH$_2$)$_5$—NH—,
—C(=O)—(CH$_2$)$_6$—NH—,
—C(=O)—(CH$_2$)$_7$—NH—,
—C(=O)—(CH$_2$)$_8$—NH—,
—C(=O)—(CH$_2$)$_2$—C(H)=C(H)—(CH$_2$)$_2$—NH—,
—NH—(CH$_2$)$_2$—O—(CH$_2$)$_2$—NH—,
—NH—(CH$_2$)$_2$—O—(CH$_2$)$_2$—O—(CH$_2$)$_2$—NH—,
—NH—(CH$_2$)$_2$—O—(CH$_2$)$_2$—O—(CH$_2$)$_2$—O—(CH$_2$)$_2$—NH—,
—NH—(CH$_2$)$_2$—NH—(CH$_2$)$_2$—NH—,
—NH—(CH$_2$)$_2$—NH—(CH$_2$)$_2$—NH—(CH$_2$)$_2$—NH—,
—NH—(CH$_2$)$_2$—NH—(CH$_2$)$_2$—NH—(CH$_2$)$_2$—NH—(CH$_2$)$_2$—NH—,
—NH—(CH$_2$)$_2$—N(CH$_3$)—,
—NH—(CH$_2$)$_3$—N(CH$_3$)—,
—NH—(CH$_2$)$_4$—N(CH$_3$)—,
—NH—(CH$_2$)$_5$—N(CH$_3$)—,
—NH—(CH$_2$)$_6$—N(CH$_3$)—,
—NH—(CH$_2$)$_7$—N(CH$_3$)—,
—NH—(CH$_2$)$_8$—N(CH$_3$)—,
—NH—(CH$_2$)$_3$—NH—(CH$_2$)$_3$—,
—NH—(CH$_2$)$_2$—C(H)=C(H)—(CH$_2$)$_2$—,
—NH—CH$_2$—CF$_2$—(CH$_2$)$_4$—,
—NH—CH$_2$—CF$_2$—(CH$_2$)$_5$—
—C(=O)—CF$_2$—(CH$_2$)$_4$—,
—C(=O)—CF$_2$—(CH$_2$)$_5$—,

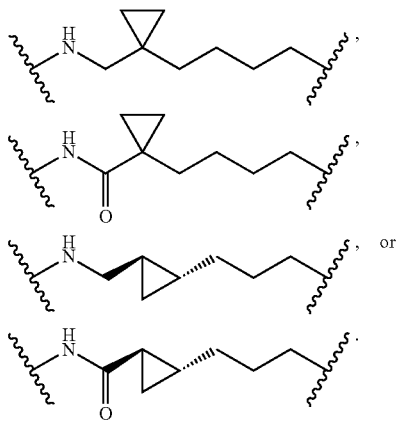

In a seventh embodiment, in any of the first, second, third, fourth, fifth, or sixth embodiments, the conjugate is of the formula:

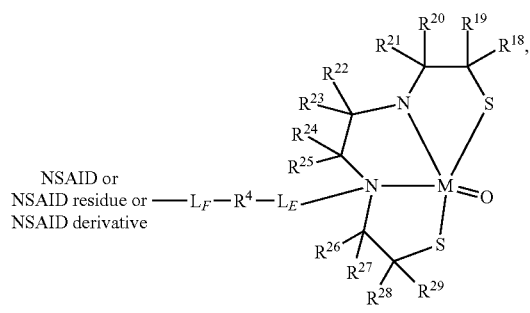

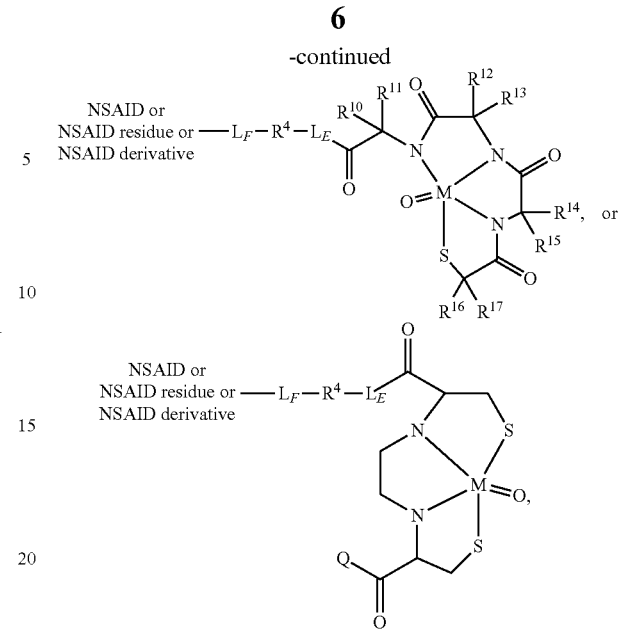

or pharmaceutically acceptable salts thereof.

In this seventh embodiment, $L_E$ is absent or is selected from the group consisting of —NH—, —N(R$^8$)—, and —C(=O)—, and R$^8$ is optionally substituted C$_1$-C$_4$ alkyl, R$^4$ is selected from the group consisting of optionally substituted C$_1$-C$_{10}$ hydrocarbylene, optionally substituted C$_2$-C$_{10}$ heterohydrocarbylene, C$_3$-C$_8$ cycloalkyl, C$_1$-C$_6$ alkyl-C$_3$-C$_8$ cycloalkyl, C$_3$-C$_8$ cycloalkyl-C$_1$-C$_6$ alkyl, C$_1$-C$_6$ alkyl-C$_3$-C$_8$ cycloalkyl-C$_1$-C$_6$ alkyl, C$_6$-C$_{10}$ aryl, C$_1$-C$_6$ alkyl-C$_6$-C$_{10}$ aryl, C$_6$-C$_{10}$ aryl-C$_1$-C$_6$ alkyl, and C$_1$-C$_6$ alkyl-C$_6$-C$_{10}$ aryl-C$_1$-C$_6$ alkyl, $L_F$ is absent or is a functional group selected from the group consisting of —(C=O)—, —O—, —N(R$^9$)—, —(C=O)N(R$^9$)—, —N(R$^9$)—(C=O)—, —(C=O)N(H)—, —N(H)—(C=O)—, —N(R$^9$)—(C=O)—(CH$_2$)—, —(SO$_2$)N(R$^9$)—, —N(R$^9$)—(SO$_2$)—, —N(R$^9$)(C=O)N(R$^9$)—, —N(R$^9$)—(C=O)—O—, —O—(C=O)N(R$^9$)—, —(CH=CH)—, or a divalent cycloalkyl or heterocyclic group, where R$^9$ is selected from the group consisting of H and optionally substituted C$_1$-C$_4$ alkyl; M is selected from the group consisting of $^{99m}$Tc, $^{52}$Mn, $^{186}$Re or $^{188}$Re; R$^{10}$, R$^{11}$, R$^{12}$, R$^{13}$, R$^{14}$, R$^1$, R$^{16}$, and R$^{17}$ are independently selected from the group consisting of hydrogen, C$_1$-C$_4$ alkyl, C$_1$-C$_4$ alkyl substituted with fluoro, hydroxy, —O—C$_1$-C$_4$ alkyl, or C$_3$-C$_6$ cycloalkyl; or, independently of the other substituents, (R$^{10}$ and R$^{11}$) together with the carbon to which they are attached independently form a C$_3$-C$_8$ cycloalkyl ring or heterocycloalkyl ring, (R$^{12}$ and R$^{13}$) together with the carbon to which they are attached independently form a C$_3$-C$_8$ cycloalkyl ring or heterocycloalkyl ring, or (R$^{14}$ and R$^{15}$) together with the carbon to which they are attached independently form a C$_3$-C$_8$ cycloalkyl ring or heterocycloalkyl ring, or (R$^{16}$ and R$^{17}$) together with the carbon to which they are attached independently form a C$_3$-C$_8$ cycloalkyl ring or heterocycloalkyl ring, with the proviso that only one of (R$^{10}$ and R$^{11}$), (R$^{12}$ and R$^{13}$), (R$^{14}$ and R$^{15}$), and (R$^{16}$ and R$^{17}$) together with the carbon to which they are attached independently form a C$_3$-C$_8$ cycloalkyl ring or heterocycloalkyl ring; R$^{18}$, R$^{19}$, R$^{20}$, R$^{21}$, R$^{22}$, R$^{23}$, R$^{24}$, R$^{25}$, R$^{26}$, R$^{27}$, R$^{28}$, and R$^{29}$ are independently selected from the group consisting of hydrogen, C$_1$-C$_4$ alkyl, C$_1$-C$_4$ alkyl substituted with fluoro, hydroxy, —O—C$_1$-C$_4$ alkyl, or C$_3$-C$_6$ cycloalkyl; or, independently of the other substituents, (R$^{18}$ and R$^{19}$)

together with the carbon to which they are attached form a C$_3$-C$_8$ cycloalkyl ring or heterocycloalkyl ring, (R$^{20}$ and R$^{21}$) together with the carbon to which they are attached form a C$_3$-C$_8$ cycloalkyl ring or heterocycloalkyl ring, or (R$^{22}$ and R$^{23}$) together with the carbon to which they are attached independently form a C$_3$-C$_8$ cycloalkyl ring or heterocycloalkyl ring, or (R$^{24}$ and R$^{25}$) together with the carbon to which they are attached independently form a C$_3$-C$_8$ cycloalkyl ring or heterocycloalkyl ring, or (R$^{26}$ and R$^{27}$) together with the carbon to which they are attached independently form a C$_3$-C$_8$ cycloalkyl ring or heterocycloalkyl ring, or (R$^{28}$ and R$^{29}$) together with the carbon to which they are attached independently form a C$_3$-C$_8$ cycloalkyl ring or heterocycloalkyl ring, with the proviso that only one of (R$^{18}$ and R$^{19}$), (R$^{20}$ and R$^{21}$), or (R$^{22}$ and R$^{23}$), or (R$^{24}$ and R$^{25}$), or (R$^{26}$ and R$^{27}$), or (R$^{28}$ and R$^{29}$) together with the carbon to which they are attached independently form a C$_3$-C$_8$ cycloalkyl ring or heterocycloalkyl ring; or, independently of the other substituents, (R$^{22}$ and R$^{23}$) together form an oxo group; Q is selected from the group consisting of OH, NH$_2$, NH(C$_1$-C$_4$ alkyl), N(C$_1$-C$_4$ alkyl)(C$_1$-C$_4$ alkyl), OCH$_3$, and OCH$_2$CH$_3$.

In an eighth embodiment, the conjugates of the seventh embodiment are of the form:

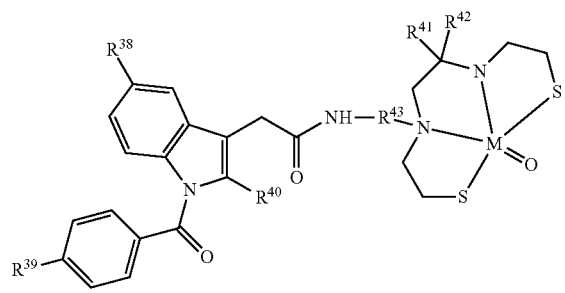

where R$^{38}$ is —O—(C$_1$-C$_4$) alkyl; R$^{39}$ is selected from the group consisting of H, F, Cl, Br, I, CH$_3$, and CF$_3$; R$^{40}$ is selected from the group consisting of H, CH$_3$, and CF$_3$; R$^{41}$ and R$^{42}$ are both H, or R$^{41}$ is H and R$^{42}$ is OH, or R$^{41}$ and R$^{42}$ together form an oxo group; R$^{43}$ is selected from the group consisting of (C$_1$-C$_{10}$) hydrocarbylene and (C$_2$-C$_{10}$) heterohydrocarbylene containing one O atom, two O atoms, one (—S(=O$_2$))— group, two (—S(=O$_2$))— groups, or one O atom and one (—S(=O$_2$))— group, where the O atom or atoms of the heteroalkylene are not bonded directly to a nitrogen atom, and where when more than one heteroatom is present, at least one carbon atom intervenes between the heteroatoms; M is selected from the group consisting of $^{99m}$Tc, $^{52}$Mn, $^{186}$Re or $^{188}$Re; or pharmaceutically acceptable salts thereof.

In a ninth embodiment, the conjugates of the eighth embodiment are of the formula:

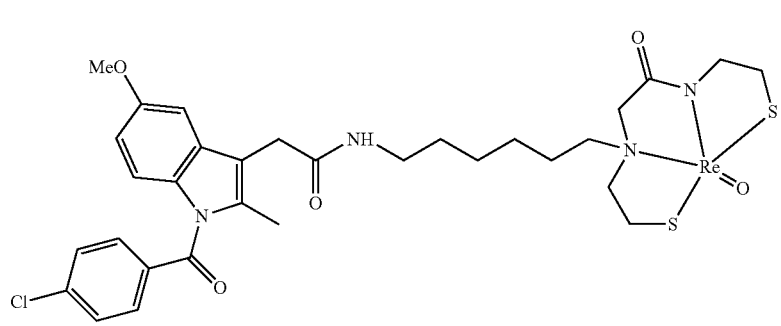

260 where Re is $^{186}$Re or $^{188}$Re; or pharmaceutically acceptable salts thereof.

In a tenth embodiment, the conjugates of the eighth embodiment are of the formula:

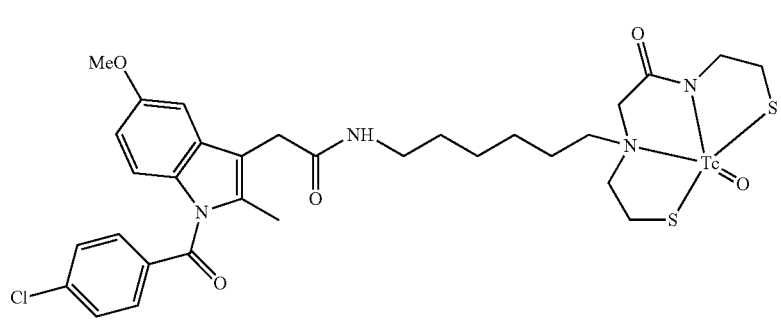

270 wherein Tc is $^{99m}$Tc; or pharmaceutically acceptable salts thereof.

In an eleventh embodiment, the conjugates of the eighth embodiment can be selected from the group consisting of the compounds:

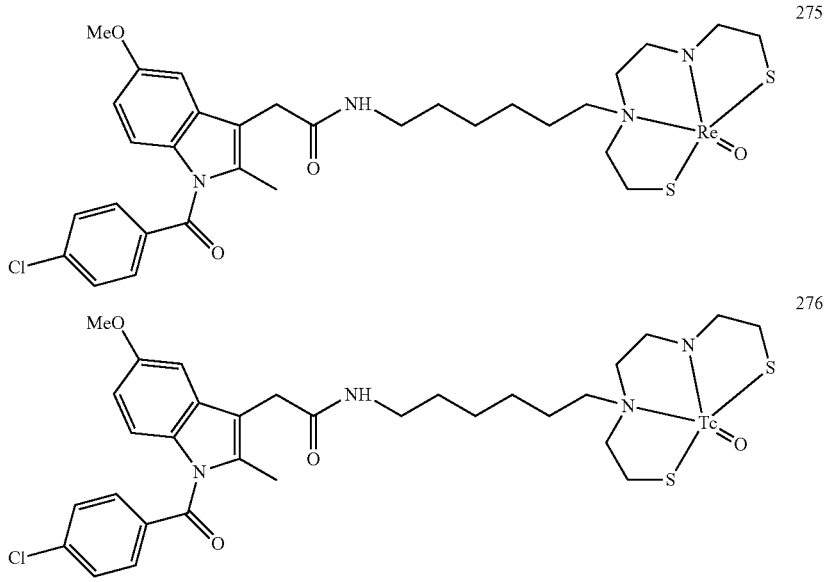

where Re is $^{186}$Re or $^{188}$Re; where Tc is $^{99m}$Tc; and pharmaceutically acceptable salts thereof.

In a twelfth embodiment, the conjugates of the first or second embodiment can be of the formula (NSAID, NSAID residue, or NSAID derivative)-(linker)-(chelator)-M-(terminal ligand)$_{z1}$ or (NSAID, NSAID residue, or NSAID derivative)-(linker)-M-(terminal ligand)$_{z2}$ where z1 is an integer between 0 and 4 inclusive; z2 is an integer between 0 and 5 inclusive; and -(linker)-(chelator)-M-(terminal ligand)$_{z1}$ or -(linker)-M-(terminal ligand)$_{z2}$ is selected from the group consisting of:

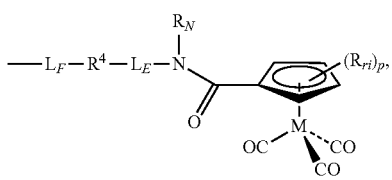

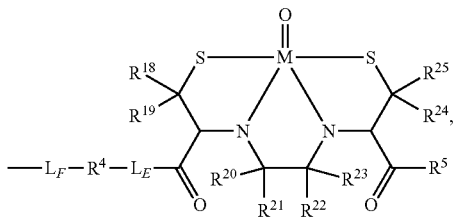

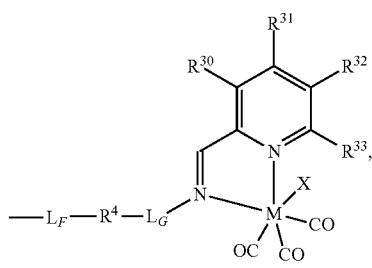

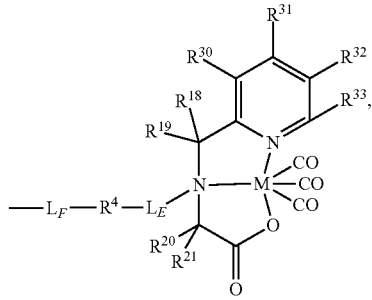

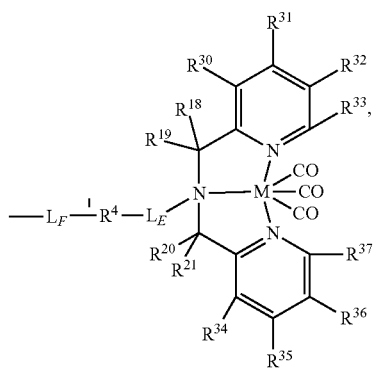

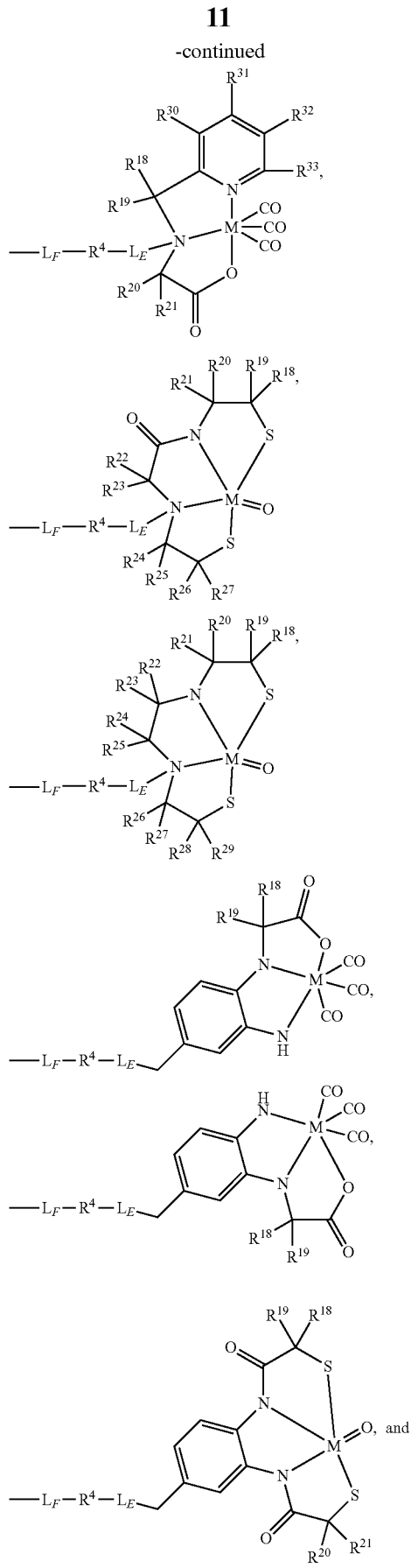

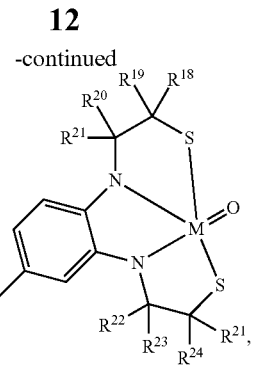

where $L_E$ is absent or is selected from the group consisting of —NH—, —N(R$^8$)—, and —(C=O)—, and R is optionally substituted $C_1$-$C_4$ alkyl, with the proviso that if the $L_E$ moiety of the group -$L_F$-R$^4$-$L_E$- would be attached to a nitrogen atom, then $L_E$ is absent; $L_G$ is absent or is selected from the group consisting of —NH—, —N(R$^8$)—, and —(C=O)—, and R$^8$ is optionally substituted $C_1$-$C_4$ alkyl; R$^4$ is selected from the group consisting of optionally substituted $C_1$-$C_{10}$ hydrocarbylene, optionally substituted $C_2$-$C_{10}$ heterohydrocarbylene, $C_3$-$C_8$ cycloalkyl, $C_1$-$C_6$ alkyl-$C_3$-$C_8$ cycloalkyl, $C_3$-$C_8$ cycloalkyl-$C_1$-$C_6$ alkyl, $C_1$-$C_6$ alkyl-$C_3$-$C_8$ cycloalkyl-$C_1$-$C_6$ alkyl, $C_6$-$C_{10}$ aryl, $C_1$-$C_6$ alkyl-$C_6$-$C_{10}$ aryl, $C_6$-$C_{10}$ aryl-$C_1$-$C_6$ alkyl, and $C_1$-$C_6$ alkyl-$C_6$-$C_{10}$ aryl-$C_1$-$C_6$ alkyl; R$^5$ is selected from the group consisting of —OH, —NH$_2$, —NH($C_1$-$C_4$ alkyl), —N($C_1$-$C_4$ alkyl)($C_1$-$C_4$ alkyl), —OCH$_3$, and —OCH$_2$CH$_3$; R$_N$ is H or ($C_1$-$C_4$ alkyl); $L_F$ is absent or is a functional group selected from the group consisting of —(C=O)—, —O—, —N(R$^9$)—, —(C=O)(N)(R$^9$)—, —N(R$^9$)—(C=O)—, —(C=O)N(H)—, —N(H)—(C=O)— —(SO$_2$)N(R$^9$)—, —N(R$^9$)—(SO$_2$)—, —N(R$^9$)(C=O)N(R$^9$)—, —N(R$^9$)—(C=O)—O—, —O—(C=O)N(R$^9$)—, —(CH=CH)—, or a divalent cycloalkyl or heterocyclic group, where R$^9$ is selected from the group consisting of H and optionally substituted $C_1$-$C_4$ alkyl; and R$^{18}$, R$^{19}$, R$^{20}$, R$^{21}$, R$^{22}$, R$^{23}$, R$^{24}$, R$^{25}$, R$^{26}$, R$^{27}$, R$^{28}$, and R$^{29}$ are independently selected from the group consisting of hydrogen, $C_1$-$C_4$ alkyl, $C_1$-$C_4$ alkyl substituted with fluoro, hydroxy, —O—$C_1$-$C_4$ alkyl, or $C_3$-$C_6$ cycloalkyl; or, independently of the other substituents, (R$^{18}$ and R$^{19}$) together with the carbon to which they are attached form a $C_3$-$C_8$ cycloalkyl ring or heterocycloalkyl ring, (R$^{20}$ and R$^{21}$) together with the carbon to which they are attached form a $C_3$-$C_8$ cycloalkyl ring or heterocycloalkyl ring, or (R$^{22}$ and R$^{23}$) together with the carbon to which they are attached independently form a $C_3$-$C_8$ cycloalkyl ring or heterocycloalkyl ring, or (R$^{24}$ and R$^{25}$) together with the carbon to which they are attached independently form a $C_3$-$C_8$ cycloalkyl ring or heterocycloalkyl ring, or (R$^{26}$ and R$^{27}$) together with the carbon to which they are attached independently form a $C_3$-$C_8$ cycloalkyl ring or heterocycloalkyl ring, or (R$^{28}$ and R$^{29}$) together with the carbon to which they are attached independently form a $C_3$-$C_8$ cycloalkyl ring or heterocycloalkyl ring, with the proviso that only one of (R$^{18}$ and R$^{19}$), (R$^{20}$ and R$^{21}$), or (R$^{22}$ and R$^{23}$), or (R$^{24}$ and R$^{25}$), or (R$^{26}$ and R$^{27}$), or (R$^{28}$ and R$^{29}$) together with the carbon to which they are attached independently form a $C_3$-$C_8$ cycloalkyl ring or heterocycloalkyl ring; R$^{30}$, R$^{31}$, R$^{32}$, and R$^{33}$ are independently selected from hydrogen and $C_1$-$C_4$ alkyl, or one pair of (R$^{30}$ and R$^{31}$), (R$^{31}$ and R$^{32}$), or (R$^{32}$ and R$^{33}$), together with the atoms to which they are attached, form a six-membered aryl ring or a five-to-six membered heteroaryl ring; R$^{34}$, R$^{35}$, R$^{36}$, and R$^{37}$ are independently selected from hydrogen and $C_1$-$C_4$ alkyl, or one pair of ($R^{34}$ and $R^{35}$), ($R^{35}$ and $R^{36}$), or ($R^{36}$ and $R^{37}$), together with the atoms to which they are attached, form a six-membered aryl ring or a five-to-six membered heteroaryl ring; M is selected from the group consisting of $^{99m}$Tc, $^{52}$Mn, $^{186}$Re and $^{188}$Re; $R_{(ri)}$ is —$CH_3$ or —$CH_2CH_3$ and p is an integer between 0 and 4 inclusive; and X is Cl or Br; or pharmaceutically acceptable salts thereof. In a further embodiment, $R^5$ is selected from the group consisting of —$NH_2$, —$NH(C_1$-$C_4$ alkyl), —$N(C_1$-$C_4$ alkyl)($C_1$-$C_4$ alkyl), —$OCH_3$, and —$OCH_2CH_3$; in yet a further embodiment, $R^5$ is selected from the group consisting of —$NH_2$, —$OCH_3$, and —$OCH_2CH_3$.

In a thirteenth embodiment, the -(linker)-(chelator)-M-(terminal ligand)$_{z1}$ or -(linker)-M-(terminal ligand)$_{z2}$ group of the conjugates of the twelfth embodiment can be selected from the group consisting of:

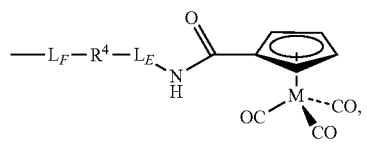

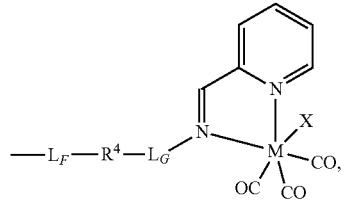

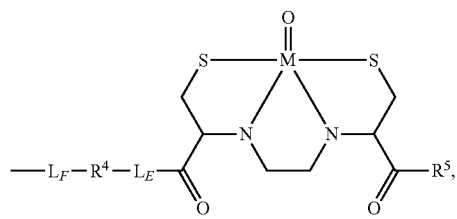

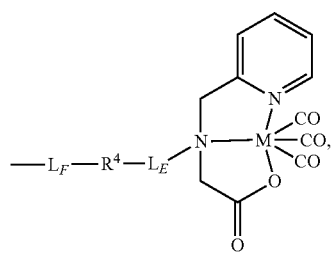

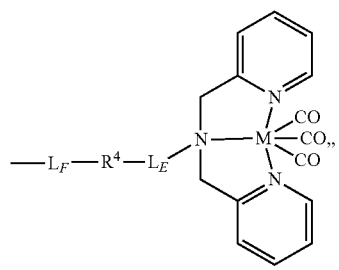

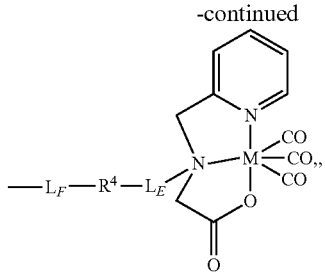

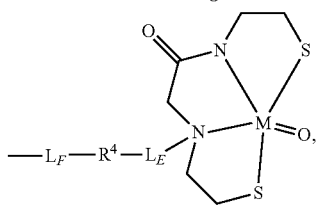

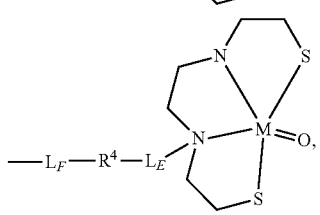

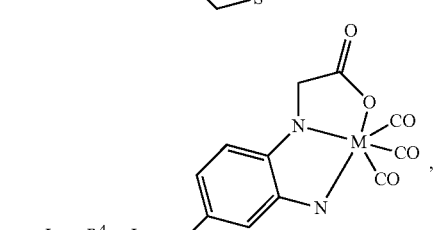

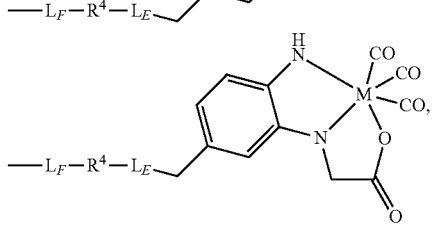

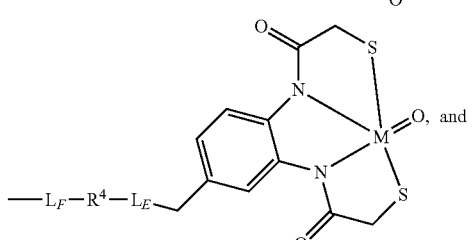

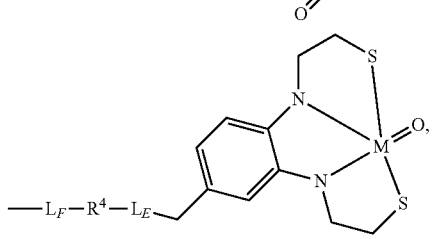

where the substituents are as indicated in the twelfth embodiment, and pharmaceutically acceptable salts thereof.

In a fourteenth embodiment, the non-steroidal anti-inflammatory drug (NSAID), residue of a NSAID, or derivative of a NSAID in any of the first, second, third, fourth, fifth, sixth, seventh, eighth, ninth, tenth, eleventh, twelfth, or thirteenth embodiments can be selected from the group consisting of:
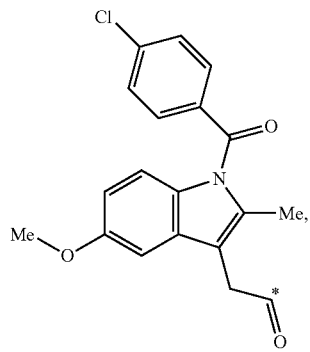
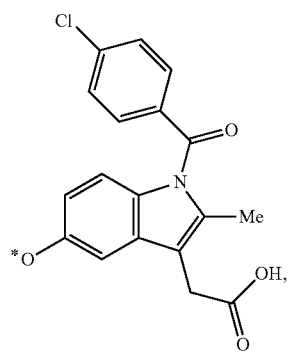
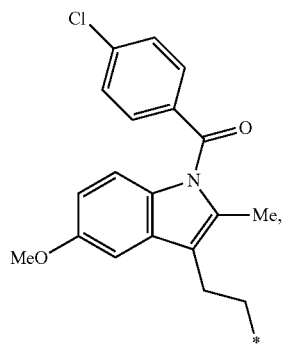
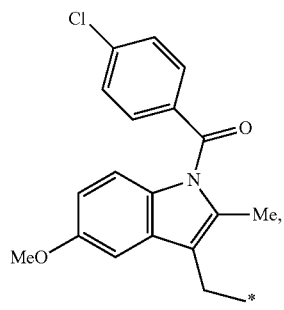
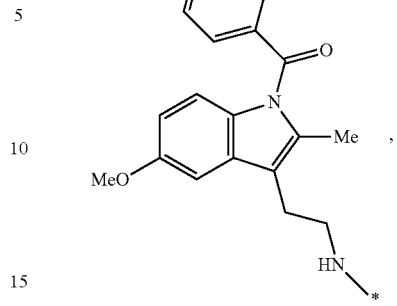
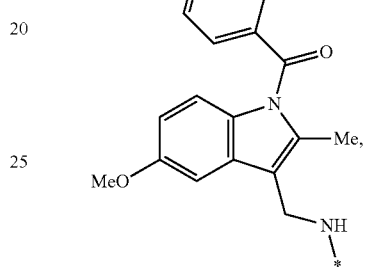
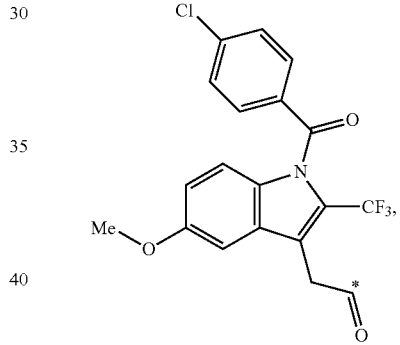
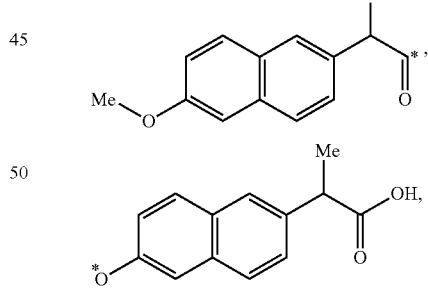
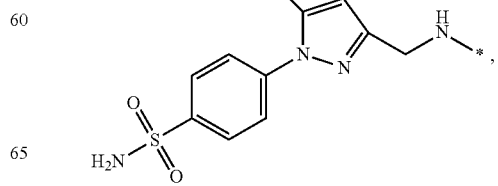

17

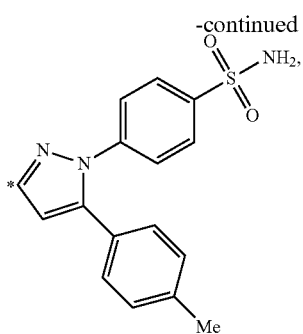

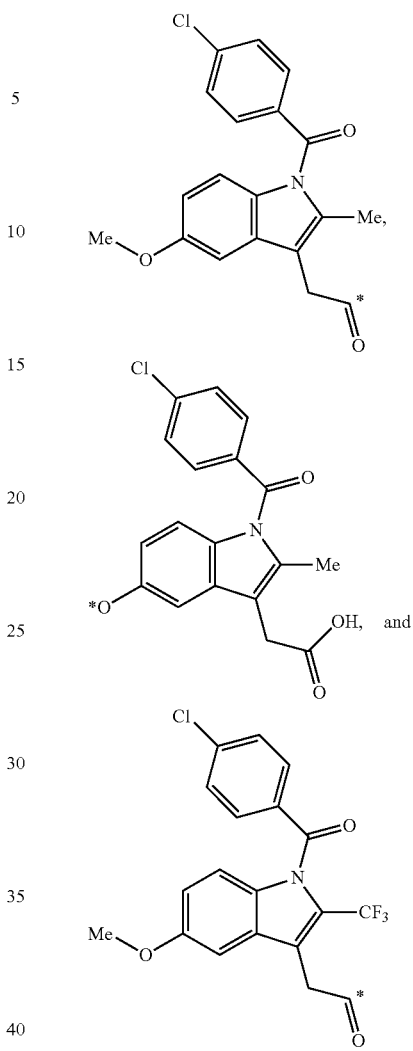

where the atom marked with an asterisk * indicates an open valence at that atom at which the NSAID, residue of the NSAID or derivative of the NSAID is attached to the remainder of the conjugate. In a fifteenth embodiment, the non-steroidal anti-inflammatory drug (NSAID), residue of a NSAID, or derivative of a NSAID in any of the first, second, third, fourth, fifth, sixth, seventh, eighth, ninth, tenth, eleventh, twelfth, or thirteenth embodiment can be selected from the group consisting of:

18 where the carbon atom or oxygen atom marked with an asterisk * indicates an open valence at that atom at which the NSAID, residue of a NSAID, or derivative of a NSAID is attached to the remainder of the conjugate.

In a sixteenth embodiment, the conjugate of the first, second, third, or fourth embodiments can be selected from the group consisting of:

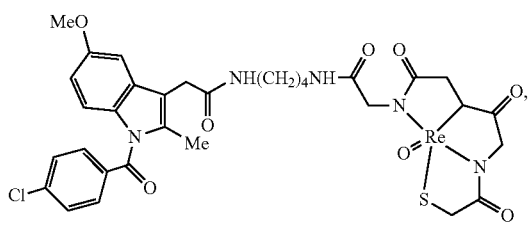

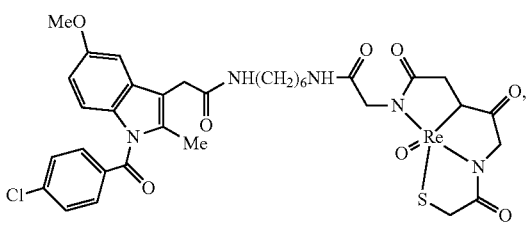

-continued
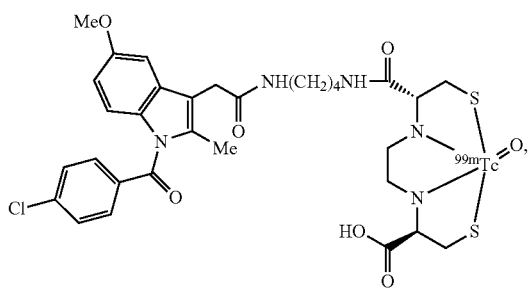
46
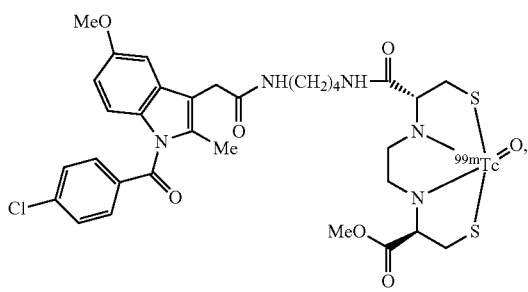
47
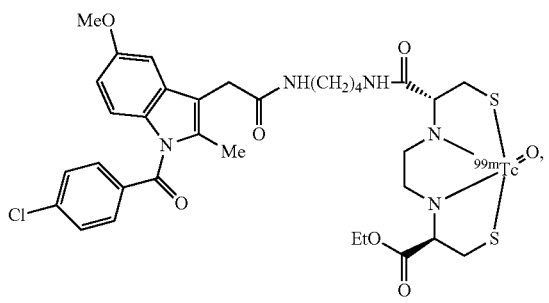
48
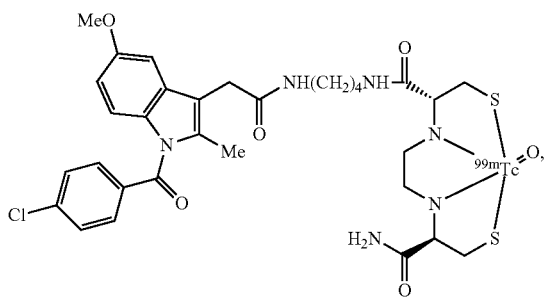
49
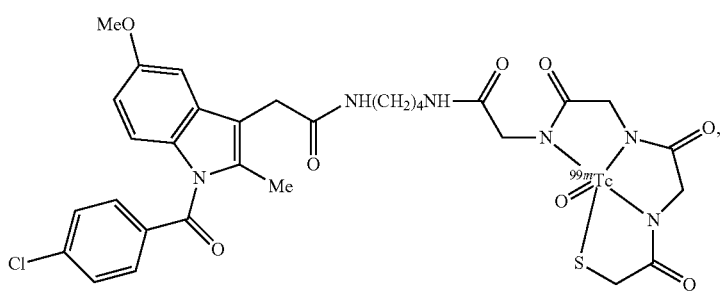
51
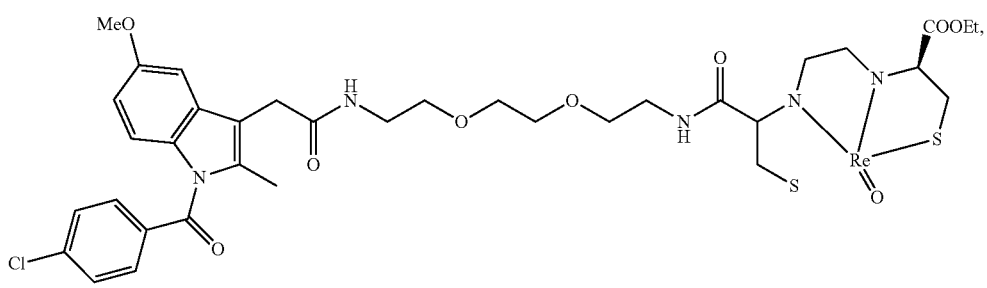
178
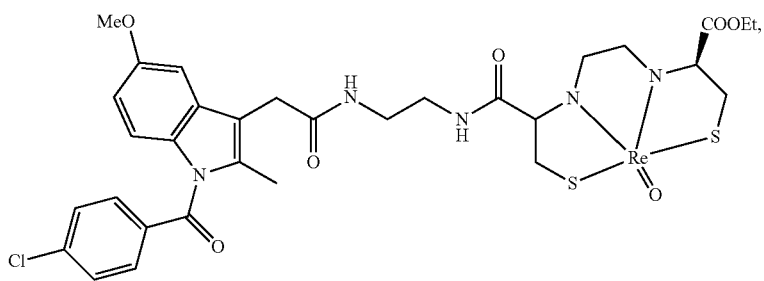
179

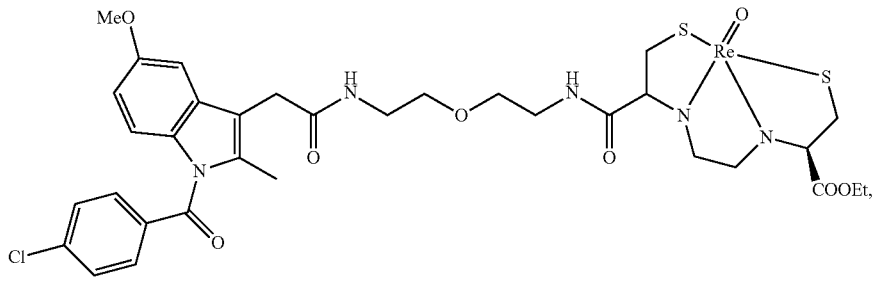
180
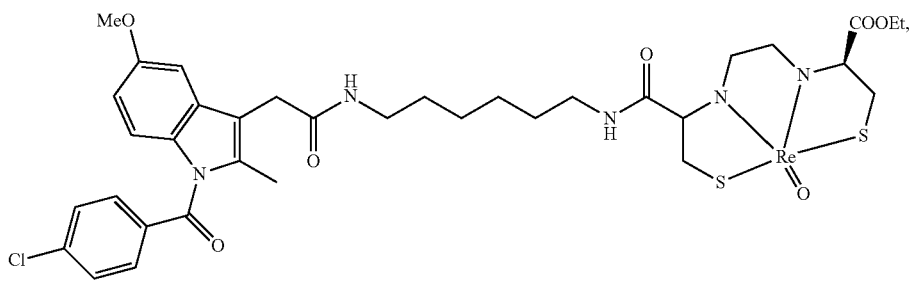
181
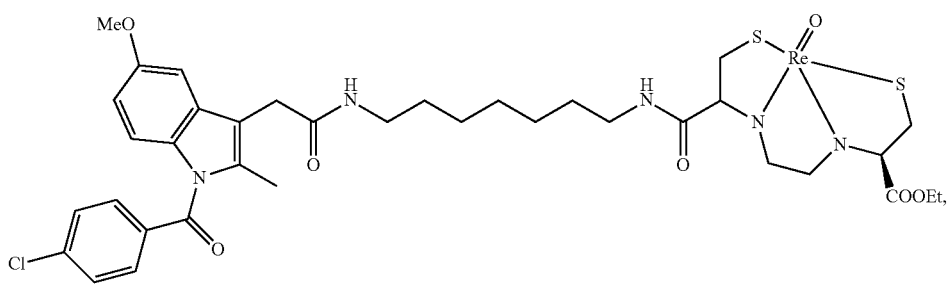
182
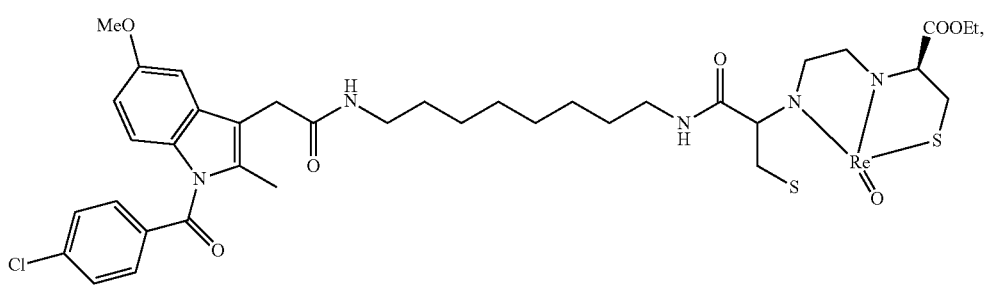
183
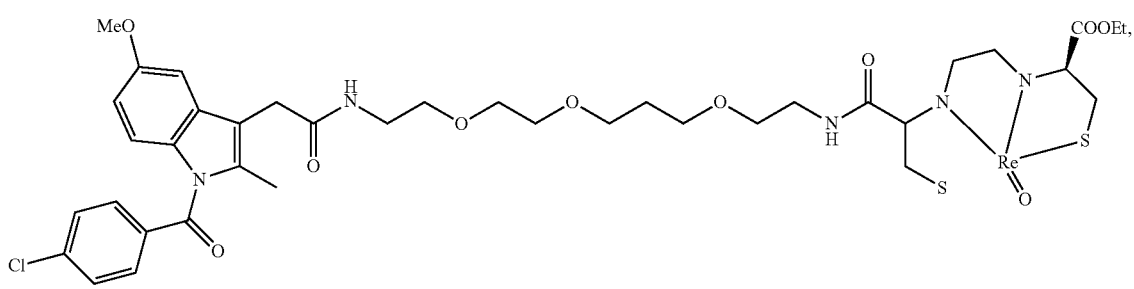
184

193
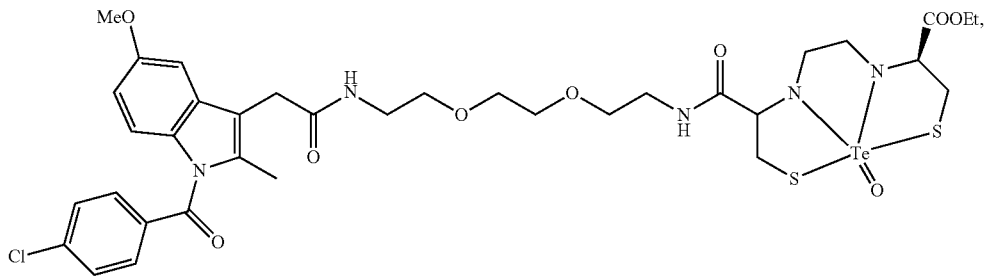
194
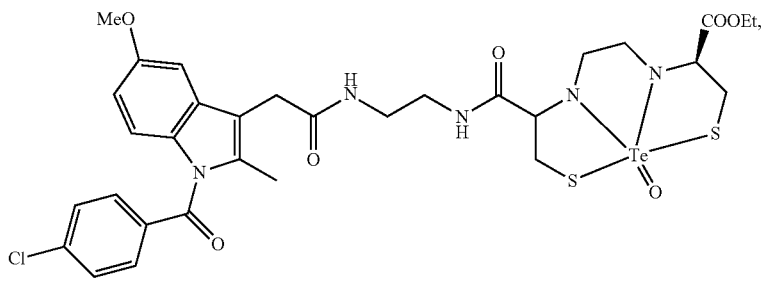
195
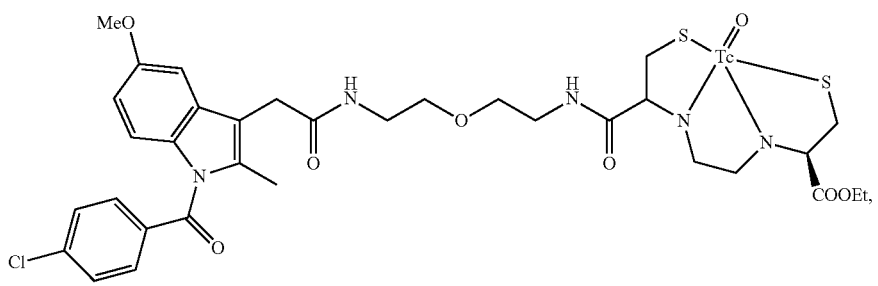
196
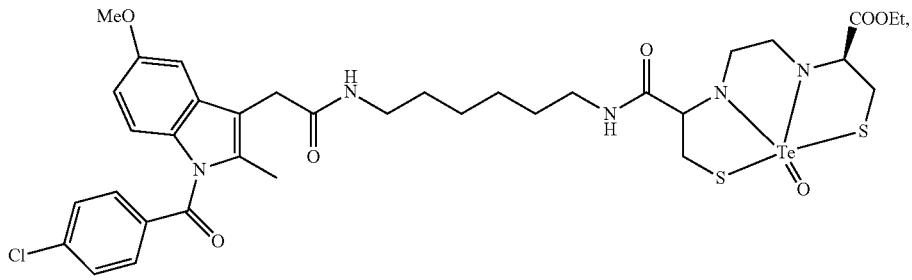
197
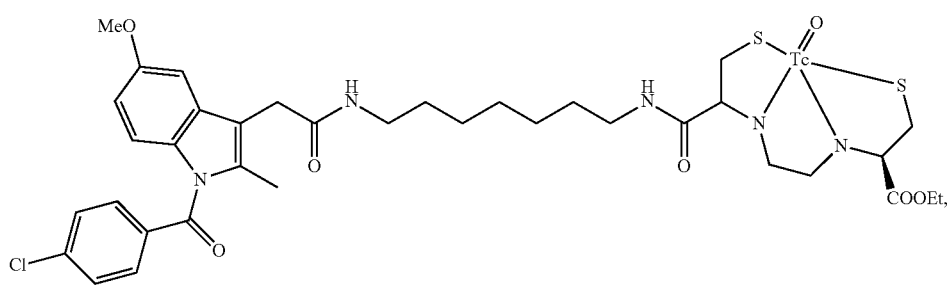

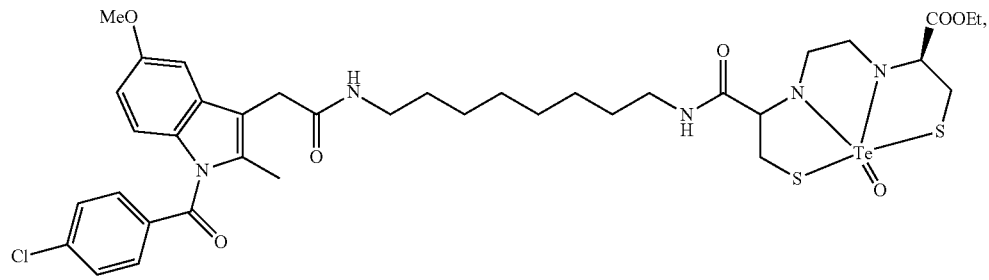
198
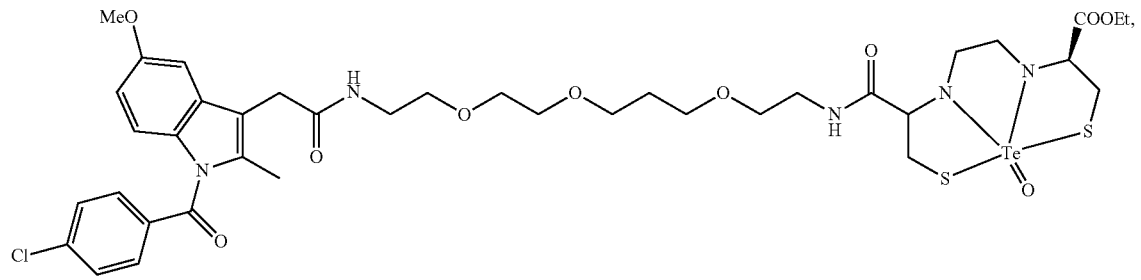
199
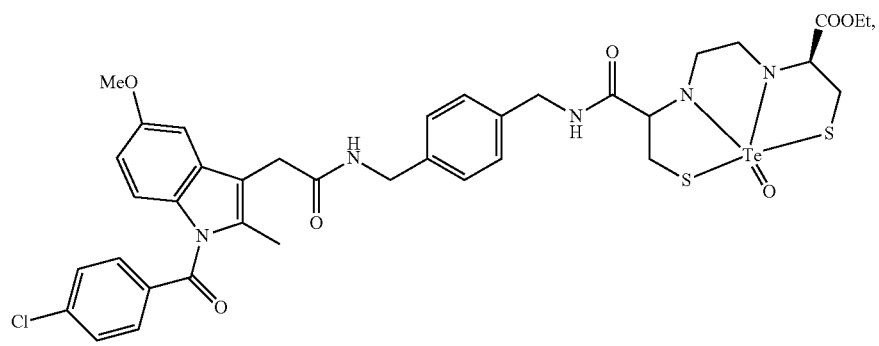
200
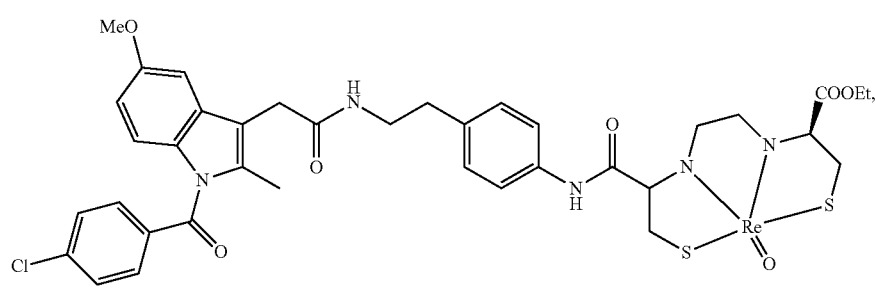
201
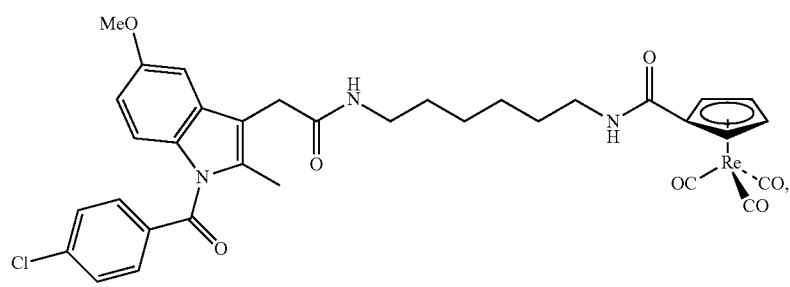
242

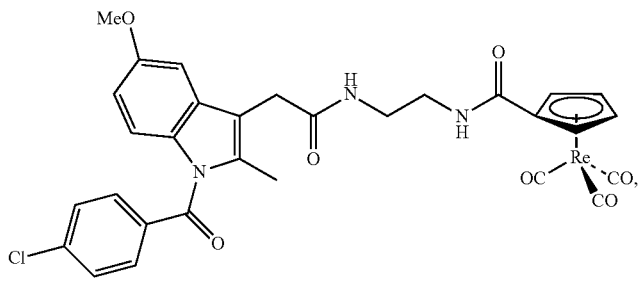
243
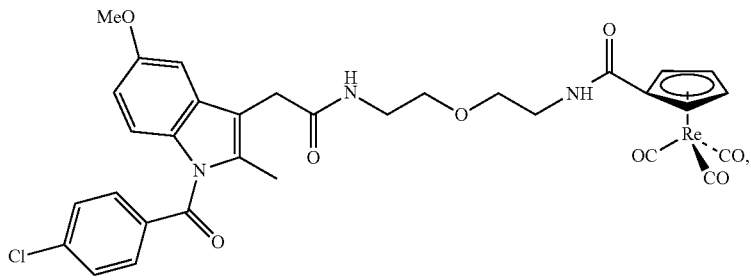
244
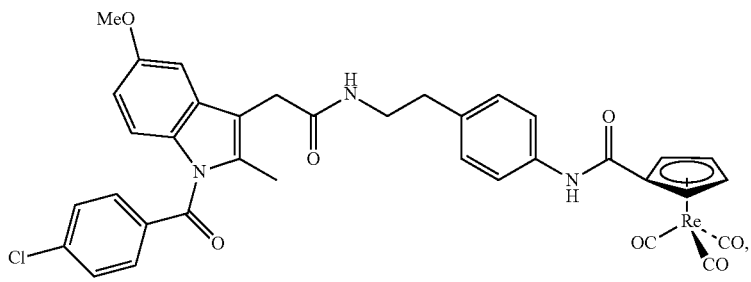
245
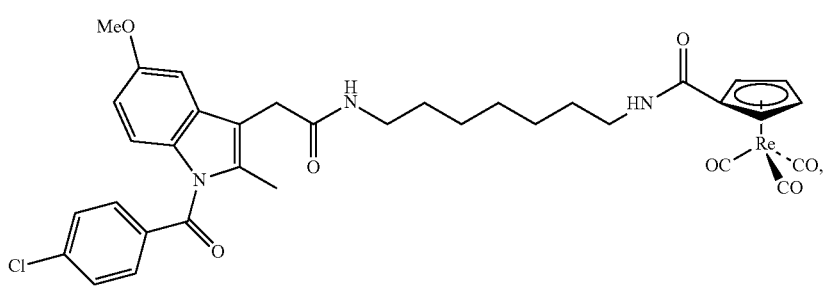
246
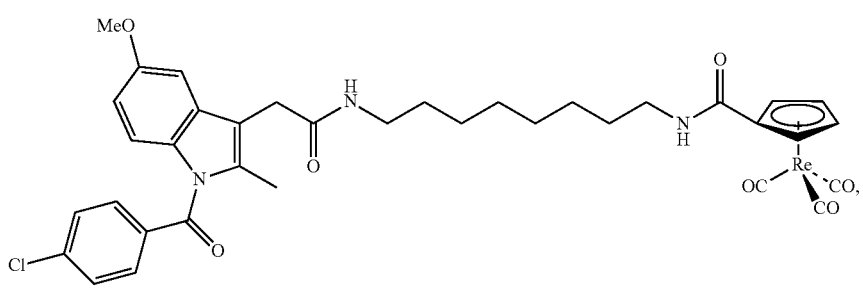
247

-continued
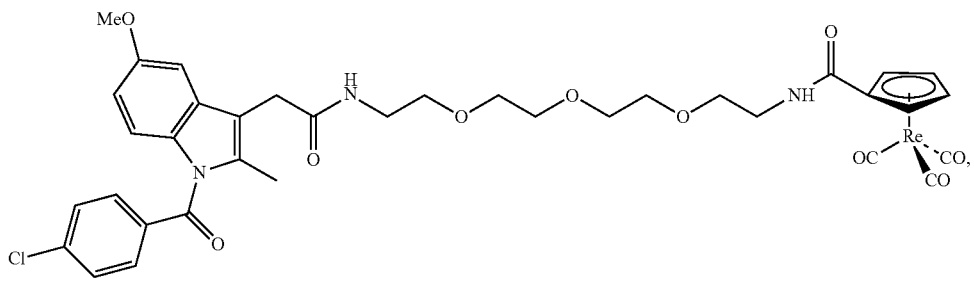
248
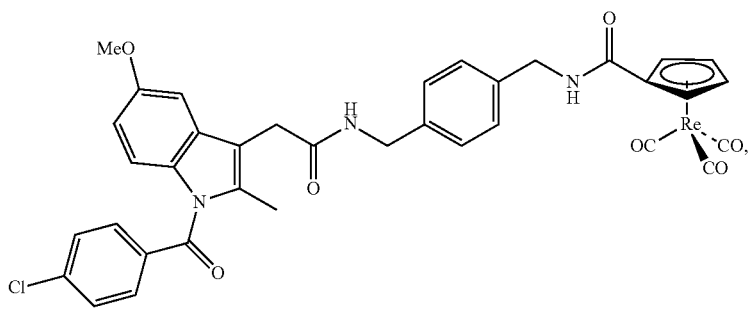
249
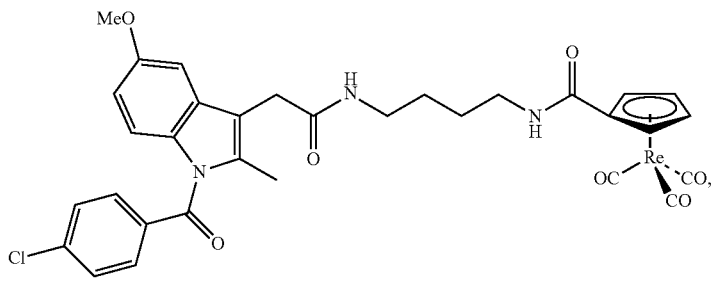
250
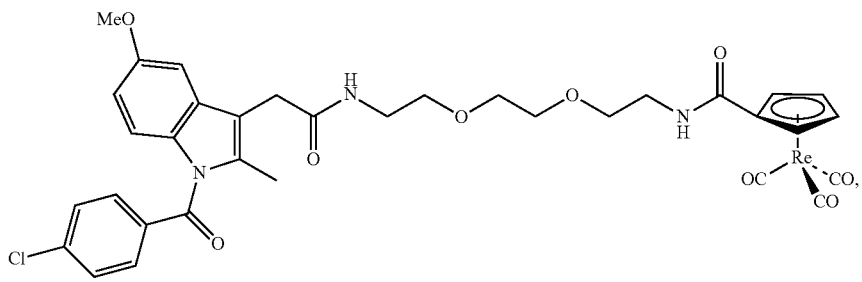
251
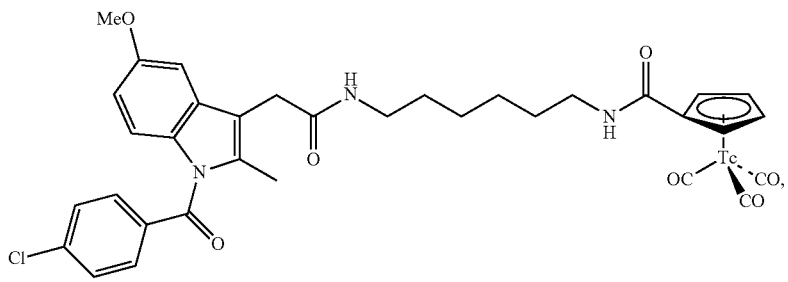
259

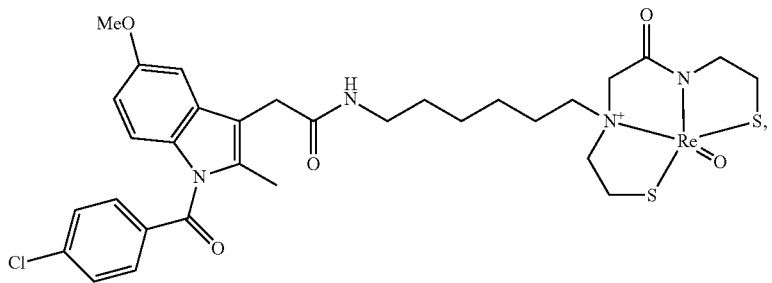
260
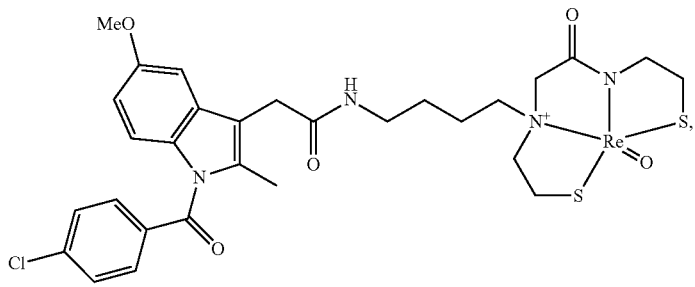
261
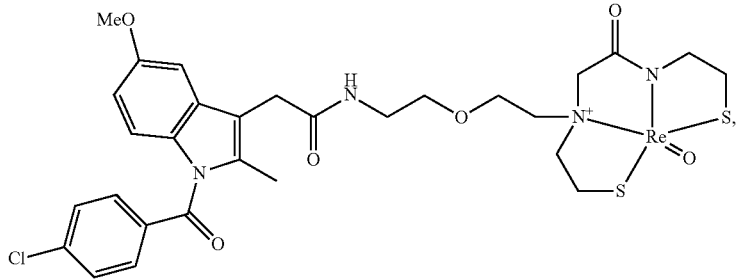
262
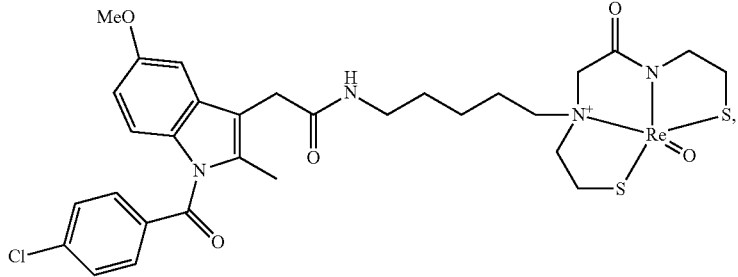
263
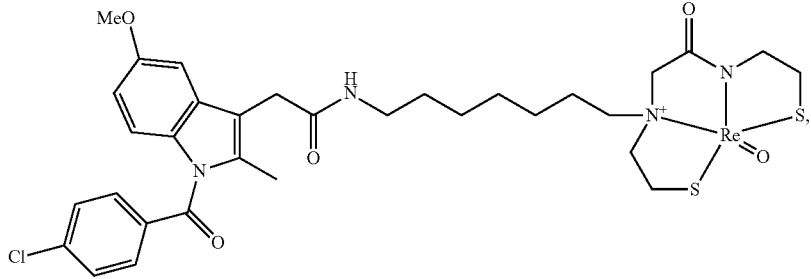
264

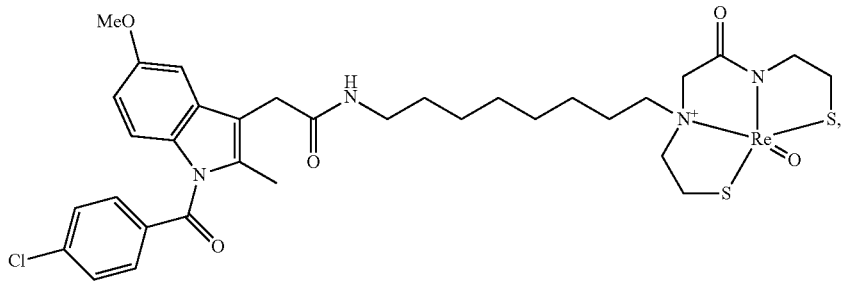
265
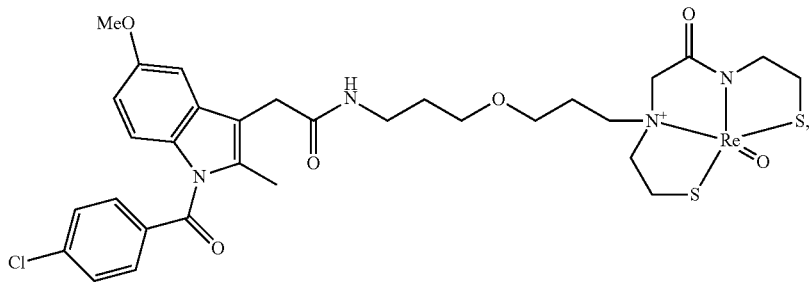
266
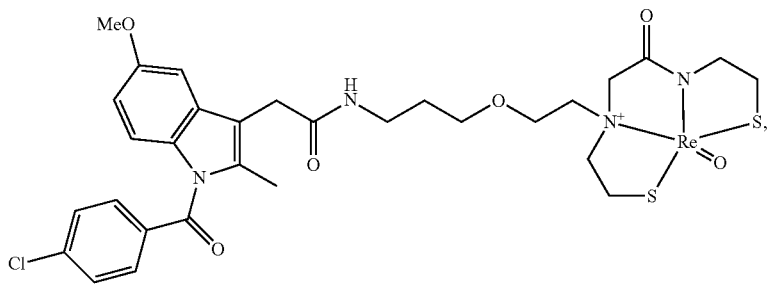
267
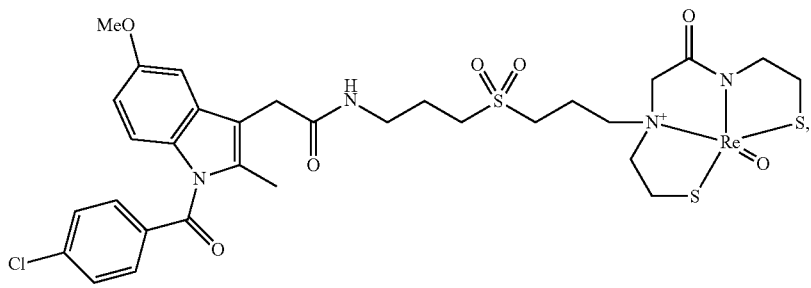
268
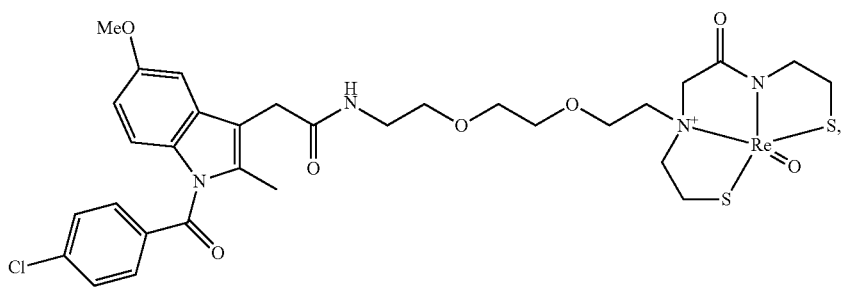
269

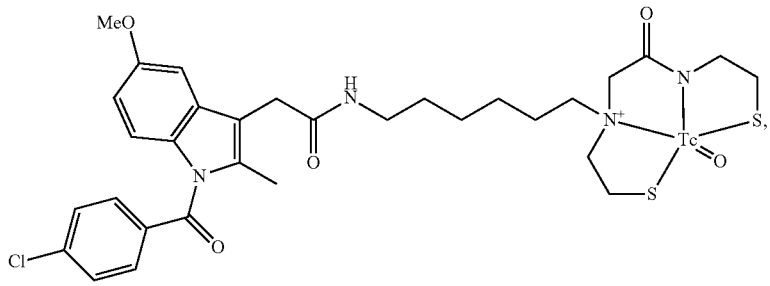
270
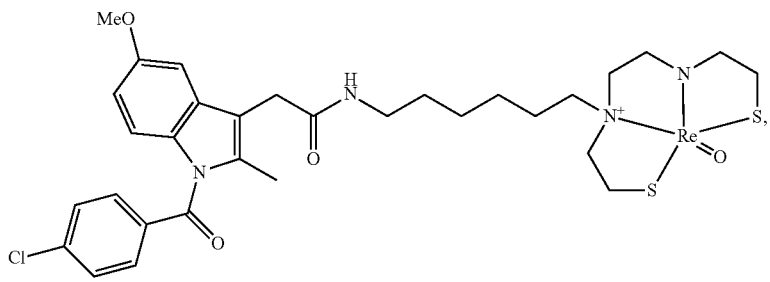
275
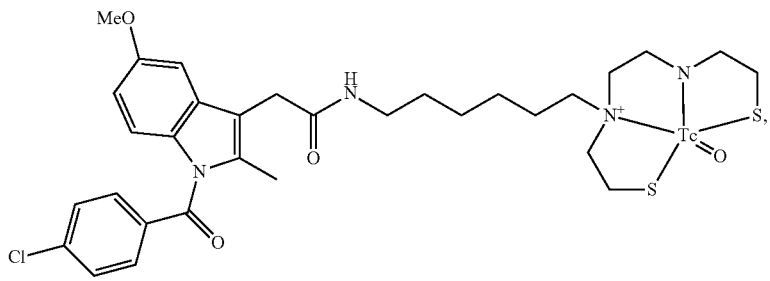
276
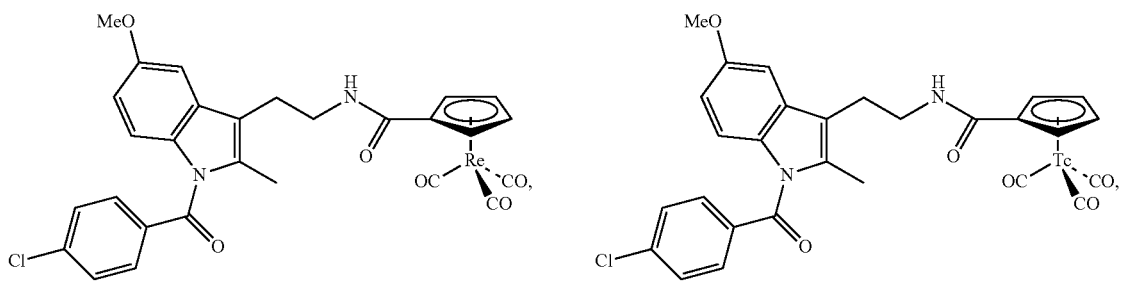
297  299
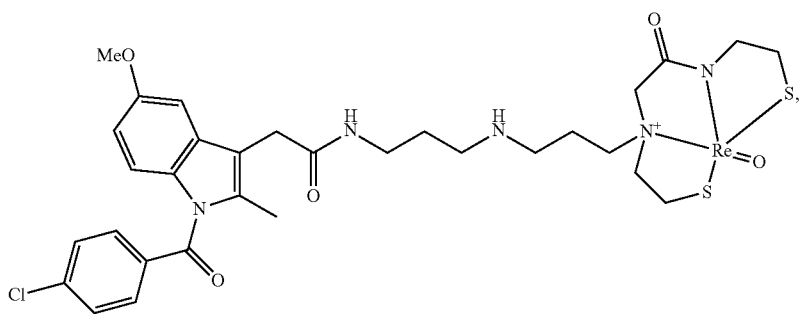
320

-continued
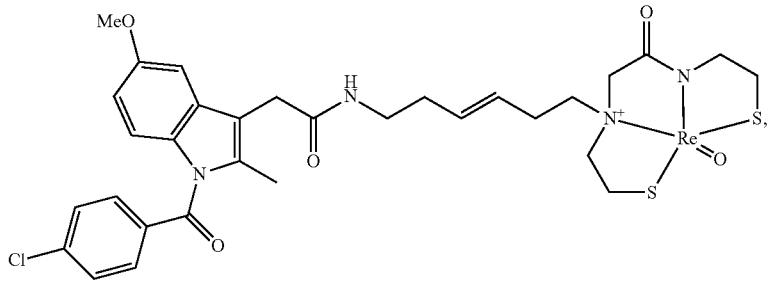
341
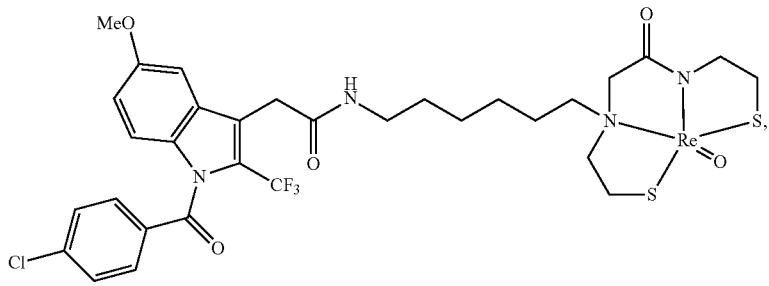
351
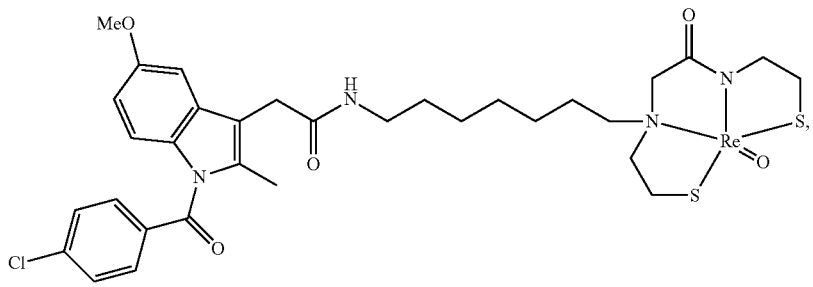
352
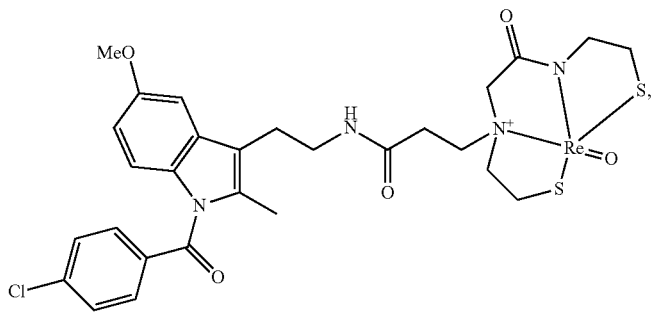
356
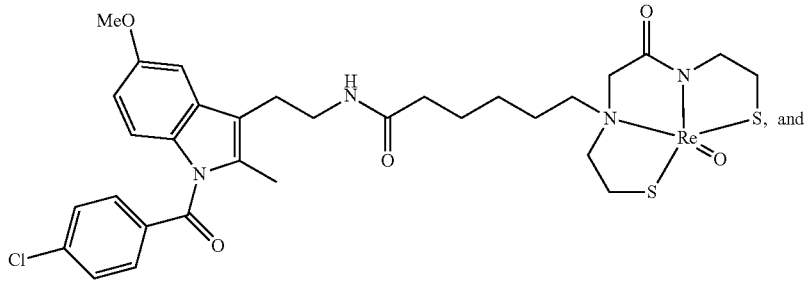
359

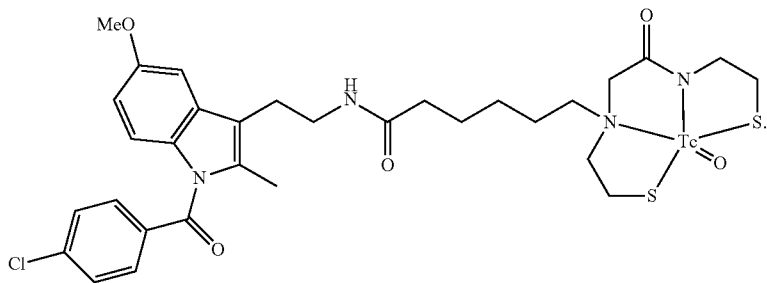
360
where Tc is $^{99m}$Tc, Re is $^{186}$Re or $^{188}$Re; and pharmaceutically acceptable salts thereof.
In a seventeenth embodiment, the conjugate of any one of the first, second, or third embodiments can be selected from the group consisting of:
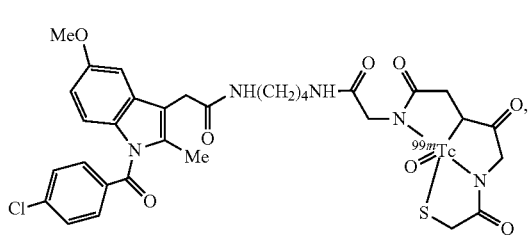
52
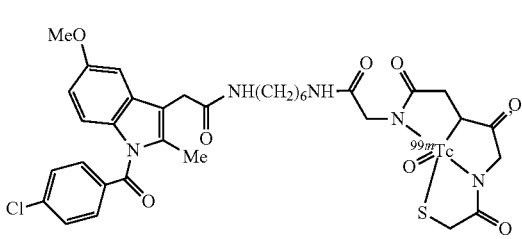
54
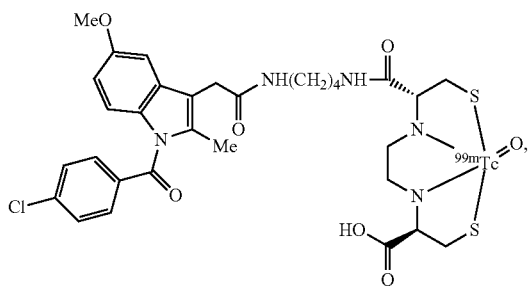
46
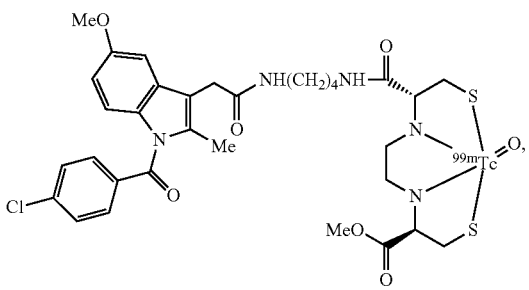
47
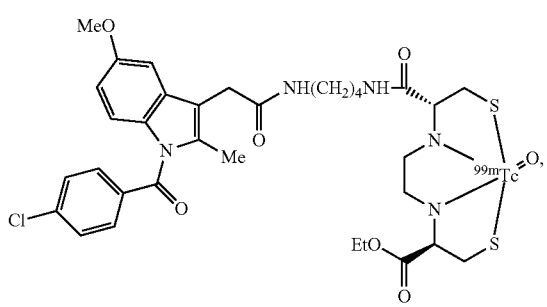
48
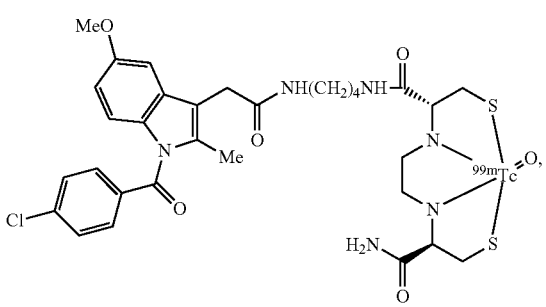
49

-continued
53
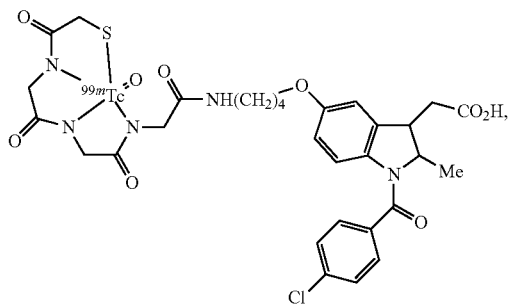
73
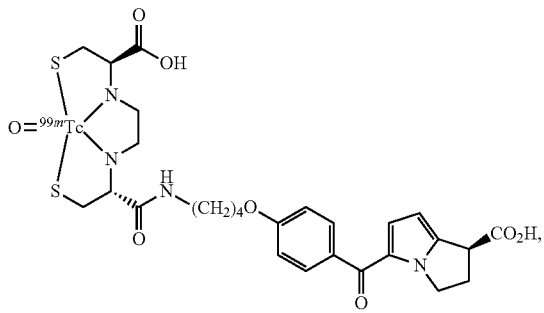
149
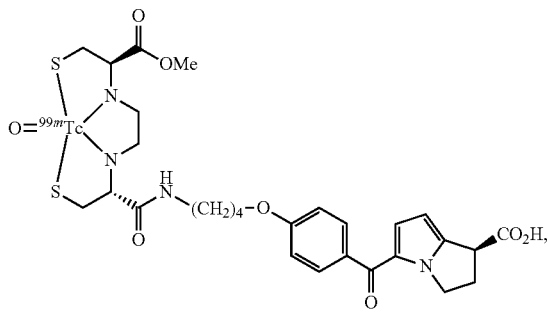
150
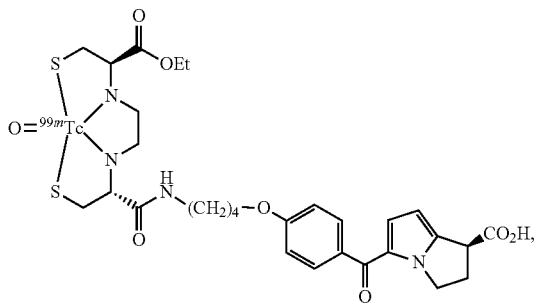
74
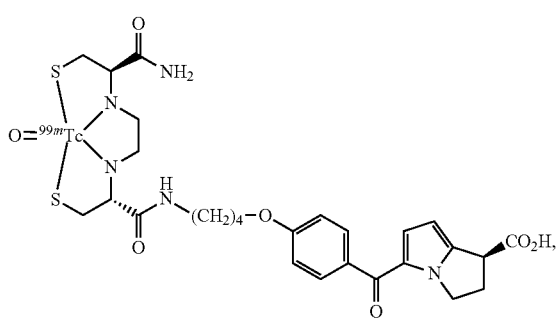
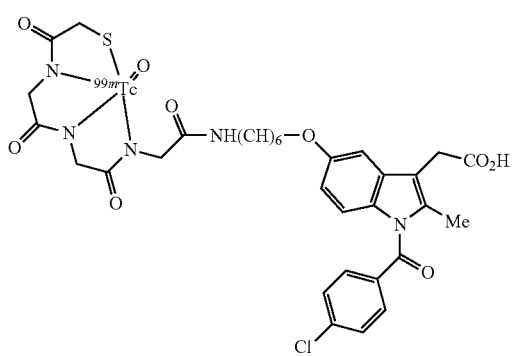
77
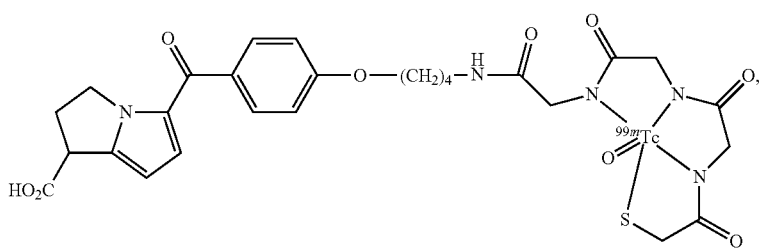
78
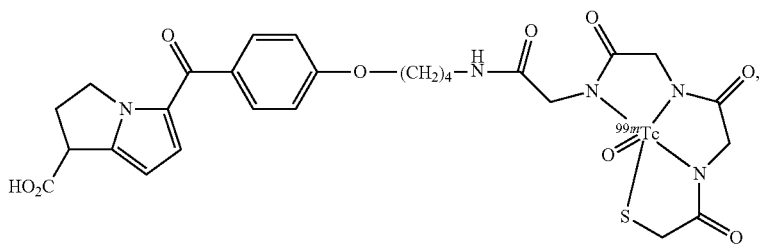

-continued
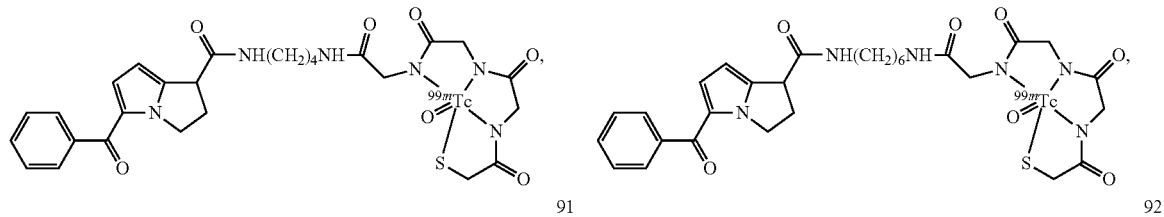
151
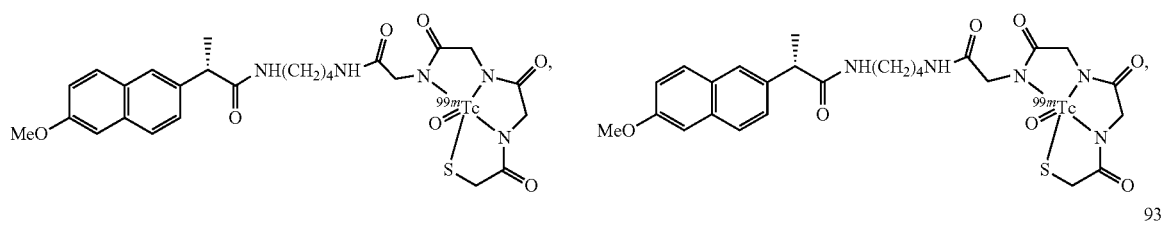
152
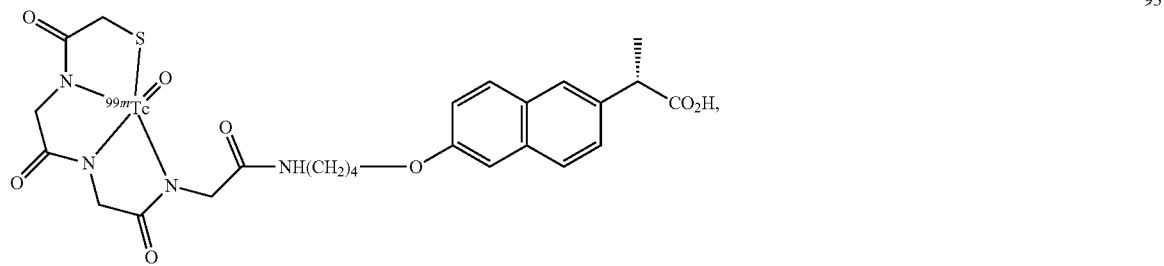
91
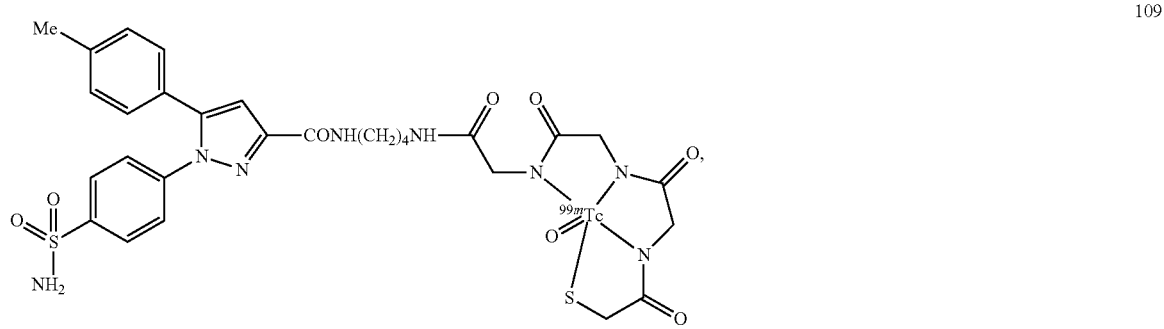
92
93
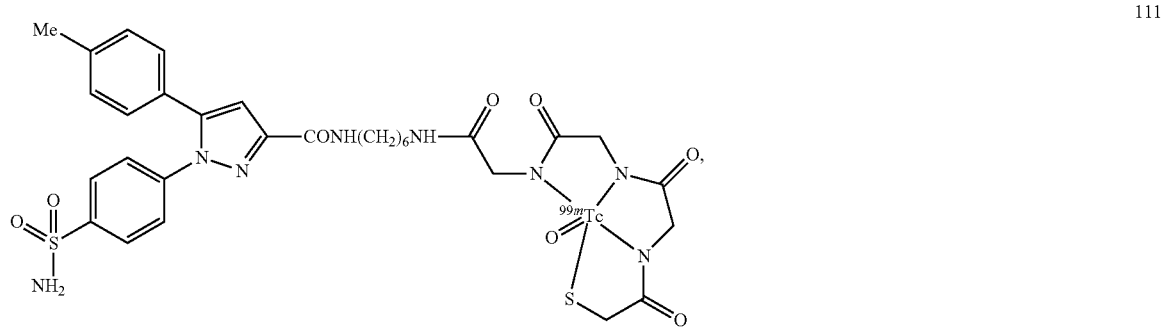
109
111
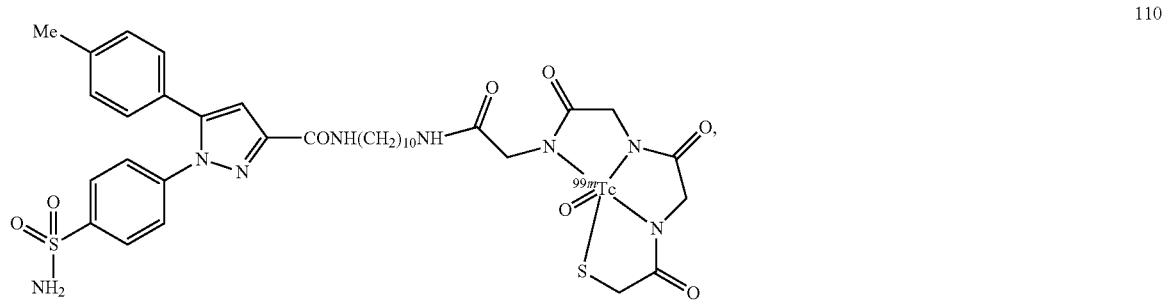
110

-continued
153
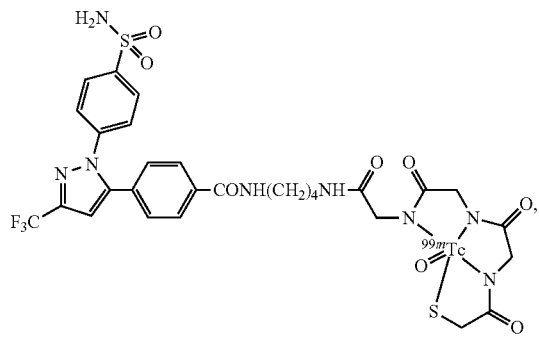
154
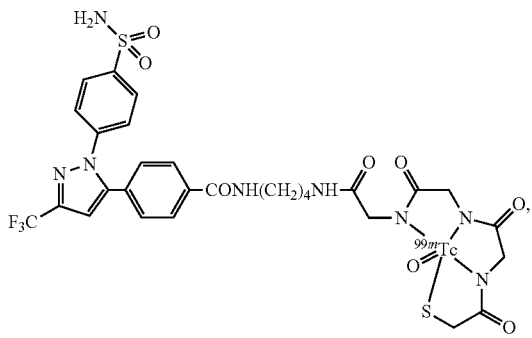
155
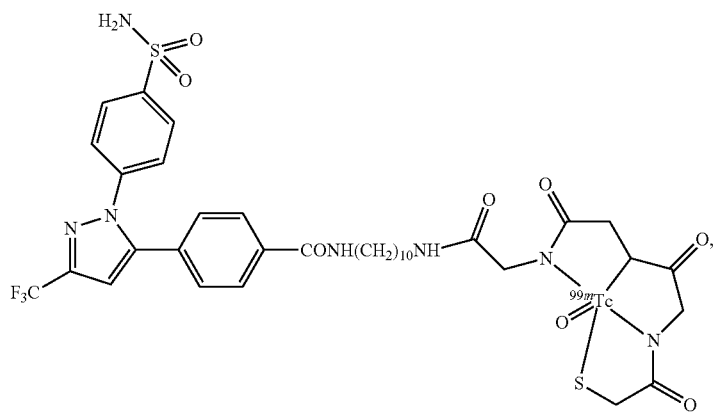
156
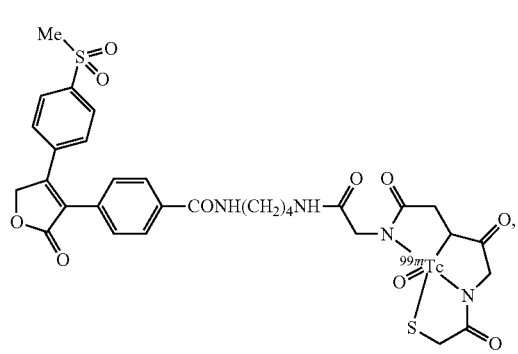
157
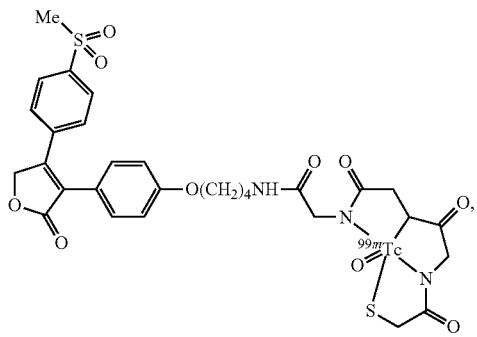
158
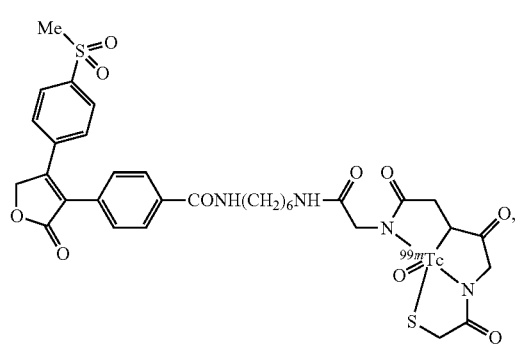
159
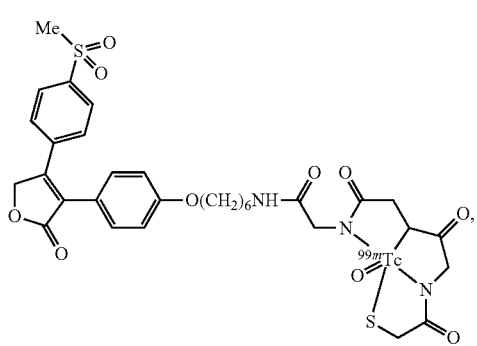

-continued
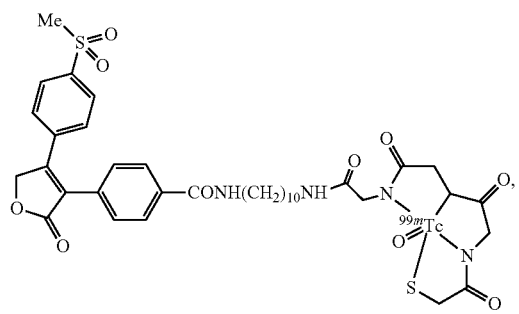
160
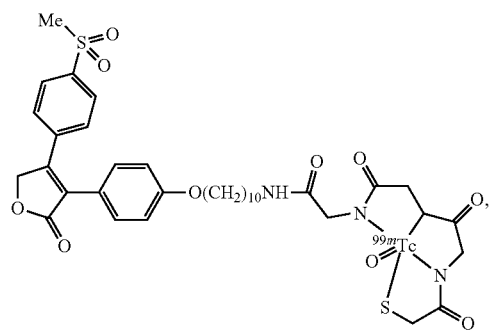
161
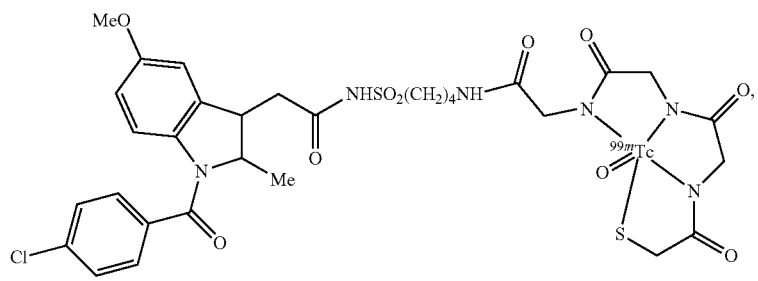
162
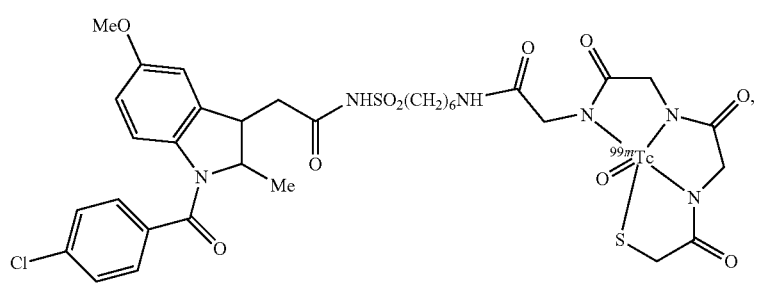
163
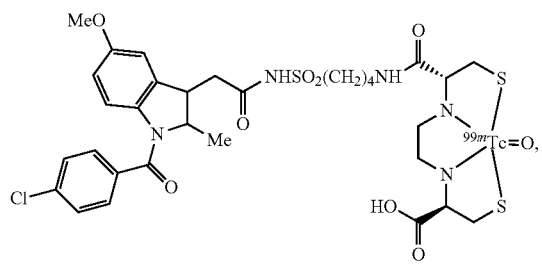
164
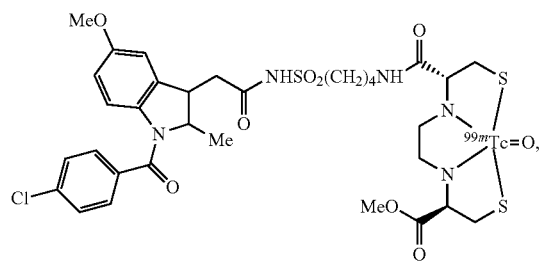
165
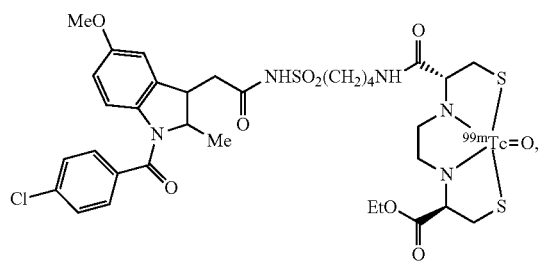
166
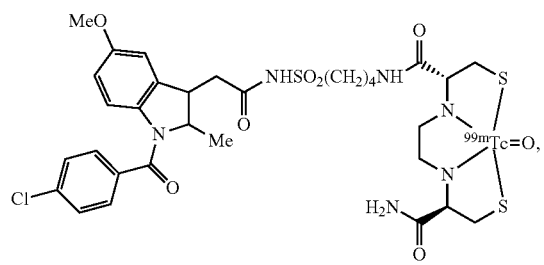
167

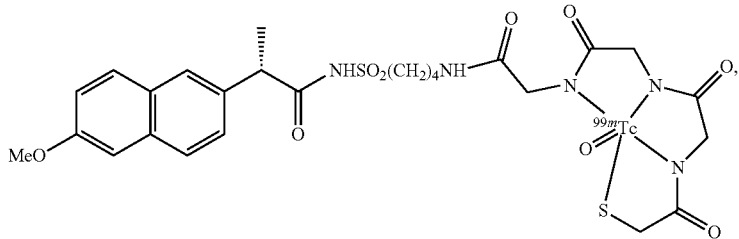
168
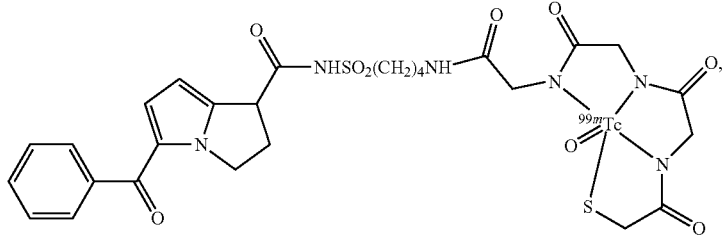
169
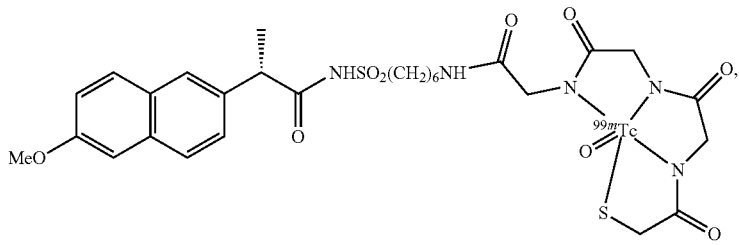
170
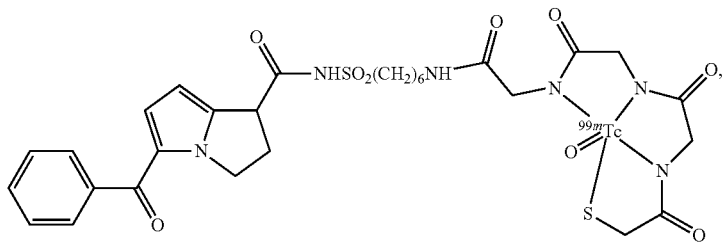
171
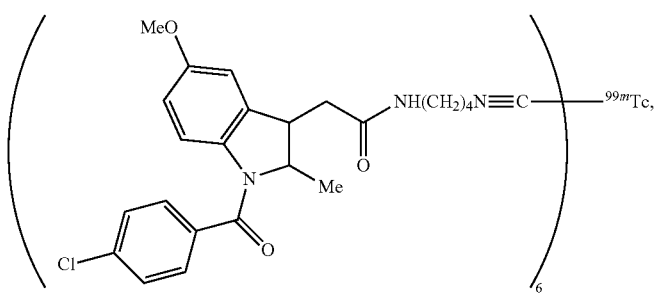
51

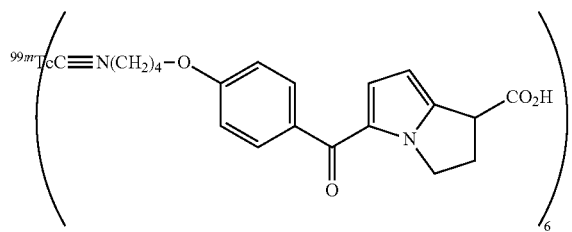
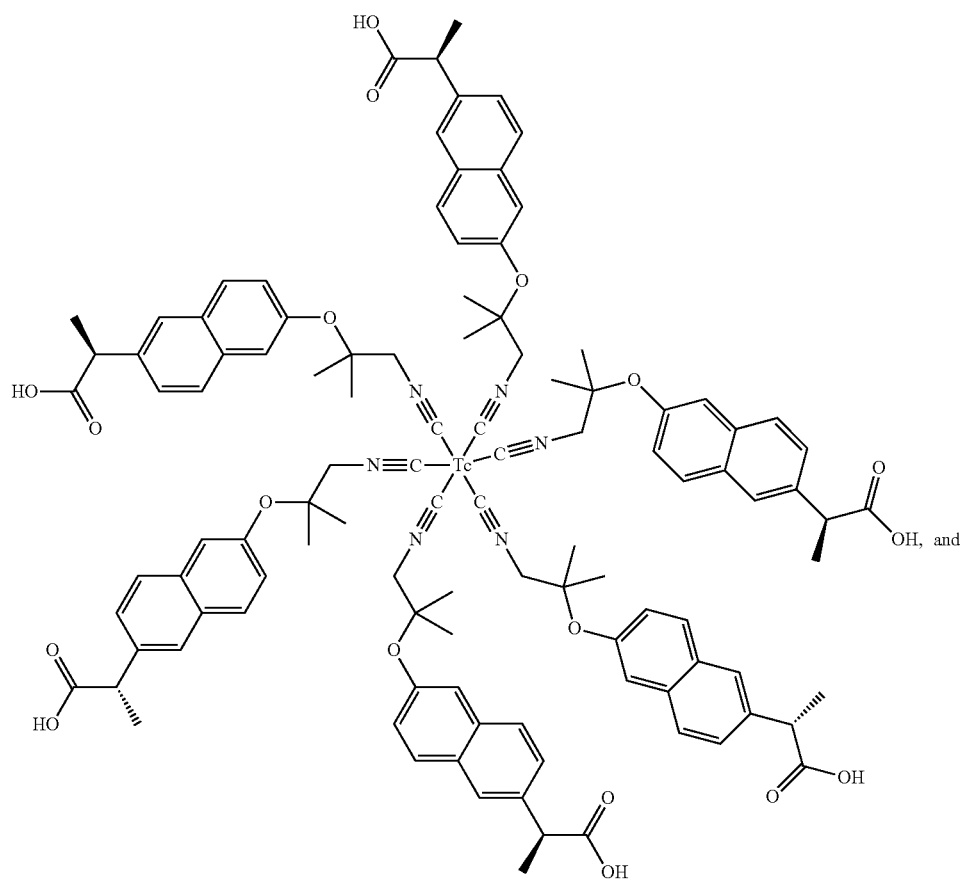

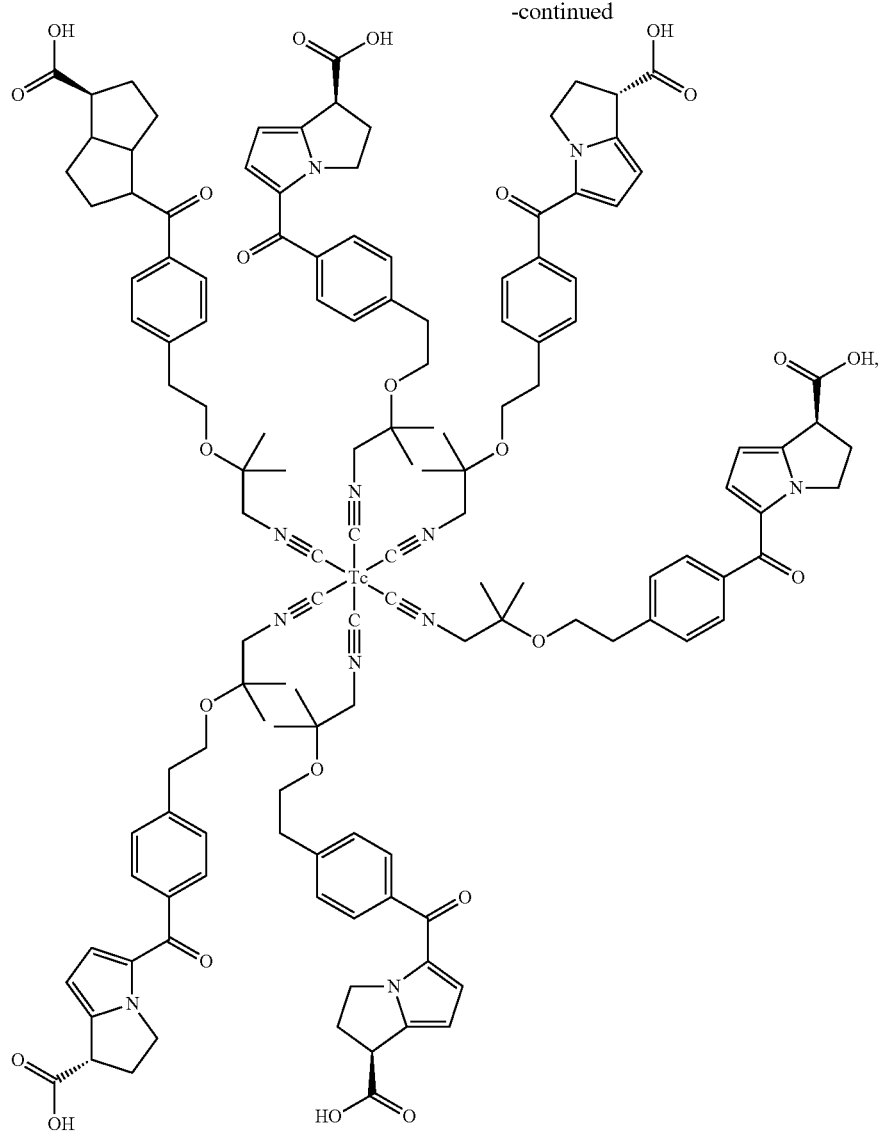
wherein Tc is $^{99m}$Tc; and pharmaceutically acceptable salts thereof.
In an eighteenth embodiment, the conjugate of any one of the first, second, or third embodiments can be selected from the group consisting of:
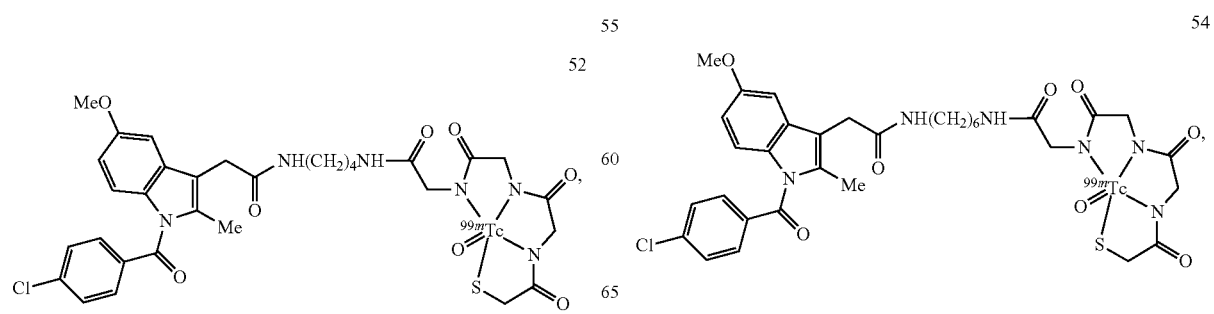
-continued

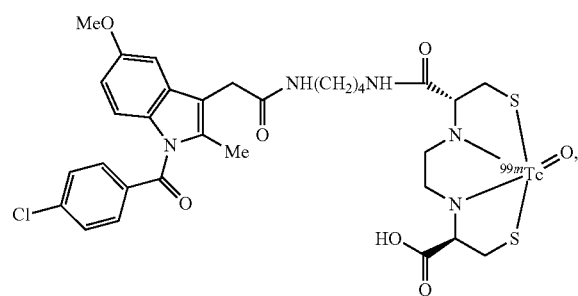
46
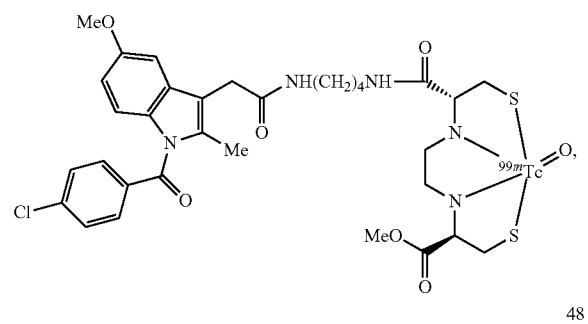
47
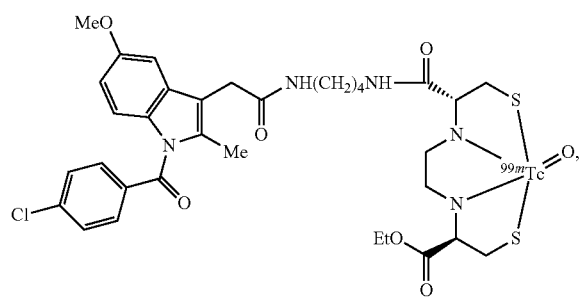
48
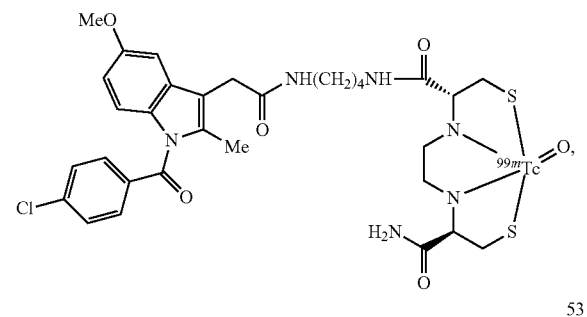
49
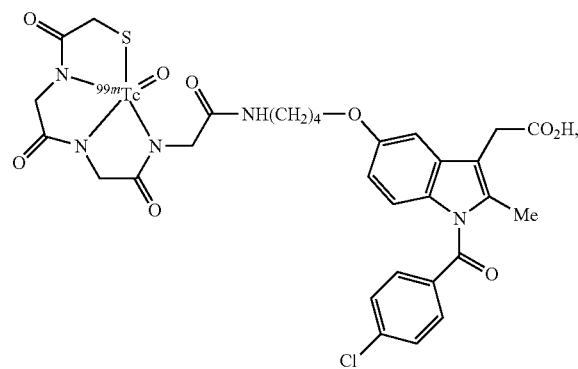
53
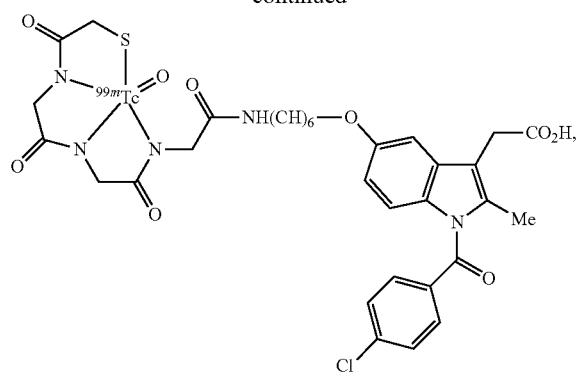
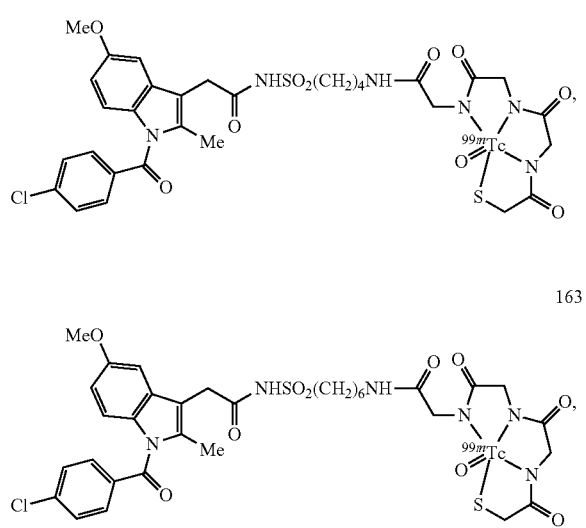
162
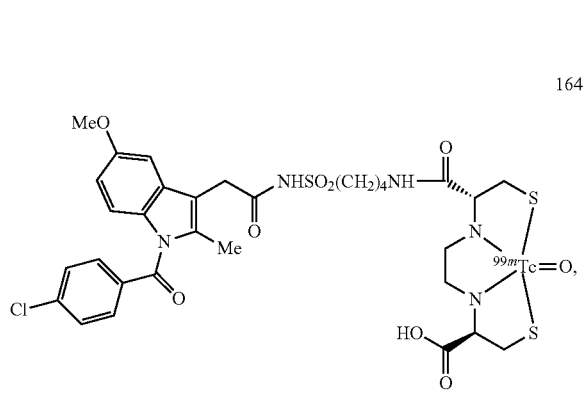
163
164
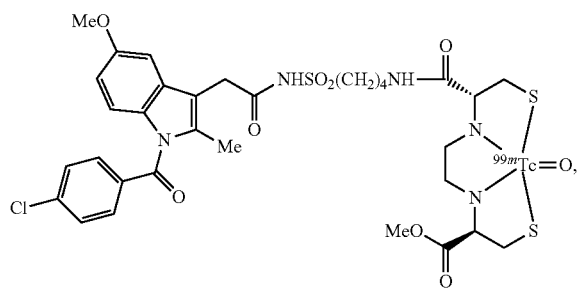
165

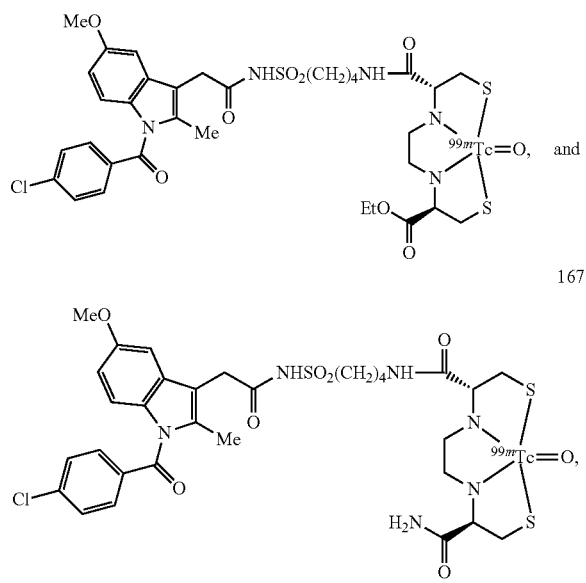

166

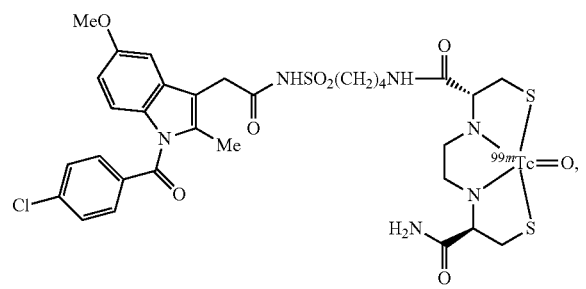

167 wherein Tc is $^{99m}$Tc; and pharmaceutically acceptable salts thereof.

In a nineteenth embodiment, the invention embraces a pharmaceutical composition comprising one or more conjugates of any one of the first, second, third, fourth, fifth, sixth, seventh, eighth, ninth, tenth, eleventh, twelfth, thirteenth, fourteenth, fifteenth, sixteenth, seventeenth, or eighteenth embodiments, and a pharmaceutically acceptable excipient.

In a twentieth embodiment, the invention embraces a method of imaging a site of pathology or suspected pathology in a subject, comprising:

a) administering one or more conjugates of any one of the first, second, third, fourth, fifth, sixth, seventh, eighth, ninth, tenth, eleventh, twelfth, thirteenth, fourteenth, fifteenth, sixteenth, seventeenth, or eighteenth embodiments, or the pharmaceutical composition of the nineteenth embodiment, to the subject, where the radioactive agent of the conjugate comprises $^{99m}$Tc, $^{52}$Mn, $^{186}$Re or $^{188}$Re; and b) generating an image of the subject or an image of a portion of the subject.

In a twentieth-first embodiment, the pathology or suspected pathology of the twentieth embodiment is a tumor or a suspected tumor.

In a twenty-second embodiment, the pathology or suspected pathology of the twentieth embodiment is pain (that is, the subject is suffering from pain).

In a twenty-third embodiment, the pathology or suspected pathology of the twentieth h embodiment is an infection or a suspected infection.

In a twenty-fourth embodiment, the invention embraces a conjugate disclosed herein which has an IC$_{50}$ for inhibition of a cyclooxygenase of less than about 2 micromolar, less than about 1 micromolar, preferably less than about 0.5 micromolar, more preferably less than about 0.3 micromolar, still more preferably less than about 0.1 micromolar, yet more preferably less than about 50 nanomolar; in a twenty-fifth embodiment, the cyclooxygenase is COX-2. In a twenty-sixth embodiment, the invention embraces a conjugate of any one of the first, second, third, fourth, fifth, sixth, seventh, eighth, ninth, tenth, eleventh, twelfth, thirteenth, fourteenth, fifteenth, sixteenth, seventeenth, or eighteenth embodiments which has an IC$_{50}$ for inhibition of a cyclooxygenase of less than about 2 micromolar, less than about 1 micromolar, preferably less than about 0.5 micromolar, more preferably less than about 0.3 micromolar, still more preferably less than about 0.1 micromolar, yet more preferably less than about 50 nanomolar; in a twenty-seventh embodiment, the cyclooxygenase is COX-2.

In some embodiments, the conjugates of the invention can be selected from the group consisting of a conjugate illustrated in FIG. 1, FIG. 2, or FIG. 3; a rhenium-containing conjugate illustrated in FIG. 1, FIG. 2, or FIG. 3; a technetium-containing conjugate illustrated in FIG. 1, FIG. 2, or FIG. 3; a technetium-99m-containing conjugate illustrated in FIG. 1, FIG. 2, or FIG. 3; or a pharmaceutically acceptable salt thereof.

In further embodiments, the invention embraces a pharmaceutical composition comprising one or more of the foregoing conjugates and a pharmaceutically acceptable excipient.

In further embodiments, the invention embraces any of the conjugates disclosed herein, with the substitution of a non-radioactive agent for the radioactive agent. Thus, for any of the generic structures or specific conjugates disclosed herein containing $^{99m}$Tc, $^{52}$Mn, $^{186}$Re, or $^{188}$Re, the invention also embraces those generic structures or specific conjugates with a non-radioactive metal, such as non-radioactive Re, such as $^{185}$Re.

In further embodiments, the invention embraces any of the conjugates disclosed herein, with the removal of the radioactive agent. Thus, for any of the generic structures or specific conjugates disclosed herein containing $^{99m}$Tc, $^{52}$Mn, $^{186}$Re, or $^{188}$Re, the invention also embraces those generic structures or specific conjugates without the metal, that is, with the uncomplexed or free chelator.

In further embodiments, the invention embraces the synthesis of any of the conjugates described herein, according to the protocols disclosed herein.

The invention also embraces methods of imaging a patient or subject. In one embodiment, the invention embraces a method of imaging a site of pathology or suspected pathology in a subject, comprising administering one or more conjugates or compositions described herein, including any of the foregoing embodiments, to the subject, wherein the radioactive agent of the conjugate comprises $^{99m}$Tc, $^{52}$Mn, $^{186}$Re, or $^{188}$Re; and generating an image of the subject or an image of a portion of the subject. The pathology or suspected pathology in the subject can be a tumor or a suspected tumor. The pathology or suspected pathology in the subject can be an infection or a suspected infection. The subject can be a subject suffering from pain.

In further embodiments, the invention embraces any of the conjugates and compositions as disclosed herein for use in imaging a subject or for diagnosing a subject. In further embodiments, the invention embraces the use in imaging or in diagnosis of any of the conjugates and compositions as disclosed herein. In further embodiments, the invention embraces the use of any of the conjugates and compositions as disclosed herein for the manufacture of a medicament for use in imaging a subject, or for use in diagnostic purposes.

In further embodiments, the invention includes conjugates where the ratio of (NSAID, NSAID residue, or NSAID derivative) to (chelating moiety) is 1:1.

Some embodiments described herein are recited as "comprising" or "comprises" with respect to their various elements. In alternative embodiments, those elements can be recited with the transitional phrase "consisting essentially of" or "consists essentially of" as applied to those elements. In further alternative embodiments, those elements can be recited with the transitional phrase "consisting of" or "consists of" as applied to those elements. Thus, for example, if a composition or method is disclosed herein as comprising A and B, the alternative embodiment for that composition or method of "consisting essentially of A and B" and the alternative embodiment for that composition or method of "consisting of A and B" are also considered to have been disclosed herein. Likewise, embodiments recited as "consisting essentially of" or "consisting of" with respect to their various elements can also be recited as "comprising" as applied to those elements. Finally, embodiments recited as "consisting essentially of" with respect to their various elements can also be recited as "consisting of" as applied to those elements, and embodiments recited as "consisting of" with respect to their various elements can also be recited as "consisting essentially of" as applied to those elements.

When a composition is described as "consisting essentially of" the listed components, the composition contains the components expressly listed, and may contain other components which do not substantially affect the condition being treated. That is, the composition either does not contain any other components which do substantially affect the condition being treated other than those components expressly listed; or, if the composition does contain extra components other than those listed which substantially affect the condition being treated, the composition does not contain a sufficient concentration or amount of those extra components to substantially affect the condition being treated. When a method is described as "consisting essentially of" the listed steps, the method contains the steps listed, and may contain other steps that do not substantially affect the condition being treated, but the method does not contain any other steps which substantially affect the condition being treated other than those steps expressly listed.

DETAILED DESCRIPTION OF THE INVENTION

Figure 1:
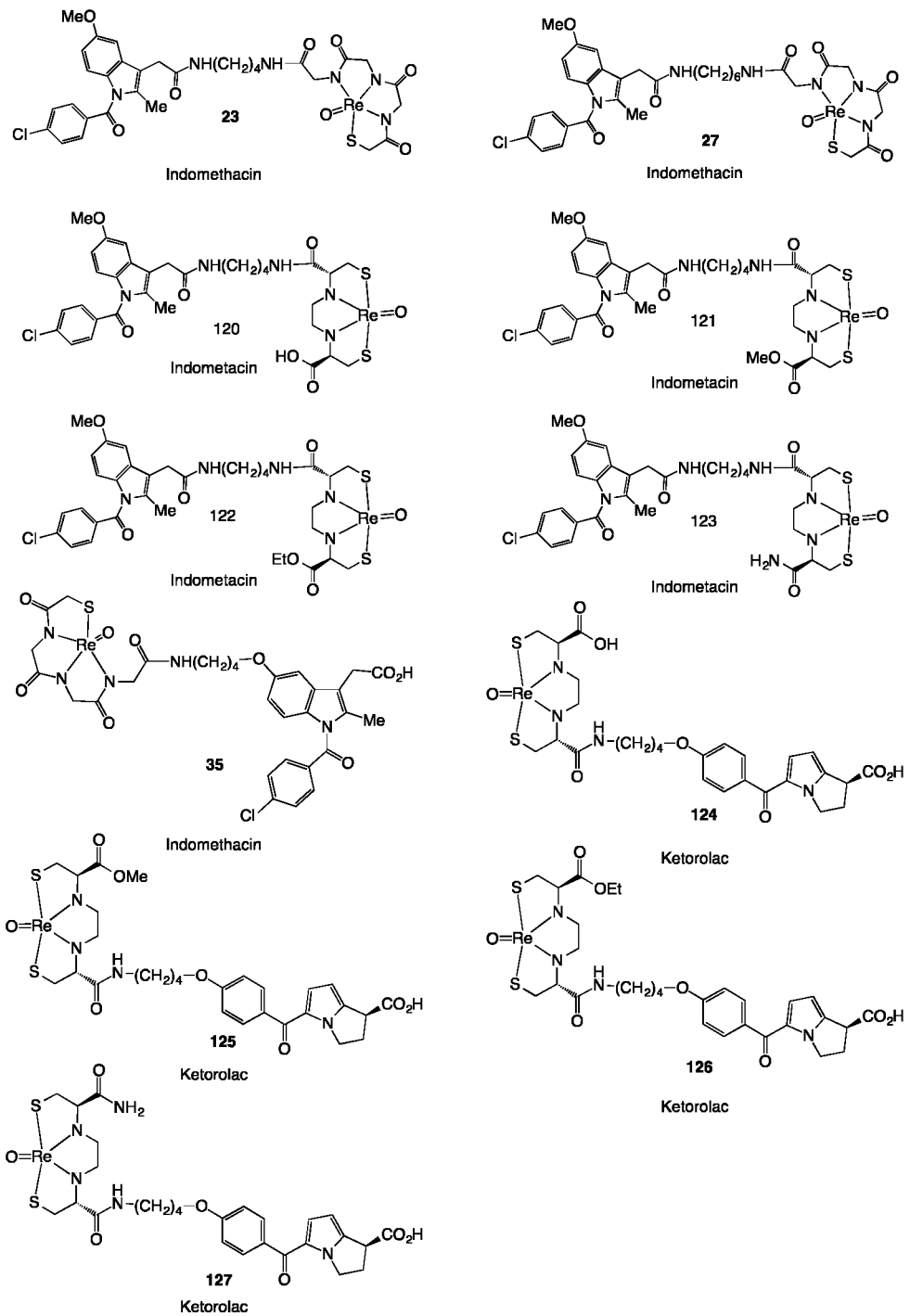
FIG. 1 illustrates various $^{99m}$Tc-containing conjugates useful in the invention.
Figure 1:
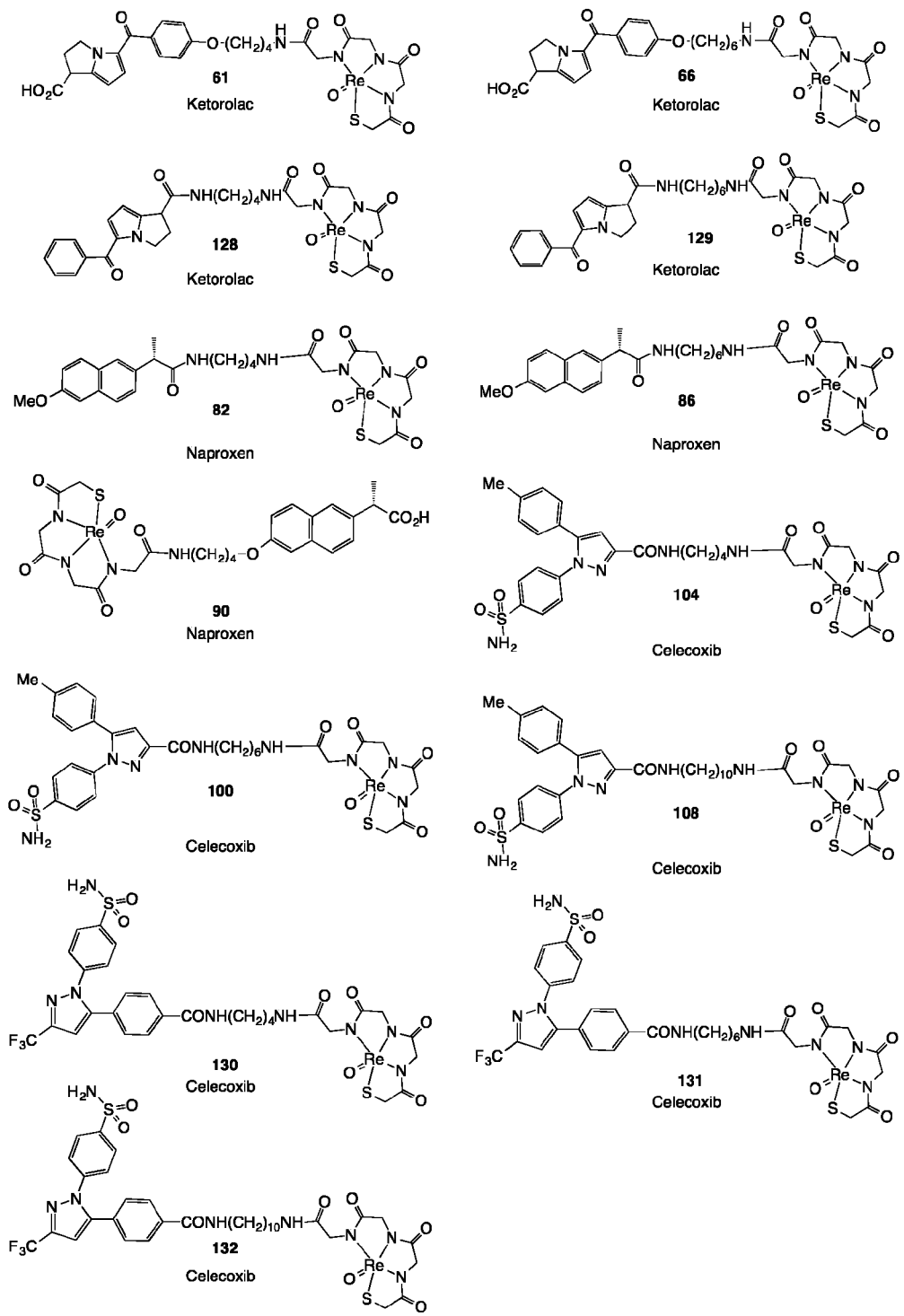
Figure 1:
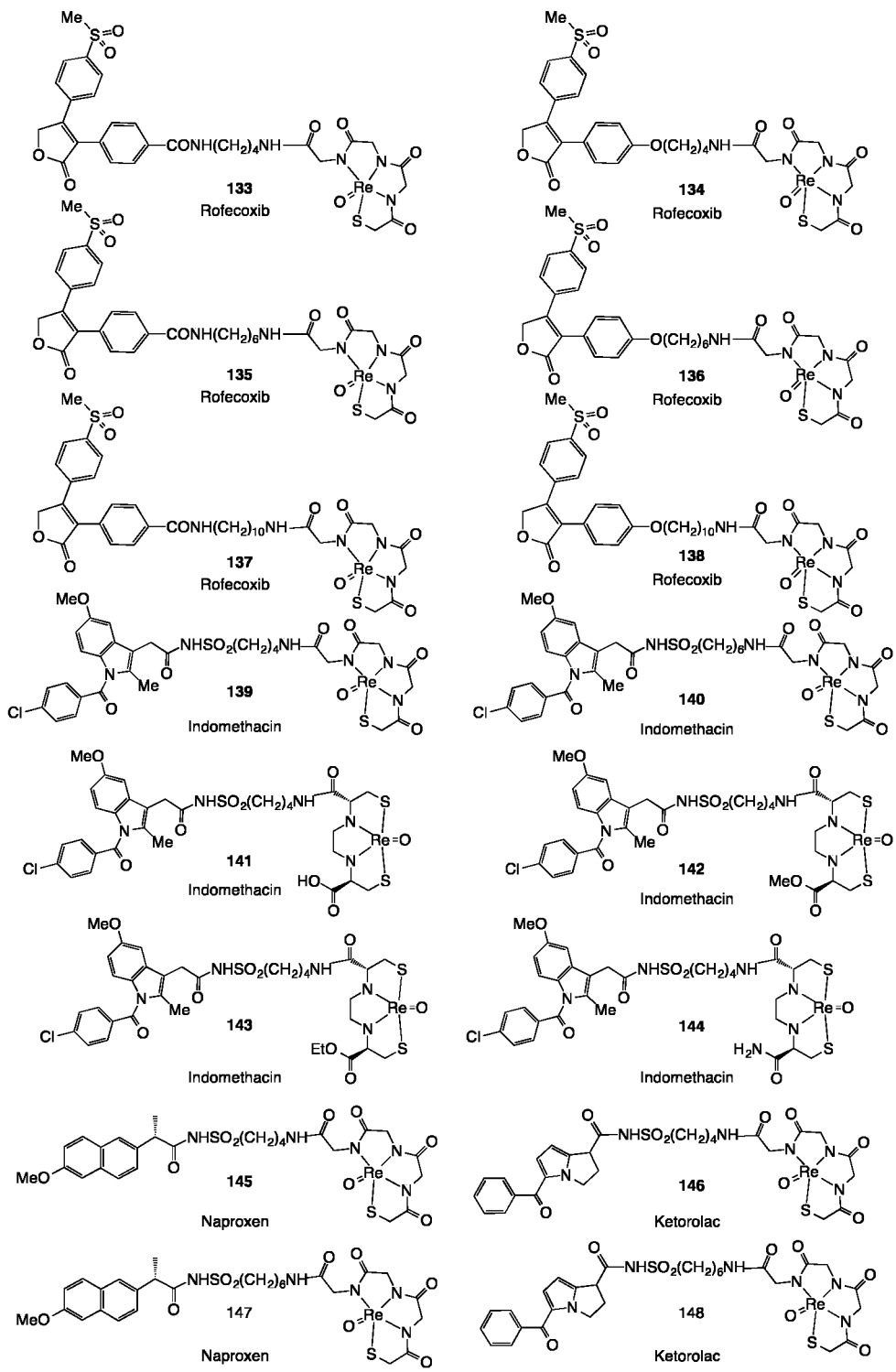

Identifying sites of pathology is important for proper diagnosis and treatment of a patient. However, it can often be difficult to pinpoint the precise location of pathology. Extensive imaging and testing may be required to accurately identify the source of pathology.

Tumor localization is an example of a condition where it can be difficult to precisely identify the area of pathology, e.g., in a patient with metastatic adenocarcinoma who presents with clear metastasis, but where the primary site of the malignancy is not known. The secondary sites of the tumor (metastases) are difficult to find in many cancer cases. This problem also occurs with "benign tumors" such as giant cell tumors, which rarely metastasize, and "quasi-malignant tumors" such as adamantinomas, which rarely metastasize early, but are known to metastasize late in their course. Because the tumor location can be extremely difficult to find, a new test which could reveal all types of tumor cells would facilitate tumor searches, whether primary tumor sites or metastatic tumor sites, and help determine the appropriate treatment.

Pain is a common symptom in medicine, and is another condition where the source of the pathology is not always readily apparent, despite thorough physical exams, laboratory studies, and radiologic studies and analysis. This is especially true for low back pain and abdominal pain. Pain in the body results from various compounds produced and released at the site of the injured area. These pain-producing compounds include bradykinins, prostaglandins, chemokines, histamine, and others. Importantly, the site at which the patient perceives the pain may not be the site of the actual injury or pathology. The term "referred pain" is used to describe pain that is perceived by the patient at a site distinct from the pathology. Referred pain can complicate diagnosis, location of the actual site of pathology, and determination of appropriate treatment.

Prostaglandins, especially the $PG_2$ group of prostaglandins, are over-expressed in tumor cells. Prostaglandins (such as the $PG_2$ group of prostaglandins) are also strongly associated with the experience of pain. Because prostaglandins are produced at the site of tumor location, actual injury, or pathology, identifying the site where prostaglandin synthesis occurs will assist in locating the precise area of pathology. Biosynthesis of the $PG_2$ prostaglandins requires the cyclooxygenase (COX) enzyme. The cyclooxygenase enzyme exists in (at least) two isoforms, COX-1, which is expressed constitutively, but which may be upregulated at sites of pain and inflammation, and COX-2, which is inducible by inflammatory stimuli. Both COX-1 and COX-2 are upregulated at tumor sites. Areas of high expression of cyclooxygenase will be associated with areas of high expression of prostaglandins, which in turn are associated with the area of pathology. Thus, pinpointing areas of high cyclooxygenase expression will enable identification of the pathological area.

The cyclooxygenase enzymes are readily inhibited by non-steroidal anti-inflammatory drugs (NSAIDs), which are sold over the counter in most countries, and also often frequently prescribed by doctors. These non-steroidal anti-inflammatory medicines include several pharmaceutical classes; each class has a number of specific drugs. If a NSAID drug is bonded or complexed to an imaging moiety, partial or total imaging of the patient provides a method of identifying sites of cyclooxygenase overexpression, prostaglandin synthesis, and inflammation, which determines the site of pathology or injury. Thus, in one embodiment, the invention encompasses conjugates of a NSAID with an imaging moiety, where said conjugate is suitable for imaging with an appropriate imaging modality.

In addition to conjugates suitable for imaging, the invention also encompasses conjugates which are not used for imaging, but which are useful surrogates for studying the chemical, biological, and pharmacokinetic properties of the conjugates suitable for imaging. For example, substitution of non-radioactive isotopes of rhenium (Re) for $^{99m}$Tc results in a conjugate which can be handled without the need for radiation protection (the most abundant rhenium isotope, $^{187}$Re, has a half-life of on the order of $10^{10}$ years, and the second most abundant rhenium isotope, $^{185}$Re, is stable). Accordingly, preparation of conjugates which have non-radioactive rhenium isotopes in place of radioactive technetium isotopes can be useful for chemical, physical, in vitro, and in vivo studies of compound properties in which the imaging properties of the conjugate are not under study, such as studies of toxicity and biological half-life, and the invention embraces both the conjugates suitable for imaging and their analogs which can be handled without radiation precautions.

The conjugates are also useful for diagnosis of infections. Infections cause cells to overexpress the COX-1 and COX-2 enzymes. The pattern distribution of the cellular influence for the three major types of infections, bacterial, tuberculosis (TB), or viral, differ in major ways. Bacterial infections (not including TB) affect COX production in the cells of most of the body's organs. The conjugates of the invention can be used for diagnosis of any bacterial infection, and are particularly useful in abscess forming bacteria, in subjects or patients with an organ-specific infection, and in aiding in diagnosis and determination of the cause of a fever of unknown origin (FUO). The organ most involved would produce more COX enzyme than the rest of the body's tissues, even though all tissues may show some increased activity.

TB infections can infect almost any organ, such as the lungs, the testes, the spinal column (such as psoas abscess), etc. Scans conducted with conjugates disclosed herein can help pinpoint the major locus of TB infection, which is especially helpful in a subject or patient with a positive skin reaction to TB (such as a positive PPD test). The primary locus for a TB infection would likely be at the site of the highest gamma count on a gamma camera when a gamma-emitting radioactive moiety is used in the conjugate.

Viral infections tend to first cause elevated COX production in the spleen to a great extent and in the stomach to a slightly lesser extent. The conjugates disclosed herein can thus be used for the screening of asymptomatic patients infected with a virus. Patients are frequently infectious even before they exhibit symptoms, such as patients with Ebola virus and other viruses. An asymptomatic patient or subject who has been exposed to such viruses, such Ebola virus, influenza viruses, or other viruses deemed sufficiently important for screening, or who has traveled in areas where outbreaks of such viruses have occurred, can be screened by administration of conjugates of the invention, followed by imaging. When a gamma-emitting radioactive moiety is used in the conjugate, a gamma scanner could detect signals above background (and thus increased COX expression) from at least the spleen and probably the stomach, indicating the presence of an infection.

Definitions

A "residue" of a non-steroidal anti-inflammatory drug (NSAID), referred to as an "NSAID residue" or "residue of a NSAID," is a portion of the NSAID, where the portion of the NSAID retains its ability to bind to cyclooxygenase. Typically, a residue of a NSAID refers to the portion of the molecule left after removal of a hydrogen, a hydroxyl, a methyl, or a methoxy group from the NSAID. The residue is then bonded or complexed together with an imaging moiety. NSAID residues also include portions of an NSAID that retains its ability to bind to cyclooxygenase, where the portion is further modified by the replacement of a hydrogen with a halogen or a trifluoromethyl group, or by the replacement of a methyl group with a trifluoromethyl group, or by the replacement of a hydroxyl group with a methoxy group. In some embodiments, the residue can be connected to a linker, which linker in turn is attached to a imaging moiety, in order to bond or complex the NSAID residue with the imaging moiety.

An NSAID derivative is an NSAID or NSAID residue which has been modified in one or more of the following manners:

a hydroxyl group has been replaced with a —O—($C_1$-$C_4$ alkyl) group, preferably a methoxy group; a halogen; a $C_1$-$C_4$ alkyl group, preferably a methyl group; or a trifluoromethyl group;

a methyl group has been replaced with a trifluoromethyl group; a $C_2$-$C_4$ alkyl group; a —O—($C_1$-$C_4$ alkyl) group, preferably a methoxy group; a halogen; or hydrogen;

a methoxy group has been replaced with a hydroxyl group, a —O—($C_2$-$C_4$ alkyl) group, a $C_1$-$C_4$ alkyl group, preferably a methyl group; a halogen, or a trifluoromethyl group;

a halogen has been replaced with a different halogen, a trifluoromethyl group, a —O—($C_1$-$C_4$ alkyl) group, preferably a methoxy group; a $C_1$-$C_4$ alkyl group, preferably a methyl group; or hydrogen;

a hydrogen has been replaced with a halogen, a methyl group, or a trifluoromethyl group;

a —COOH group has been replaced with a —NH$_2$ group, or a —C(=O)—O— group has been replaced by a —NH— group;

a —COOH group has been replaced with a —CH$_2$NH$_2$ group, or a —C(=O)—O— group has been replaced by an —CH$_2$NH— group;

an amino group has been replaced by a carboxyl group;

a trifluoromethyl group has been replaced with a —CH$_2$NH$_2$ group or a —CH$_2$NH— group.

"Bonded or complexed" indicates that the NSAID, NSAID residue, or NSAID derivative is associated with the imaging moiety in a manner such that the imaging moiety can be localized along with the NSAID, NSAID residue, or NSAID derivative to the intended site, such that the imaging moiety can indicate where the NSAID, NSAID residue, or NSAID derivative bonded or complexed to the imaging moiety has concentrated. "Bonded or complexed" embraces any manner of association sufficiently stable for the foregoing purpose, whether such association is via a covalent bond, an ionic bond, a coordination bond (coordinate covalent bond or dative bond), a donor-acceptor complex, or any other association of NSAID, NSAID residue, or NSAID derivative and imaging moiety which has suitable stability. In one embodiment, "bonded or complexed" can indicate a covalent bond. In another embodiment, "bonded or complexed" can indicate a coordination bond. In another embodiment, "bonded or complexed" can indicate an ionic bond. In another embodiment, "bonded or complexed" can indicate a donor-acceptor complex.

"Alkyl" is intended to embrace a univalent saturated linear or branched hydrocarbon chain having the number of carbon atoms specified, or if no number is specified, having 1 to 8 carbon atoms. "Alkylene" refers to a similar group, which is divalent. "Optionally substituted" alkyl refers to either an unsubstituted alkyl group, or an alkyl group substituted with one or more substituents (such as one, two, three, four, or five substituents) selected from the group consisting of —OH, —($C_1$-$C_4$ alkyl)-OH, halo, fluoro, chloro, bromo, iodo, —($C_1$-$C_4$ alkyl), —($C_1$-$C_4$) haloalkyl, —($C_1$-$C_4$) perhaloalkyl, —O—($C_1$-$C_4$ alkyl), —O—($C_1$-$C_4$ haloalkyl), —O—($C_1$-$C_4$ perhaloalkyl), —($C_1$-$C_4$) perfluoroalkyl, —(C=O)—($C_1$-$C_4$) alkyl, —(C=O)—($C_1$-$C_4$) haloalkyl, —(C=O)—($C_1$-$C_4$) perhaloalkyl, —NH$_2$, —NH($C_1$-$C_4$ alkyl), —N($C_1$-$C_4$ alkyl)($C_1$-$C_4$ alkyl) (where each $C_1$-$C_4$ alkyl is chosen independently of the other), —NO$_2$, —CN, isocyano (NC—), oxo (=O), —C(=O)H, —C(=O)—($C_1$-$C_4$ alkyl), —COOH, —C(=O)—O—($C_1$-$C_4$ alkyl), —C(=O)NH$_2$, —C(=O)NH($C_1$-$C_4$ alkyl), —C(=O)N($C_1$-$C_4$ alkyl)($C_1$-$C_4$ alkyl) (where each $C_1$-$C_4$ alkyl is chosen independently of the other), —SH, —($C_1$-$C_4$ alkyl)-SH, —S—($C_1$-$C_4$ alkyl), —S(=O)—($C_1$-$C_4$ alkyl), —$SO_2$—($C_1$-$C_4$ alkyl), and —$SO_2$—($C_1$-$C_4$ perfluoroalkyl). Examples of such substituents are —$CH_3$, —$CH_2CH_3$, —$CF_3$, —$CH_2CF_3$, —$CF_2CF_3$, —$OCH_3$, —$NH(CH_3)$, —$N(CH_3)_2$, —$SCH_3$, and $SO_2CH_3$. "Optionally substituted alkylene" groups can be unsubstituted, or substituted in the same manner as substituted alkyl groups.

"Cycloalkyl" is intended to embrace a univalent saturated cyclic hydrocarbon chain having the number of carbon atoms specified, or if no number is specified, having 3 to 10 carbon atoms, or 3 to 8 carbon atoms, preferably 3 to 6 carbon atoms. "Cycloalkylene" refers to a similar group, which is divalent. Cycloalkyl and cycloalkylene groups can be unsubstituted, or substituted in the same manner as substituted alkyl groups.

"Alkenyl" is intended to embrace a univalent linear or branched hydrocarbon chain having at least one carbon-carbon double bond, and having the number of carbon atoms specified, or if no number is specified, having 2 to 8 carbon atoms. "Alkenylene" refers to a similar group, which is divalent. Alkenyl and alkenylene groups can be unsubstituted, or substituted in the same manner as substituted alkyl groups where chemically possible.

"Cycloalkenyl" is intended to embrace a univalent cyclic hydrocarbon chain having at least one carbon-carbon double bond and having the number of carbon atoms specified, or if no number is specified, having 4 to 10 carbon atoms, or 4 to 8 carbon atoms, or 4 to 6 carbon atoms. "Cycloalkenylene" refers to a similar group, which is divalent. Cycloalkenyl and cycloalkenylene groups can be unsubstituted, or substituted in the same manner as substituted alkyl groups where chemically possible.

"Alkynyl" is intended to embrace a univalent linear or branched hydrocarbon chain having at least one carbon-carbon triple bond, and having the number of carbon atoms specified, or if no number is specified, having 2 to 8 carbon atoms. "Alkynylene" refers to a similar group, which is divalent. Alkynyl and alkynylene groups can be unsubstituted, or substituted in the same manner as substituted alkyl groups where chemically possible.

"Aryl" is defined as a univalent aromatic ring system. Aryl groups include monocyclic aromatic rings and polycyclic aromatic ring systems containing the number of carbon atoms specified, or if no number is specified, containing six to twenty carbon atoms. In other embodiments, aryl groups may contain six to ten carbon atoms. In some embodiments, aryl groups can be unsubstituted. In other embodiments, aryl groups can be substituted with, for example, one, two, or three substituents independently selected from the group consisting of —OH, —($C_1$-$C_4$ alkyl)-OH, halo, fluoro, chloro, bromo, iodo, —($C_1$-$C_4$ alkyl), —($C_1$-$C_4$) haloalkyl, —($C_1$-$C_4$) perhaloalkyl, —O—($C_1$-$C_4$ alkyl), —O—($C_1$-$C_4$ haloalkyl), —O—($C_1$-$C_4$ perhaloalkyl), —($C_1$-$C_4$) perfluoroalkyl, —(C=O)—($C_1$-$C_4$) alkyl, —(C=O)—($C_1$-$C_4$) haloalkyl, —(C=O)—($C_1$-$C_4$) perhaloalkyl, —$NH_2$, —NH($C_1$-$C_4$ alkyl), —N($C_1$-$C_4$ alkyl)($C_1$-$C_4$ alkyl) (where each $C_1$-$C_4$ alkyl is chosen independently of the other), —$NO_2$, —CN, (NC—), —C(=O)H, —C(=O)—($C_1$-$C_4$ alkyl), —COOH, —C(=O)—O—($C_1$-$C_4$ alkyl), —C(=O)$NH_2$, —C(=O)ONH($C_1$-$C_4$ alkyl), —C(=O)N($C_1$-$C_4$ alkyl)($C_1$-$C_4$ alkyl) (where each $C_1$-$C_4$ alkyl is chosen independently of the other), —SH, —($C_1$-$C_4$ alkyl)-SH and —S—$C_1$-$C_4$ alkyl. "Arylene" refers to a similar group, which is divalent.

"Hydrocarbyl" is defined as a univalent hydrocarbon group, that is, a group comprised of hydrogen and carbon, whether aliphatic or aromatic, acyclic or cyclic, or any combination of, or all of, aliphatic, aromatic, acyclic and cyclic. Hydrocarbyl groups have the number of carbon atoms specified, or if no number is specified, having 1 to 10 carbon atoms. "Hydrocarbylene" refers to a similar group, which is divalent. Hydrocarbyl and hydrocarbylene groups can be unsubstituted, or substituted in the same manner as substituted alkyl groups where chemically possible.

"Heterocycle" or a "heterocyclic group" is defined as a ring system which contains the number of carbon atoms specified, and one or more heteroatoms (such as one to six heteroatoms, or one to three heteroatoms, or one heteroatom), where heteroatoms include, but are not limited to, oxygen, nitrogen, sulfur, and phosphorus. "Heteroaryl" is defined as an aromatic ring system which contains the number of carbon atoms specified, and one or more heteroatoms (such as one to six heteroatoms, or one to three heteroatoms, or one heteroatom), where heteroatoms include, but are not limited to, oxygen, nitrogen, sulfur, and phosphorus; heteroaryl groups are a subset of heterocyclic groups. In some embodiments, heteroatoms for heterocyclyl and heteroaryl groups are selected from the group consisting of oxygen and nitrogen. In various embodiments, heterocyclic groups may contain two to twenty carbon atoms and one to six heteroatoms, two to twelve carbon atoms and one to four heteroatoms, two to twelve carbon atoms and one to three heteroatoms, two to ten carbon atoms and one to three heteroatoms, two to six carbon atoms and one to three heteroatoms, or two to six carbon atoms and two to four heteroatoms. In some embodiments, heterocyclic groups can be unsubstituted. In other embodiments, heterocyclic groups can be substituted on any chemically possible valence with for example, one, two, or three substituents independently selected from the group consisting of —OH, —($C_1$-$C_4$ alkyl)-OH, halo, fluoro, chloro, bromo, iodo, —($C_1$-$C_4$ alkyl), —($C_1$-$C_4$) haloalkyl, —($C_1$-$C_4$) perhaloalkyl, —O—($C_1$-$C_4$ alkyl), —O—($C_1$-$C_4$ haloalkyl), —O—($C_1$-$C_4$ perhaloalkyl), —($C_1$-$C_4$) perfluoroalkyl, —(C=O)—($C_1$-$C_4$) alkyl, —(C=O)—($C_1$-$C_4$) haloalkyl, —(C=O)—($C_1$-$C_4$) perhaloalkyl, —$NH_2$, —NH($C_1$-$C_4$ alkyl), —N($C_1$-$C_4$ alkyl) ($C_1$-$C_4$ alkyl) (where each $C_1$-$C_4$ alkyl is chosen independently of the other), —$NO_2$, —CN, (NC—), —C(=O)H, —C(=O)—($C_1$-$C_4$ alkyl), —COOH, —C(=O)—O—($C_1$-$C_4$ alkyl), —C(=O)$NH_2$, —C(=O)ONH($C_1$-$C_4$ alkyl), —C(=O)N($C_1$-$C_4$ alkyl)($C_1$-$C_4$ alkyl) (where each $C_1$-$C_4$ alkyl is chosen independently of the other), —SH, —($C_1$-$C_4$ alkyl)-SH and —S—$C_1$-$C_4$ alkyl. Examples of heterocycles include aziridine, oxirane, oxetane, azetidine, pyrrolidine, pyrrole, tetrahydrofuran, furan, thiolane, thiophene, imidazolidine, imidazole, pyrazolidine, pyrazole, 1,2,3-triazole, 1,2,4-triazole, piperidine, pyridine, pyran, piperazine, and morpholine.

A "heterohydrocarbyl" group is defined as a univalent hydrocarbyl group, where one or more of the carbon atoms have been independently replaced by a heteroatom at any chemically possible location, where heteroatoms include, but are not limited to, oxygen, nitrogen, sulfur, and phosphorus. Heterohydrocarbyl groups have the number of carbon atoms specified, or if no number is specified, having 1 to 10 carbon atoms, and also at least one heteroatom, such as 1 to 5 heteroatoms, 1 to 4 heteroatoms, 1 to 3 heteroatoms, 1 to 2 heteroatoms, or one heteroatom. "Heterohydrocarbylene" refers to a similar group, which is divalent. Heterohydrocarbyl and heterohydrocarbylene groups can be unsubstituted, or substituted in the same manner as substituted alkyl groups where chemically possible. Examples of heterohydrocarbyl and heterohydrocarbylene groups include, but are not limited to, ethylene glycol and polyethylene glycol moieties, such as (—CH$_2$CH$_2$—O)$_n$—H (a monovalent heterohydrocarbyl group) and (—CH$_2$CH$_2$—O—)$_n$ (a divalent heterohydrocarbylene group) where n is an integer from 1 to 12 inclusive, and propylene glycol and polypropylene glycol moieties, such as (—CH$_2$CH(CH$_3$)—O—)$_n$—H (a monovalent heterohydrocarbyl group) and (—CH$_2$CH(CH$_3$)—O—)$_n$-(a divalent heterohydrocarbylene group) where n is an integer from 1 to 12 inclusive. For heterohydrocarbyl groups, when more than one heteroatom is present, at least one carbon atom intervenes between any two heteroatoms.

The various groups described above can be attached to the remainder of the molecule at any chemically possible location on the fragment, including attachment via a substituent when the group is substituted. For the purposes of drawing the structures, groups are typically attached by replacement of a hydrogen, hydroxyl, methyl, or methoxy group on a "complete" molecule to generate the appropriate fragment, and a bond is drawn from the open valence on the fragment to the remainder of the molecule. For example, attachment of the heteroalkyl group —CH$_2$—O—CH$_3$ proceeds by removal of a hydrogen from one of the methyl groups of CH$_3$—O—CH$_3$, to generate the heteroalkyl fragment —CH$_2$—O—CH$_3$, from which a bond is drawn from the open valence to the remainder of the molecule.

Reference to "about" a value or parameter herein includes (and describes) variations that are directed to that value or parameter per se. For example, description referring to "about X" includes description of "X".

The terms "a" or "an," as used in herein means one or more, unless the context clearly indicates otherwise.

By "subject," "individual," or "patient" is meant an individual organism, preferably a vertebrate, more preferably a mammal, most preferably a human.

The description is intended to embrace all salts of the compounds described herein, as well as methods of using such salts of the compounds. In one embodiment, the salts of the compounds comprise pharmaceutically acceptable salts. Pharmaceutically acceptable salts are those salts which can be administered as drugs or pharmaceuticals to humans and/or animals and which, upon administration, retain at least some of the biological activity of the free compound (neutral compound or non-salt compound). The desired salt of a basic compound may be prepared by methods known to those of skill in the art by treating the compound with an acid. Examples of inorganic acids include, but are not limited to, hydrochloric acid, hydrobromic acid, sulfuric acid, nitric acid, and phosphoric acid. Examples of organic acids include, but are not limited to, formic acid, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, sulfonic acids, and salicylic acid. Salts of basic compounds with amino acids, such as aspartate salts and glutamate salts, can also be prepared. The desired salt of an acidic compound can be prepared by methods known to those of skill in the art by treating the compound with a base. Examples of inorganic salts of acid compounds include, but are not limited to, alkali metal and alkaline earth salts, such as sodium salts, potassium salts, magnesium salts, and calcium salts; ammonium salts; and aluminum salts. Examples of organic salts of acid compounds include, but are not limited to, procaine, dibenzylamine, N-ethylpiperidine, N,N'-dibenzylethylenediamine, and triethylamine salts. Salts of acidic compounds with amino acids, such as lysine salts, can also be prepared. For lists of pharmaceutically acceptable salts, see, for example, P. H. Stahl and C. G. Wermuth (eds.) "Handbook of Pharmaceutical Salts, Properties, Selection and Use" Wiley-VCH, 2011 (ISBN: 978-3-90639-051-2). Several pharmaceutically acceptable salts are also disclosed in Berge, J. Pharm. Sci. 66:1 (1977).

The invention also includes, where chemically possible, all stereoisomers and geometric isomers of the compounds, including diastereomers, enantiomers, and cis/trans (E/Z) isomers. The invention also includes mixtures of stereoisomers and/or geometric isomers in any ratio, including, but not limited to, racemic mixtures. Unless stereochemistry is explicitly indicated in a structure, the structure is intended to embrace all possible stereoisomers of the compound depicted. If stereochemistry is explicitly indicated for one portion or portions of a molecule, but not for another portion or portions of a molecule, the structure is intended to embrace all possible stereoisomers for the portion or portions where stereochemistry is not explicitly indicated.

Unless a specific isotope is indicated, the invention includes all isotopologues of the compounds disclosed herein, such as, for example, deuterated derivatives of the compounds (where H can be $^2$H, i.e., D).

The following abbreviations may be used herein:
~ about
+ve or pos. ion positive ion
Δ heat
AA Arachidonic acid
Ac Acetyl
ACN acetonitrile
Ac$_2$O acetic anhydride
aq aqueous
AcOH acetic acid
Bn benzyl
Boc tert-butyloxycarbonyl
BOP-Cl Bis(2-oxo-3-oxazolidinyl)phosphinic chloride
BSA bovine serum albumin
Bu butyl
Bz benzoyl
Calcd or Calc'd calculated
Conc. concentrated
COX cyclooxygenase, prostaglandin-endoperoxide synthase
d day(s)
DCE dichloroethane
DCM dichloromethane
DEA diethylamine
DEAD Diethyl azodicarboxylate
DIEA or DIPEA diisopropylethylamine
DMAP 4-dimethylaminopyridine
DME 1,2-dimethoxyethane
DMF N,N-dimethylformamide
DMSO dimethyl sulfoxide
EDC or EDCI N-ethyl-N'-(3-dimethylaminopropyl)carbodiimide
EIA Enzyme immunoassay
eq equivalent
ESI or ES electrospray ionization
Et ethyl
Et$_2$O diethyl ether
Et$_3$N triethylamine
EtOAc ethyl acetate
EtOH ethyl alcohol
g gram(s)
h hour(s)
HATU O-(7-azabenzotriazol-1-yl)-N,N,N',N'-tetramethyluronium hexafluorophosphate
HBTU O-benzotriazole-N,N,N',N'-tetramethyl-uronium hexafluorophosphate Hex hexanes
HMPA hexamethylphosphoramide
HOAt 1-hydroxy-7-azabenzotriazole
HOBt hydroxybenzotriazole
HPLC high pressure liquid chromatography
IPA or iPrOH isopropyl alcohol
KOAc potassium acetate
LCMS, LC-MS or LC/MS liquid chromatography mass spectrometry
LDA lithium diisopropylamide
LHMDS or LiHMDS lithium hexamethyldisilazide
M molar (mol L$^{-1}$)
Me methyl
MeCN acetonitrile
MeI iodomethane
MeOH methyl alcohol
mg milligram(s)
min minute(s)
mL milliliter(s)
M mole(s)
MS mass spectrometry
MsCl methanesulfonyl chloride
MTBE or MtBE methyl tert-butyl ether
m/z mass-to-charge ratio
NaHMDS sodium hexamethyldisilazide
NaOtBu sodium tert-butoxide
NBS N-bromosuccinimide
NCS N-chlorosuccinimide
nBuLi n-butyl lithium
NMO N-methylmorpholine-N-oxide
NMP 1-methyl-2-pyrrolidinone
NMR nuclear magnetic resonance
PE Petroleum ether, CAS Number: 101316-46-5
PG Prostaglandin or prostaglandins
PGE2 Prostaglandin E2
PGF2α Prostaglandin F2α
PGH2 Prostaglandin H2
PBS phosphate buffered saline
PMB para-methoxybenzyl, 4-methoxybenzyl
Pr propyl
Prep-HPLC Preparative high pressure liquid chromatography
ppm parts per million
p-tol para-toluoyl
rac racemic
RP-HPLC or RPHPLC reversed phase high pressure liquid chromatography
RT or rt or r.t. room temperature
sat. or sat'd or satd saturated
TBAF tetrabutylammonium fluoride
TBDMS tert-butyldimethylsilyl
TBDMS-Cl tert-butyldimethylsilyl chloride
TBDPS tert-butyldiphenylsilyl
TEMPO (2,2,6,6-tetramethylpiperidin-1-yl)oxidanyl
tert or t tertiary
TFA triflouroacetic acid
THF tetrahydrofuran
TLC thin layer chromatography
TMS trimethylsilyl or trimethylsilane
$t_R$ retention time
tBuOH tert-butyl alcohol
v/v volume per volume
Non-Steroidal Anti-Inflammatory Drugs (NSAIDs)

Non-steroidal anti-inflammatory drugs (NSAIDs) are commonly used to treat pain and inflammation, which occur due to many diseases, such as those involving tumors. NSAIDs which can be used in the invention include:

salicylates, such as aspirin (acetylsalicylic acid), diflunisal, salsalate, and choline magnesium trisalicylate;

propionic acid derivatives, such as ibuprofen, dexibuprofen, naproxen, fenoprofen, ketoprofen, dexketoprofen, flurbiprofen, oxaprozin, and loxoprofen;

acetic acid derivatives, such as indomethacin, tolmetin, sulindac, etodolac, ketorolac, diclofenac, aceclofenac, and nabumetone;

enolic acid (oxicam) derivatives, such as piroxicam, meloxicam, tenoxicam, droxicam, lornoxicam, and isoxicam;

anthranilic acid derivatives (fenamates), such as mefenamic acid, meclofenamic acid, flufenamic acid, and tolfenamic acid;

selective COX-2 inhibitors (coxibs, several of which are not approved, or have been withdrawn, in various countries), such as celecoxib, rofecoxib, valdecoxib, parecoxib, lumiracoxib, etoricoxib, and firocoxib (firocoxib approved for equine and canine use only);

sulfonanilides such as nimesulide (which should be used cautiously due to the risk of liver damage); and licofelone, which is both a cyclooxygenase and lipoxygenase inhibitor.

When forming a conjugate of a NSAID compound, typically a bond to an atom or atoms on the NSAID compound is replaced with a bond to a linking group in order to facilitate bonding or complexing the NSAID, NSAID residue, or NSAID derivative to the imaging moiety. Thus, for example, linking an amine-containing linker to a carboxylic acid-containing NSAID compound can be accomplished by condensing the amine and carboxylic acid to form an amide group. The bond to the —OH portion of the —COOH group has been replaced with a bond to the nitrogen atom of the amine-containing linker. "NSAID residue" refers to the portion of the NSAID molecule that remains and which is attached to the linker, and, as defined previously, retains its ability to bind to cyclooxygenase. The NSAID residue need not bind to COX with the same affinity or specificity as the NSAID from which the residue is derived, as long as sufficient binding affinity remains for the purposes of the invention. A derivative of a NSAID includes an NSAID or NSAID residue that has been modified as defined herein, and the NSAID derivative portion of the conjugate need not bind to COX with the same affinity or specificity as the NSAID which was modified to form the derivative, as long as sufficient binding affinity remains for the purposes of the invention.

Linker Groups and Linker/Chelator Groups for Attachment of Imaging Moieties to NSAID Compounds; General and Exemplary Forms of Conjugates An imaging moiety can be bonded or complexed to a NSAID compound by using an appropriate linker (also referred to as a linking group). The linker must be capable of being bonded or complexed to both the NSAID compound, or to a residue or derivative of the NSAID compound, and bonded or complexed to the imaging moiety, for the purpose of localizing the imaging moiety to the site where the NSAID compound or residue or derivative of the NSAID compound concentrates when administered to a patient. In various non-limiting embodiments, a linker group covalently bound to both the NSAID and the imaging moiety, or a linker group covalently bound to the NSAID and bonded or complexed via a coordination bond to the imaging moiety, or a linker group covalently bound to the NSAID and bonded or complexed via an ionic bond to the imaging moiety, can be used. The linker should preferably be bonded or complexed to the NSAID molecule or residue or derivative of the NSAID at a site as distant as possible from the region of the NSAID or residue or derivative of the NSAID that binds to cyclooxygenase, in order to preserve the ability of the NSAID or residue or derivative of the NSAID to bind to cyclooxygenase. However, any attachment to the NSAID molecule or residue or derivative of the NSAID, which attachment does not render the conjugate unsuitable for its purpose, can be used.

The linker also needs to bind or complex with the imaging moiety. One particularly useful imaging moiety is the metastable isotope of technetium-99, referred to as $^{99m}$Tc, Tc99m, or Tc-99m. $^{99m}$Tc decays to $^{99}$Tc with a half-life of about 6 hours, via gamma emission at an energy of about 140 keV. $^{99m}$Tc is often used in a complex with six methoxyisobutylisonitrile (MIBI) ligands, which is often referred to as $^{99m}$Tc-MIBI, technetium Tc99m Sestamibi, or $^{99m}$Tc sestamibi (sold as CARDIOLITE, a registered trademark of Lantheus Medical Imaging, Inc., North Billerica, Mass.). This compound has the following structure:

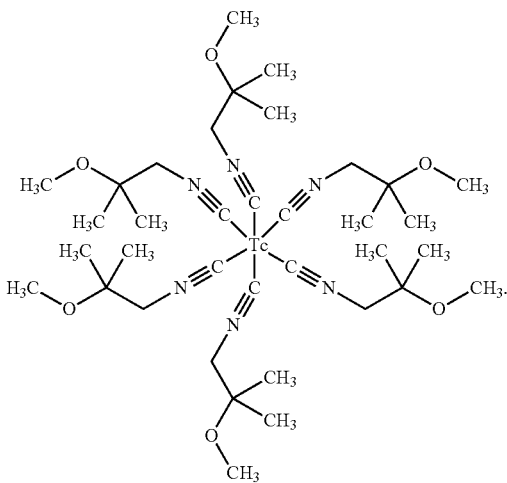

Modification of a NSAID with a linker such as

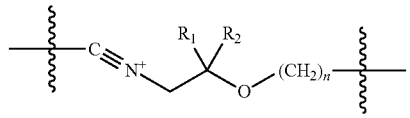

enables the linker to bind to a radioactive tracer moiety, such as $^{99m}$Tc, via the isocyano group, while the remaining open valence on the linker will allow attachment of a NSAID or a residue or derivative of a NSAID. For example, the structure below can be attached to a radioactive tracer moiety, such as $^{99m}$Tc:

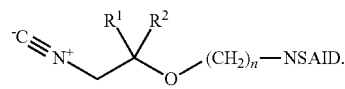

where $R^1$, $R^2$, and $R^3$ can be independently selected from the group consisting of hydrogen, $C_1$-$C_4$ alkyl, $C_1$-$C_4$ alkyl substituted with hydroxy, fluoro, —O—$C_1$-$C_4$ alkyl, or $C_3$-$C_6$ cycloalkyl, or $R^1$ and $R^2$ together with the carbon to which they are attached form a $C_3$-$C_8$ cycloalkyl ring or heterocycloalkyl ring, while n is an integer selected from 0 to 4, inclusive.

The linker itself may be capable of bonding to or complexing the radioactive agent, as with the methoxyisobutylisonitrile ligands above which directly bond to $^{99m}$Tc. In other embodiments, the imaging moiety comprises a chelating group and the radioactive agent, and may further comprise additional groups, such as ligands, bound or complexed to the radioactive agent. Chelating groups can comprise a number of ligand systems known to the skilled artisan, such as those described in e.g. Jirgens, S. et al., J. Organomet. Chem. (2014), 751, 83-89 and Liu, G. et al. Anticancer Agents Med. Chem. (2007), 7(3): 367-377.

In some embodiments, when a linker is used to link a NSAID, NSAID residue, or NSAID derivative to an imaging moiety, the linker can be selected from the group consisting of an optionally substituted $C_1$-$C_{40}$ hydrocarbylene group; an optionally substituted $C_2$-$C_{40}$ heterohydrocarbylene group; and a linker of the form -$L_E$-$R_4$-$L_F$-, where $L_E$ is absent or is selected from the group consisting of —NH— and —N($R^8$)—, $R^8$ is optionally substituted $C_1$-$C_4$ alkyl, $R^4$ is selected from the group consisting of optionally substituted $C_1$-$C_{40}$ hydrocarbylene and optionally substituted $C_2$-$C_{40}$ heterohydrocarbylene, $C_3$-$C_8$ cycloalkyl, $C_1$-$C_6$ alkyl-$C_3$-$C_8$ cycloalkyl, $C_3$-$C_8$ cycloalkyl-$C_1$-$C_6$ alkyl, $C_1$-$C_6$ alkyl-$C_3$-$C_8$ cycloalkyl-$C_1$-$C_6$ alkyl, $C_6$-$C_{10}$ aryl, $C_1$-$C_6$ alkyl-$C_6$-$C_{10}$ aryl, $C_6$-$C_{10}$ aryl-$C_1$-$C_6$ alkyl, and $C_1$-$C_6$ alkyl-$C_6$-$C_{10}$ aryl-$C_1$-$C_6$ alkyl; and $L_F$ is absent or is a functional group selected from the group consisting of —(C=O)—, —O—, —N($R^9$)—, —(C=O)N($R^9$)—, —N($R^9$)—(C=O)—, —(SO$_2$)N($R^9$)—, —N($R^9$)—(SO$_2$)—, —N($R^9$)(C=O)N($R^9$)—, —N($R^9$)—(C=O)—O—, —O—(C=O)N($R^9$)—, —(CH=CH)—, or a divalent cycloalkyl or heterocyclic group such as 1,2,3-triazole or 1,2,4-triazole, where $R^9$ is selected from the group consisting of H and optionally substituted $C_1$-$C_4$ alkyl.

In other embodiments, when a linker is used to link a NSAID, NSAID residue, or NSAID derivative to an imaging moiety, the linker can be selected from the group consisting of an optionally substituted $C_1$-$C_{10}$ hydrocarbylene group; an optionally substituted $C_2$-$C_{10}$ heterohydrocarbylene group; and a linker of the form -$L_E$-$R^4$-$L_F$-; where $L_E$ is absent or is selected from the group consisting of —NH—, —N($R^8$)—, and —C(=O)—, and $R^8$ is optionally substituted $C_1$-$C_4$ alkyl, $R^4$ is selected from the group consisting of optionally substituted $C_1$-$C_{10}$ hydrocarbylene, optionally substituted $C_2$-$C_{10}$ heterohydrocarbylene, $C_3$-$C_8$ cycloalkyl, $C_1$-$C_6$ alkyl-$C_3$-$C_8$ cycloalkyl, $C_3$-$C_8$ cycloalkyl-$C_1$-$C_6$ alkyl, $C_1$-$C_6$ alkyl-$C_3$-$C_8$ cycloalkyl-$C_1$-$C_6$ alkyl, $C_6$-$C_{10}$ aryl, $C_1$-$C_6$ alkyl-$C_6$-$C_{10}$ aryl, $C_6$-$C_{10}$ aryl-$C_1$-$C_6$ alkyl, and $C_1$-$C_6$ alkyl-$C_6$-$C_{10}$ aryl-$C_1$-$C_6$ alkyl, and $L_F$ is absent or is a functional group selected from the group consisting of —(C=O)—, —O—, —N($R^9$)—, —(C=O)N($R^9$)—, —N($R^9$)—(C=O)—, —(C=O)N(H)—, —N(H)—(C=O)—, —N($R^9$)—(C=O)—(CH$_2$)—, —(SO$_2$)N($R^9$)—, —N($R^9$)—(SO$_2$)—, —N($R^9$)(C=O)N($R^9$)—, —N($R^9$)—(C=O)—O—, —O—(C=O)N($R^9$)—, —(CH=CH)—, or a divalent cycloalkyl or heterocyclic group, where $R^9$ is selected from the group consisting of H and optionally substituted $C_1$-$C_4$ alkyl.

A useful chelating group for preparation of conjugates is the tetradentate mertiatide group (N—[N—[N-[(acetylthio)acetyl]glycyl]glycyl]-glycine; Fritzberg et al., J. Nuclear Medicine (1986) 27(1):111-116), having the structure:

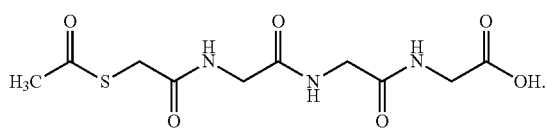 [SMILES: CC(=O)SCC(=O)NCC(=O)NCC(=O)NCC(=O)O]

For example, the following structure shows metal complexed with a group derived from mertiatide to form an imaging moiety:

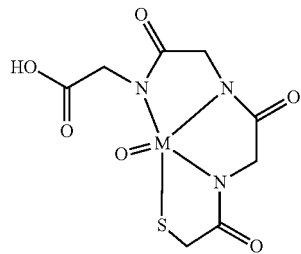

where M indicates a cationic metal ion, where the metal ion also bears an oxo group (for example, M=O can be $^{99m}$Tc=O or Re=O). The carboxylic acid functionality of the complex allows for a wide range of coupling reactions in order to attach the imaging moiety to the remainder of the molecule. Typically, the mertiatide peptide is coupled via its carboxylate group prior to introduction of the metal ion or metal-oxo ion. Once the mertiatide peptide is complexed to the metal ion (or metal-oxo ion), it can be referred to either as "mertiatide complexed to the metal ion (or metal-oxo ion)," or as a group derived from mertiatide. That is, a group bound or complexed to a metal ion or metal-oxo ion which is referred to as "derived" from a specific moiety refers to the group after it has complexed with the metal ion or metal-oxo ion. Alternatively, the group which binds or complexes to the metal ion or metal-oxo ion can be referred to by the same name in its free, uncomplexed form and in its complexed form with the metal; for example, "mertiatide group" can refer to both a mertiatide group without a complexed metal or metal-oxo ion, and also a mertiatide group which has complexed with a metal or metal-oxo ion.

A mertiatide-based group of the form:

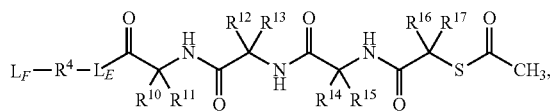

such as

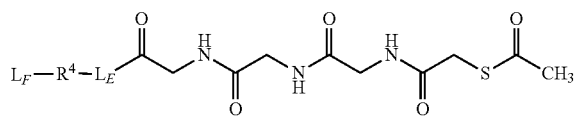

can be used in conjugates of the invention, where $L_E$ is absent or is selected from the group consisting of —NH— and —N($R^8$)—, where $R^8$ is optionally substituted $C_1$-$C_4$ alkyl, $R^4$ is selected from the group consisting of optionally substituted $C_1$-$C_{30}$ hydrocarbylene, optionally substituted $C_2$-$C_{30}$ heterohydrocarbylene group (such as $C_1$-$C_{12}$ alkylene), $C_3$-$C_8$ cycloalkyl, $C_1$-$C_6$ alkyl-$C_3$-$C_8$ cycloalkyl, $C_3$-$C_8$ cycloalkyl-$C_1$-$C_6$ alkyl, $C_1$-$C_6$ alkyl-$C_3$-$C_8$ cycloalkyl-$C_1$-$C_6$ alkyl, $C_6$-$C_{10}$ aryl, $C_1$-$C_6$ alkyl-$C_6$-$C_{10}$ aryl, $C_6$-$C_{10}$ aryl-$C_1$-$C_6$ alkyl, and $C_1$-$C_6$ alkyl-$C_6$-$C_{10}$ aryl-$C_1$-$C_6$ alkyl; and $L_F$ is absent or is a functional group selected from the group consisting of —(C=O)—, —O—, —N($R^9$)—, —(C=O)N($R^9$)—, —N($R^9$)—(C=O)—, —(C=O)N(H)—, —N(H)—(C=O)—, —(SO$_2$)N($R^9$)—, —N($R^9$)—(SO$_2$)—, —N($R^9$)(C=O)N($R^9$)—, —N($R^9$)—(C=O)—O—, and —O—(C=O)N($R^9$)— where one valence of $L_F$ (when $L_F$ is present) is attached to the $R^4$ group and the other valence is attached to the NSAID or residue or derivative of a NSAID; and where each $R^9$ is independently selected from the group consisting of H and optionally substituted $C_1$-$C_4$ alkyl. In one embodiment, $R^9$ is H. The substituents $R^{10}$, $R^{11}$, $R^{12}$, $R^{13}$, $R^{14}$, $R^{15}$, $R^{16}$, and $R^{17}$ are independently selected from the group consisting of hydrogen, $C_1$-$C_4$ alkyl, $C_1$-$C_4$ alkyl substituted with fluoro, hydroxy, —O—$C_1$-$C_4$ alkyl, or $C_3$-$C_6$ cycloalkyl; or, independently of the other substituents, ($R^{10}$ and $R^{11}$) together with the carbon to which they are attached independently form a $C_3$-$C_8$ cycloalkyl ring or heterocycloalkyl ring, ($R^{12}$ and $R^{13}$) together with the carbon to which they are attached independently form a $C_3$-$C_8$ cycloalkyl ring or heterocycloalkyl ring, or ($R^{14}$ and $R^{15}$) together with the carbon to which they are attached independently form a $C_3$-$C_8$ cycloalkyl ring or heterocycloalkyl ring, or ($R^{16}$ and $R^{17}$) together with the carbon to which they are attached independently form a $C_3$-$C_8$ cycloalkyl ring or heterocycloalkyl ring. In some embodiments, only one of ($R^{10}$ and $R^{11}$), ($R^{12}$ and $R^{13}$), ($R^{14}$ and $R^{15}$), and ($R^{16}$ and $R^{17}$) together with the carbon to which they are attached independently form a $C_3$-$C_8$ cycloalkyl ring or heterocycloalkyl ring; that is, only one of the four pairs of substituents forms a spiro ring, and the remaining three pairs do not form a spiro ring.

TechneScan MAG3™ is a commercially available kit for preparing $^{99m}$Tc-mertiatide conjugates, and is sold by Mallinckrodt Pharmaceuticals (catalog number N096B0, National Drug Code 00019N096B0), 675 McDonnell Blvd., St. Louis, Mo. 63042, USA. The kit vials contain betiatide, stannous chloride dihydrate (SnCl$_2$.2H$_2$O), sodium tartrate dihydrate, and lactose monohydrate. Betiatide, which is N-[(benzoylthio)acetyl]glycylglycylglycine, reacts with sodium pertechnetate $^{99m}$Tc to form $^{99m}$Tc-mertiatide.

Yet another useful chelating group for preparation of conjugates is based on the tetradentate ethylenedicysteine group:

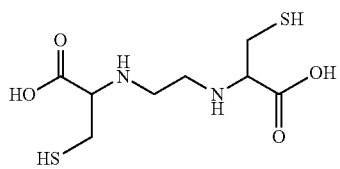 [SMILES: O=C(O)C(CS)NCCNC(CS)C(=O)O]

or, in stereospecific form using L-cysteine (having the R configuration at the alpha carbon):

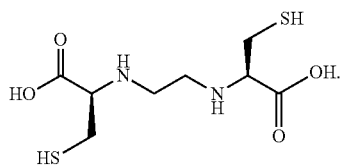

The following structure shows a metal ion complexed with a linker derived from ethylenedicysteine:

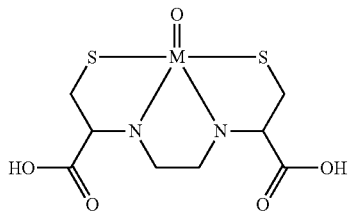

where M indicates a cationic metal ion, where the metal ion also bears an oxo group (for example, M=O can be $^{99m}$Tc=O or Re=O). Again, the carboxylic acid functionalities of the complex allows for a wide range of coupling reactions. One of the carboxylic acid functionalities can be blocked, for example as an amide:

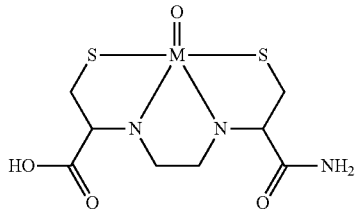

while the remaining carboxylic acid group can be used for attachment to the remainder of the molecule.

An ethylenedicysteine-based linker-imaging moiety of the form:

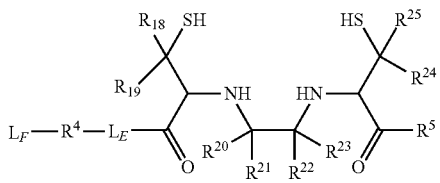

can be used in conjugates of the invention, where $L_E$ is absent or is selected from the group consisting of —NH— and —N(R$^8$)—, where R$^8$ is optionally substituted $C_1$-$C_4$ alkyl, R$^4$ is selected from the group consisting of optionally substituted $C_1$-$C_{30}$ hydrocarbylene, optionally substituted $C_2$-$C_{30}$ heterohydrocarbylene group (such as $C_1$-$C_{12}$ alkylene), $C_3$-$C_8$ cycloalkyl, $C_1$-$C_6$ alkyl-$C_3$-$C_8$ cycloalkyl, $C_3$-$C_8$ cycloalkyl-$C_1$-$C_6$ alkyl, $C_1$-$C_6$ alkyl-$C_3$-$C_8$ cycloalkyl-$C_1$-$C_6$ alkyl, $C_6$-$C_{10}$ aryl, $C_1$-$C_6$ alkyl-$C_6$-$C_{10}$ aryl, $C_6$-$C_{10}$ aryl-$C_1$-$C_6$ alkyl, and $C_1$-$C_6$ alkyl-$C_6$-$C_{10}$ aryl-$C_1$-$C_6$ alkyl, R$^5$ is —OH, —OR$^6$, —NH$_2$, —NHR$^6$, or —NR$^6$R$^7$, R$^6$ and R$^7$ are independently selected from $C_1$-$C_4$ alkyl, and $L_F$ is absent or is a functional group selected from the group consisting of —(C=O)—, —O—, —N(R$^9$)—, —(C=O)N(R$^9$)—, —N(R$^9$)—(C=O)—, —(C=O)N(H)—, —N(H)—(C=O)—, —(SO$_2$)N(R$^9$)—, —N(R$^9$)(SO$_2$)—, —N(R$^9$)—(C=O)—N(R$^9$)—, —N(R$^9$)—(C=O)—O—, and —O—(C=O)N(R$^9$)— where one valence of $L_F$ (when $L_F$ is present) is attached to the R$^4$ group and the other valence is attached to the NSAID or residue or derivative of a NSAID; and where each R$^9$ is independently selected from the group consisting of H and optionally substituted $C_1$-$C_4$ alkyl. In one embodiment, R$^9$ is H. The substituents R$^{18}$, R$^{19}$, R$^{20}$, R$^{21}$, R$^{22}$, R$^{23}$, R$^{24}$, and R$^{25}$ are independently selected from the group consisting of hydrogen, $C_1$-$C_4$ alkyl, $C_1$-$C_4$ alkyl substituted with fluoro, hydroxy, —O—$C_1$-$C_4$ alkyl, or $C_3$-$C_6$ cycloalkyl; or, independently of the other substituents, (R$^{18}$ and R$^{19}$) together with the carbon to which they are attached form a $C_3$-$C_8$ cycloalkyl ring or heterocycloalkyl ring, (R$^{20}$ and R$^{21}$) together with the carbon to which they are attached form a $C_3$-$C_8$ cycloalkyl ring or heterocycloalkyl ring, or (R$^{22}$ and R$^{23}$) together with the carbon to which they are attached independently form a $C_3$-$C_8$ cycloalkyl ring or heterocycloalkyl ring, or (R$^{24}$ and R$^{25}$) together with the carbon to which they are attached independently form a $C_3$-$C_8$ cycloalkyl ring or heterocycloalkyl ring. In some embodiments, only one of (R$^{18}$ and R$^{19}$), (R$^{20}$ and R$^{21}$), or (R$^{22}$ and R$^{23}$), or (R$^{24}$ and R$^{25}$) together with the carbon to which they are attached independently form a $C_3$-$C_8$ cycloalkyl ring or heterocycloalkyl ring; that is, only one of the four pairs of substituents forms a spiro ring, and the remaining three pairs do not form a spiro ring. In a further embodiment, R$^5$ is selected from the group consisting of —NH$_2$, —NH($C_1$-$C_4$ alkyl), —N($C_1$-$C_4$ alkyl)($C_1$-$C_4$ alkyl), —OCH$_3$, and —OCH$_2$CH$_3$; in yet a further embodiment, R$^5$ is selected from the group consisting of —NH$_2$, —OCH$_3$, and —OCH$_2$CH$_3$.

It should be noted that the mertiatide fragment:

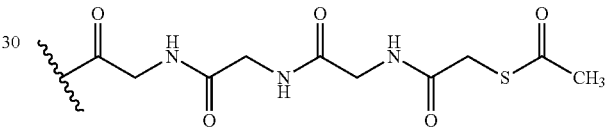

is a $C_{10}$ heterohydrocarbyl group (specifically, $C_{10}$ heteroalkyl) with three nitrogen atoms and a sulfur atom in the chain, and five oxo substituents, while the ethylenedicysteine fragment:

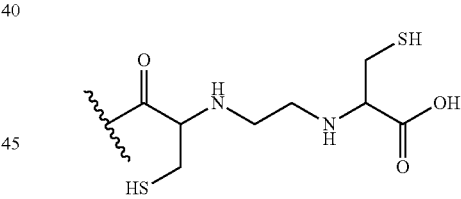

is a $C_6$ heterohydrocarbyl group (specifically, $C_6$ heteroalkyl); following the chain from the first thiol-substituted carbon to the second thiol-substituted carbon, the ethylenedicysteine fragment has two nitrogen atoms in the chain, two —SH substituents on the first and last carbons in the chain, one —COOH substituent, and a second —COOH substituent which is linked to the remainder of the molecule by removal of the —OH group of the carboxyl. Alternatively, the ethylenedicysteine fragment can be considered as a 3,6-diazaoctane (i.e., heteroalkyl) with thiol substituents on the 1 and 8 carbons, a carboxy substituent on the 7 carbon, and a —C(=O)—OH or —C(=O)—H moiety on the 2 carbon, where the —OH or —H, respectively, has been removed for attachment to the remainder of the molecule.

In one embodiment, where the linker(s) is (are) capable of directly binding to or chelating the metal of the imaging moiety, the invention comprises compounds of the formula:

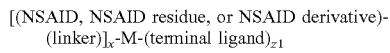

where "NSAID, NSAID residue, or NSAID derivative" refers to a NSAID or a residue or derivative of a NSAID, M is selected from the group consisting of $^{99m}$Tc, $^{52}$Mn, and Re, x is an integer between 1 and 6 inclusive, z1 is an integer between 0 and 5 inclusive, and the sum of x and z1 is less than or equal to 6, and "terminal ligand" is a ligand that coordinates to M, but which does not have a NSAID attached to it. The linker or linkers may be monodentate or polydentate for M. The terminal ligand or ligands may be monodentate or polydentate for M. When more than one terminal ligand is present, all of the ligands can be identical groups, all of the ligands can be different groups, or some of the ligands can be identical groups and some can be different groups. It should be noted that some monodentate ligands, such as the oxo ligand, =O, can occupy more than one valence on the metal ion; that is, there can be multiple bonds between some monodentate ligands, such as the oxo ligand, =O, and the metal atom.

In one embodiment, where the linker(s) is (are) capable of directly binding to or chelating the metal of the imaging moiety, and where both the linker(s) and the terminal ligand(s) are monodentate and occupy only one valence per linker and one valence per terminal ligand, the invention comprises compounds of the formula:

[(NSAID, NSAID residue, or NSAID derivative)-monodentate linker]$_x$-M-(terminal monodentate ligand), where "NSAID, NSAID residue, or NSAID derivative" refers to a NSAID or a residue or derivative of a NSAID, M is selected from the group consisting of $^{99m}$Tc, $^{52}$Mn, and Re, x is an integer between 1 and 6 inclusive, y is an integer between 0 and 5 inclusive, and x+y=6, and "terminal ligand" is a ligand that coordinates to $^{99m}$Tc, $^{52}$Mn, or Re, but which does not have a NSAID or a residue or derivative of a NSAID attached to it.

Chelating groups (including linkers, where the linker is capable of chelation) and terminal ligands may be monodentate or polydentate, with the condition that the chelating group or groups and terminal ligand or ligands must together satisfy the valency of the metal atom to which they are bonded. For example, in the following compound:

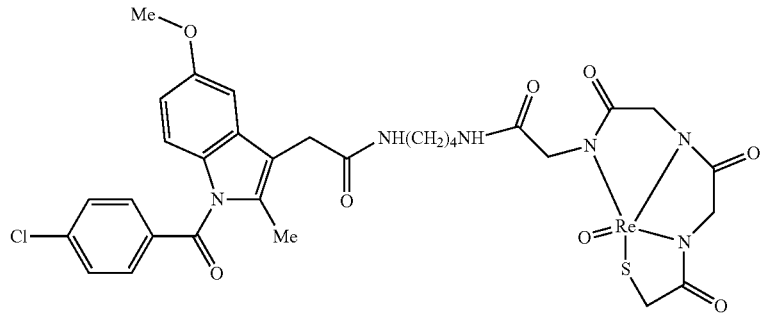

the mertiatide moiety is tetradentate and occupies four valences of the rhenium ion, while the monodentate oxo ligand occupies two valences of the rhenium ion, thus together satisfying the valency of the Re(VI) ion.

In the formula:

(NSAID, NSAID derivative, or NSAID residue)-(linker)-(chelating group)-M-(terminal ligand)$_{z2}$, which can be written as the three individual formulas:

(NSAID)-(linker)-(chelating group)-M-(terminal ligand)$_{z2}$ (NSAID derivative)-(linker)-(chelating group)-M-(terminal ligand)$_{z2}$ (NSAID residue)-(linker)-(chelating group)-M-(terminal ligand)$_{z2}$, and where z2 is an integer between 0 and 4 inclusive, the chelating group binds the radioactive agent M by two or more bonds. When two or more terminal ligands are present, two or more of the terminal ligands can be combined to form an additional chelating group or groups.

Examples of terminal ligands include: halo (—X), fluoro (—F), chloro (—Cl), bromo (—Br), iodo (—I), oxo (=O), cyano (—CN), isocyano (—NC), hydroxyl (—OH), with oxo being a preferred terminal ligand; and substituted isocyano ligands of the form:

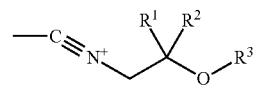

where $R^1$, $R^2$, and $R^3$ can be independently selected from the group consisting of hydrogen, $C_1$-$C_4$ alkyl, $C_1$-$C_4$ alkyl substituted with hydroxy, fluoro, —O—$C_1$-$C_4$ alkyl, or $C_3$-$C_6$ cycloalkyl, or $R^1$ and $R^2$ together with the carbon to which they are attached form a $C_3$-$C_8$ cycloalkyl ring or heterocycloalkyl ring, such as

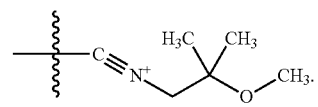 [SMILES: *C#[N+]CC(C)(C)OC]

These substituted isocyano ligands are preferred when the NSAID linker is also an isocyano ligand.

Examples of cyclooxygenase inhibitors with a linker which incorporates a ligand to bind $^{99m}$Tc, which can be used as the moiety [(NSAID, NSAID residue, or NSAID derivative)-linker] include, but are not limited to:

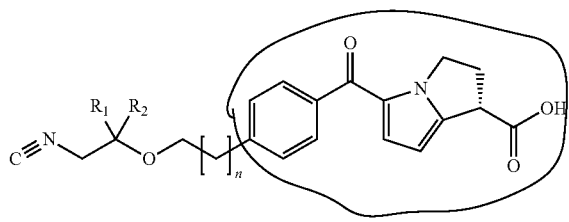

where the encircled portion represents a residue of ketorolac (where one of the hydrogens on the phenyl ring of ketorolac has been replaced by the linker);

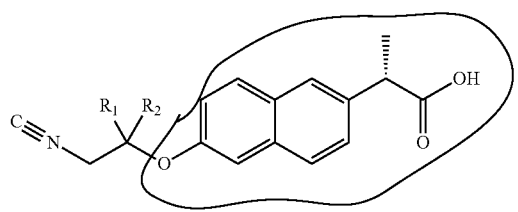

where the encircled portion represents a residue of naproxen (where the methyl of the methoxy group of naproxen has been replaced by the linker);

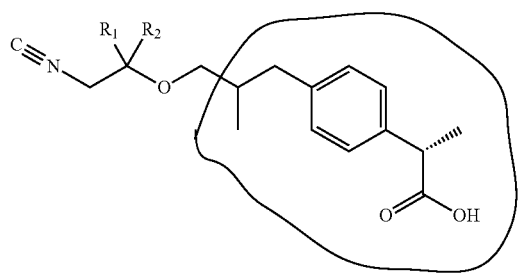

where the encircled portion represents a residue of ibuprofen (where one of the methyl groups of the (2-methylpropyl) group of ibuprofen has been replaced by the linker); and

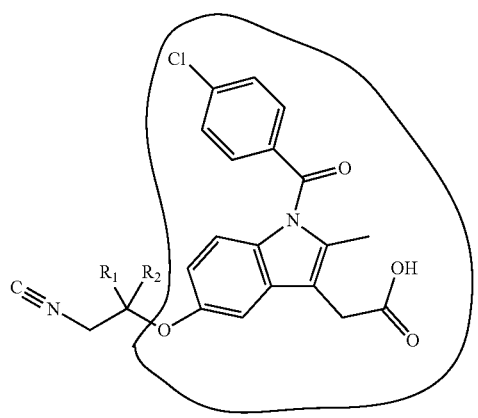

where the encircled portion represents a residue of indomethacin (where the methyl of the methoxy group of indomethacin has been replaced by the linker). The linkers are attached as indicated above in order to preserve the pharmacophoric portions of the NSAID.

In some embodiments, when x is two or greater, all of the NSAID, NSAID residue, or NSAID derivatives in the x subunits [(NSAID, NSAID residue, or NSAID derivative)-linker] are the same NSAID, NSAID residue, or NSAID derivative. In some embodiments, when x is two or greater, at least one of the NSAID, NSAID residue, or NSAID derivatives in the x subunits of [(NSAID, NSAID residue, or NSAID derivative)-linker] is different than the remaining NSAID(s) or NSAID residue(s) in the remaining subunits of [(NSAID, NSAID residue, or NSAID derivative)-linker]. In some embodiments, when x is two or greater, each of the NSAID, NSAID residue, or NSAID derivatives in the x subunits of [(NSAID, NSAID residue, or NSAID derivative)-linker] is different than the remaining NSAID(s) or NSAID residue(s) in the other subunits of [(NSAID, NSAID residue, or NSAID derivative)-linker].

Exemplary conjugates of the invention can be of the form:

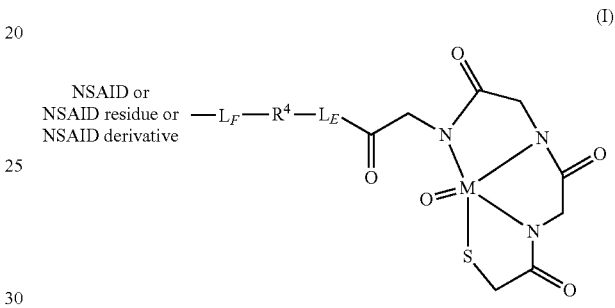

(I)

where $L_E$ is absent or is selected from the group consisting of —NH— and —N($R^8$)—, where $R^8$ is optionally substituted $C_1$-$C_4$ alkyl, $R^4$ is selected from the group consisting of optionally substituted $C_1$-$C_{30}$ hydrocarbylene and optionally substituted $C_2$-$C_{30}$ heterohydrocarbylene group (such as $C_1$-$C_{12}$ alkylene), $C_3$-$C_8$ cycloalkyl, $C_1$-$C_6$ alkyl-$C_3$-$C_8$ cycloalkyl, $C_3$-$C_8$ cycloalkyl-$C_1$-$C_6$ alkyl, $C_1$-$C_6$ alkyl-$C_3$-$C_8$ cycloalkyl-$C_1$-$C_6$ alkyl, $C_6$-$C_{10}$ aryl, $C_1$-$C_6$ alkyl-$C_6$-$C_{10}$ aryl, $C_6$-$C_{10}$ aryl-$C_1$-$C_6$ alkyl, and $C_1$-$C_6$ alkyl-$C_6$-$C_{10}$ aryl-$C_1$-$C_6$ alkyl; $L_F$ is absent or is a functional group selected from the group consisting of —(C=O)—, —O—, —N($R^9$)—, —(C=O)N($R^9$)—, —N($R^9$)—(C=O)—, —(C=O)N(H)—, —N(H)—(C=O)—, —($SO_2$)N($R^9$)—, —N($R^9$)—($SO_2$)—, —N($R^9$)(C=O)N($R^9$)—, —N($R^9$)—(C=O)—O—, and —O—(C=O)N($R^9$)— where one valence of $L_F$ (when $L_F$ is present) is attached to the $R^4$ group and the other valence is attached to the NSAID or residue or derivative of a NSAID; and where each $R^9$ is independently selected from the group consisting of H and optionally substituted $C_1$-$C_4$ alkyl (in one embodiment, $R^9$ is H), and M is selected from the group consisting of $^{99m}$Tc, $^{52}$Mn, and Re, where Re can be $^{186}$Re or $^{188}$Re.

Examples of specific conjugates of this form include:

23

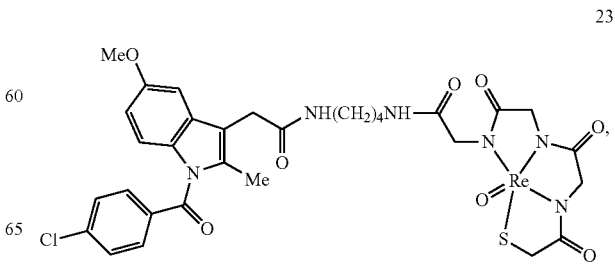

-continued

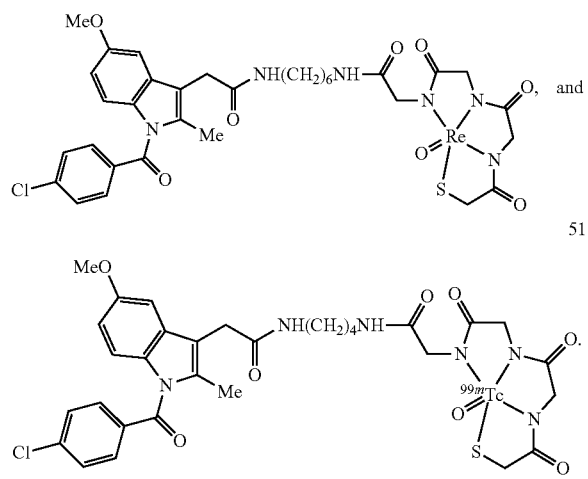

Further exemplary conjugates of the invention can be of the form:

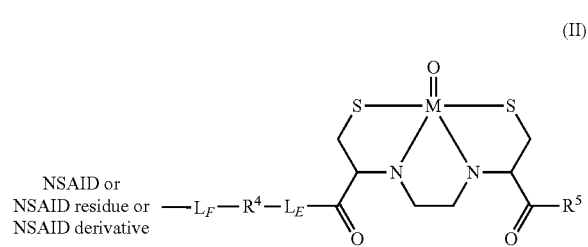

where $L_E$ is absent or is selected from the group consisting of —NH— and —N(R$^8$)—, where R$^8$ is optionally substituted $C_1$-$C_4$ alkyl, R$^4$ is selected from the group consisting of optionally substituted $C_1$-$C_{30}$ hydrocarbylene, optionally substituted $C_2$-$C_{30}$ heterohydrocarbylene group (such as $C_1$-$C_{12}$ alkylene), $C_3$-$C_8$ cycloalkyl, $C_1$-$C_6$ alkyl-$C_3$-$C_8$ cycloalkyl, $C_3$-$C_8$ cycloalkyl-$C_1$-$C_6$ alkyl, $C_1$-$C_6$ alkyl-$C_3$-$C_8$ cycloalkyl-$C_1$-$C_6$ alkyl, $C_6$-$C_{10}$ aryl, $C_1$-$C_6$ alkyl-$C_6$-$C_{10}$ aryl, $C_6$-$C_{10}$ aryl-$C_1$-$C_6$ alkyl, and $C_1$-$C_6$ alkyl-$C_6$-$C_{10}$ aryl-$C_1$-$C_6$ alkyl; R$^5$ is —OH, —NH$_2$, —NH($C_1$-$C_4$ alkyl), or —N($C_1$-$C_4$ alkyl)($C_1$-$C_4$ alkyl), $L_F$ is absent or is a functional group selected from the group consisting of —(C=O)—, —O—, —N(R$^9$)—, —(C=O)N(R$^9$)—, —N(R$^9$)—(C=O)—, —(C=O)N(H)—, —N(H)—(C=O)—, —(SO$_2$)N(R$^9$)—, —N(R$^9$)—(SO$_2$)—, —N(R$^9$)(C=O)N(R$^9$)—, —N(R$^9$)—(C=O)—O—, and —O—(C=O)N(R$^9$)— where one valence of $L_F$ (when $L_F$ is present) is attached to the R$^4$ group and the other valence is attached to the NSAID or residue or derivative of a NSAID; and where each R$^9$ is independently selected from the group consisting of H and optionally substituted $C_1$-$C_4$ alkyl (in one embodiment, R$^9$ is H); and M is selected from the group consisting of $^{99m}$Tc, $^{52}$Mn, and Re, where Re can be $^{186}$Re or $^{188}$Re. In a further embodiment, R$^5$ is selected from the group consisting of —NH$_2$, —NH($C_1$-$C_4$ alkyl), —N($C_1$-$C_4$ alkyl)($C_1$-$C_4$ alkyl), —OCH$_3$, and —OCH$_2$CH$_3$; in yet a further embodiment, R$^5$ is selected from the group consisting of —NH$_2$, —OCH$_3$, and —OCH$_2$CH$_3$.

Examples of specific conjugates of this form include:

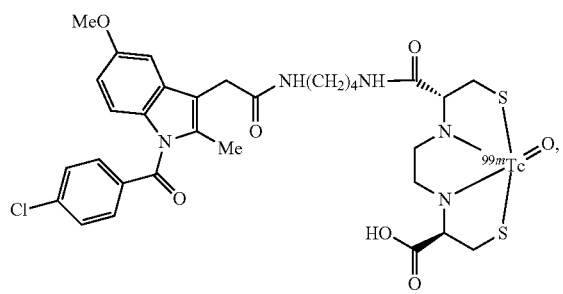

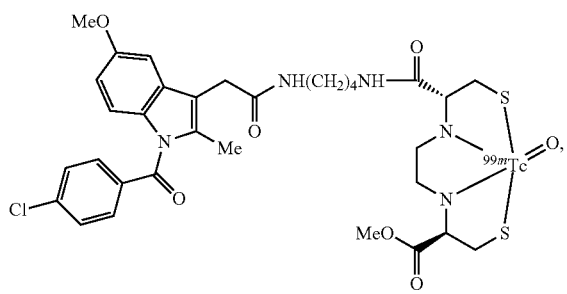

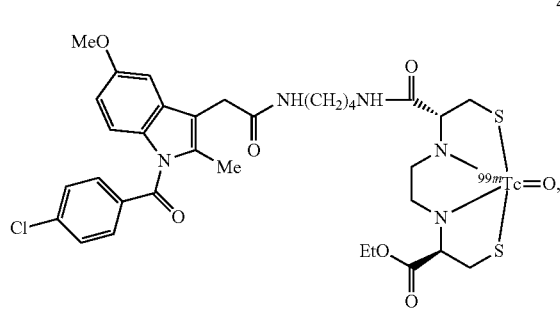

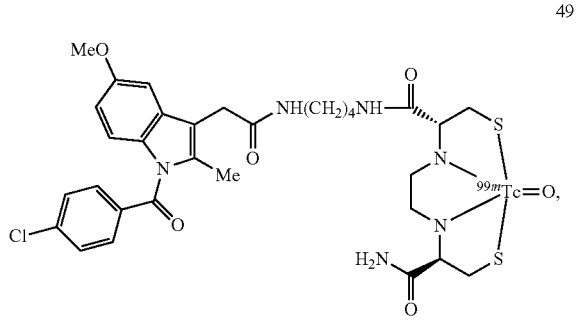

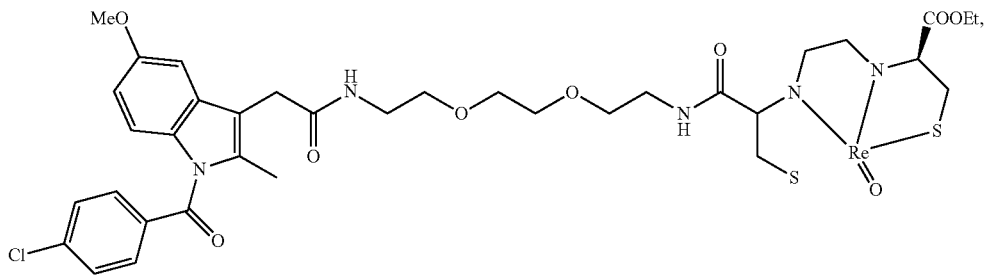
178
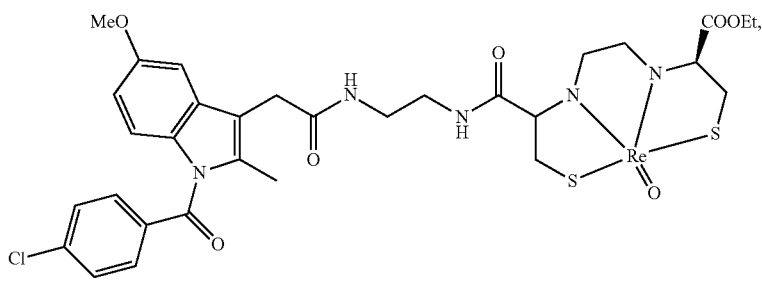
179
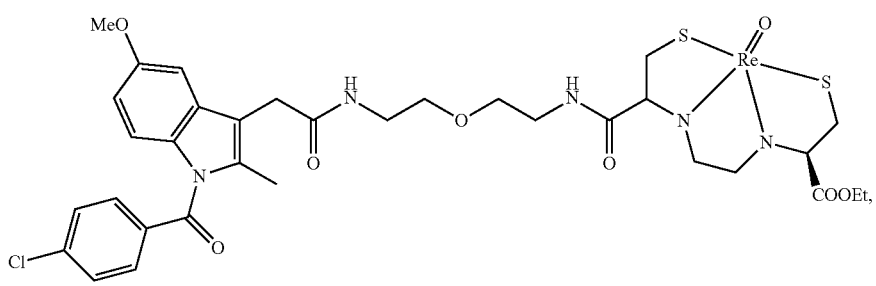
180
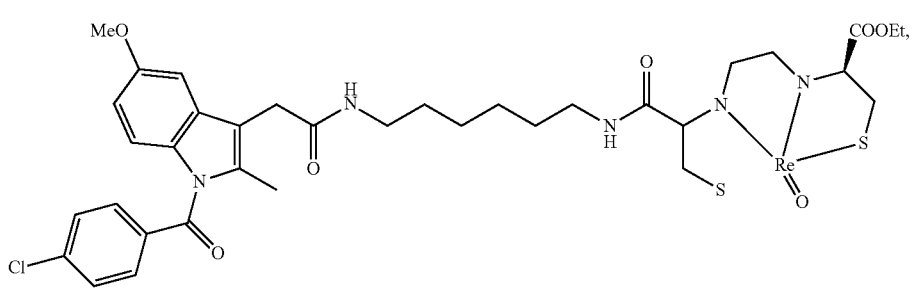
181
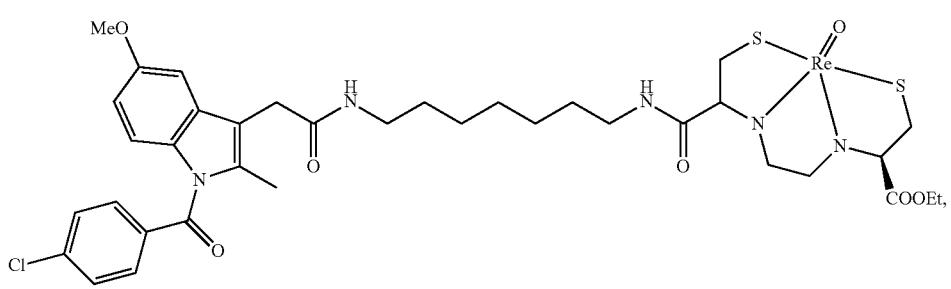
182

183
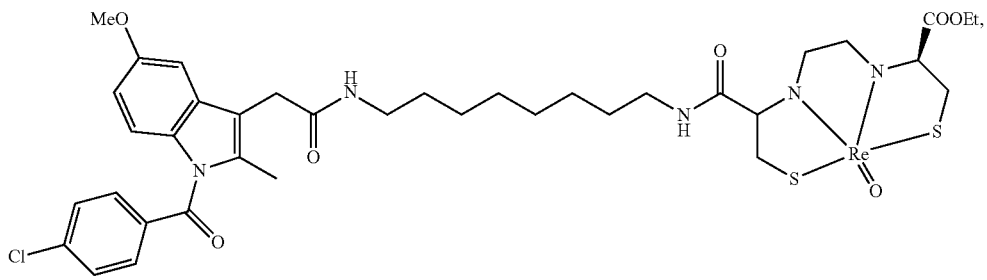
184
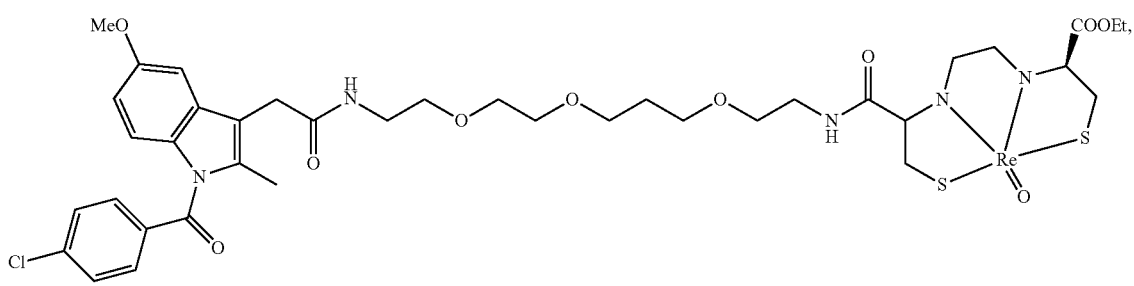
193
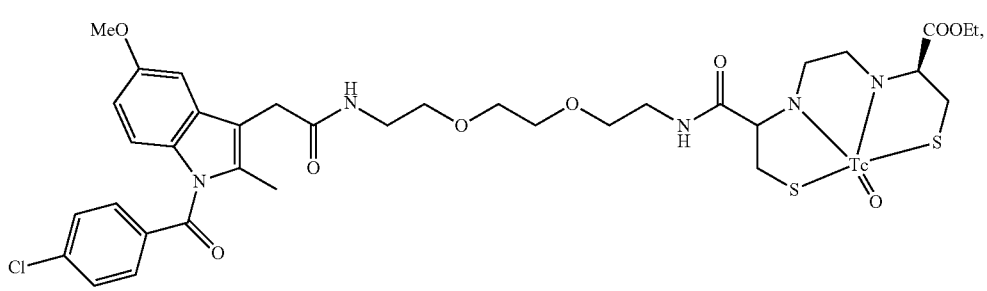
194
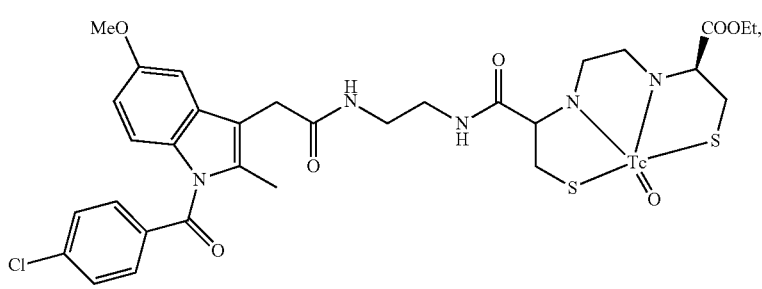
195
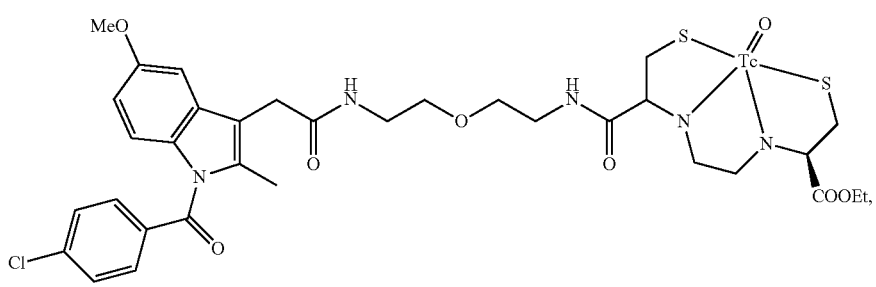

196
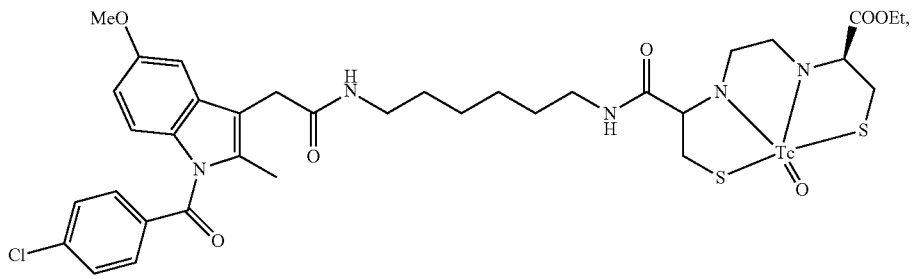
197
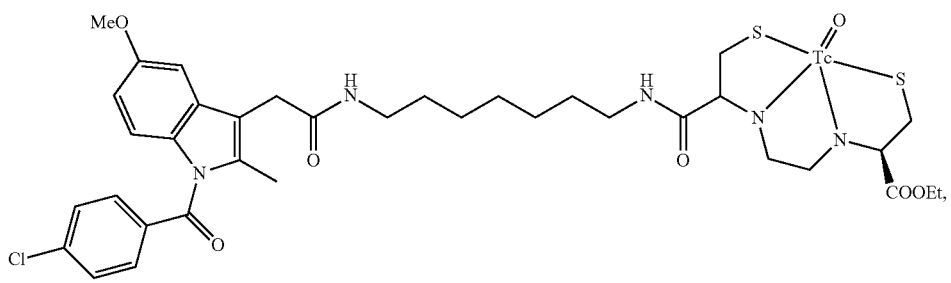
198
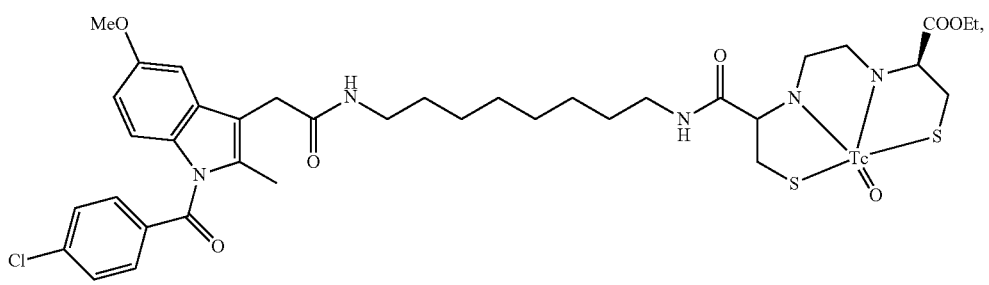
199
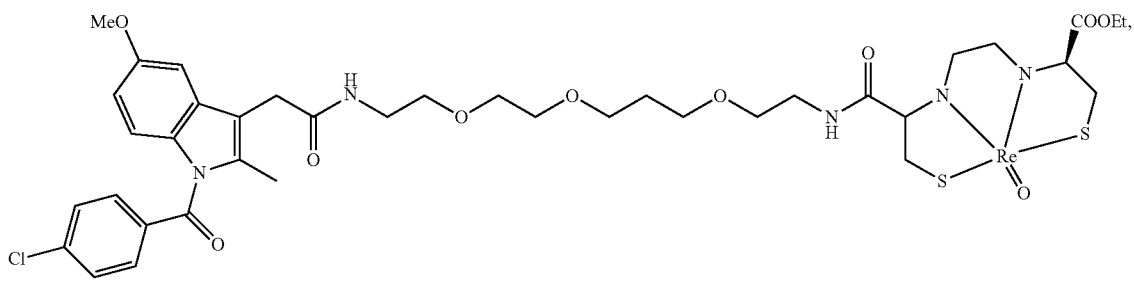
200
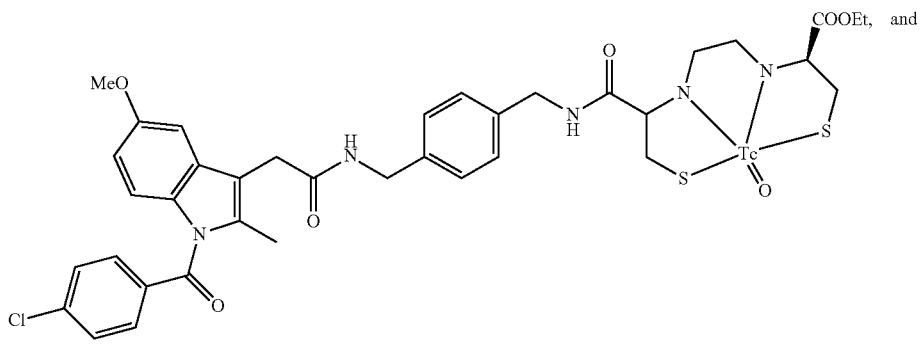
and

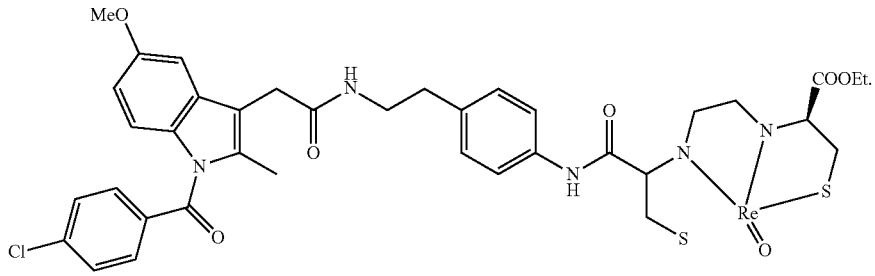

201

Further exemplary conjugates of the invention can be of the form:

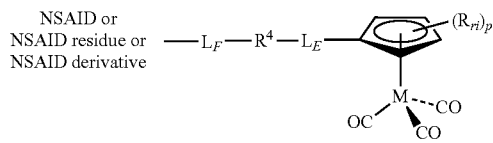

where $L_E$ is absent or is selected from the group consisting of —NH— and —N(R$^8$)—, where R$^8$ is optionally substituted $C_1$-$C_4$ alkyl, R$^4$ is selected from the group consisting of optionally substituted $C_1$-$C_{30}$ hydrocarbylene, optionally substituted $C_2$-$C_{30}$ heterohydrocarbylene group (such as $C_1$-$C_{12}$ alkylene), $C_3$-$C_8$ cycloalkyl, $C_1$-$C_6$ alkyl-$C_3$-$C_8$ cycloalkyl, $C_3$-$C_8$ cycloalkyl-$C_1$-$C_6$ alkyl, $C_1$-$C_6$ alkyl-$C_3$-$C_8$ cycloalkyl-$C_1$-$C_6$ alkyl, $C_6$-$C_{10}$ aryl, $C_1$-$C_6$ alkyl-$C_6$-$C_{10}$ aryl, $C_6$-$C_{10}$ aryl-$C_1$-$C_6$ alkyl, and $C_1$-$C_6$ alkyl-$C_6$-$C_{10}$ aryl-$C_1$-$C_6$ alkyl; R$^5$ is —OH, —NH$_2$, —NH($C_1$-$C_4$ alkyl), or —N($C_1$-$C_4$ alkyl)($C_1$-$C_4$ alkyl), $L_F$ is absent or is a functional group selected from the group consisting of —(C=O)—, —O—, —N(R$^9$)—, —(C=O)N(R$^9$)—, —N(R$^9$)—(C=O)—, —(C=O)N(H)—, —N(H)—(C=O)—, —(SO$_2$)N(R$^9$)—, —N(R$^9$)—(SO$_2$)—, —N(R$^9$)(C=O)N(R$^9$)—, —N(R$^9$)—(C=O)—O—, and —O—(C=O)N(R$^9$)— where one valence of $L_F$ (when $L_F$ is present) is attached to the R$^4$ group and the other valence is attached to the NSAID or residue or derivative of a NSAID; and where each R$^9$ is independently selected from the group consisting of H and optionally substituted $C_1$-$C_4$ alkyl (in one embodiment, R$^9$ is H); R$_{(ri)}$ is —CH$_3$ or —CH$_2$CH$_3$ and p is an integer between 0 and 4 inclusive; and M is selected from the group consisting of $^{99m}$Tc, $^{52}$Mn, and Re, where Re can be $^{186}$Re or $^{188}$Re. In a further embodiment, R$^5$ is selected from the group consisting of —NH$_2$, —NH($C_1$-$C_4$ alkyl), —N($C_1$-$C_4$ alkyl)($C_1$-$C_4$ alkyl), —OCH$_3$, and —OCH$_2$CH$_3$; in yet a further embodiment, R$^5$ is selected from the group consisting of —NH$_2$, —OCH$_3$, and —OCH$_2$CH$_3$.

Examples of specific conjugates of this form include:

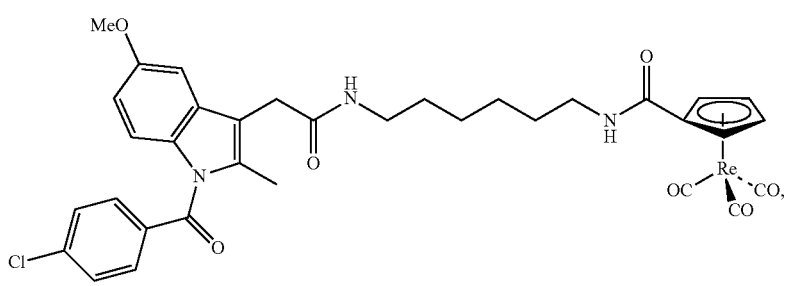

242

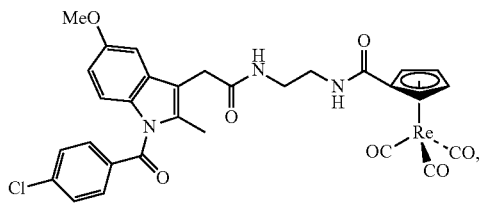

243

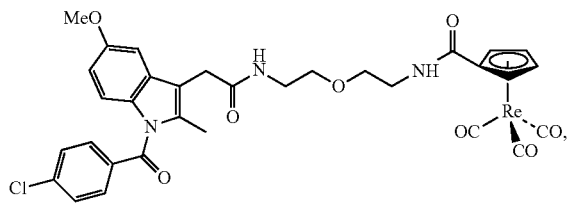

244

245
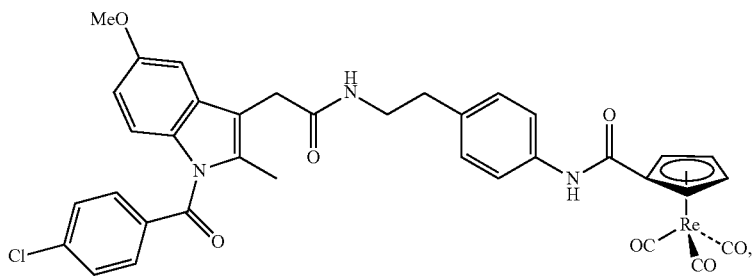
246
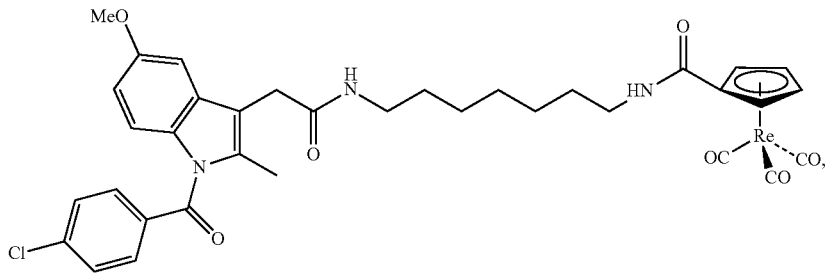
247
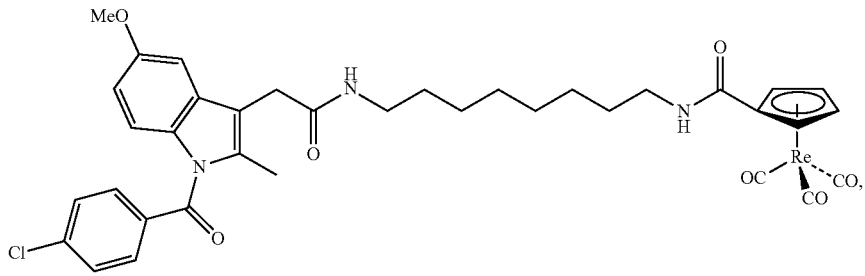
248
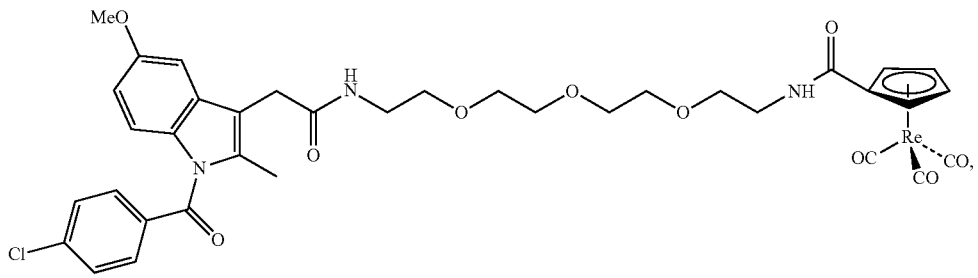
249 250
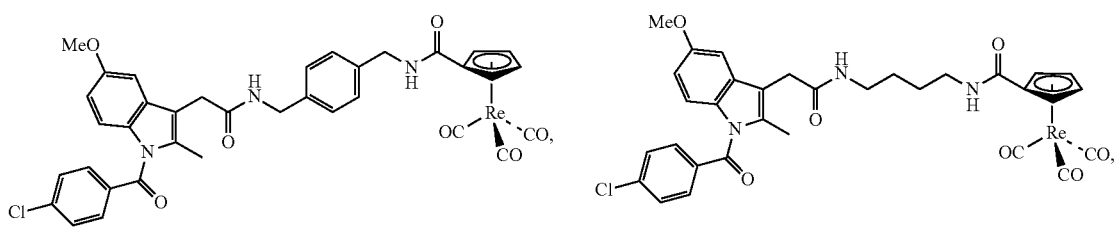
251
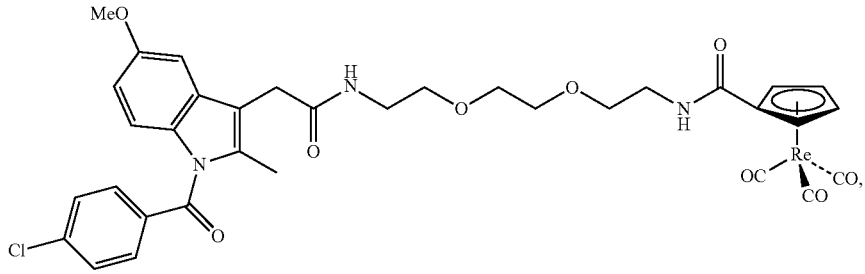

-continued

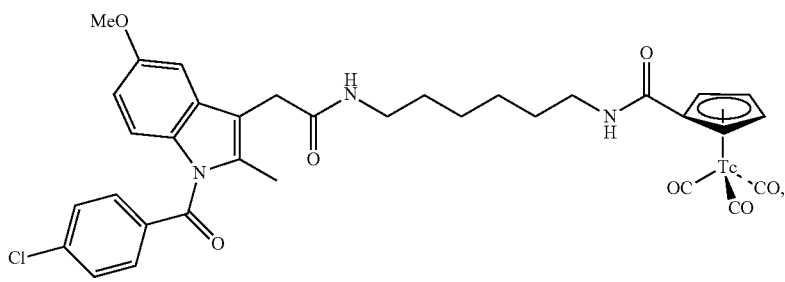

254

Further exemplary conjugates of the invention can be of the form:

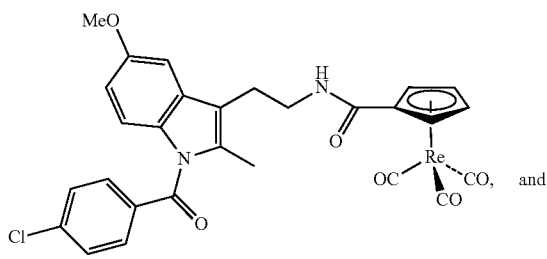

297

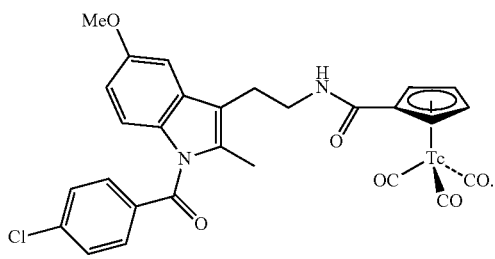

299 and where $L_E$ is absent or is selected from the group consisting of —NH— and —N(R$^8$)—, where R is optionally substituted C$_1$-C$_4$ alkyl, R$^4$ is selected from the group consisting of optionally substituted C$_1$-C$_{30}$ hydrocarbylene, optionally substituted C$_2$-C$_{30}$ heterohydrocarbylene group (such as C$_1$-C$_{12}$ alkylene), C$_3$-C$_8$ cycloalkyl, C$_1$-C$_6$ alkyl-C$_3$-C$_8$ cycloalkyl, C$_3$-C$_8$ cycloalkyl-C$_1$-C$_6$ alkyl, C$_1$-C$_6$ alkyl-C$_3$-C$_8$ cycloalkyl-C$_1$-C$_6$ alkyl, C$_6$-C$_{10}$ aryl, C$_1$-C$_6$ alkyl-C$_6$-C$_{10}$ aryl, C$_6$-C$_{10}$ aryl-C$_1$-C$_6$ alkyl, and C$_1$-C$_6$ alkyl-C$_6$-C$_{10}$ aryl-C$_1$-C$_6$ alkyl; R$^5$ is —OH, —NH$_2$, —NH(C$_1$-C$_4$ alkyl), or —N(C$_1$-C$_4$ alkyl)(C$_1$-C$_4$ alkyl), L$_F$ is absent or is a functional group selected from the group consisting of —(C=O)—, —O—, —N(R$^9$)—, —(C=O)N(R$^9$)—, —N(R$^9$)—(C=O)—, —(C=O)N(H)—, —N(H)—(C=O)—, —(SO$_2$)N(R$^9$)—, —N(R$^9$)—(SO$_2$)—, —N(R$^9$)(C=O)N(R$^9$)—, —N(R$^9$)—(C=O)—O—, and —O—(C=O)N(R$^9$)— where one valence of L$_F$ (when L$_F$ is present) is attached to the R$^4$ group and the other valence is attached to the NSAID or residue or derivative of a NSAID; and where each R$^9$ is independently selected from the group consisting of H and optionally substituted C$_1$-C$_4$ alkyl (in one embodiment, R$^9$ is H); and M is selected from the group consisting of $^{99m}$Tc, $^{52}$Mn, and Re, where Re can be $^{186}$Re or $^{188}$Re. In a further embodiment, R$^5$ is selected from the group consisting of —NH$_2$, —NH(C$_1$-C$_4$ alkyl), —N(C$_1$-C$_4$ alkyl)(C$_1$-C$_4$ alkyl), —OCH$_3$, and —OCH$_2$CH$_3$; in yet a further embodiment, R$^5$ is selected from the group consisting of —NH$_2$, —OCH$_3$, and —OCH$_2$CH$_3$.

Examples of specific conjugates of this form include:

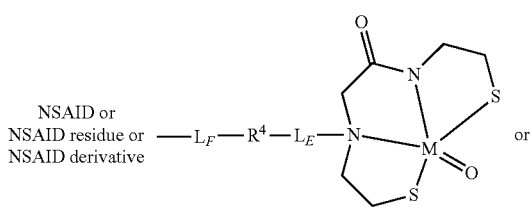

260

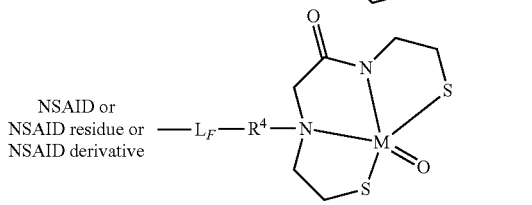

261

262

263
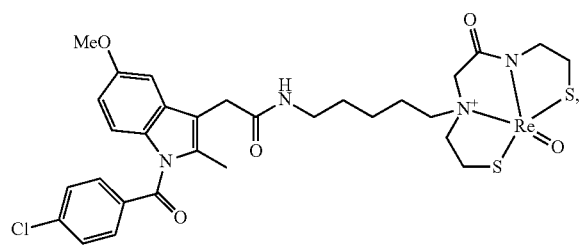
264
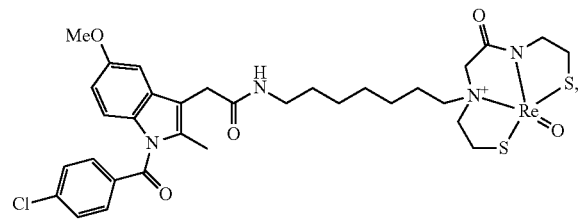
265
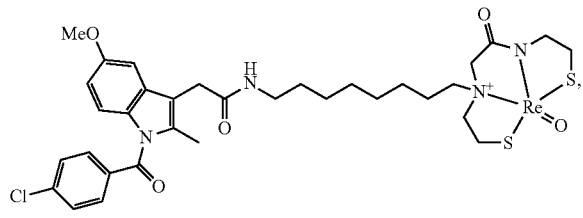
266
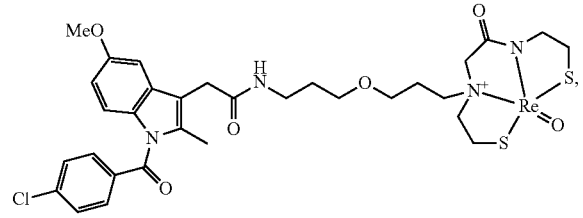
267
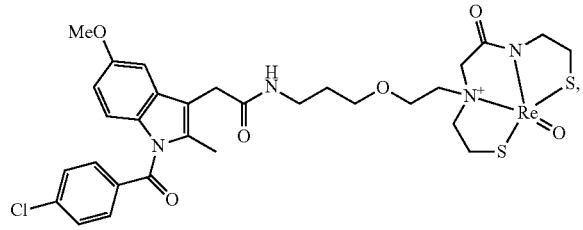
268
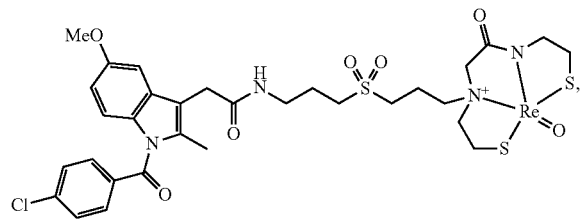
269
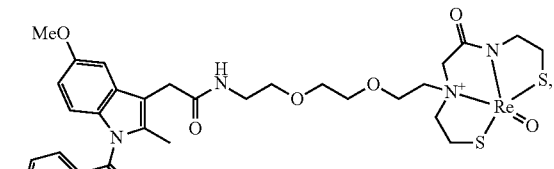
270
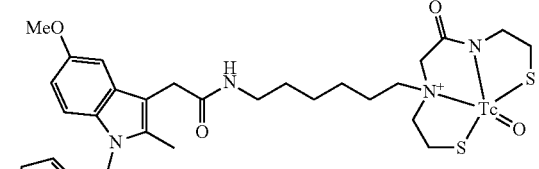
320
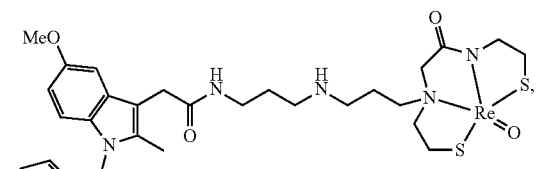
341
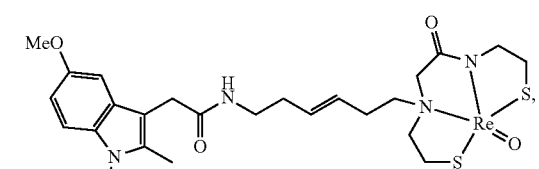
351
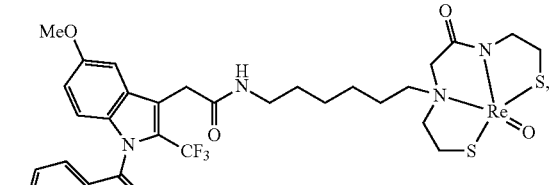
352
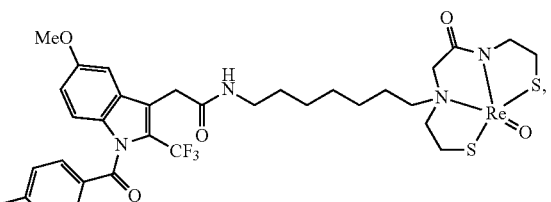

-continued

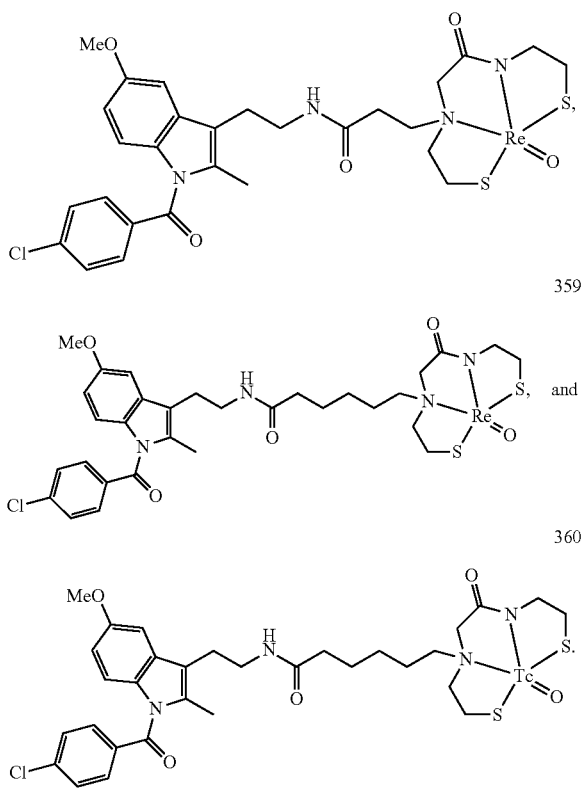

356

359

Further exemplary conjugates of the invention can be of the form:

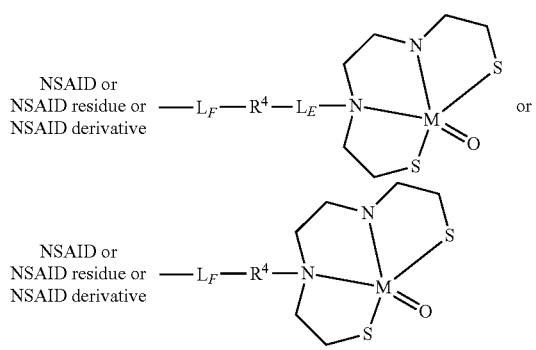

where $L_E$ is absent or is selected from the group consisting of —NH— and —N(R$^8$)—, where R$^8$ is optionally substituted $C_1$-$C_4$ alkyl, R$^4$ is selected from the group consisting of optionally substituted $C_1$-$C_{30}$ hydrocarbylene, optionally substituted $C_2$-$C_{30}$ heterohydrocarbylene group (such as $C_1$-$C_{12}$ alkylene), $C_3$-$C_8$ cycloalkyl, $C_1$-$C_6$ alkyl-$C_3$-$C_8$ cycloalkyl, $C_3$-$C_8$ cycloalkyl-$C_1$-$C_6$ alkyl, $C_1$-$C_6$ alkyl-$C_3$-$C_8$ cycloalkyl-$C_1$-$C_6$ alkyl, $C_6$-$C_{10}$ aryl, $C_1$-$C_6$ alkyl-$C_6$-$C_{10}$ aryl, $C_6$-$C_{10}$ aryl-$C_1$-$C_6$ alkyl, and $C_1$-$C_6$ alkyl-$C_6$-$C_{10}$ aryl-$C_1$-$C_6$ alkyl; R$^5$ is —OH, —NH$_2$, —NH($C_1$-$C_4$ alkyl), or —N($C_1$-$C_4$ alkyl)($C_1$-$C_4$ alkyl), $L_F$ is absent or is a functional group selected from the group consisting of —(C=O)—, —O—, —N(R$^9$)—, —(C=O)N(R$^9$)—, —(C=O)N(H)—, —N(H)—(C=O)—, —N(R$^9$)(C=O)—, —(SO$_2$)N(R$^9$)—, —N(R$^9$)—(SO$_2$)—, —N(R$^9$)(C=O)N(R$^9$)—, —N(R$^9$)—(C=O)—O—, and —O—(C=O)N(R$^9$)— where one valence of $L_F$ (when $L_F$ is present) is attached to the R$^4$ group and the other valence is attached to the NSAID or residue or derivative of a NSAID; and where each R$^9$ is independently selected from the group consisting of H and optionally substituted $C_1$-$C_4$ alkyl (in one embodiment, R$^9$ is H); and M is selected from the group consisting of $^{99m}$Tc, $^{52}$Mn, and Re, where Re can be $^{186}$Re or $^{188}$Re. In a further embodiment, R$^5$ is selected from the group consisting of —NH$_2$, —NH($C_1$-$C_4$ alkyl), —N($C_1$-$C_4$ alkyl)($C_1$-$C_4$ alkyl), —OCH$_3$, and —OCH$_2$CH$_3$; in yet a further embodiment, R$^5$ is selected from the group consisting of —NH$_2$, —OCH$_3$, and —OCH$_2$CH$_3$.

Examples of specific conjugates of this form include:

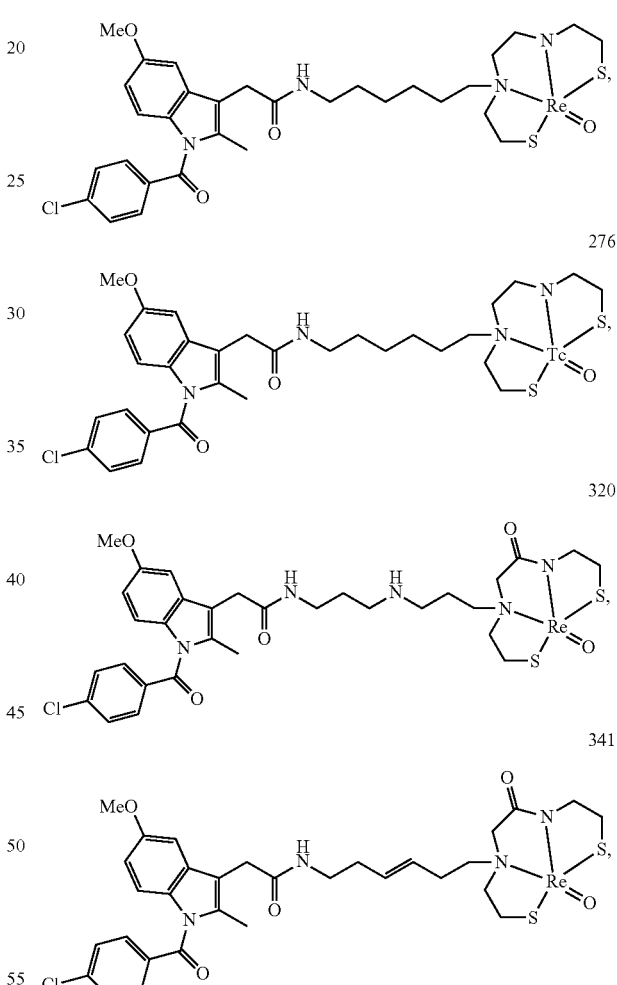

275

276

320

341

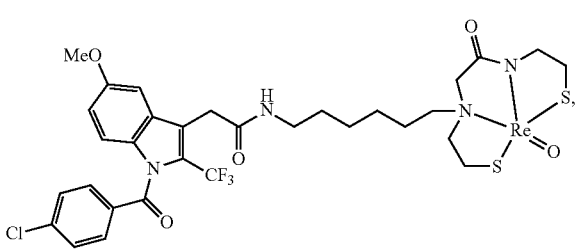

351

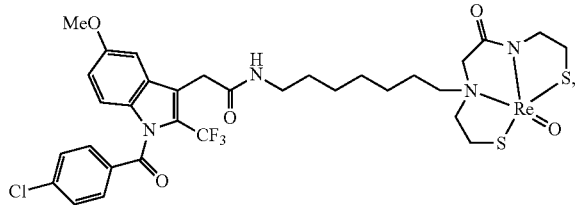

352

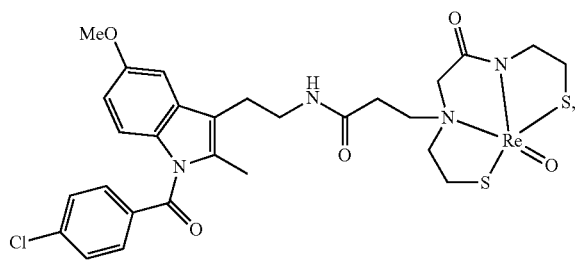

356

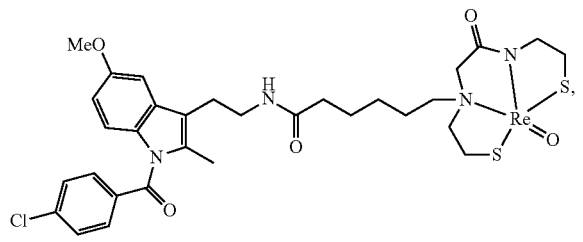

359

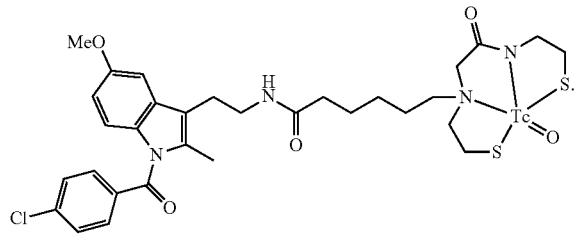

360

All pharmaceutically acceptable salts of all of the above general and specific compounds are also included in this disclosure.

Figure 2:
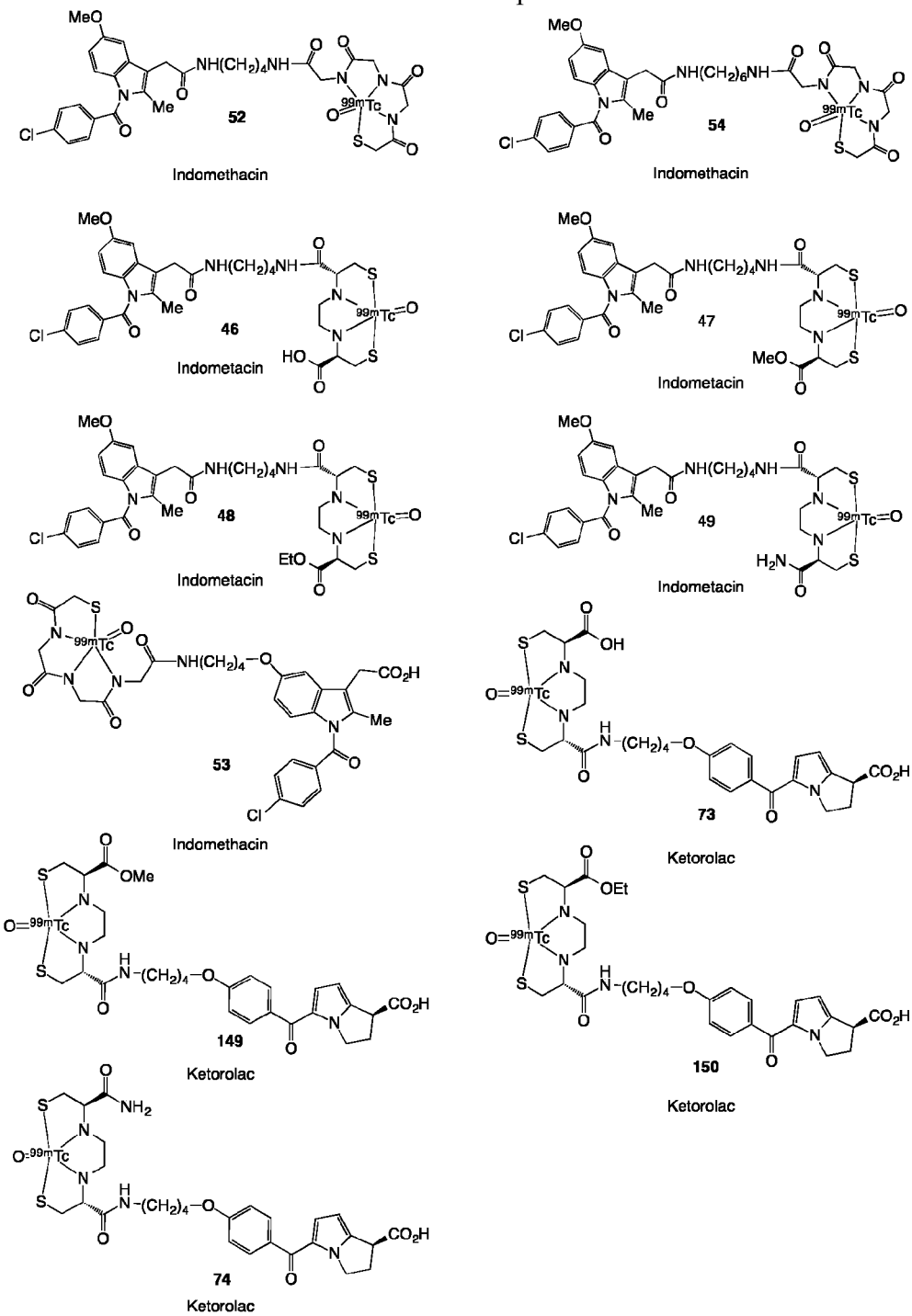
FIG. 2 illustrates various rhenium-containing conjugates.
Figure 2:
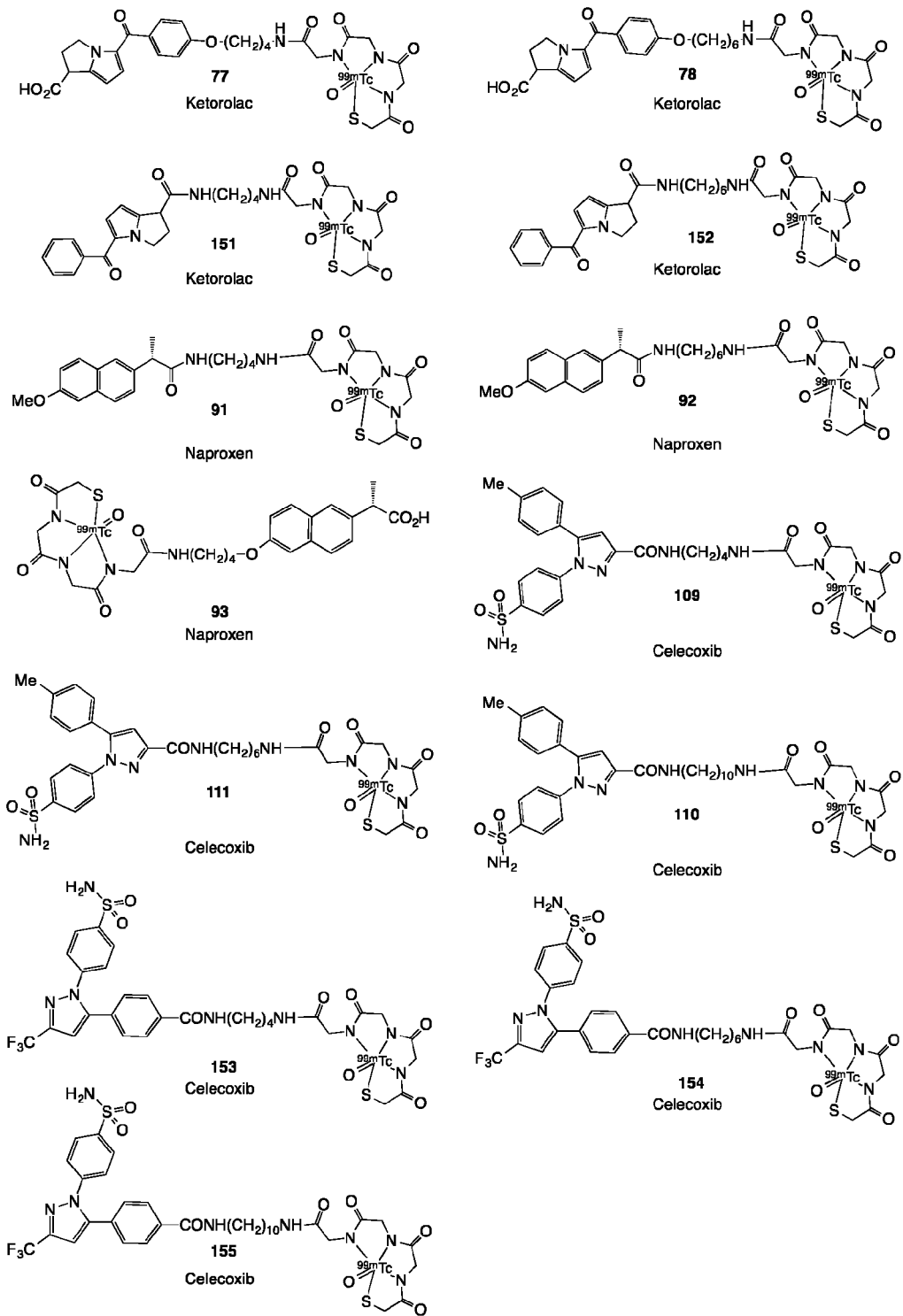
Figure 2:
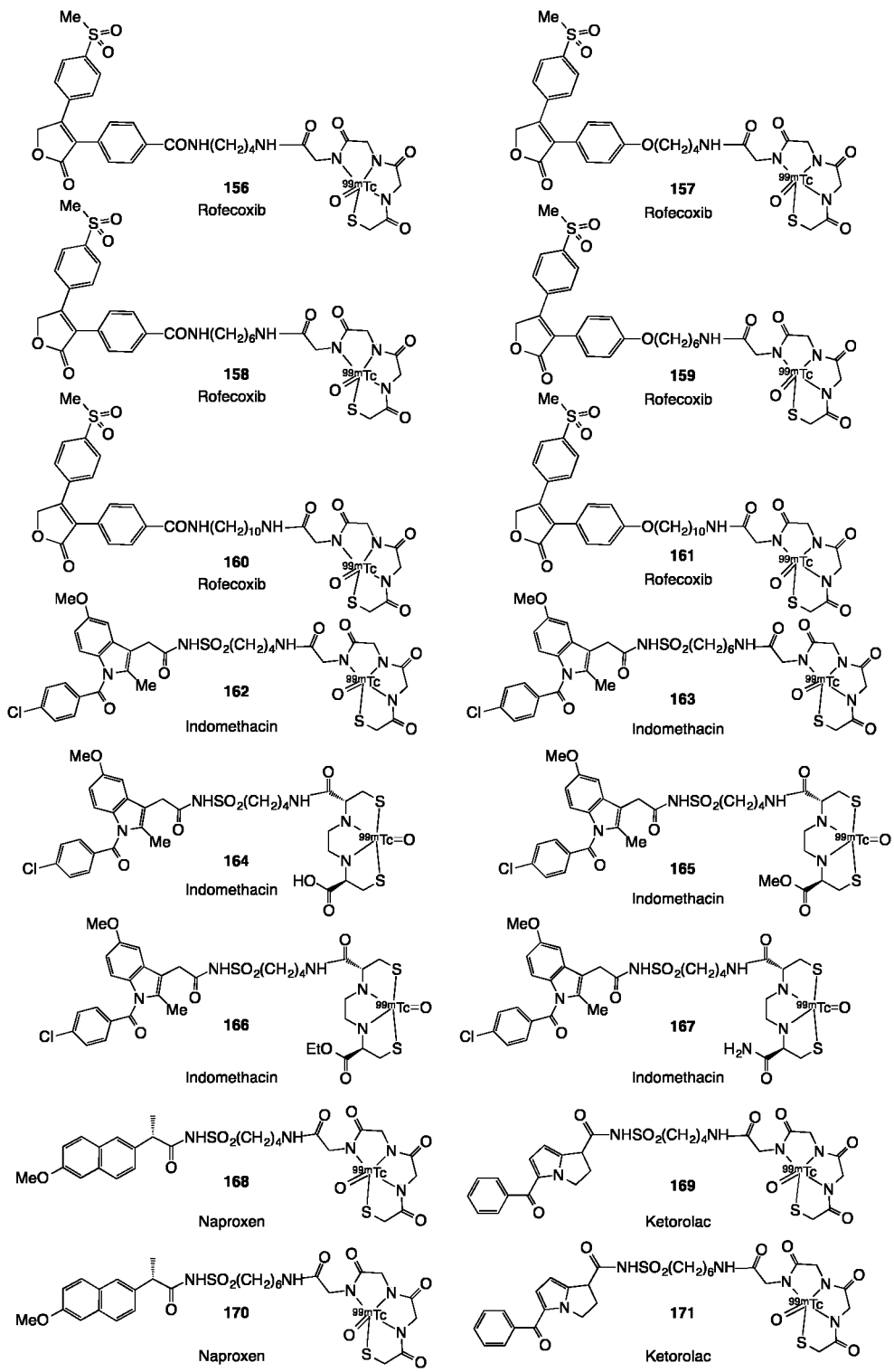
Figure 2:
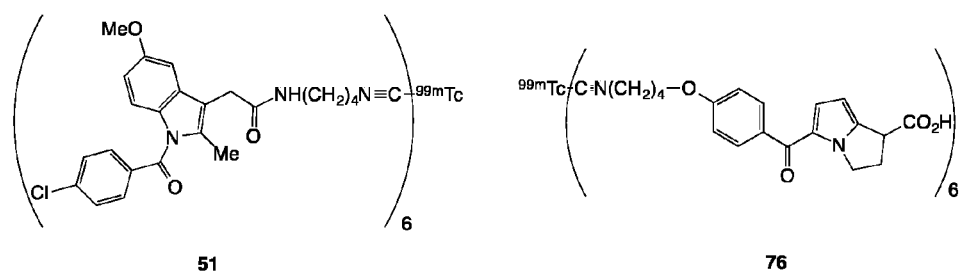
Figure 3A:
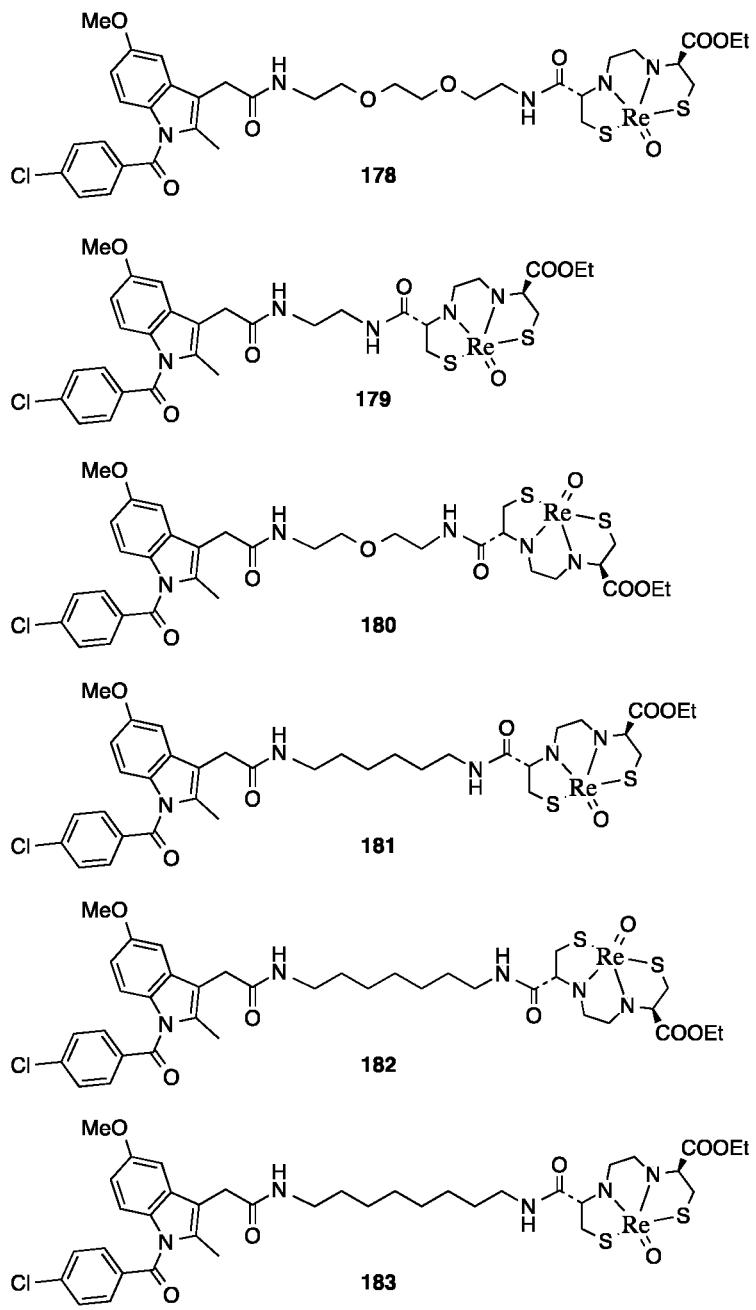
FIG. 3 (3A-3S) illustrates various rhenium-containing and $^{99m}$Tc-containing conjugates.
Figure 3B:
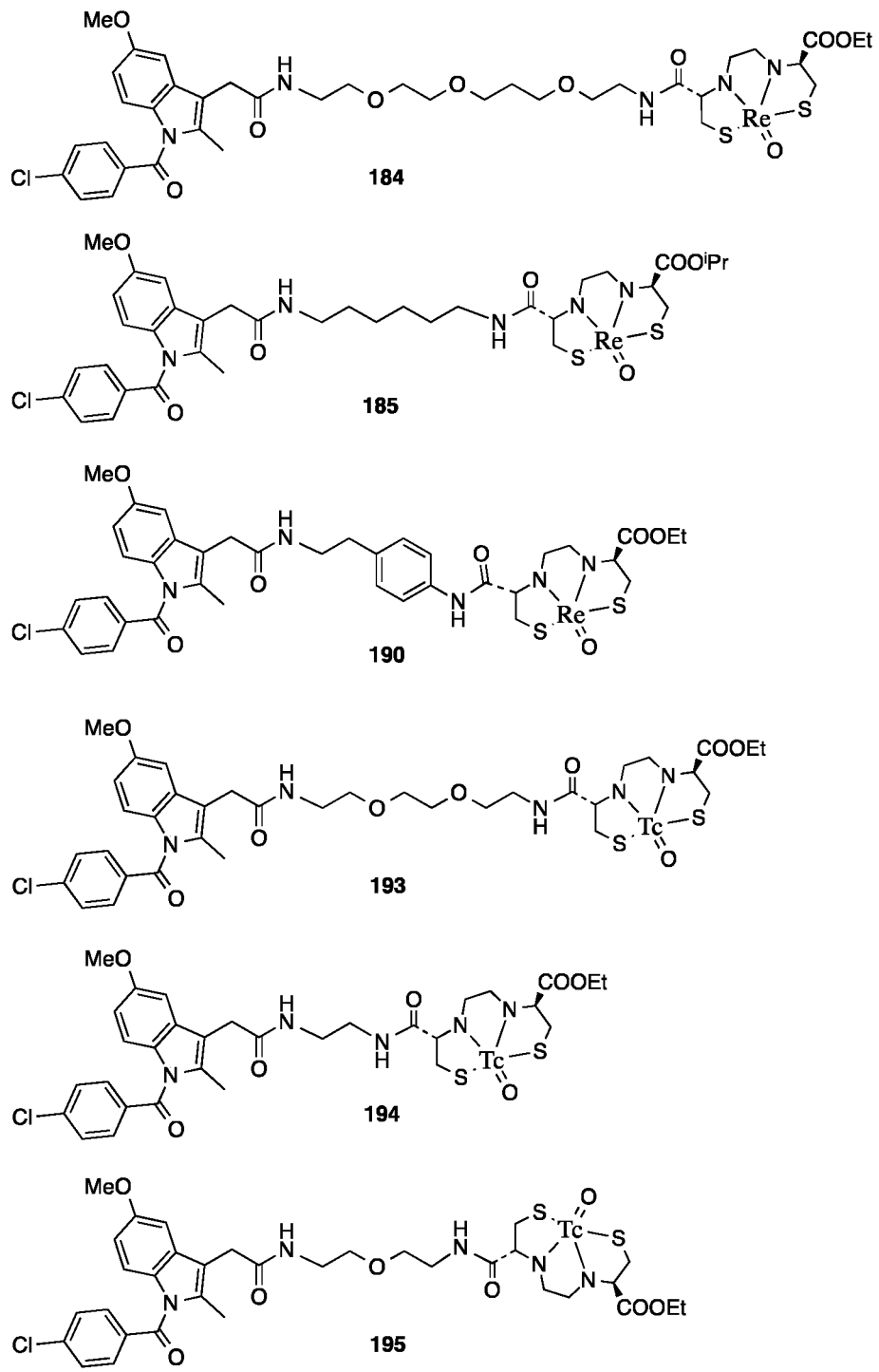
Figure 3C:
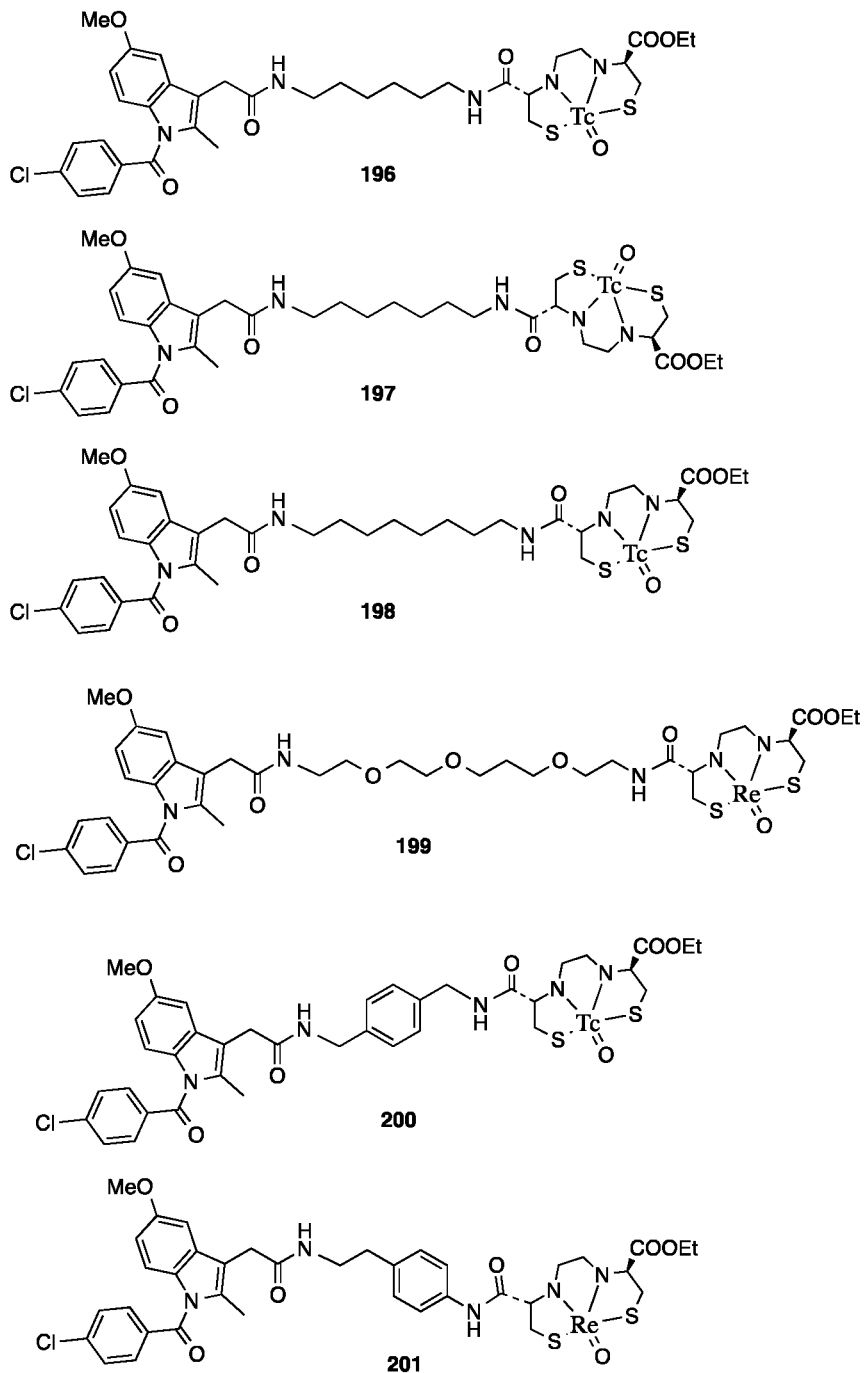
Figure 3D:
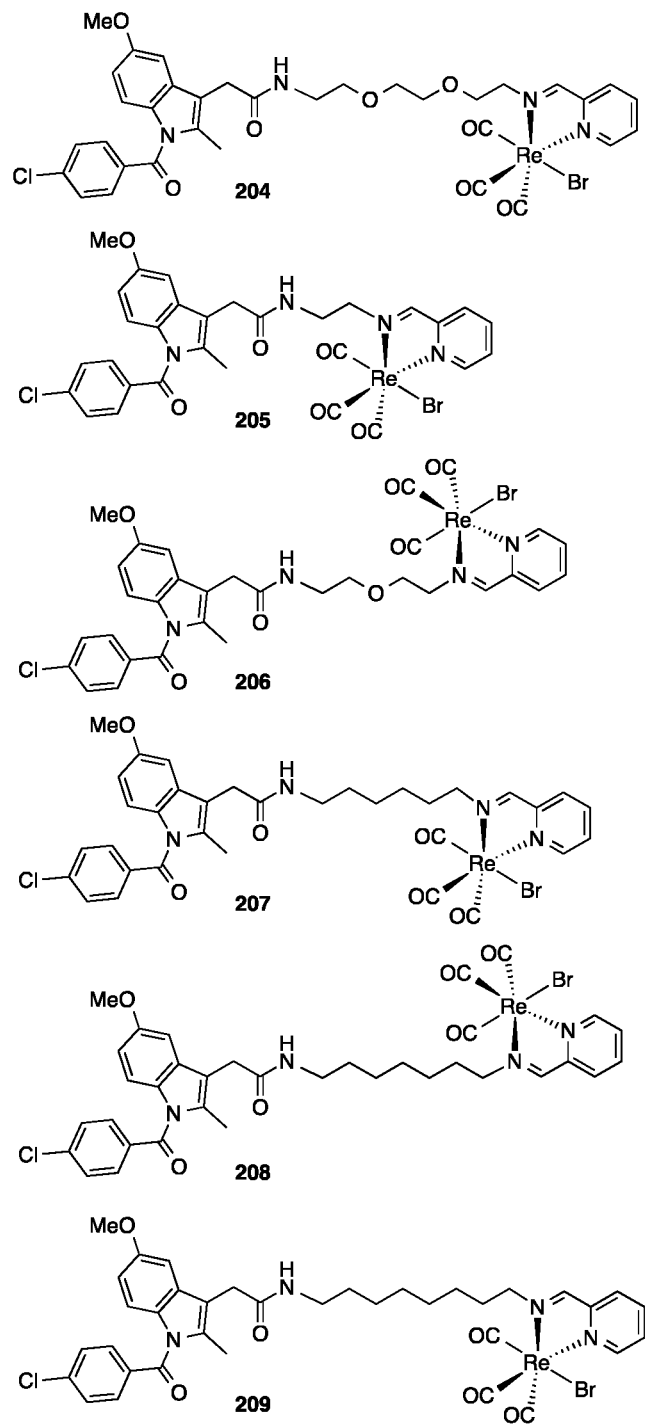
Figure 3E:
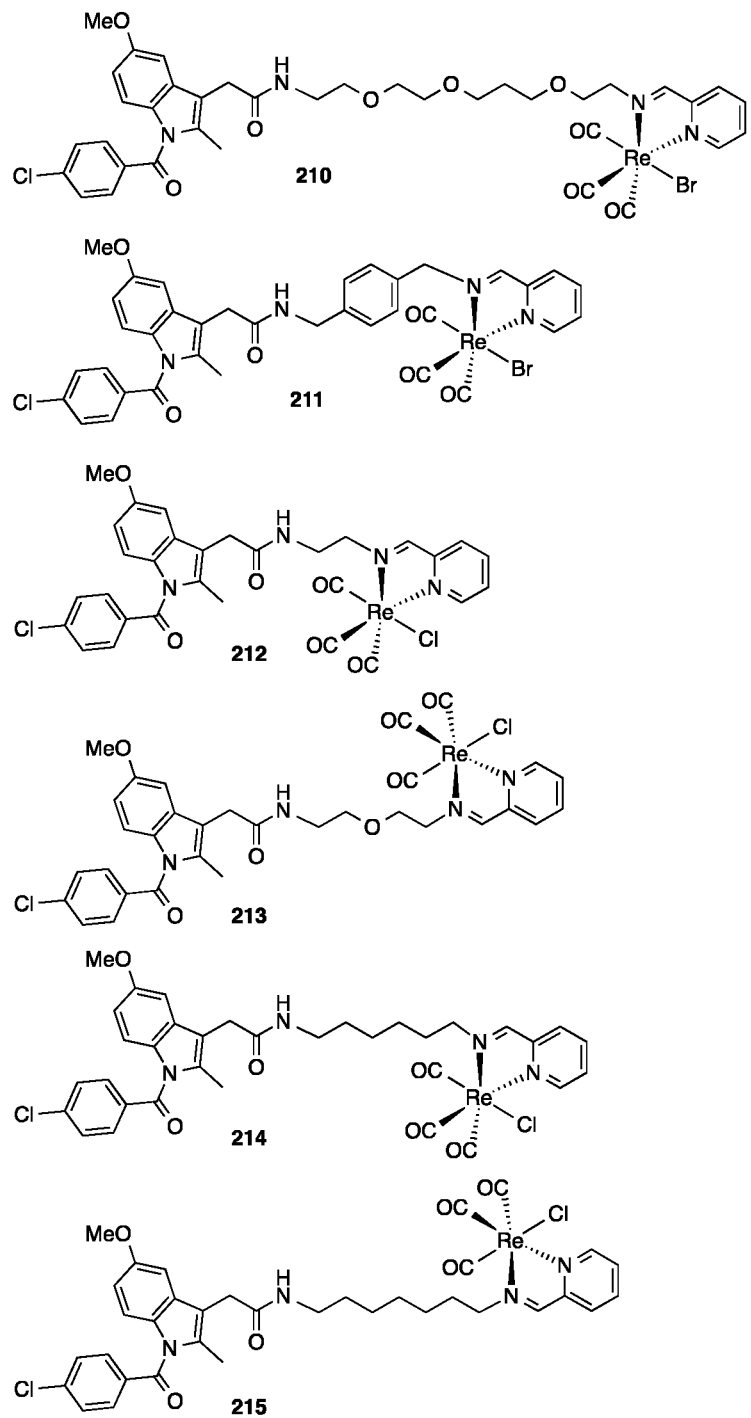
Figure 3F:
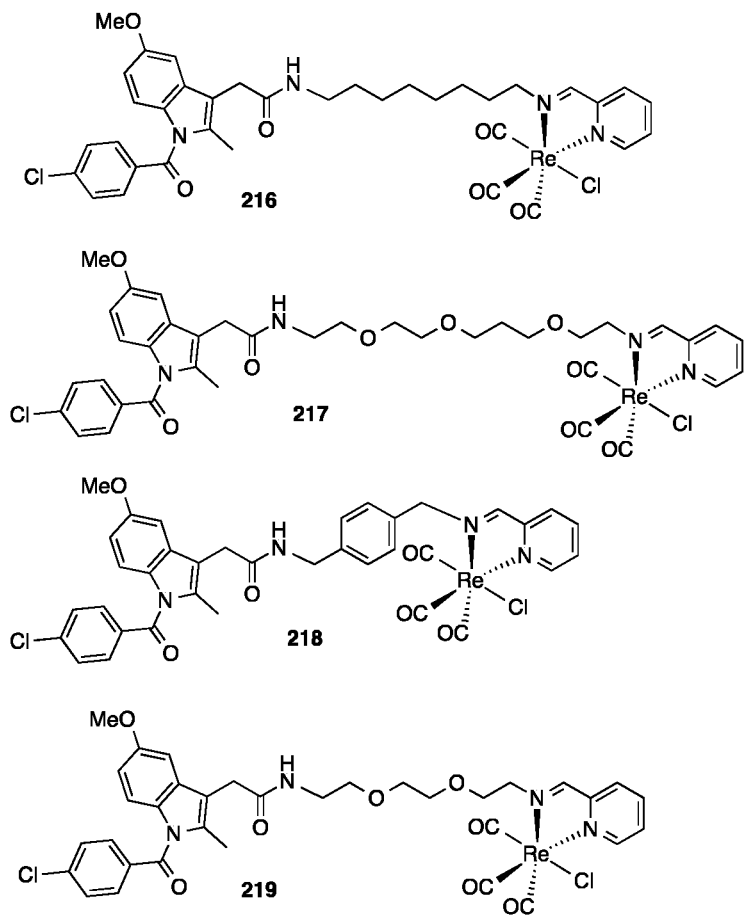
Figure 3G:
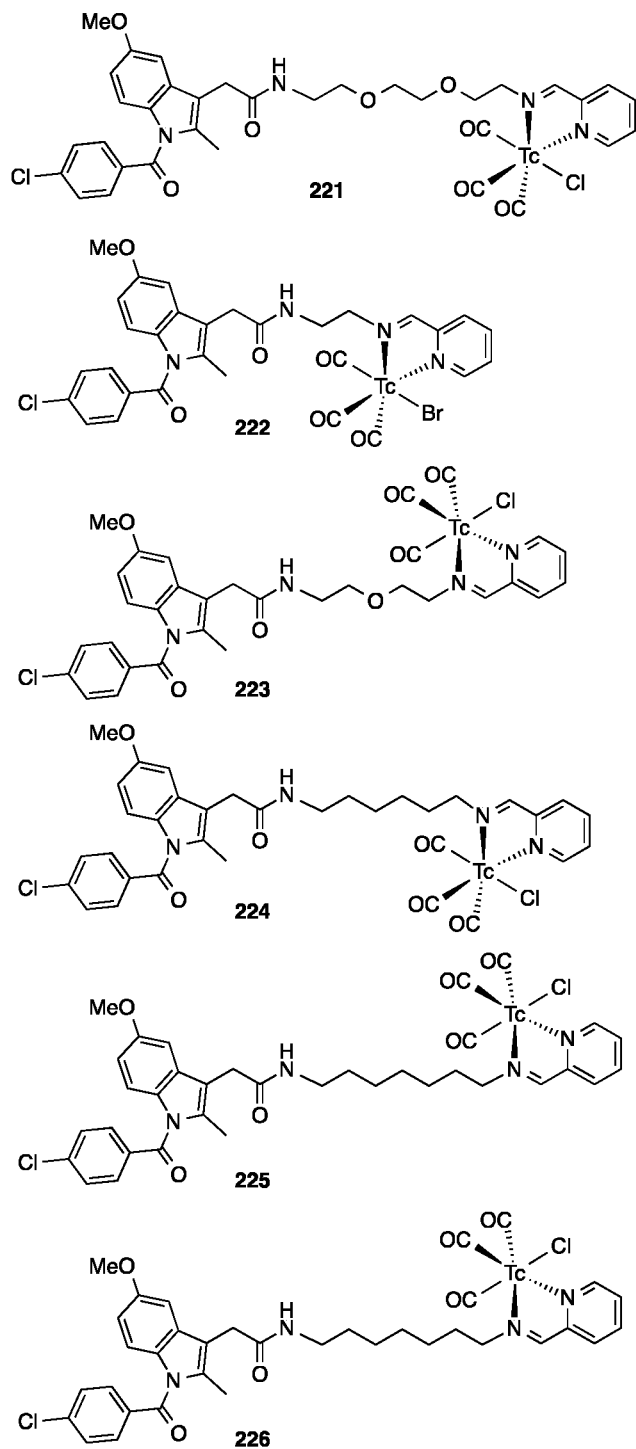
Figure 3H:
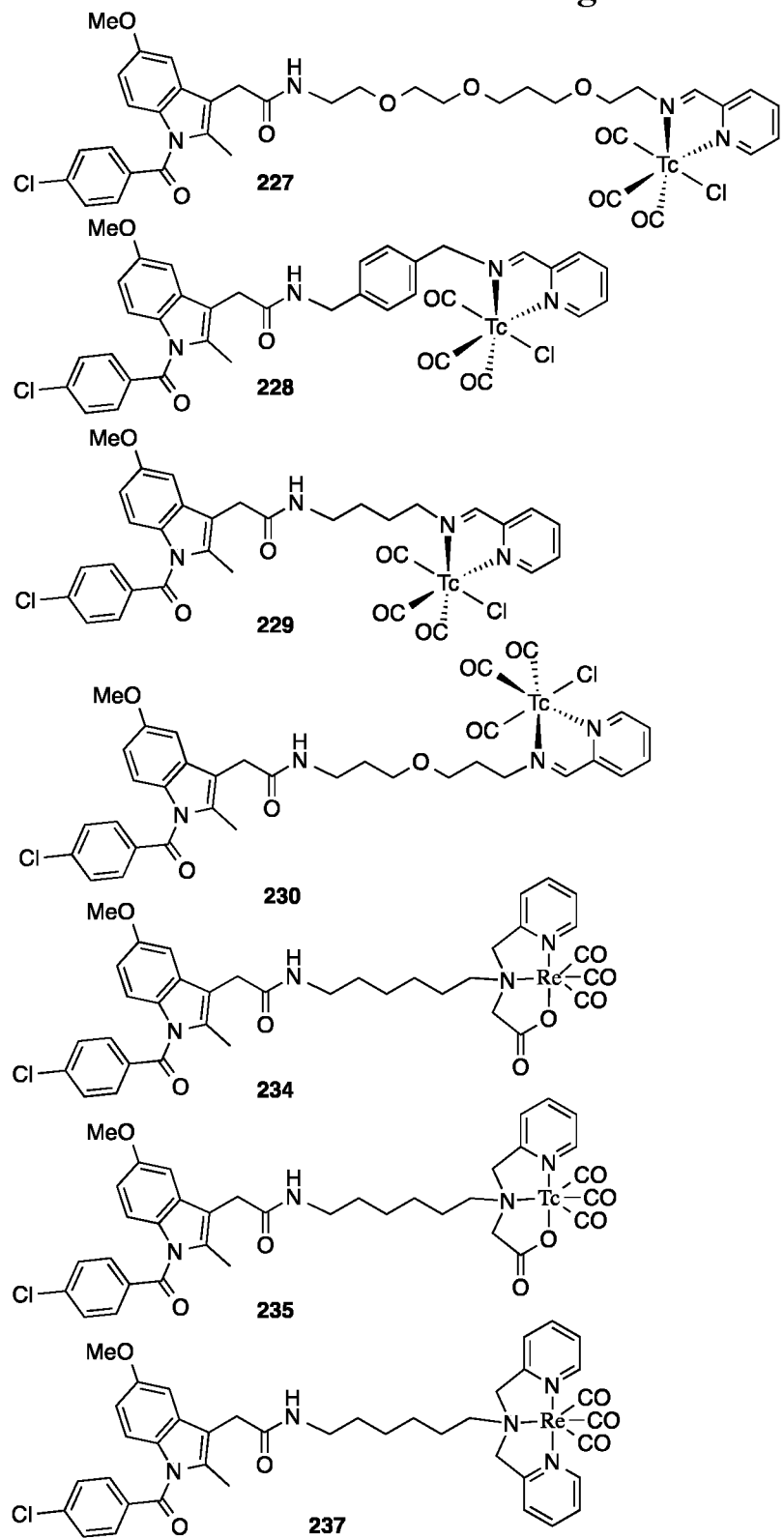
Figure 3I:
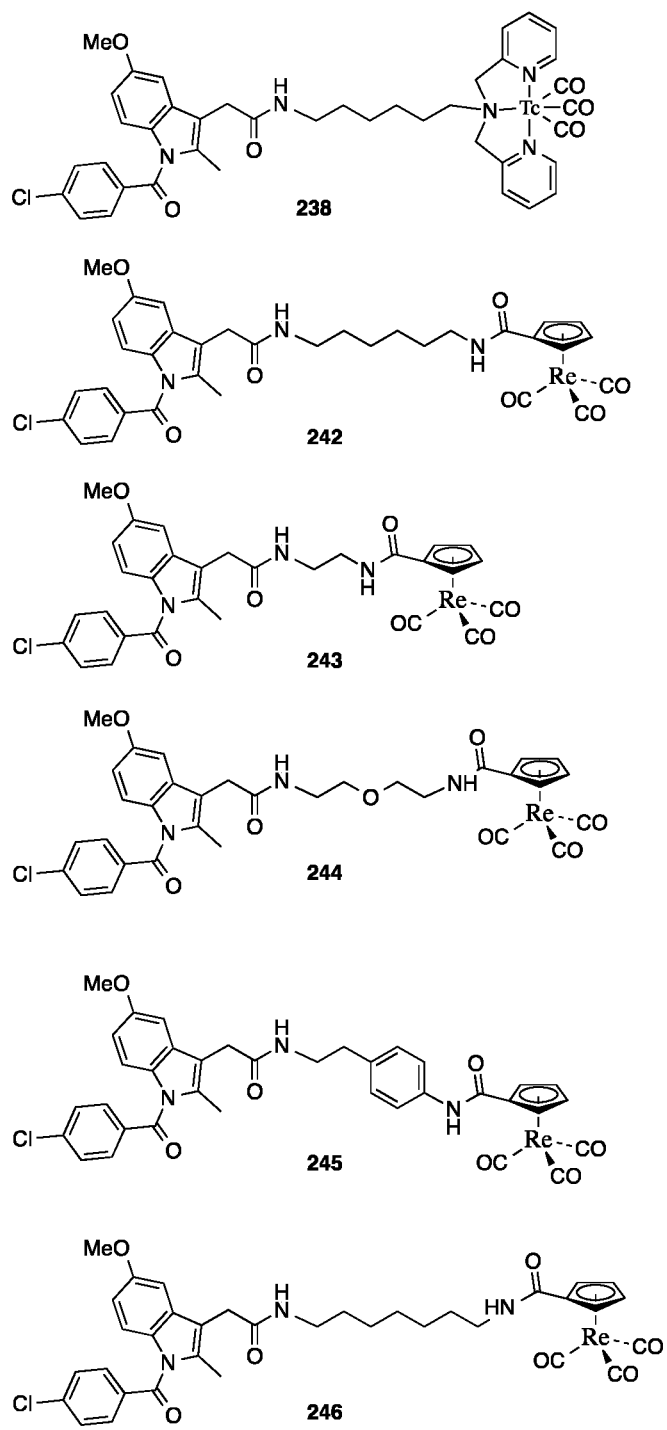
Figure 3J:
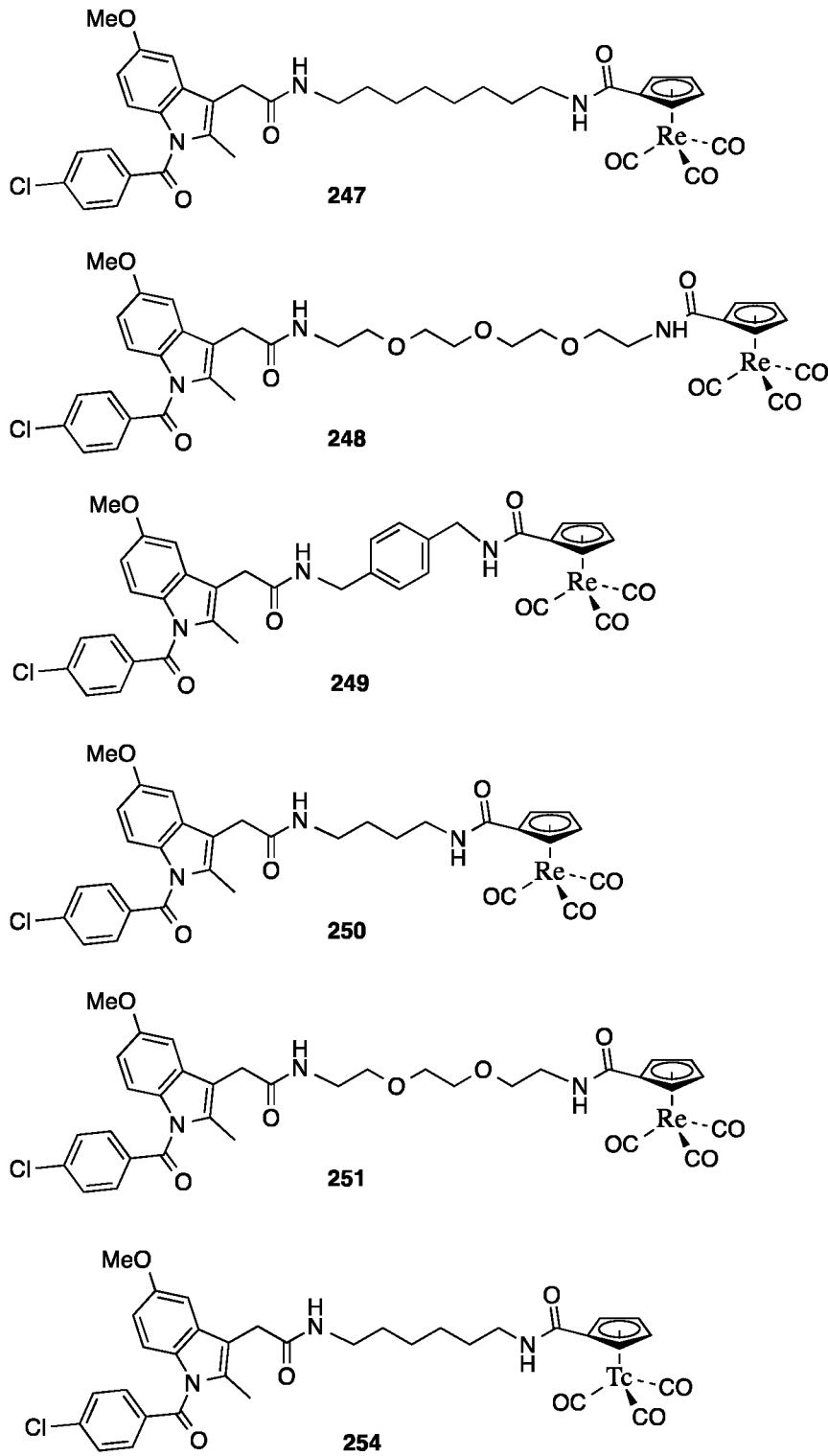
Figure 3K:
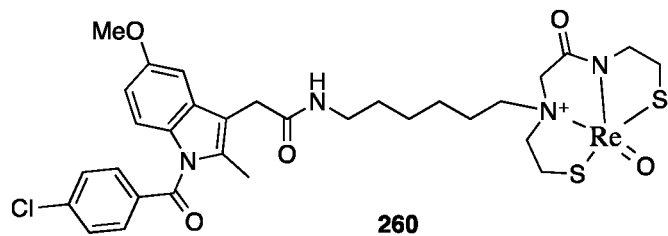
Figure 3K:
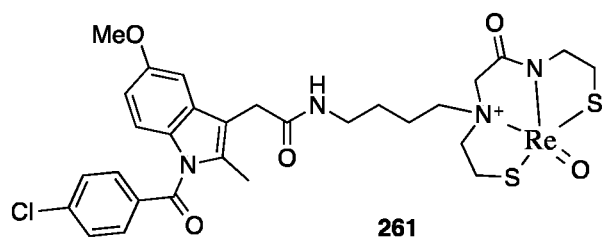
Figure 3K:
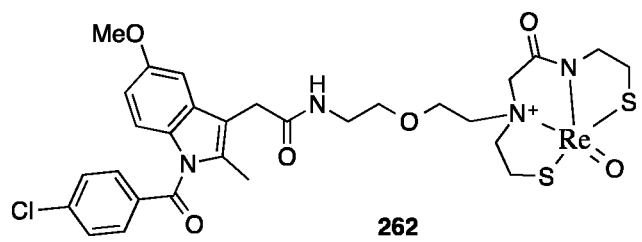
Figure 3K:
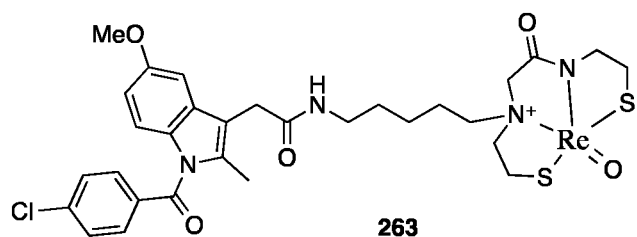
Figure 3K:
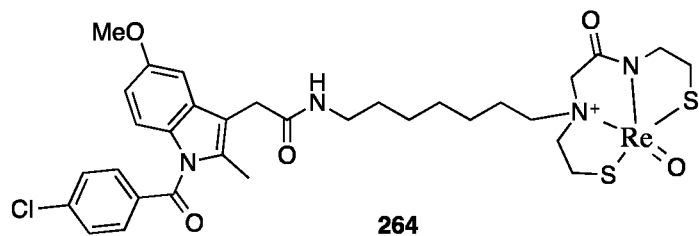
Figure 3K:
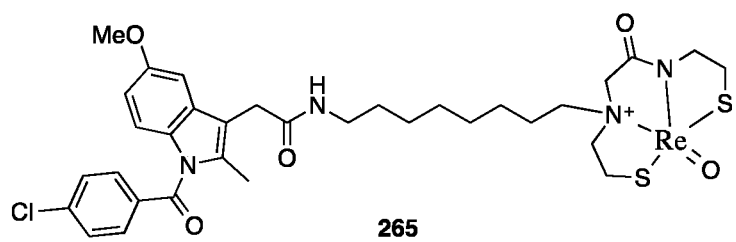
Figure 3L:
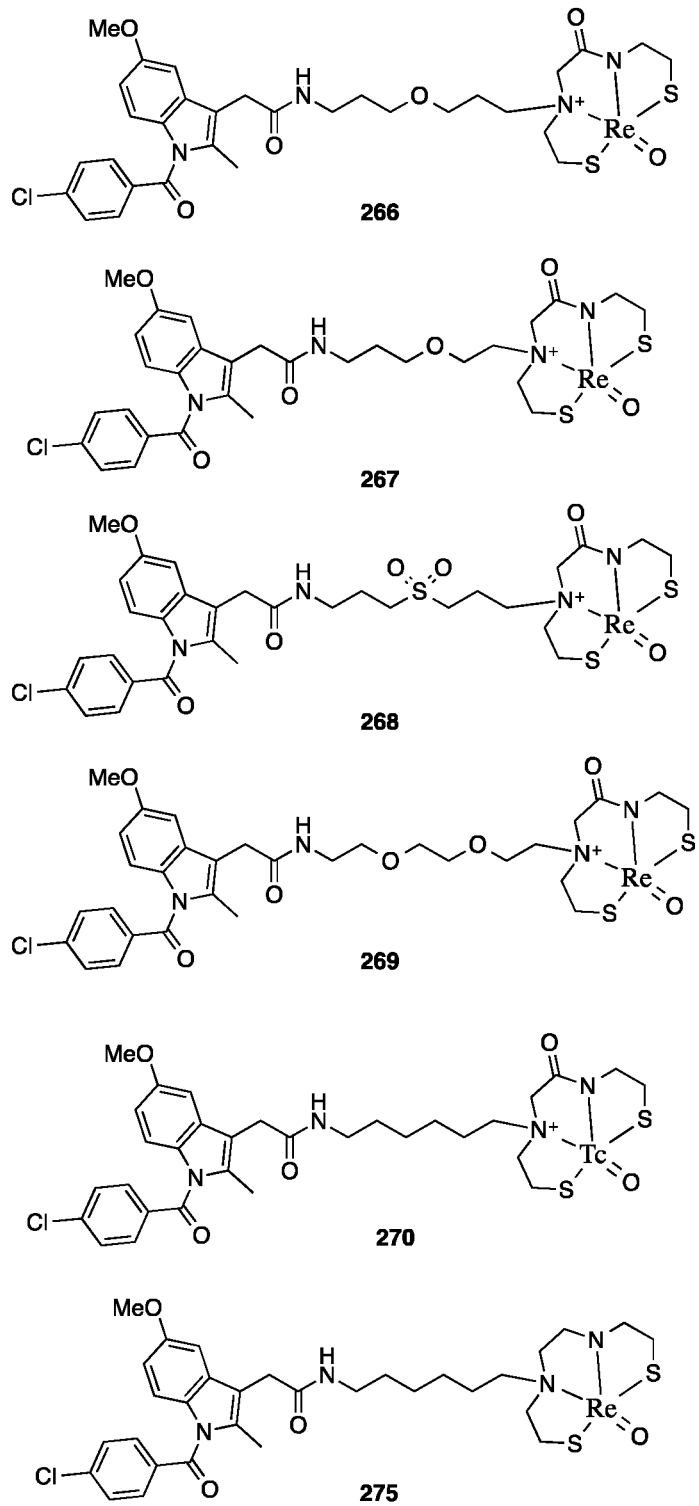
Figure 3M:
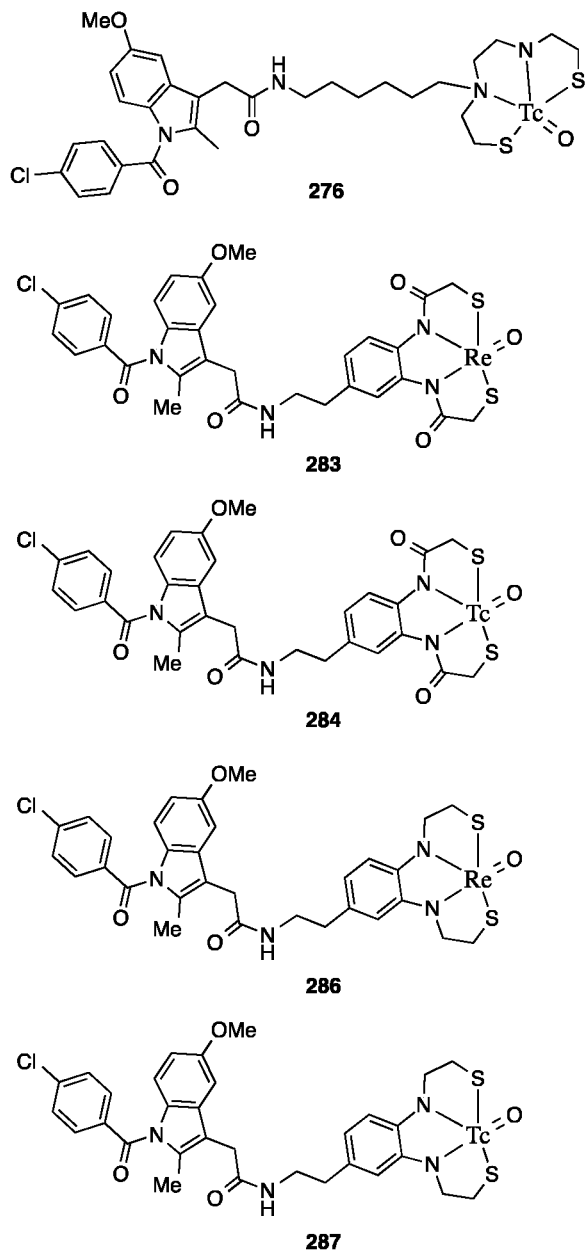
Figure 3N:
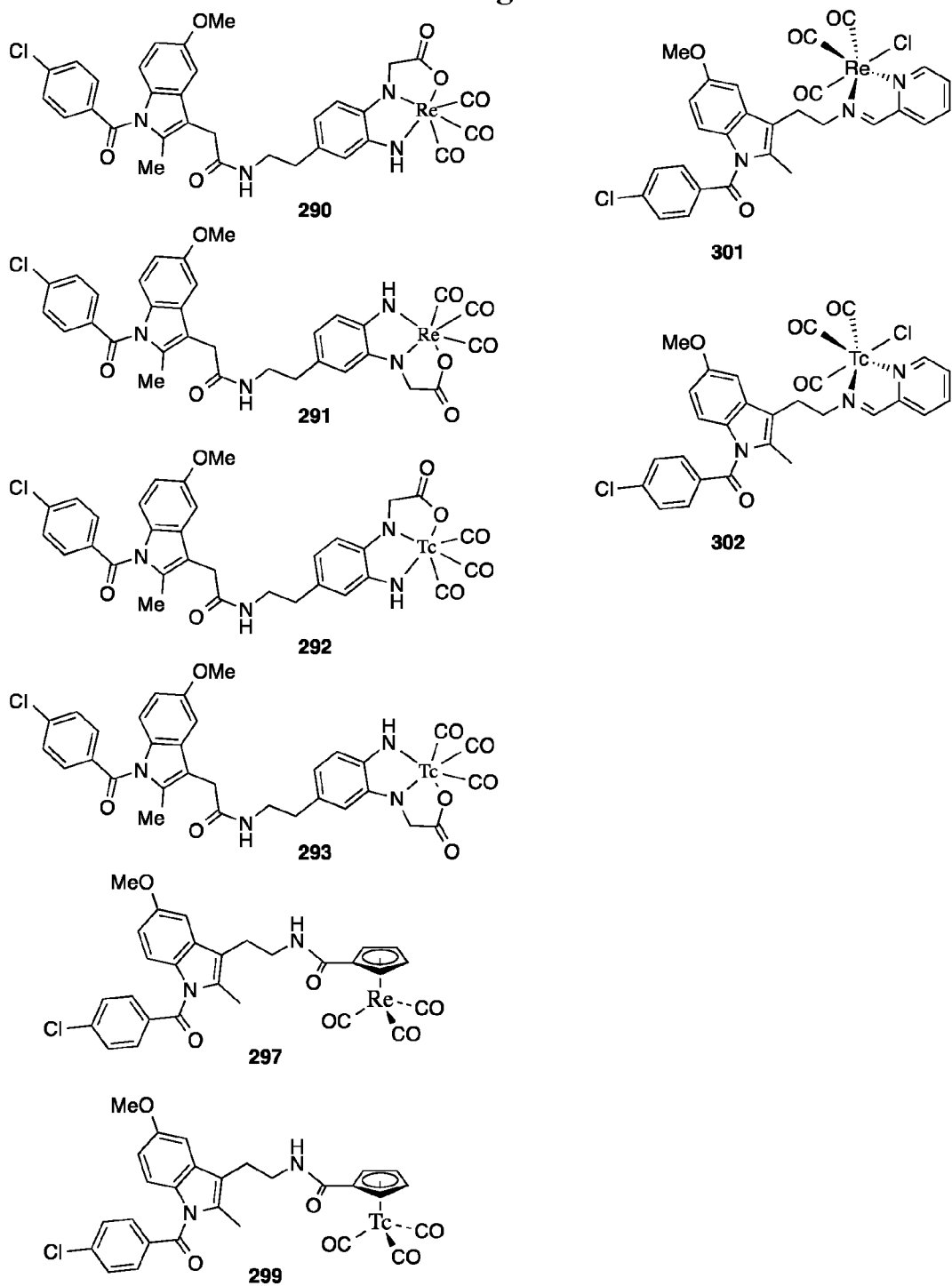
Figure 3O:
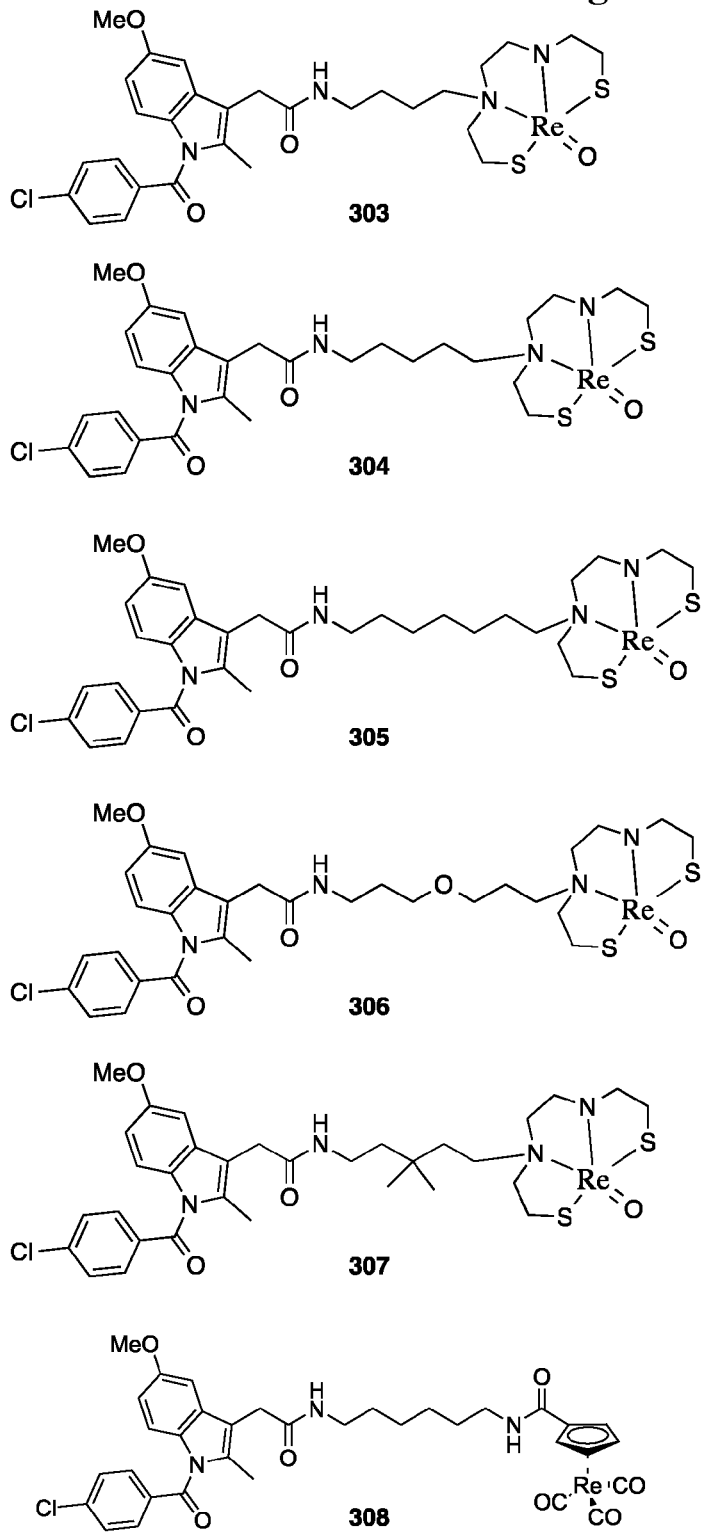
Figure 3P:
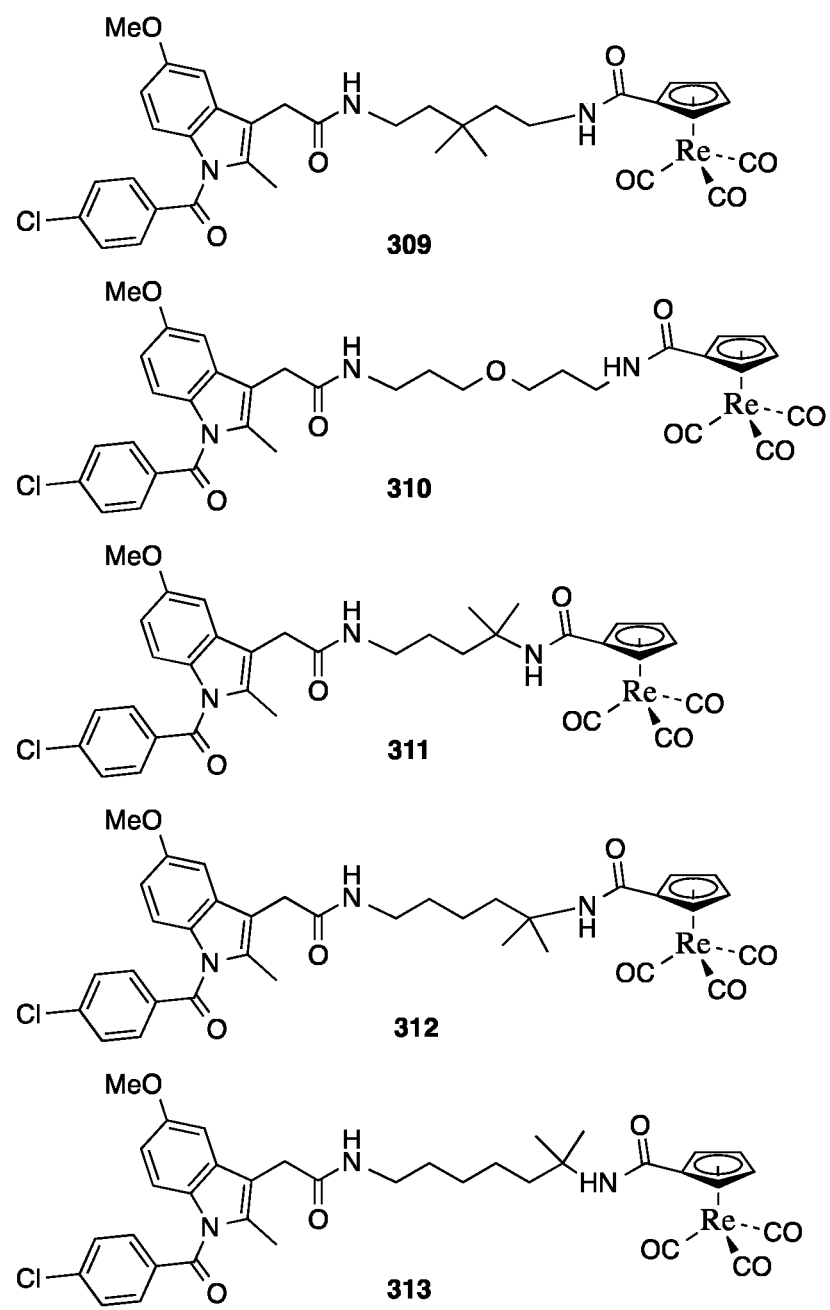
Figure 3Q:
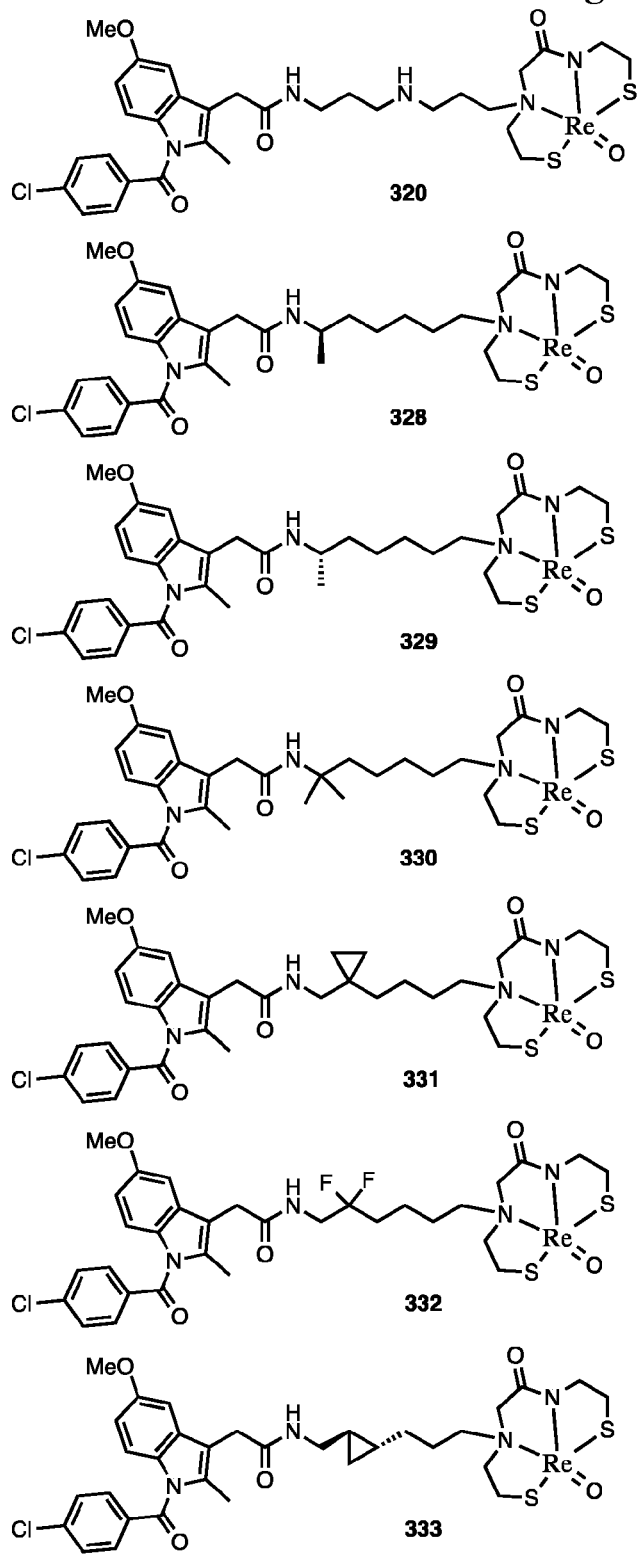
Figure 3R:
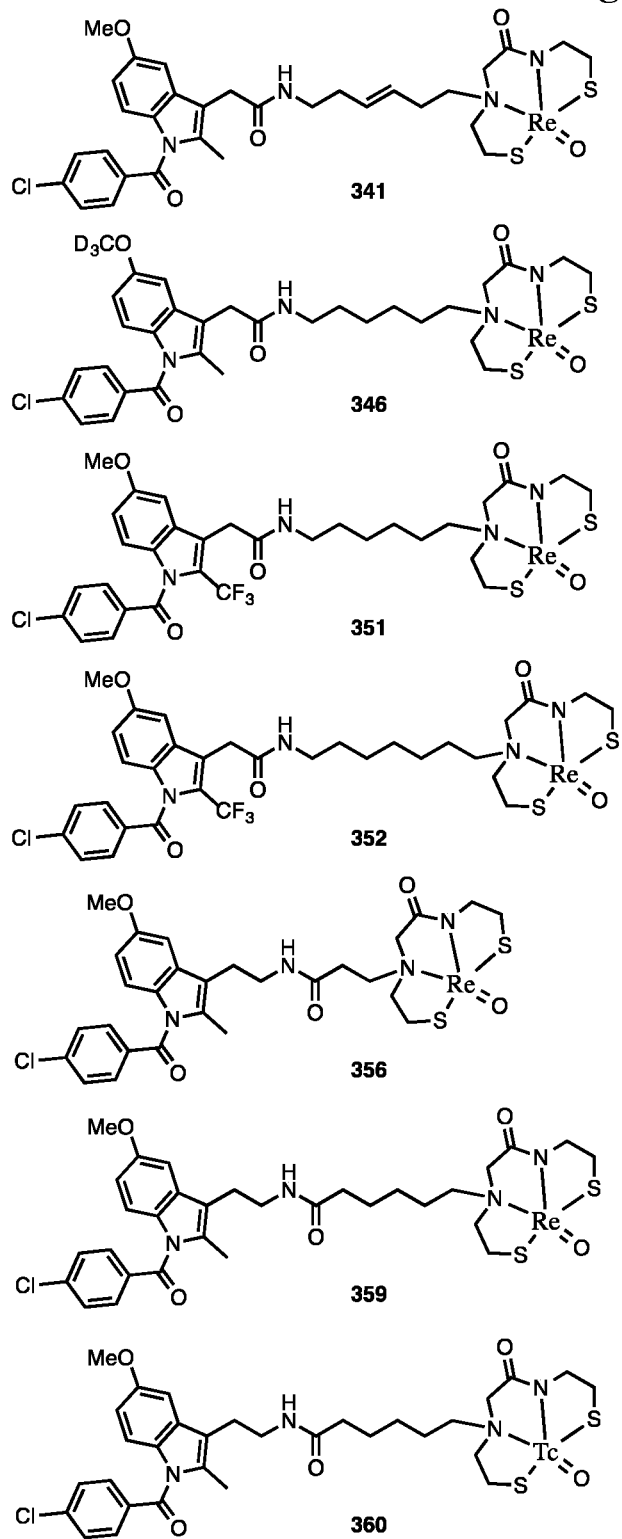
Figure 3S:
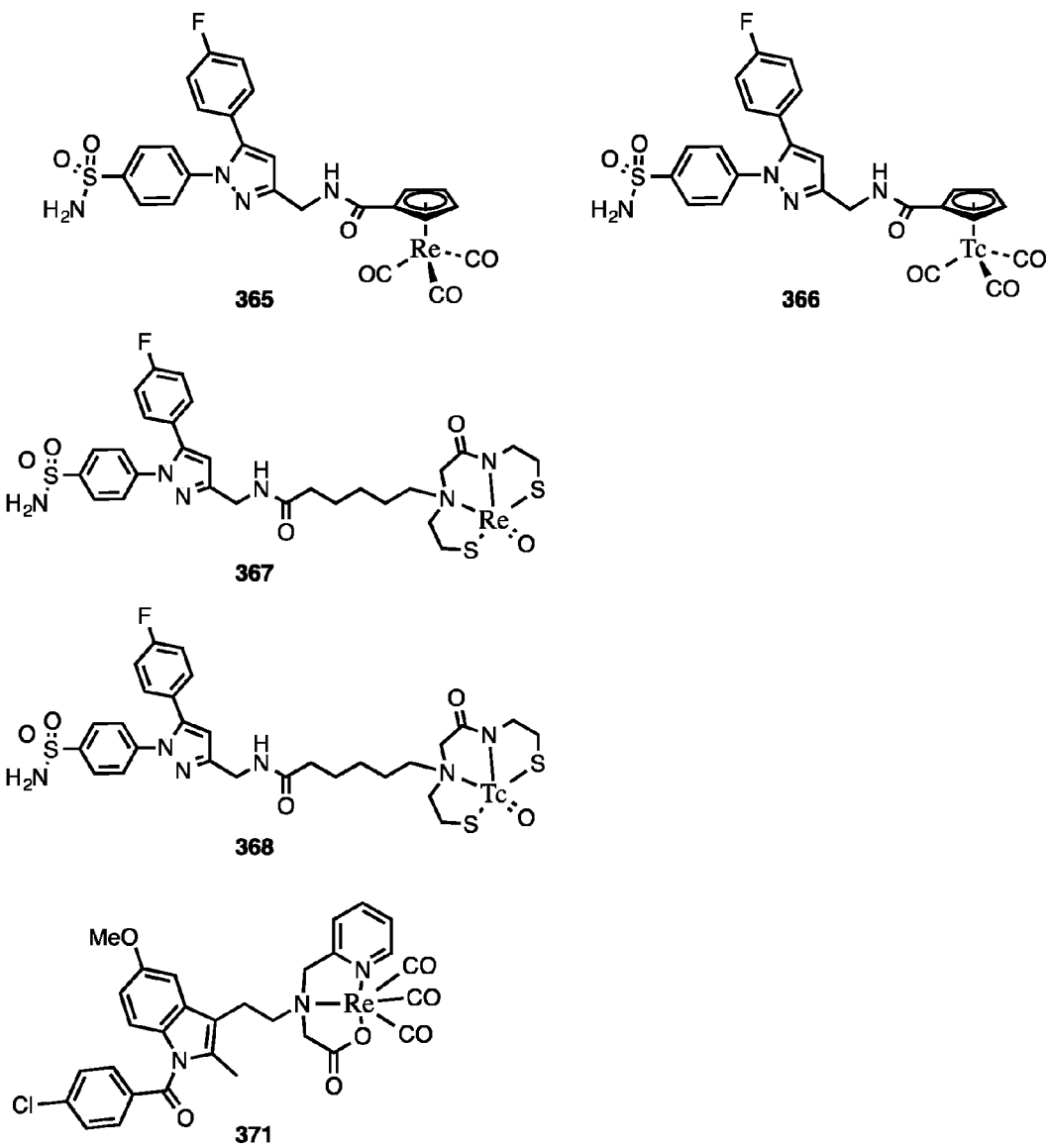

Specific exemplary technetium conjugates of the invention are disclosed in the Examples and in FIG. 1. Specific exemplary rhenium conjugates of the invention are disclosed in the Examples and in FIG. 2. Further specific conjugates of the invention are disclosed in the Examples and in FIG. 3.

Formulations and Routes of Administration

The compounds of the invention, that is, any conjugates of the invention disclosed herein, used in the methods of the invention may be administered in any suitable form that will provide sufficient levels of the compounds for the purposes of imaging. Intravenous administration is a useful route of administration, although other parenteral routes can also be employed, where parenteral as used herein includes subcutaneous injections, intravenous injection, intraarterial injection, intramuscular injection, intrasternal injection, intraperitoneal injection, or infusion techniques. The compounds can also be administered orally or enterally, which is a preferred route when compatible with the absorption of the compound and with imaging requirements. Where the pharmacokinetics of the compounds are suitable, the compounds can also be administered sublingually, by buccal administration, subcutaneously, by spinal administration, by epidural administration, by administration to cerebral ventricles, by inhalation (e.g. as mists or sprays), rectally, or topically in unit dosage formulations containing conventional nontoxic pharmaceutically acceptable carriers, excipients, adjuvants, and vehicles as desired. The compounds may be administered directly to a specific or affected organ or tissue. The compounds are mixed with pharmaceutically acceptable carriers, excipients, adjuvants, and vehicles appropriate for the desired route of administration.

In certain embodiments of the invention, especially those embodiments where a formulation is used for injection or other parenteral administration, including the routes listed herein, but also including any other route of administration described herein (such as oral, enteric, gastric, etc.), the formulations and preparations used in the methods of the invention are sterile. Sterile pharmaceutical formulations are compounded or manufactured according to pharmaceutical-grade sterilization standards (United States Pharmacopeia Chapters 797, 1072, and 1211; California Business & Professions Code 4127.7; 16 California Code of Regulations 1751, 21 Code of Federal Regulations 211) known to those of skill in the art.

Oral administration is advantageous due to its ease of implementation and patient compliance. If a patient has difficulty swallowing, introduction of medicine via feeding tube, feeding syringe, or gastrostomy can be employed in order to accomplish enteric administration. The active compound (and, if present, other co-administered agents) can be enterally administered in any other pharmaceutically acceptable carrier suitable for formulation for administration via feeding tube, feeding syringe, or gastrostomy.

Intravenous administration can also be used advantageously, for delivery of the conjugates of the invention to the bloodstream as quickly as possible and to circumvent the need for absorption from the gastrointestinal tract.

The compounds described for use herein can be administered in solid form, in liquid form, in aerosol form, or in the form of tablets, pills, powder mixtures, capsules, granules, injectables, solutions, suppositories, enemas, colonic irrigations, emulsions, dispersions, food premixes, and in other forms suitable for the route of administration. The compounds can also be administered in liposome formulations. The compounds can also be administered as prodrugs, where the prodrug undergoes transformation in the treated subject to a therapeutically effective form. Additional methods of administration are known in the art.

Injectable preparations, for example, sterile injectable aqueous or oleaginous suspensions, may be formulated according to methods known in the art using suitable dispersing or wetting agents and suspending agents. The sterile injectable preparation may also be a sterile injectable solution or suspension in a nontoxic parenterally acceptable diluent or solvent, for example, as a solution in propylene glycol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono or di-glycerides. In addition, fatty acids such as oleic acid find use in the preparation of injectables.

Solid dosage forms for oral administration may include capsules, tablets, pills, powders, and granules. In such solid dosage forms, the active compound may be admixed with at least one inert diluent such as sucrose, lactose, or starch. Such dosage forms may also comprise additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, cyclodextrins, and sweetening, flavoring, and perfuming agents. Alternatively, the compound may also be administered in neat form if suitable.

The compounds for use in the present invention can also be administered in the form of liposomes. As is known in the art, liposomes are generally derived from phospholipids or other lipid substances. Liposomes are formed by mono or multilamellar hydrated liquid crystals that are dispersed in an aqueous medium. Any non-toxic, physiologically acceptable and metabolizable lipid capable of forming liposomes can be used. The present compositions in liposome form can contain, in addition to a compound for use in the present invention, stabilizers, preservatives, excipients, and the like. The preferred lipids are the phospholipids and phosphatidyl cholines (lecithins), both natural and synthetic. Methods to form liposomes are known in the art. See, for example, Prescott, Ed., Methods in Cell Biology, Volume XIV, Academic Press, New York, N.W., p. 33 et seq (1976).

The amount of active ingredient that may be combined with the carrier materials to produce a single dosage form can vary depending upon the patient to which the active ingredient is administered and the particular mode of administration. It will be understood, however, that the specific dose level for any particular patient will depend upon a variety of factors including the specific compound employed; the age, body weight, body area, body mass index (BMI), general health, sex, and diet of the patient; the time of administration and route of administration used; the rate of excretion; and the drug combination, if any, used. The compounds can be administered in a unit dosage formulation. The pharmaceutical unit dosage chosen is fabricated and administered to provide sufficient concentration of drug for imaging a patient.

While the compounds for use in the present invention can be administered as the sole active pharmaceutical agent, they can also be used in combination with one or more other agents. When additional active agents are used in combination with the compounds for use in the present invention, the additional active agents may generally be employed in therapeutic amounts as indicated in the Physicians' Desk Reference (PDR) 53rd Edition (1999), which is incorporated herein by reference, or such therapeutically useful amounts as would be known to one of ordinary skill in the art, or as are determined empirically for each patient.

Combinations of the NSAID conjugates can also be used. Combining two or more conjugates of different NSAIDs or residues or derivative s of NSAIDs can provide advantages over using a single conjugate. Advantages can include the ability to tune pharmacokinetics and pharmacodynamics, to adjust the solubility of the overall composition and/or its components, to adjust the half-life of total conjugate in the body, to enhance imaging contrast and/or definition, to adjust binding kinetics to COX, to adjust binding affinity to COX, or to enhance the stability of the composition either in storage or in use. The two or more conjugates can be combined in solution form such as those solution forms described above (such as in a sterile solution for IV administration), or in solid form such as those solid forms as described above (such as pill or tablet form). The two or more conjugates can be mixed together shortly before administration and administered together. The two or more conjugates can be administered simultaneously, either by the same route of administration or by different routes of administration. The two or more conjugates can be administered consecutively, either by the same route of administration or by different routes of administration. In one embodiment, a kit form can contain two or more conjugates as individual conjugates, with printed or electronic instructions for administration either as a mixture of conjugates, as separate conjugates administered simultaneously, or as separate conjugates administered consecutively. Where three or more conjugates are administered, they can be administered as a mixture of conjugates, as separate conjugates administered simultaneously, as separate conjugates administered consecutively, as separate conjugates where two or more may be administered simultaneously with the remainder administered consecutively before or after the simultaneous administration, or any other possible combination of mixed administration, simultaneous administration, and consecutive administration.

Imaging Techniques

The conjugates can be used with any suitable imaging technique. Images of a subject, or of a portion of a subject such as the arm, leg, or any specific region of the body of the subject, can be generated using gamma cameras, planar gamma imaging, scintigraphic imaging, SPECT imaging (single photon emission computed tomography), and other radiographic or tomographic imaging techniques. Exemplary imaging methods that can be used are described in Pacelli et al., *J. Label. Compd. Radiopharm.* 57:317-322 (2014); de Vries et al., *J Nucl. Med.* 44:1700-1706 (2003); Tietz et al., *Current Medicinal Chemistry*, 20, 4350-4369 (2013); Sogbein et al., *Biomed. Res. Int.*, Sogbein, Oyebola O. et al., *BioMed Research International*, 2014:942960, doi: 10.1155/2014/942960; and Wemick, M. N. and Aarsvold, J. N., *Emission Tomography: The Fundamentals of PET and SPECT*, San Diego: Elsevier Academic Press, 2004.

Kits

Further embodiments of the invention embrace one or more kit forms which can contain one or more conjugates as disclosed herein. The kit can contain printed or electronic instructions for administration of the conjugate. In further embodiments, the kit can contain one or more compounds as disclosed herein which lacks the radioactive agent, with printed or electronic instructions for adding the radioactive agent to constitute one or more conjugates of the invention.

The following examples are intended to illustrate, but not limit, the invention.

EXAMPLES

Synthetic Examples

Example 1

General method for the synthesis of tetrakis(((2-((6-((S)-1-carboxyethyl)naphthalen-2-yl)oxy)-2-methyl-propyl)-1λ4-azanylidyne)methyl)copper (2)

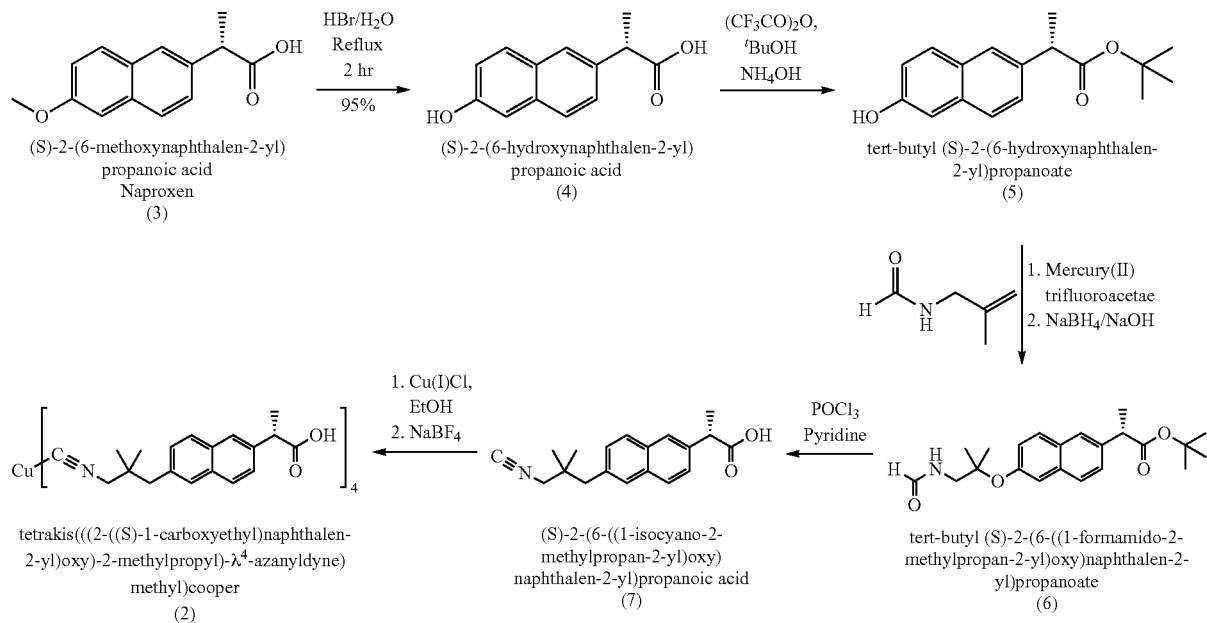

Scheme 1

Synthesis of (S)-2-(6-hydroxynaphthalen-2-yl)propanoic acid (4)

As described in del Amo, V., McGlone, A. P., Soriano, J. M. & Davis, A. P. "*Two-colour screening in combinatorial chemistry: prospecting for enantioselectivity in a library of steroid-based receptors.*" Tetrahedron 65, 6370-6381 (2009), (S)-2-(6-methoxynaphthalen-2-yl)propanoic acid (Naproxen) (3) (3.0 g, 13.0 mmol) is suspended in HBr (48% w/w in water, 120 mL) and heated at reflux for 2 h. The mixture is allowed to warm to room temperature and filtered. The solid is washed with chilled water to afford the title product (S)-2-(6-hydroxynaphthalen-2-yl)propanoic acid (4).

Synthesis of tert-butyl(S)-2-(6-hydroxynaphthalen-2-yl)propanoate (5)

As described in del Amo, V., McGlone, A. P., Soriano, J. M. & Davis, A. P. "*Two-colour screening in combinatorial chemistry: prospecting for enantioselectivity in a library of steroid-based receptors.*" Tetrahedron 65, 6370-6381 (2009), the carboxylic acid (4) (2.39 g, 11.05 mmol) is dissolved in dry THF (110 mL) under a nitrogen atmosphere. The solution is cooled to 0° C., then trifluoroacetic anhydride (13.93 g, 9.42 mL, 66.32 mmol) is added drop wise and the mixture is further stirred for 4 h maintaining the temperature below 5° C. tert-Butanol (32 mL) is added drop wise and the resulting mixture is then allowed to rise to room temperature and is vigorously stirred overnight. The reaction is cooled again to ice-bath temperature and $NH_4OH$ (35% in water, 6 mL) is added drop wise. When the addition is finished the mixture is allowed to rise to room temperature again and is finally stirred for a further 30 min before the volatiles are evaporated under vacuum. The crude residue is triturated with boiling DCM and the crystalline solid formed is removed by filtration. The filtrate is washed with saturated aqueous $NaHCO_3$ and dried over $MgSO_4$, then the solvent is evaporated under reduced pressure to give the tert-butyl ester (5). An analytical sample can be prepared by crystallizing (5) from hot benzene/hexane.

Synthesis of tert-butyl(S)-2-(6-((1-formamido-2-methylpropan-2-yl)oxy)naphthalen-2-yl)propanoate (6)

Using the method of Al-Ktaifani, M. M., Nakawa, A. a., Tabbaa, Z. a. & Namou, A. a. "Synthesis of 2-methyl-2-propoxypropyl isocyanide and its Cu(I) tetrafluoroborate complex." Chem. Pap. 62, 329-333 (2008): in general, mercuric(II)trifluoroacetate and N-(2-methyl-2-propenyl)formamide (Synthesized by the method of van Wyk, A. J. et al. "*Synthesis and $^{99m}Tc$ labelling of MMI (MIBI) and its ethyl analogue EMI.*" Int. J. Radiat. Appl. Instrumentation. Part A. Appl. Radiat. Isot. 42, 687-689 (1991)) and tert-butyl(S)-2-(6-hydroxynaphthalen-2-yl)propanoate (5) are dissolved in THF and stirred at room temperature. The mixture is cooled down in an ice bath and NaOH pellets in isopropanol are added slowly. Subsequently, NaBH$_4$ was added to the mixture, which was stirred for 18 h. The solution was passed through a column of Celite® (J.T. Baker, Phillipsberg, N.J., diatomaceous earth) to remove elemental Hg to yield tert-butyl(S)-2-(6-((1-formamido-2-methylpropan-2-yl)oxy)naphthalen-2-yl)propanoate (6).

Synthesis of (S)-2-(6-((1-isocyano-2-methylpropan-2-yl)oxy)naphthalen-2-yl)propanoic acid (7)

tert-Butyl (S)-2-(6-((1-formamido-2-methylpropan-2-yl)oxy)naphthalen-2-yl)propanoate (6) is dissolved in pyridine and benzene. The solution is cooled to 0° C. and POCl$_3$ is subsequently added drop wise. The reaction is quenched by pouring over ice and the product is extracted into CH$_2$Cl$_2$.

Synthesis of tetrakis(((2-((6-((S)-1-carboxyethyl)naphthalen-2-yl)oxy)-2-methylpropyl)-14-azanylidyne)methyl)copper (2)

Based on the method of Al-Ktaifani, M. M., Nakawa, A. a., Tabbaa, Z. a. & Namou, A. a. "Synthesis of 2-methyl-2-propoxypropyl isocyanide and its Cu(I) tetrafluoroborate complex." Chem. Pap. 62, 329-333 (2008): synthesis of (2) is realized by heating a mixture of (7) and freshly crystallized CuCl in degassed dry EtOH at 50° C. in an ampoule for 1 h. A solution of NaBF$_4$ in water is added in one portion, solvents are removed under reduced pressure, and the resultant crude product is dissolved in EtOH and the NaCl generated is separated by filtration. The solvent is removed to get the product (2).

Example 2

Synthesis of tetrakis(((2-(4-((S)-1-carboxy-2,3-dihydro-1H-pyrrolizine-5-carbonyl)phenethoxy)-2-methylprop yl)-14-azanylidyne)methyl)copper (16)

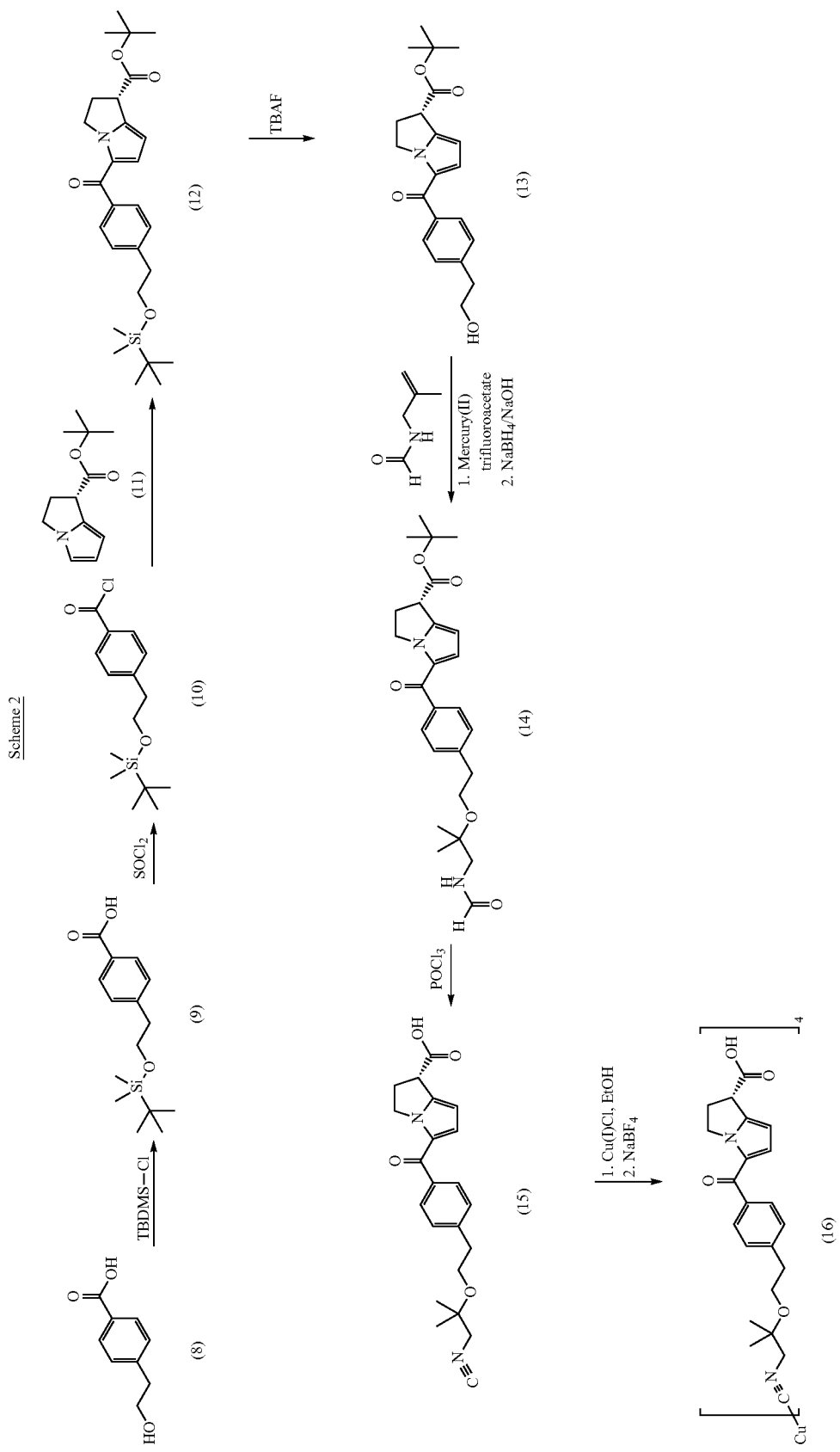

Synthesis of 4-(2-((tert-butyldimethylsilyl)oxy)ethyl)benzoic acid (9)

Commercially available 4-(2-hydroxyethyl)benzoic acid (8) is protected as the TBDMS ether using standard conditions (see, for example, *Greene's Protective Groups in Organic Synthesis*, 4th Edition. Peter G. M. Wuts, Theodora W. Greene; John Wiley & Sons, Inc.; ISBN: 978-0-471-69754-1).

Synthesis of 4-(2-((tert-butyldimethylsilyl)oxy)ethyl)benzoyl chloride (10)

4-(2-((tert-butyldimethylsilyl)oxy)ethyl)benzoic acid (9) is converted to its acid chloride using standard conditions.

Synthesis of tert-butyl (S)-5-(4-(2-((tert-butyldimethylsilyl)oxy)ethyl)benzoyl)-2,3-dihydro-1H-pyrrolizine-1-carboxylate (12) Components (10) and tert-butyl (S)-2,3-dihydro-1H-pyrrolizine-1-carboxylate (11) are coupled using the methods of either Muchowski et al. or Baran et al. (for the chiral synthesis) of (12) (Muchowski, J. M. et al., "Synthesis and antiinflammatory and analgesic activity of 5-aroyl-1,2-dihydro-3H-pyrrolo[1,2-a]pyrrole-1-carboxylic acids and related compounds," *J. Med. Chem.* 28, 1037-49 (1985); Baran, P. S., Richter, J. M. and Lin, D. W., "Direct coupling of pyrroles with carbonyl compounds: short enantioselective synthesis of (S)-ketorolac," *Angew. Chem. Int. Ed. Engl.* 44, 609-12 (2005)).

Synthesis of tert-butyl (S)-5-(4-(2-hydroxyethyl)benzoyl)-2,3-dihydro-1H-pyrrolizine-1-carboxylate (13) Compound (12) is deprotected with TBAF using standard methods to yield (13).

tert-butyl(S)-5-(4-(2-((1-formamido-2-methylpropan-2-yl)oxy)ethyl)benzoyl)-2,3-dihydro-1H-pyrrolizine-1-carboxylate (14)

Using the method of Al-Ktaifani, M. M., Nakawa, A. A., Tabbaa, Z. A. and Namou, A. A., "Synthesis of 2-methyl-2-propoxypropyl isocyanide and its Cu(I) tetrafluoroborate complex," *Chem. Pap.* 62, 329-333 (2008).

In general, mercuric(II)trifluoroacetate and N-(2-methyl-2-propenyl)formamide (Synthesized by the method of van Wyk, A. J. et al. "Synthesis and $^{99m}Tc$ labelling of MMI (MIBI) and its ethyl analogue EMI." *Int. J. Radiat. Appl. Instrumentation.* Part A. *Appl. Radiat. Isot.* 42, 687-689 (1991)) and tert-butyl (S)-5-(4-(2-hydroxyethyl)benzoyl)-2,3-dihydro-1H-pyrrolizine-1-carboxylate (13) are dissolved in THF and stirred at room temperature. The mixture is cooled down in an ice bath and NaOH pellets in isopropanol are added slowly. Subsequently, NaBH$_4$ was added to the mixture, which was stirred for 18 h. The solution was passed through a column of Celite® (J. T. Baker, Phillipsberg, N.J., diatomaceous earth) to remove elemental Hg to yield tert-butyl (S)-5-(4-(2-((1-formamido-2-methylpropan-2-yl)oxy)ethyl)benzoyl)-2,3-dihydro-1H-pyrrolizine-1-carboxylate (14).

Synthesis of (S)-5-(4-(2-((1-isocyano-2-methylpropan-2-yl)oxy)ethyl)benzoyl)-2,3-dihydro-1H-pyrrolizine-1-carboxylic acid (15) tert-butyl (S)-5-(4-(2-((1-formamido-2-methylpropan-2-yl)oxy)ethyl)benzoyl)-2,3-dihydro-1H-pyrrolizine-1-carboxylate (14) is dissolved in pyridine and benzene. The solution is cooled to 0° C. and POCl$_3$ is subsequently added drop wise. The reaction is quenched by pouring over ice and extracting the product into CH$_2$Cl$_2$.

Synthesis of tetrakis(((2-(4-((S)-1-carboxy-2,3-dihydro-1H-pyrrolizine-5-carbonyl)phenethoxy)-2-methylprop yl)-14-azanylidyne)methyl)copper (16) Based on the method of Al-Ktaifani, M. M., Nakawa, A. A., Tabbaa, Z. A. and Namou, A. A., "Synthesis of 2-methyl-2-propoxypropyl isocyanide and its Cu(I) tetrafluoroborate complex." *Chem. Pap.* 62, 329-333 (2008). Synthesis of (16) is realized by heating a mixture of (15) and freshly crystallized CuCl in degassed dry EtOH at 50° C. in an ampoule for 1 h. A solution of NaBF$_4$ in water is added in one portion, solvents are removed under vacuum, with the resultant crude product dissolved in EtOH and the NaCl generated was separated by filtration. The solvent was removed to get the product (16).

Example 3

Synthesis of hexakis(((2-((6-((S)-1-carboxyethyl)naphthalen-2-yl)oxy)-2-methylpropyl)-14-azanylidyne)methyl)technetium (1)

Scheme 3

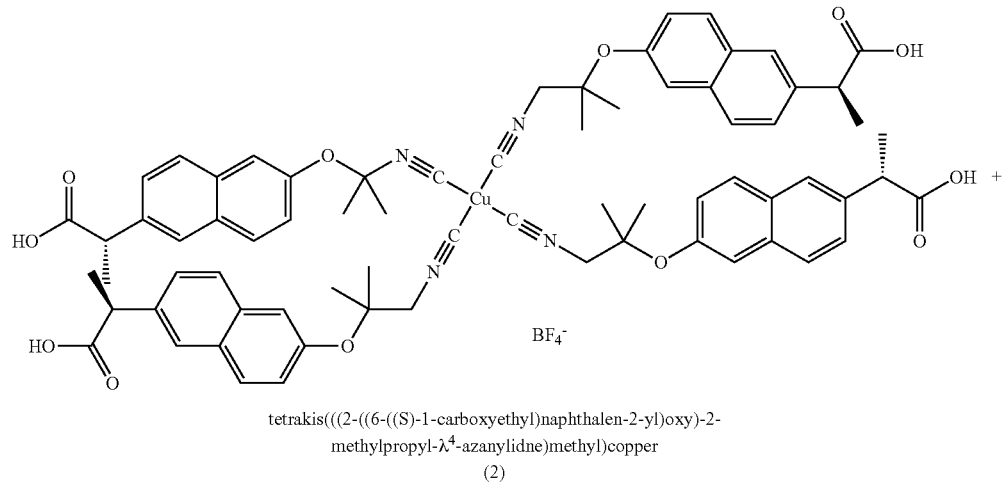

tetrakis(((2-((6-((S)-1-carboxyethyl)naphthalen-2-yl)oxy)-2-methylpropyl-$\lambda^4$-azanylidne)methyl)copper (2)

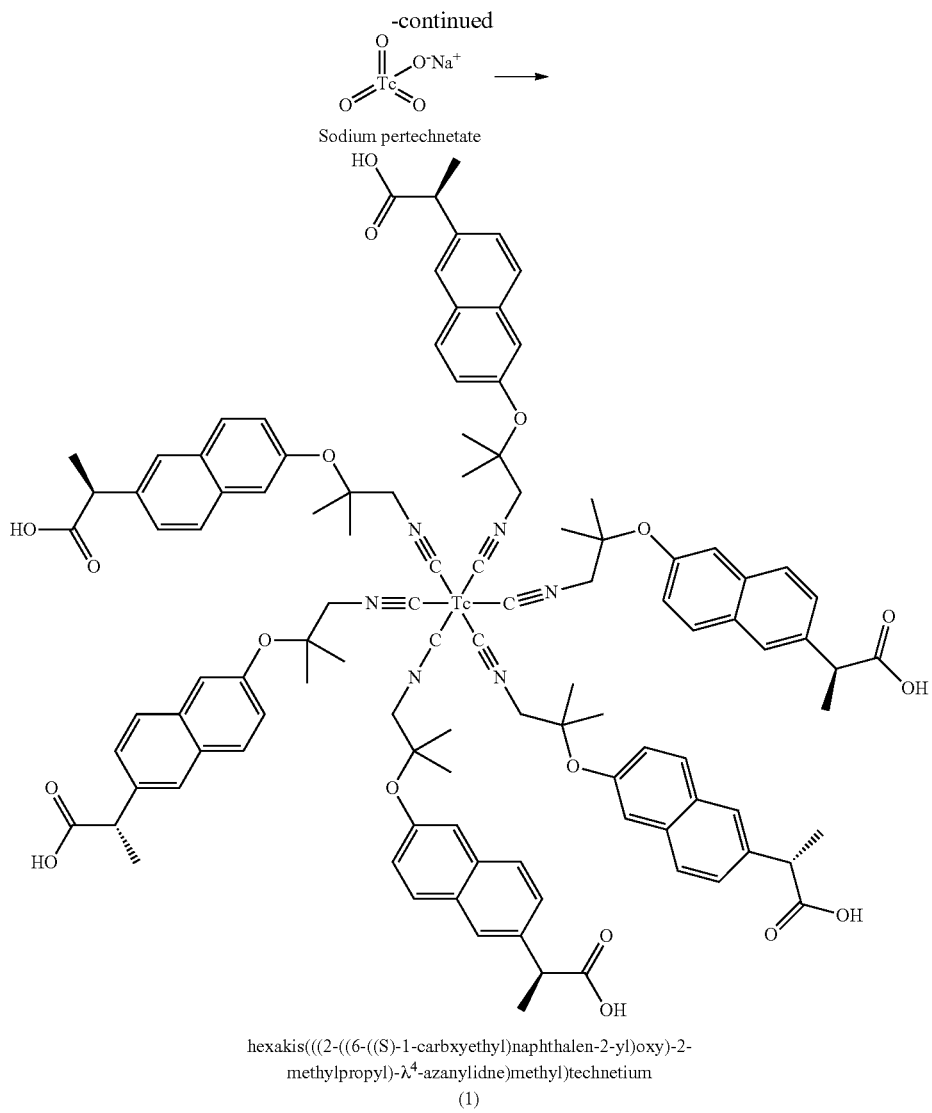

hexakis(((2-((6-((S)-1-carbxyethyl)naphthalen-2-yl)oxy)-2-methylpropyl)-λ⁴-azanylidne)methyl)technetium (1)

A vial is prepared containing a sterile, non-pyrogenic, lyophilized mixture of:

Tetrakis(((2-((6-((S)-1-carboxyethyl)naphthalen-2-yl)oxy)-2-methylpropyl)-14-azanylidyne)methyl) Copper (I) tetrafluoroborate—1.0 mg Sodium Citrate Dihydrate—2.6 mg L-Cysteine Hydrochloride Monohydrate—1.0 mg Mannitol—20 mg Stannous Chloride, Dihydrate, minimum (SnCl$_2$.2H$_2$O)—0.025 mg Stannous Chloride, Dihydrate, (SnCl$_2$.2H$_2$O)—0.075 mg Tin Chloride (stannous and stannic) Dihydrate, maximum (as SnCl$_2$.2H$_2$O)—0.086 mg.

Prior to lyophilization the pH is 5.3 to 5.9. The contents of the vial are lyophilized and stored under nitrogen.

Reconstitution with sterile, non-pyrogenic, oxidant-free Sodium Pertechnetate Tc99m Injection forms the compound (1), which is administered by intravenous injection for diagnostic use (see Scheme 2). The specific steps for reconstitution are:

Place the vial in a suitable radiation shield with a fitted radiation cap.

With a sterile shielded syringe, aseptically obtain additive-free, sterile, non-pyrogenic Sodium Pertechnetate Tc99m Injection [925-5550 MBq, (25-150 mCi)] in approximately 1 to 3 mL.

Aseptically add the Sodium Pertechnetate Tc99m Injection to the vial in the lead shield. Without withdrawing the needle, remove an equal volume of headspace to maintain atmospheric pressure within the vial.

Shake vigorously, about 5 to 10 quick upward-downward motions.

Remove the vial from the lead shield and place upright in an appropriately shielded and contained boiling water bath, such that the vial is suspended above the bottom of the bath, and boil for 10 minutes. Timing for 10 minutes is begun as soon as the water begins to boil again. Do not allow the boiling water to come in contact with the aluminum crimp.

Remove the vial from the water bath, place in the lead shield and allow to cool for fifteen minutes.

Using proper shielding, the vial contents should be visually inspected. Use only if the solution is clear and free of particulate matter and discoloration.

Assay the reaction vial using a suitable radioactivity calibration system. Record the Technetium Tc99m concentration, total volume, assay time and date, expiration time and lot number on the vial shield label and affix the label to the shield.

Store the reaction vial containing the Technetium Tc99m (1) at 15° C. to 25° C. until use; at such time the product should be aseptically withdrawn. Technetium Tc99m (1) should be used within six hours of preparation. The vial contains no preservative.

The pH of the reconstituted product is 5.5 (5.0-6.0). No bacteriostatic preservative is present. The precise structure of the technetium complex (1) is Tc99m[IBN]$_6^+$ where IBN is (S)-2-(6-((1-isocyano-2-methylpropan-2-yl)oxy)naphthalen-2-yl)propanoic acid.

Example 4

Synthesis of Hexakis(((2-(4-((S)-1-carboxy-2,3-dihydro-1H-pyrrolizine-5-carbonyl)phenethoxy)-2-methylpropyl)-14-azanylidyne)methyl)technetium (17)

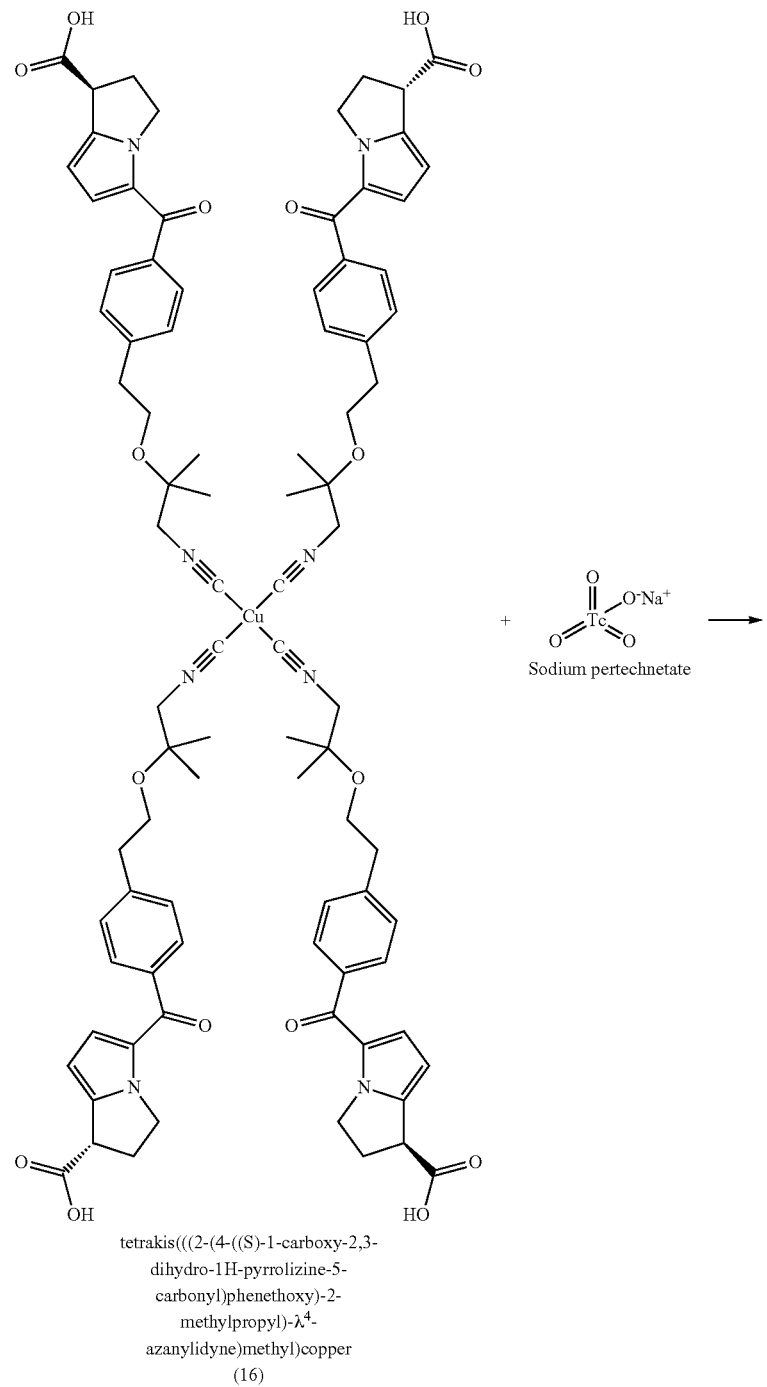

tetrakis(((2-(4-((S)-1-carboxy-2,3-dihydro-1H-pyrrolizine-5-carbonyl)phenethoxy)-2-methylpropyl)-λ$^4$-azanylidyne)methyl)copper (16)

-continued

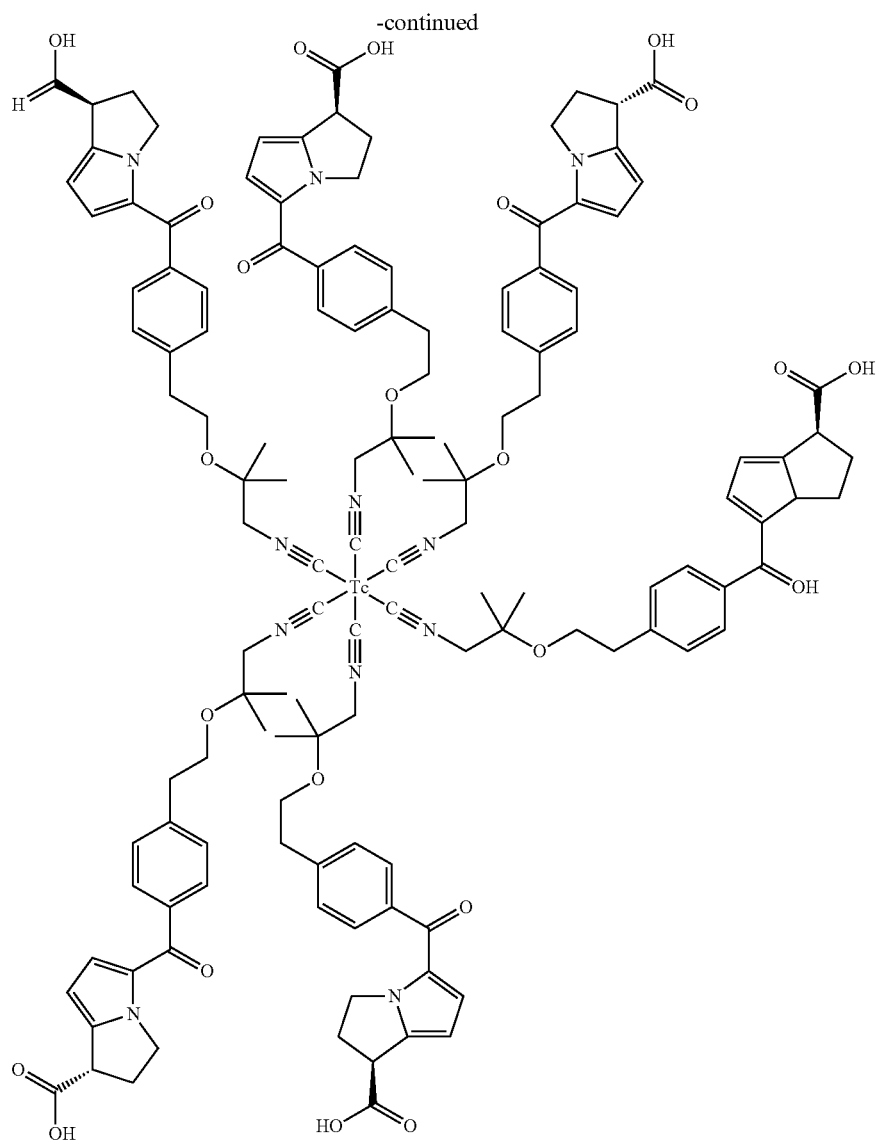

hexakis(((2-(4-((S)-1-carboxy-2,3-dihydro-1H-pyrrolizine-5-carbonyl)phenethoxy)-2-methylpropyl)-λ⁴-azanylidyne)methyl)technetium (17)

Hexakis(((2-(4-((S)-1-carboxy-2,3-dihydro-1H-pyrrolizine-5-carbonyl)phenethoxy)-2-methylpropyl)-14-azanylidyne)methyl)technetium (17) is prepared using the same procedure as in Example 3, starting from tetrakis(((2-(4-((S)-1-carboxy-2,3-dihydro-1H-pyrrolizine-5-carbonyl) phenethoxy)-2-methylprop yl)-14-azanylidyne)methyl)copper (16).

Example 5
Synthesis of Indomethacin Derivatives
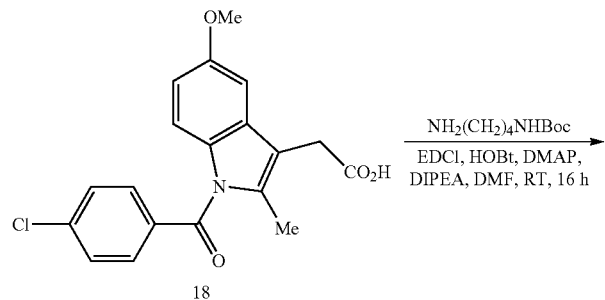
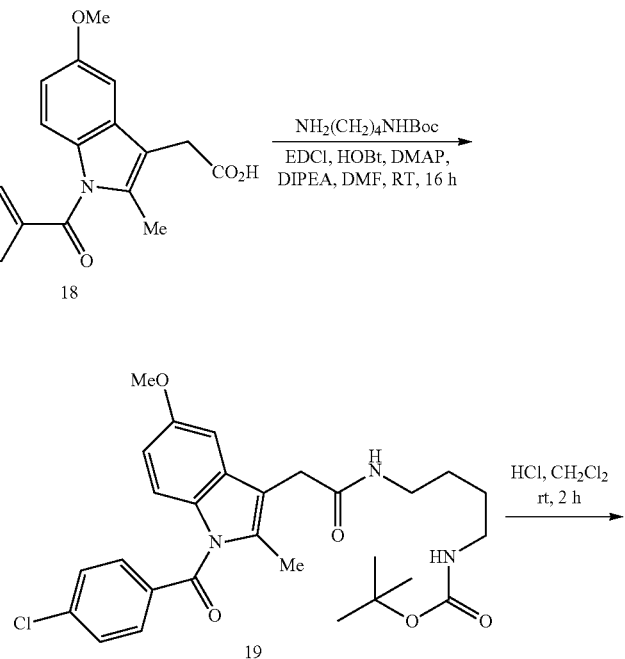
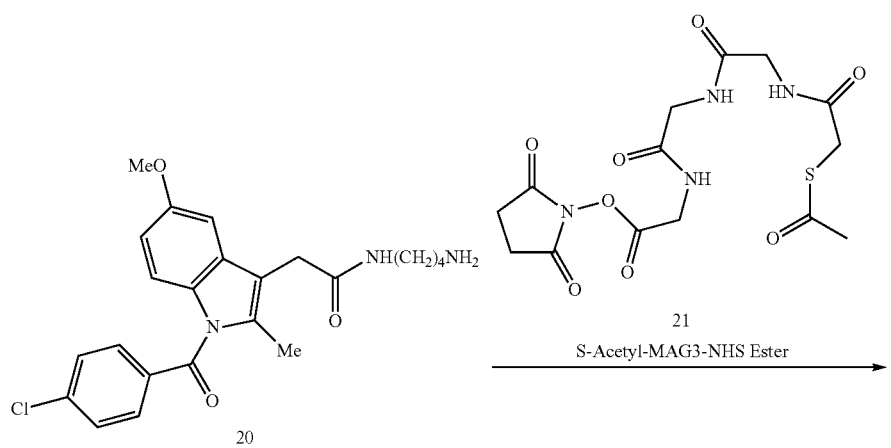
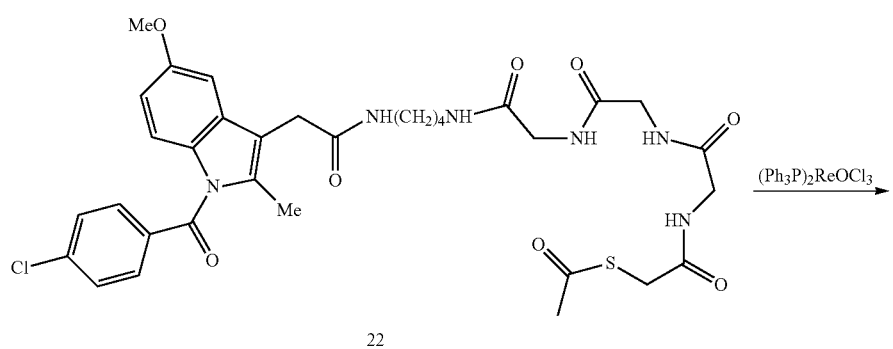

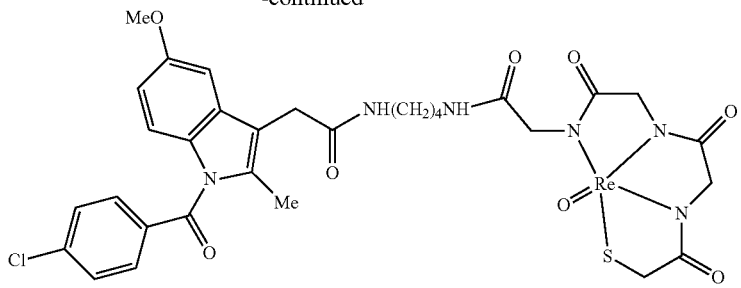

23

Amine 20 is readily synthesized by using protocols available in the following publications: (1) Uddin, Md. Jashim, et al. *Bioconjugate Chemistry* (2013), 24(4), 712-723; (2) Zlatopolskiy, Boris D., et al. *Chemical Communications* (2012), 48(57), 7134-7136; (3) U.S. Pat. Appl. Publ. 2005/0002859 (2005); (4) U.S. Pat. Appl. Publ. 2007/0292352 (2007); (5) Uddin, Md. Jashim, et al. *Journal of Labelled Compounds and Radiopharmaceuticals* (2009), 52(9), 387-393; and (6) Uddin, Md. Jashim, et al. *Bioorganic & Medicinal Chemistry Letters* (2010), 20(5), 1787-1791.

Alternatively, amine 20 can be synthesized by the following procedure:

To a stirred solution of indomethacin 18 (2 g, 5.6 mmol) in DMF (50 mL) was added tert-butyl 4-aminobutylcarbamate (2 g, 11.2 mmol), HOBt (2.3 g, 16.8 mmol), DIPEA (3.6 g, 28 mmol) and EDCI (2.1 g, 11.2 mmol, 2 eq) at rt. The resultant mixture was stirred at rt for 16 h. The mixture was washed with 100 mL saturated LiCl solution and extracted with EtOAc (3×100 mL). The organic layers were combined, concentrated and crystallized from n-hexane to give 19 as a yellow solid. LC-MS: m/z=428 (M−100+H)$^+$; H-NMR (400 MHz, CDCl$_3$) δ: 7.68 (d, 2H, J=8.8 Hz), 7.50 (d, 2H, J=8.4 Hz), 6.90 (m, 2H), 6.71 (d, 2H, J=2.4 Hz), 5.79 (s, 1H), 4.59 (s, 1H), 3.82 (s, 3H), 3.63 (s, 2H), 3.22 (m, 2H), 3.06 (m, 2H), 2.39 (s, 3H), 1.41 (m, 12H).

To a stirred solution of 19 (2 g, 3.7 mmol) in DCM (20 mL), a solution of HCl in dioxane (4M, 7.5 mL) was added dropwise. The resultant solution was stirred at rt for 2 h. Removal of solvent under reduced pressure afforded 20 as a yellow residue, which was used without further purification. LC-MS: m/z=428 (M−36+H)$^+$; H-NMR (400 MHz, DMSO-d$_6$) δ: 8.26 (s, 1H), 8.07 (s, 3H), 7.68 (m, 4H), 7.18 (d, 1H, J=2.4 Hz), 6.94 (d, 2H, J=8 Hz), 6.71 (d, 1H, J=2.8 Hz), 3.77 (s, 3H), 3.56 (s, 2H), 3.07 (d, 2H, J=6 Hz), 2.76 (d, 2H, J=6.4 Hz), 2.24 (s, 3H), 1.57 (m, 2H), 1.48 (m, 2H).

Indomethacin derivative 22 is made following the procedure in: Wang Y, et al. Nat Protoc. (2007), 2(4): 972-8. The reagent S-Acetyl-MAG3-NHS ester is available commercially (KeraFAST Inc., Boston, Mass., USA; catalog no. ES1001; see the supplier web site: www.kerafast.com/p-1447-s-acetyl-mag3-nhs-ester.aspx?gclid=Cj0KEQjwur2eBRDtvMS0gIuS-dYBEiQANBPMR3SKY-ABw0HCC08Gud53dB29wsldYYUl3UeQFvVxc_ga-AiIA8P8HAQ; see also Winnard P. et al., Nucl Med Biol. (1997), 24(5): 425-32; Wang Y. et al., Nat. Protoc. (2007) 2(4): 972-8; Rusckowski M. et al., Cancer Biotherapy & Radiopharmaceuticals (2007), 22(4): 564-72; and Wang Y. et al., European J. Nucl. Med. Mol. Imag. (2009), 36(12): 1977-86).

Indomethacin derivative 23 is made following the procedure in Ono, et al. Bioorg. Med. Chem. Lett. (2010), 20, 5743-5748. The reagent Trichlorooxobis(triphenylphosphine)rhenium(V), (PPh3)$_2$ReOCl$_3$, is commercially available (Sigma-Aldrich, Saint Louis, Mo., USA; catalog no. 370193).

Alternatively, compound 23 can be synthesized using the following procedure: To a stirred solution of compound 22 (100 mg, 0.14 mmol) in NMP (15 mL), (PPh$_3$)$_2$ReOCl$_3$ (Sigma-Aldrich, Order #370193, 106 mg, 0.127 mmol) was added. The mixture was stirred at 80° C. for 48 h. The solution was purified by Prep-HPLC (Column: Acquity BEH C18, Waters Corp, solvent A: Water (10 mM NH$_4$HCO$_3$), solvent B: MeCN) to give compound 23 as a solid. LC-MS: m/z=871 (M+H)$^+$; H-NMR (400 MHz, DMSO-d$_6$) δ: 8.00 (m, 1H), 7.70-7.63 (m, 4H), 7.20 (m, 1H), 7.11 (m, 1H), 6.95 (d, 1H, J=8.8 Hz), 6.71 (d, 1H, J=2 Hz), 4.82 (d, 1H, J=16 Hz), 4.55 (d, 1H, J=17.6 Hz), 4.41 (d, 1H, J=16 Hz), 3.80 (m, 4H), 3.65 (d, 1H, J=16.8 Hz), 3.48 (s, 2H), 3.03 (m, 4H), 2.22 (s, 3H), 1.36 (s, 4H). $^{13}$C-NMR (400 MHz, DMSO-d$_6$) δ: 192.27, 191.61, 188.45, 170.13, 169.65, 168.32, 156.01, 137.97, 135.53, 134.77, 131.61, 130.72, 129.49, 115.00, 111.76, 102.30, 58.45, 56.21, 55.90, 53.08, 39.94, 38.53, 31.61, 27.12, 26.91, 13.84.

Example 6

Synthesis of Indomethacin Derivatives

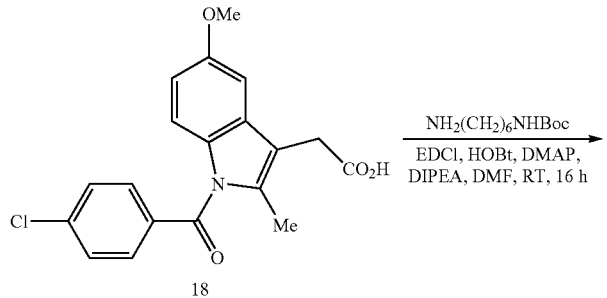

18

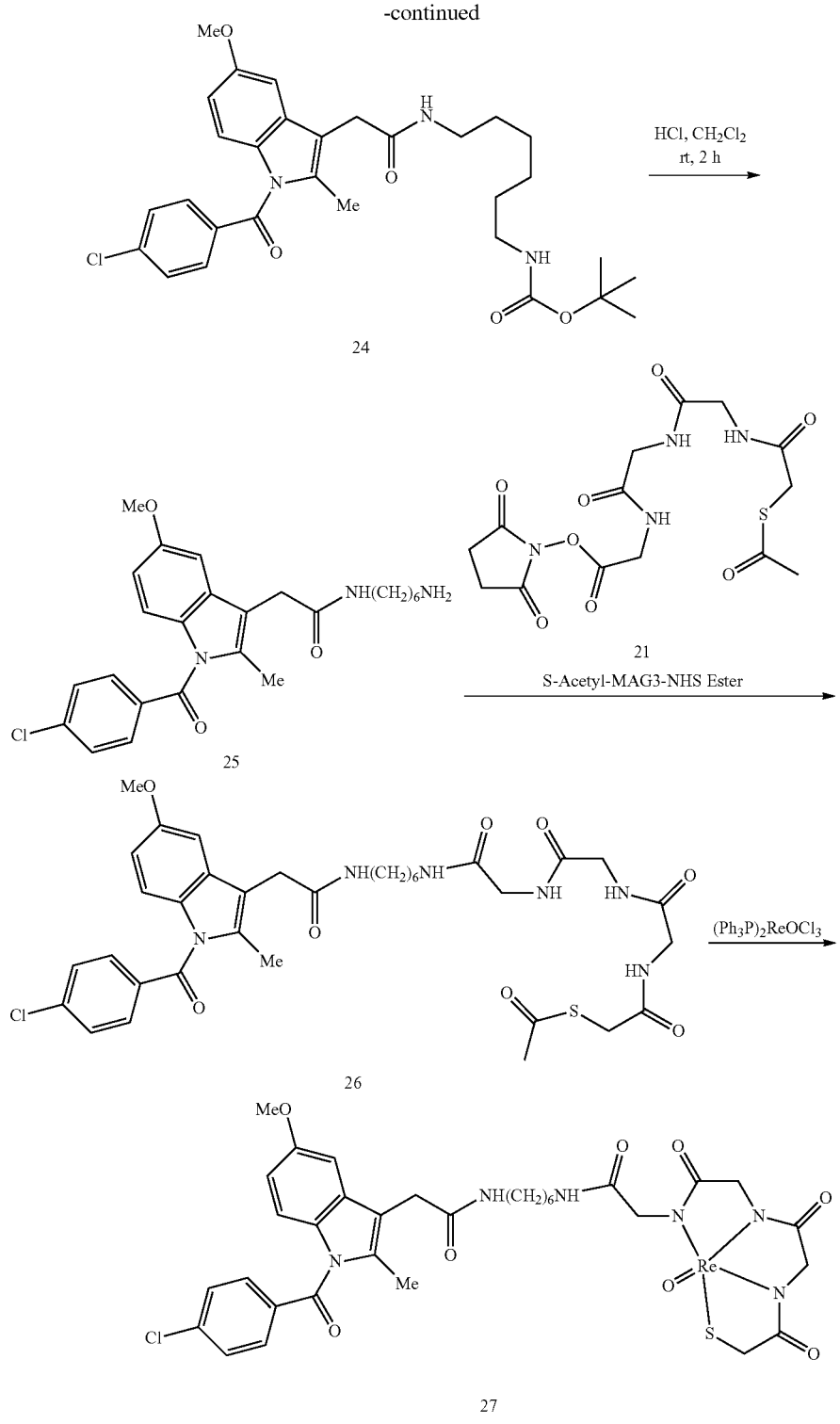

Similarly as Example 5, amine 25 has been reported in the following articles: (1) Uddin, Md. Jashim, et al. *Bioconjugate Chemistry* (2013), 24(4), 712-723. (2) Hua Zhang, et al. *J. Am. Chem. Soc.* (2013), 135, 11663-11669 (3) Hua Zhang, et al. *J. Am. Chem. Soc.* (2013), 135, 17469-17475.

Alternatively, amine 25 can be synthesized by the following procedure: To a mixture of indomethacin (11.8 g, 33 mmol), tert-butyl 6-aminohexylcarbamate (CAS No. 51857-17-1) (8.5 g, 39 mmol) and HATU (18.8 g, 50 mmol) in DMF (200 mL) was added TEA (10.1 g, 0.1 mol). The mixture was stirred at rt for 4 h and poured onto ice water (300 mL). The precipitate was collected by filtration and dried to give compound 24 as a solid. LC-MS: m/z=456.3 (M−100+H; H-NMR (400 MHz, DMSO-$d_6$) δ: 8.00 (br s, 1H), 7.77-7.63 (m, 4H), 7.11 (d, J=2.4 Hz, 1H), 6.95-6.93

(m, 1H), 6.74-6.69 (m, 2H), 3.76 (s, 3H), 3.48 (s, 2H), 3.06-3.01 (m, 2H), 2.88-2.83 (m, 2H), 2.23 (s, 3H), 1.36 (s, 9H), 1.33-1.18 (m, 8H).

A mixture of compound 24 (10 g, 18 mmol) in HCl/dioxane (3M, 150 mL) was stirred at rt for 2 h. The mixture was concentrated to give compound 25 as white solid, which was in the next step without further purification. LC-MS: m/z=456.3 (M+H)$^+$; H NMR (400 MHz, CD3OD) δ: 7.72 (d, J=8.4 Hz, 2H), 7.59 (d, J=8.4 Hz, 2H), 7.03 (d, J=2.4 Hz, 1H), 6.95 (d, J=9.2 Hz, 1H), 6.73-6.70 (m, 1H), 3.83 (s, 3H), 3.63 (s, 2H), 3.34-3.23 (m, 2H), 2.91-2.85 (m, 2H), 2.34 (s, 3H), 1.62-1.37 (m, 8H).

Indomethacin derivative 26 is made following the procedure in: Wang Y, et al. Nat Protoc. (2007), 2(4): 972-8. The reagent S-Acetyl-MAG3-NHS ester is available commercially (KeraFAST Inc., Boston, Mass., USA; catalog no. ES1001; see the supplier web site: www.kerafast.com/p-1447-s-acetyl-mag3-nhs-ester.aspx?gclid=Cj0KEQjwur2eBRDtvMS0gIuS-dYBEiQANBPMR3SKY-ABw0HCC08Gud53dB29wsldYYUl3UeQFvVxc_gaAiIA8P8HAQ; see also Winnard P. et al., Nucl. Med Biol. (1997), 24(5): 425-32; Wang Y. et al., Nat. Protoc. (2007), 2(4): 972-8; Rusckowski M. et al., Cancer Biotherapy & Radiopharmaceuticals (2007), 22(4): 564-72; and Wang Y. et al., European J. Nucl. Med. Mol. Imag.; (2009), 36(12): 1977-86).

Indomethacin derivative 27 is made following the procedure in: Ono, et al. Bioorg. Med. Chem. Lett. (2010), 20, 5743-5748. The reagent Trichlorooxobis(triphenylphosphine)rhenium(V) is commercially available (Sigma-Aldrich, Saint Louis, Mo., USA; catalog no. 370193).

Alternatively, compound 27 can be synthesized using the following procedure: A mixture of compound 26 (200 mg, 0.27 mmol) and (Ph$_3$P)$_2$ReOCl$_3$ (337 mg, 0.41 mmol) in NMP (10 mL) was stirred for 16 h at 100° C. The solution was directly purified by Prep-HPLC (Column: Acquity BEH C18, Waters Corp, solvent A: water containing 10 mM NH$_4$HCO$_3$, solvent B: ACN) to give 27 as a solid. LC-MS: m/z=899.2 MS (M–H)$^-$; H-NMR (400 MHz, DMSO-d$_6$) δ: 8.00 (s, 1H), 7.70-7.63 (m, 4H), 7.16-7.11 (m, 2H), 6.94 (d, J=8.8 Hz, 1H), 6.71-6.69 (m, 1H), 4.78 (d, J=16.4 Hz, 1H), 4.52 (d, J=18.0 Hz, 1H), 4.38 (d, J=16.0 Hz, 1H), 4.16-4.10 (m, 3H), 3.79-3.75 (m, 4H), 3.63 (d, J=17.2 Hz, 1H), 3.47 (s, 2H), 3.03-2.98 (m, 4H), 2.22 (s, 3H), 1.36-1.20 (m, 8H).

Example 7

Synthesis of Indomethacin Derivatives

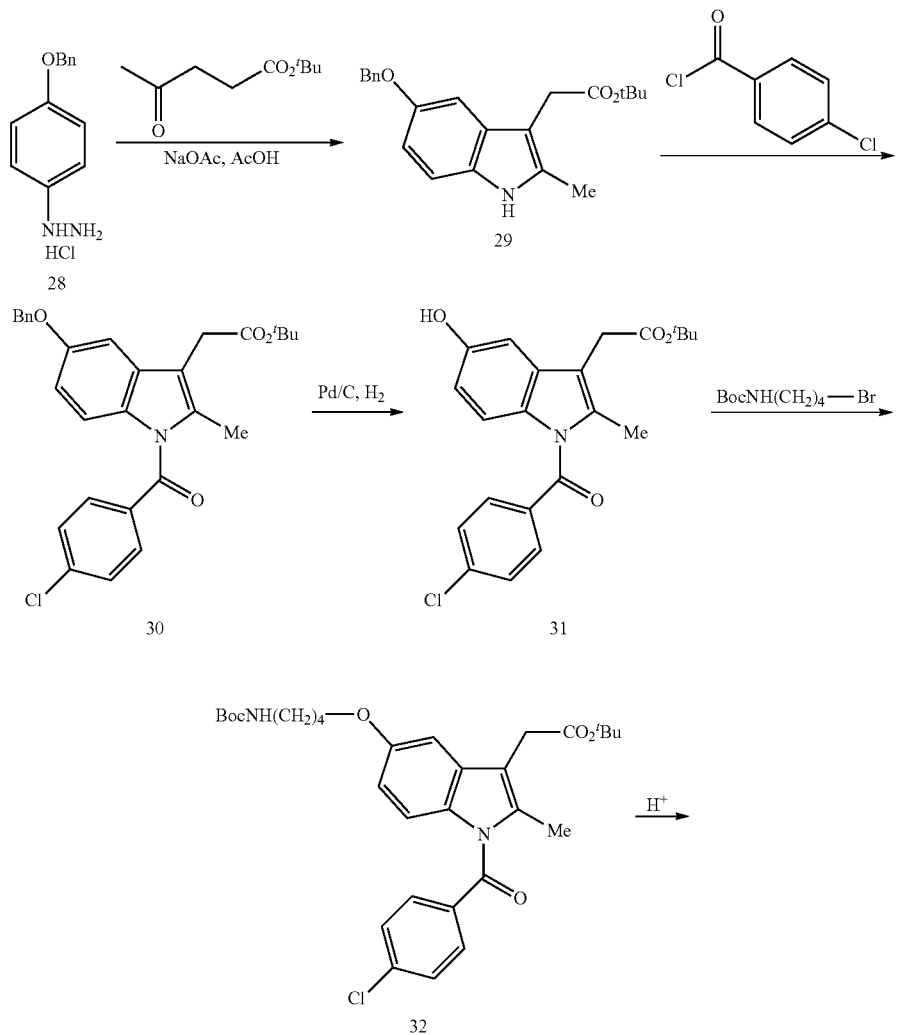

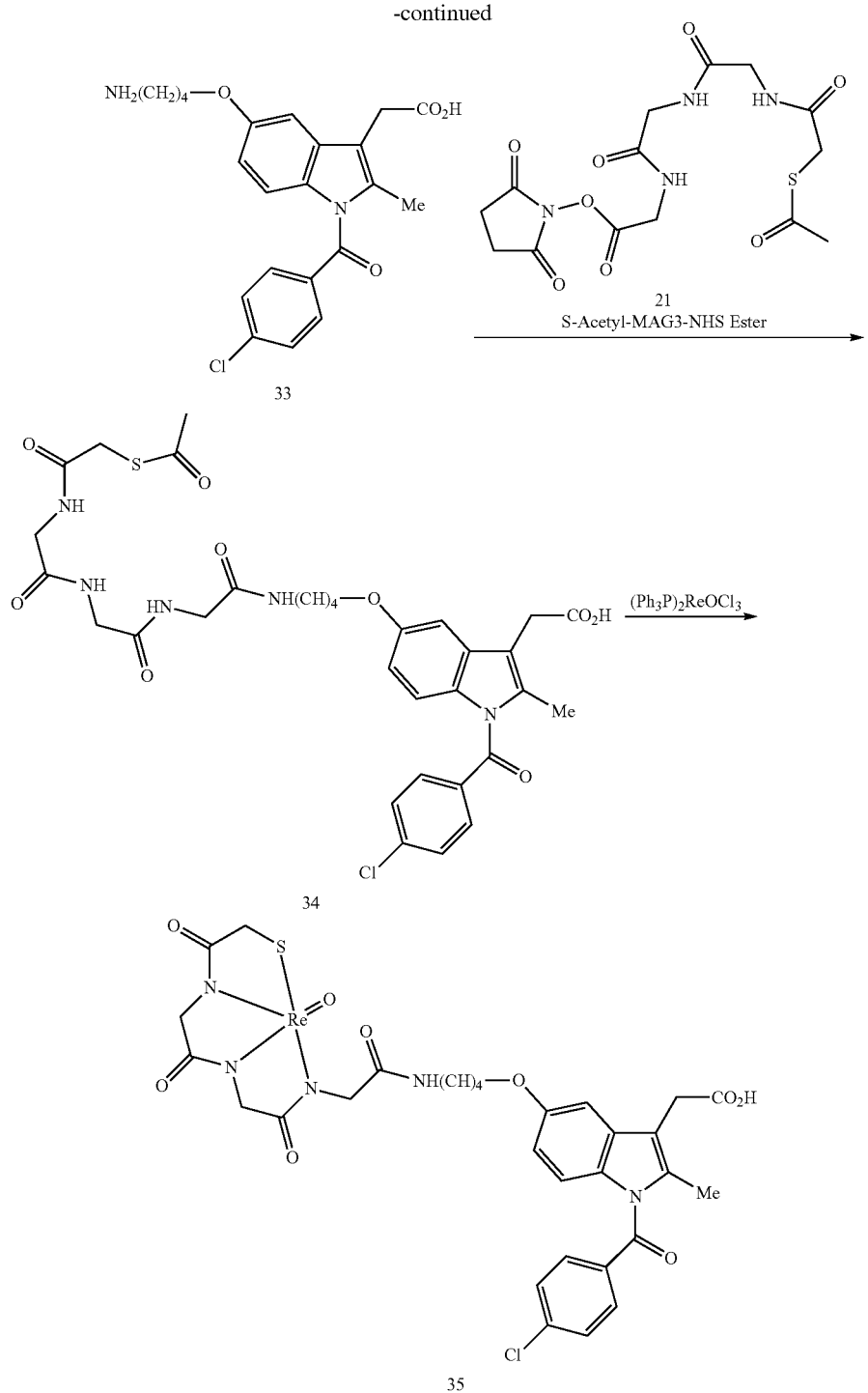

Compound 31 has been reported by Yoriko Iwata, et al. *J. Med. Chem.* (2001), 44, 1718-1728 and is readily synthesized from the commercially available hydrazine 28 through the Fisher indole synthesis with levulinic acid. Alkylation of 31 with 'BocNH(CH$_2$)$_4$Br and deprotection of the 'BOC amine and the tBu-ester leads to amino acid 33 which can be reacted with NHS—S-Acetyl-MAG3 following the procedure in: Wang Y, et al. Nat Protoc. 2007; 2(4), 972-8 to afford 34. The reagent S-Acetyl-MAG3-NHS ester is available commercially (KeraFAST Inc., Boston, Mass., USA; catalog no. ES1001; see the supplier web site: www.kerafast.com/p-1447-s-acetyl-mag3-nhs-ester.aspx?gclid=Cj0KEQjwur2eBRDtvMS0gIuS-dYBEiQANBPMR3SKY-ABw0HCC08Gud53dB29wsldYYUl3UeQFvVxc_gaAiIA8P8HAQ; see also Winnard P. et al., Nucl. Med. Biol. (1997), 24(5): 425-32; Wang Y. et al., Nat. Protoc. (2007), 2(4): 972-8; Rusckowski M. et al., Cancer Biotherapy & Radiopharmaceuticals (2007), 22(4): 564-72; and Wang Y. et al., European J. Nucl. Med. Mol. Imag. (2009), 36(12): 1977-86).

The rhenium-indomethacin derivative 35 is made following the procedure in: Ono, et al. Bioorg. Med. Chem. Lett. (2010), 20, 5743-5748. The reagent trichlorooxobis(triphenylphosphine)rhenium(V) is commercially available (Sigma-Aldrich, Saint Louis, Mo., USA; catalog no. 370193).
Example 7b
Synthesis of Indomethacin Derivatives
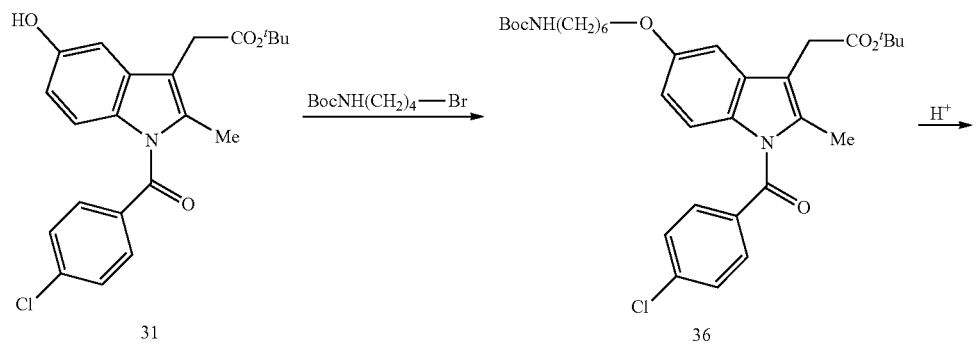
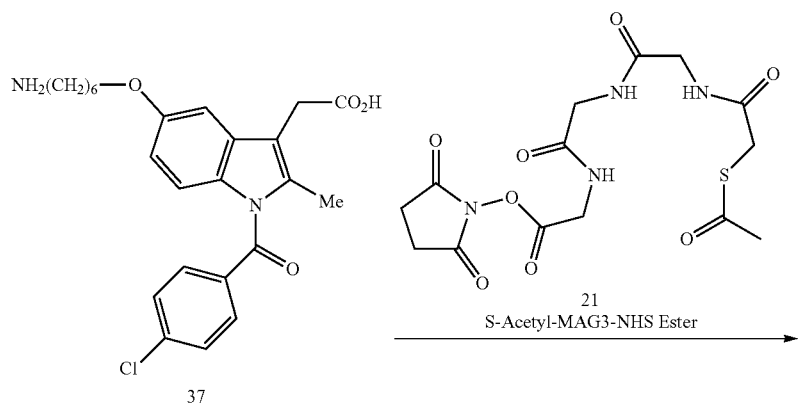
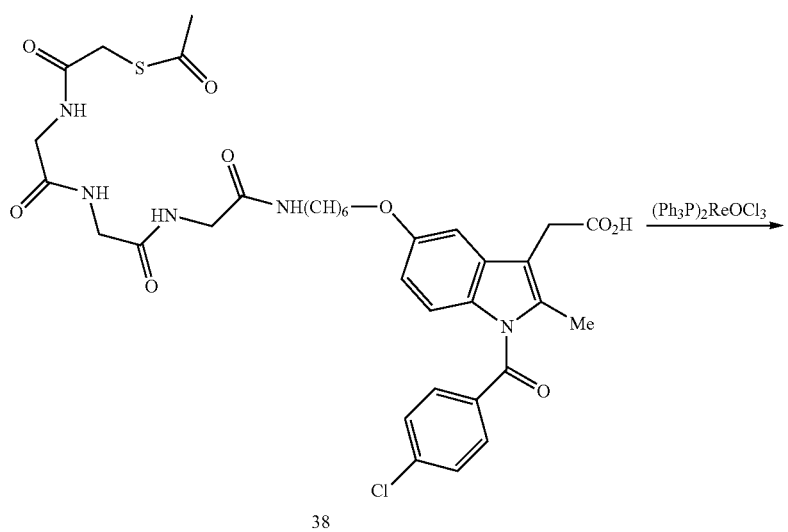

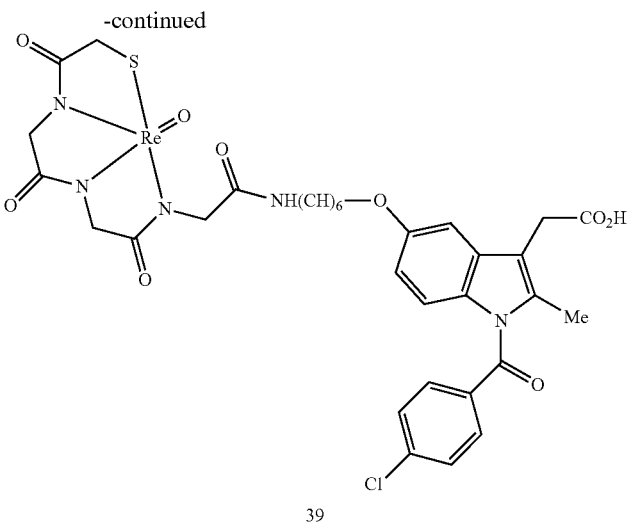
39
Compound 39 is prepared by a procedure similar to the one described in Example 7, substituting 'BocNH(CH)₄Br with 'BocNH(CH) NH(CH)₆₆Br.
Example 8
Synthesis of Ethylenedicysteine Indomethacin Derivatives 40, 41, 42, and 43
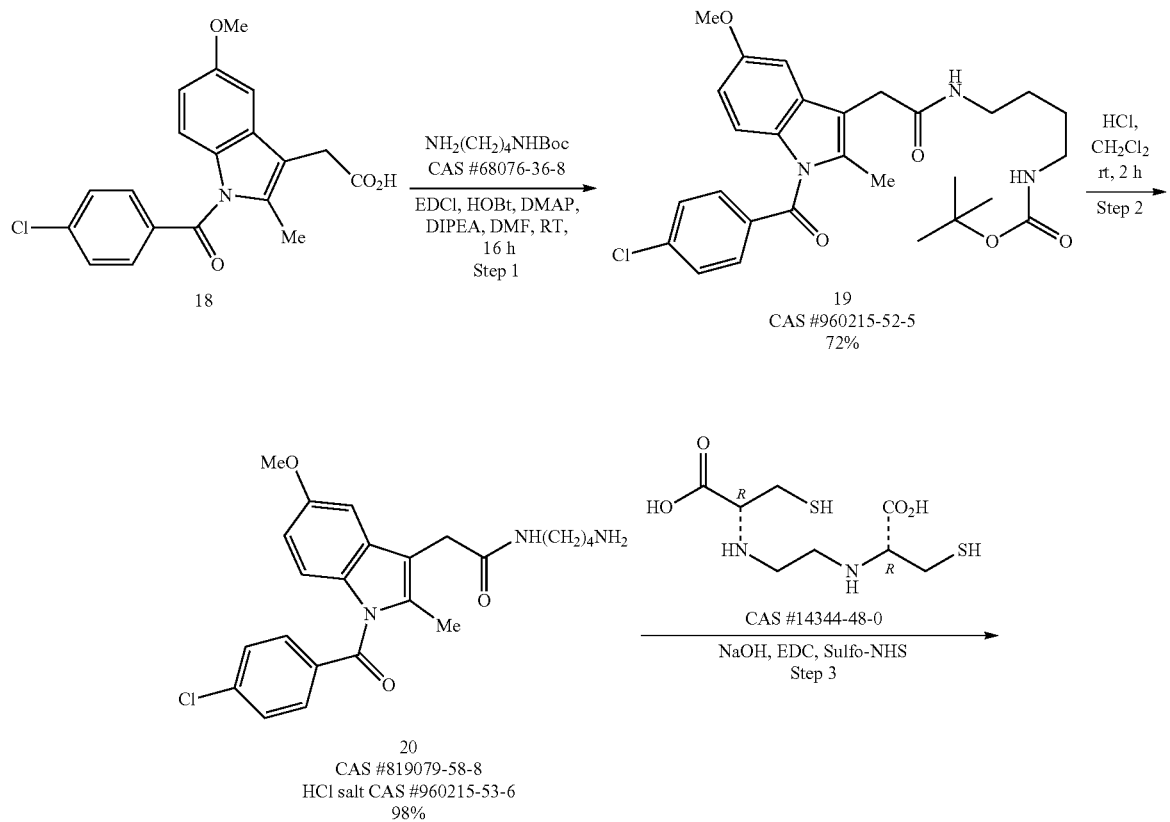

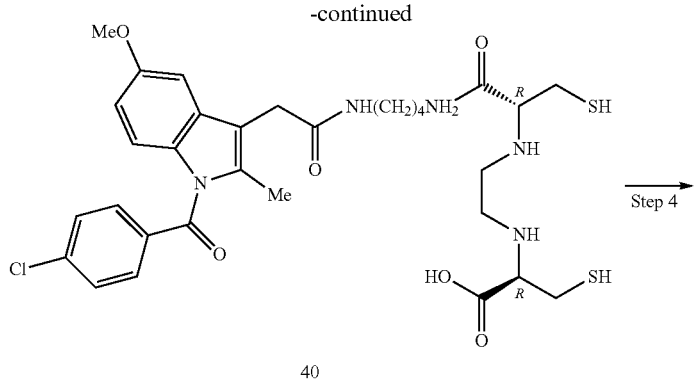

40

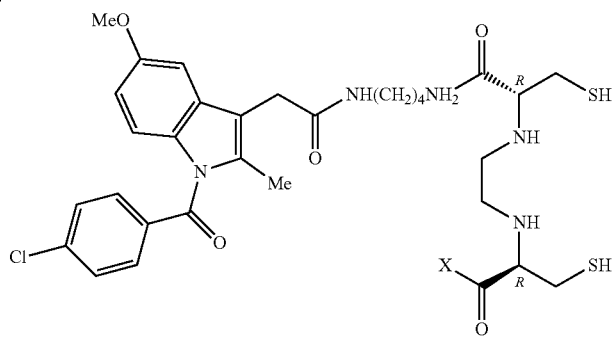

41 X = OMe
42 X = OEt
43 X = NH₂

Part 1: Synthesis of Ethylenedicysteine Indomethacin Derivatives 40, 41, 42, and 43

Amine 20 is prepared as described in Example 5.

Indomethacin derivative 40 is made from amine 20 by amide coupling with ethylenedicysteine (CAS #14344-48-0). The reaction of ethylenedicysteine with primary amines is described in the literature, see e.g. Yang et al., US 2004/6692724.

Derivative 41 is made by reacting 40 with diazomethane or TMS-diazomethane. Analog 42 is made by treating 40 with EtOH/HCl or EtOH/TMSCl. Derivative 43 is made from 40 by reaction with NH₃ in the presence of a dehydrating agent or by a similar method well known to a person skilled in the art.

Example 8b

Synthesis of Isocyano Indomethacin Derivative 45

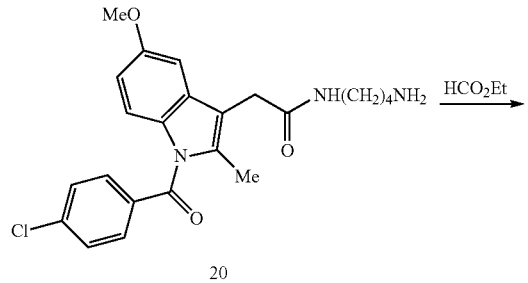

20

-continued

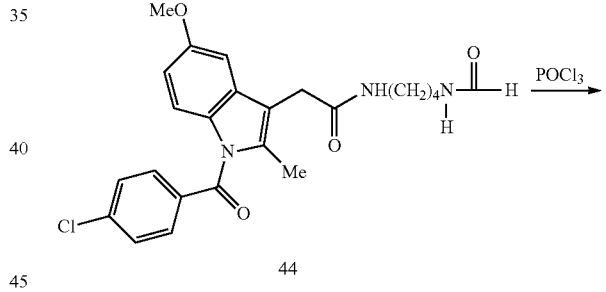

44

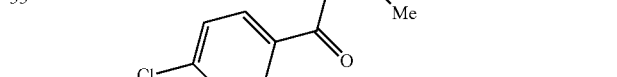

45

The isocyano compound 45 is prepared by formylating amine 20 to yield 44, followed by dehydration of 44 with POCl₃ to give 45.

Example 8c
Synthesis of $^{99m}$Tc Indomethacin Derivative 50b
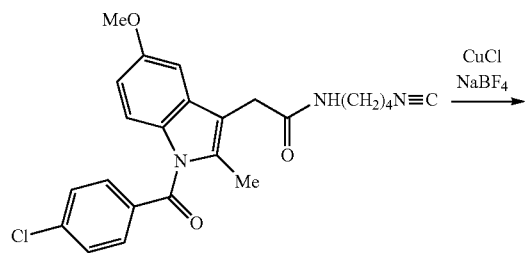
41
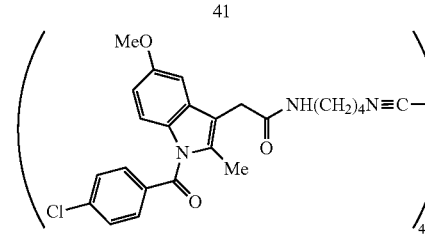
50a
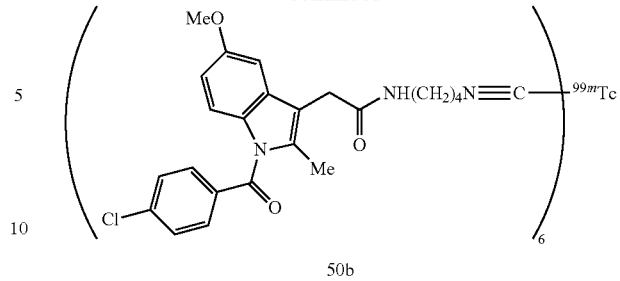
50b
Compound 50b is prepared from compound 41 in a manner analogous to the procedure in Example 2.
Example 9
Synthesis of $^{99m}$Tc Indomethacin Derivatives: 46, 47, 48, and 49
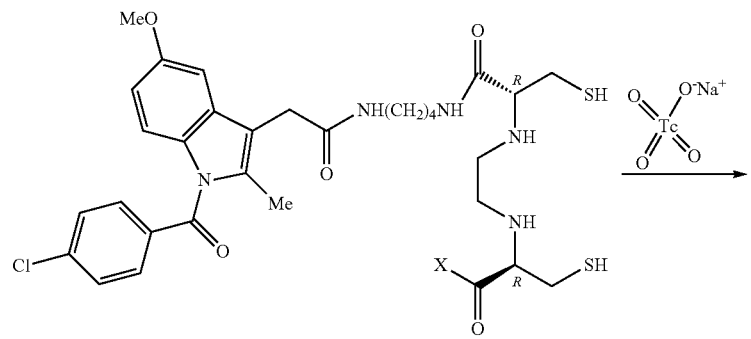
40 X = OH
41 X = OMe
42 X = OEt
43 X = NH$_2$
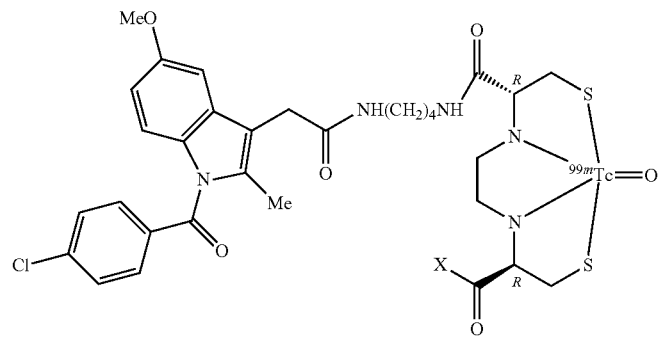
46 X = OH
47 X = OMe
48 X = OEt
49 X = NH$_2$ Compounds 46, 47, 48, and 49 are prepared from compounds 42, 43, 44, and 45, respectively, by treating with sodium pertechnetate as described in Example 3.

Example 10

Synthesis of $^{99m}$Tc Indomethacin MAG3 Analog (51)

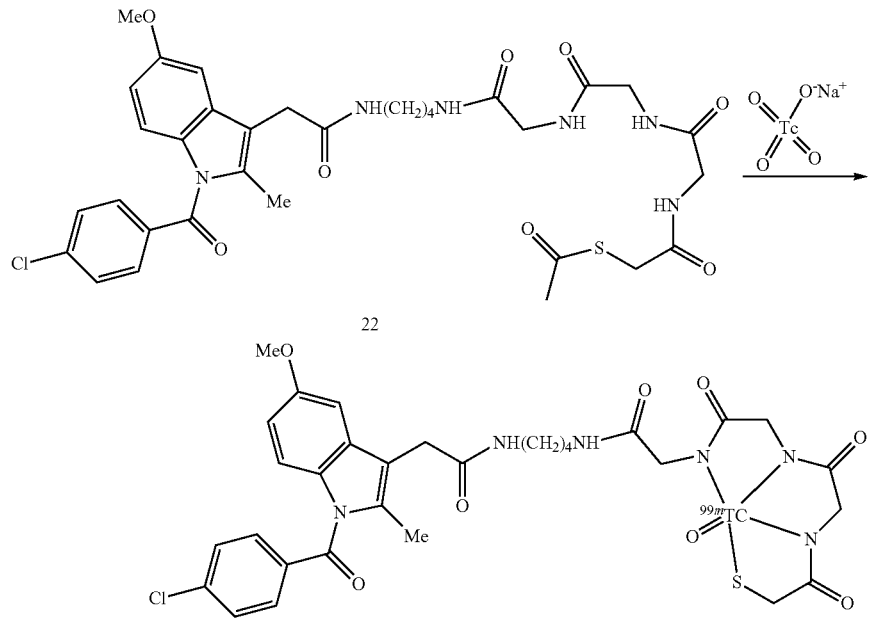

Compound 51 is prepared by combining, in a reaction vial, 1 mg of 22, between 0.05 mg (minimum) stannous chloride dihydrate ($SnCl_2 \cdot 2H_2O$) and 0.2 mg (maximum) total tin expressed as stannous chloride dihydrate ($SnCl_2 \cdot 2H_2O$), 40 mg sodium tartrate dehydrate ($Na_2C_4H_2O_6 \cdot 2H_2O$), and 20 mg lactose monohydrate. The pH of the reconstituted drug is between 5.0 and 6.0. A solubilizing agent and a bacteriostatic agent are optionally used depending on the need.

The preparation of compound 51 is analogous to the preparation of Technetium Tc 99m Mertiatide using the TechneScan MAG3™ Kit. Details of the preparation are at URL www.mallinckrodt.com/WorkArea/DownloadAsset.aspx?id=616.

Example 11

Synthesis of $^{99m}$Tc Indomethacin MAG3 Analog (52)

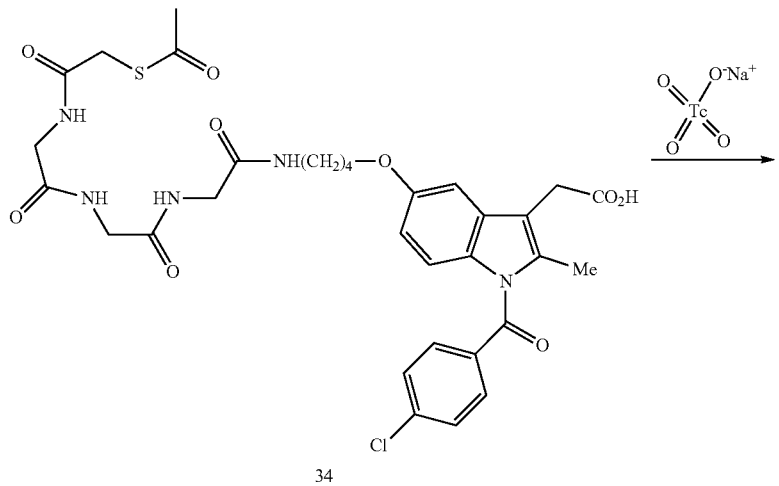

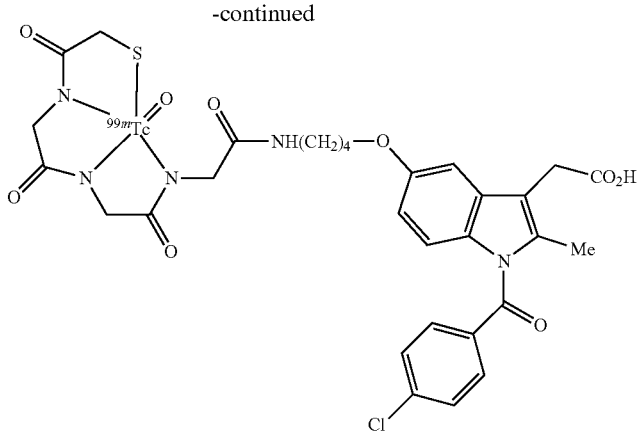
52
Compound 52 is prepared from compound 34 using a procedure similar to the one described in Example 10.
Example 11b
Synthesis of $^{99m}$Tc Indomethacin MAG3 Analog (53)
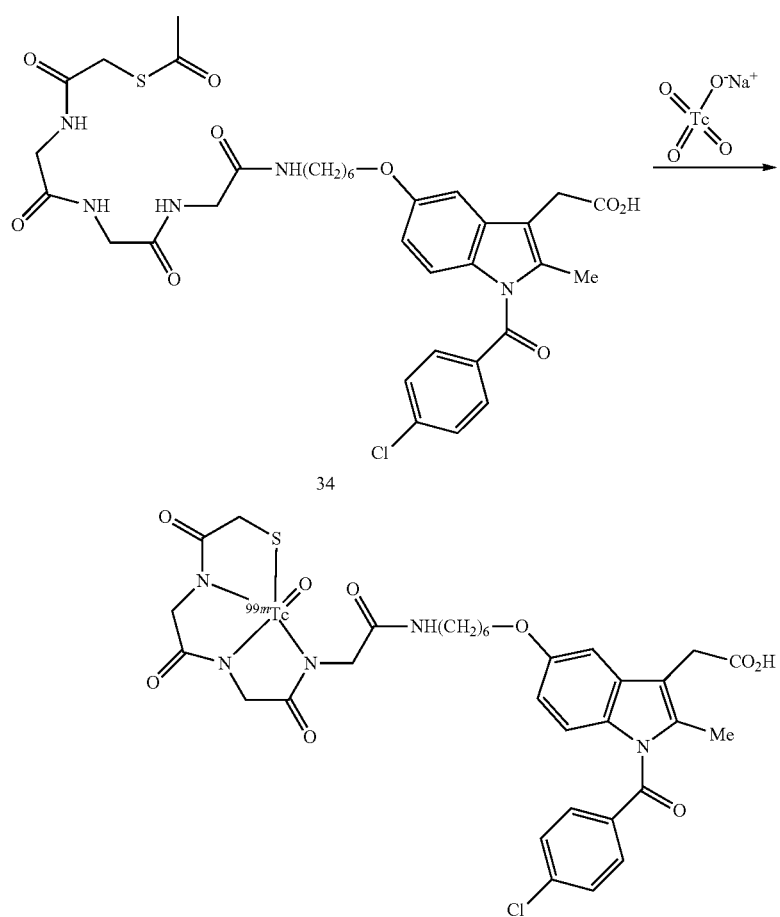

Compound 53 is prepared from compound 34 using a procedure similar to the one described in Example 10.
Example 12
Synthesis of $^{99m}$Tc Indomethacin MAG3 Analog (54)
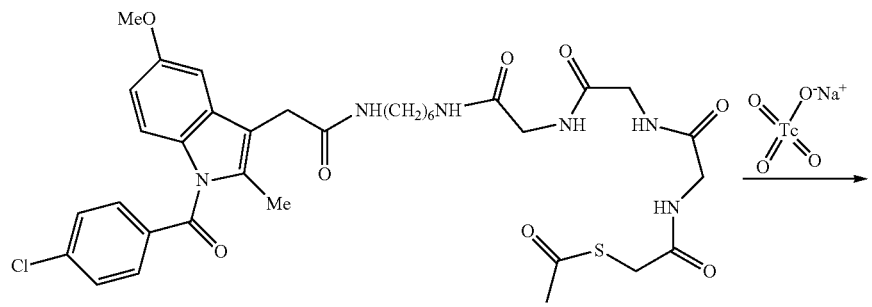
26
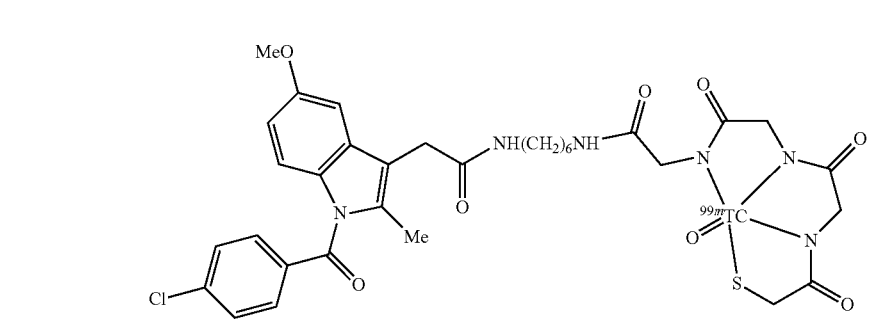
54
Compound 54 is prepared from compound 26 using a procedure similar to the one described in Example 10.
Example 13
Synthesis of Ketorolac MAG3 Ligand
Part 1
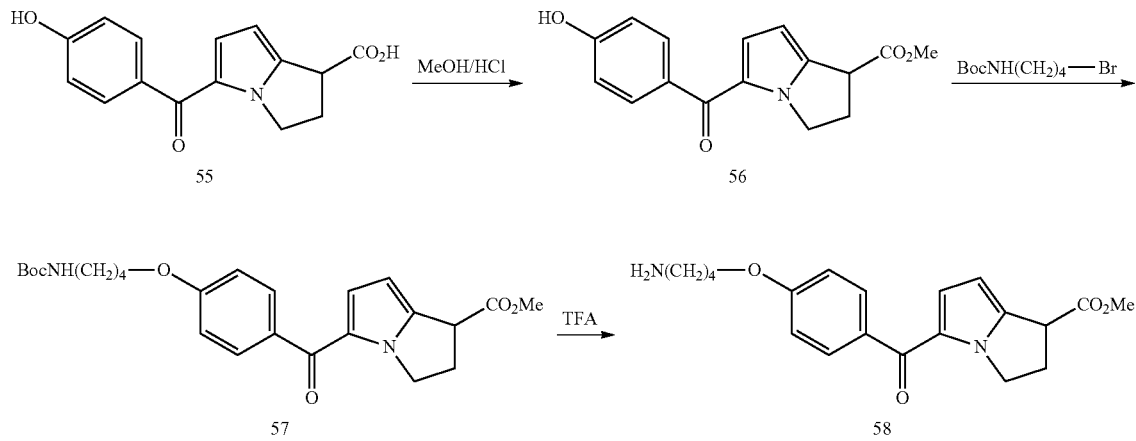

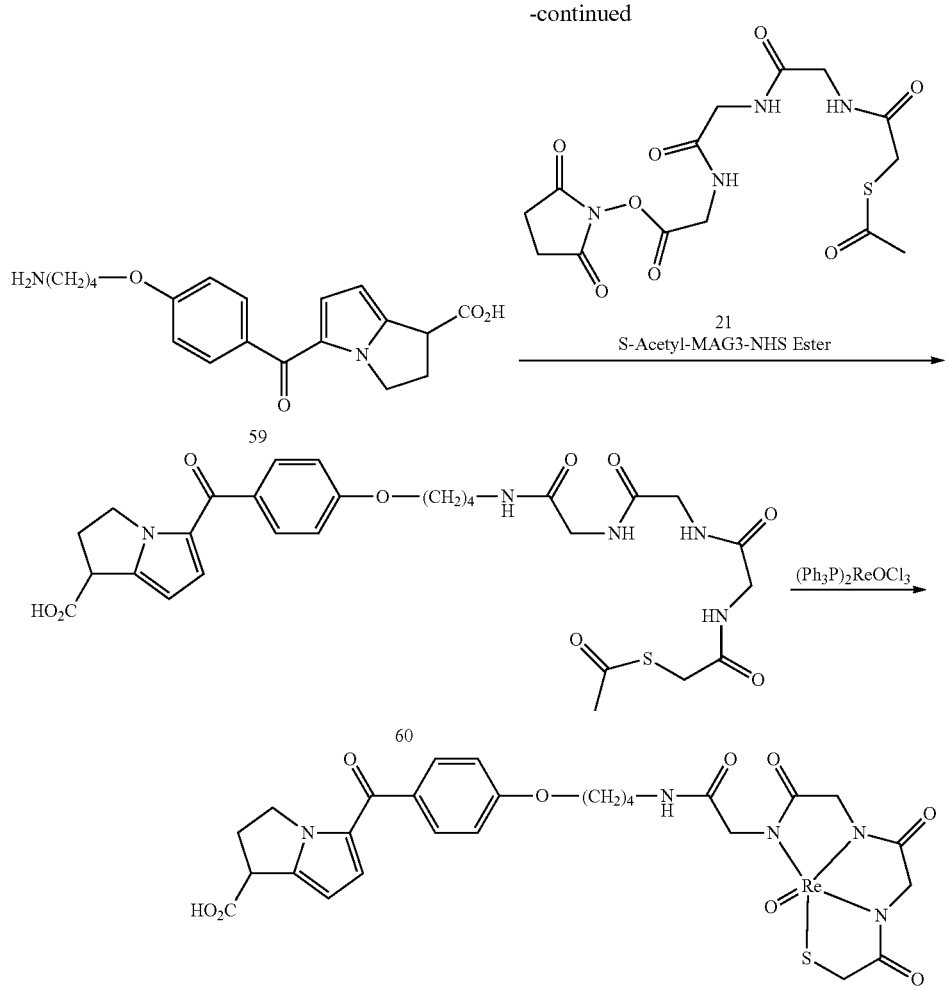
Compound 61 is prepared from compound 55 by first protecting the acid functionality of 55 via acid-catalyzed esterification to give 56, and then using a procedure analogous to that given in Example 7.
Example 14
Synthesis of Ketorolac Hexanoic MAG Re Ligand
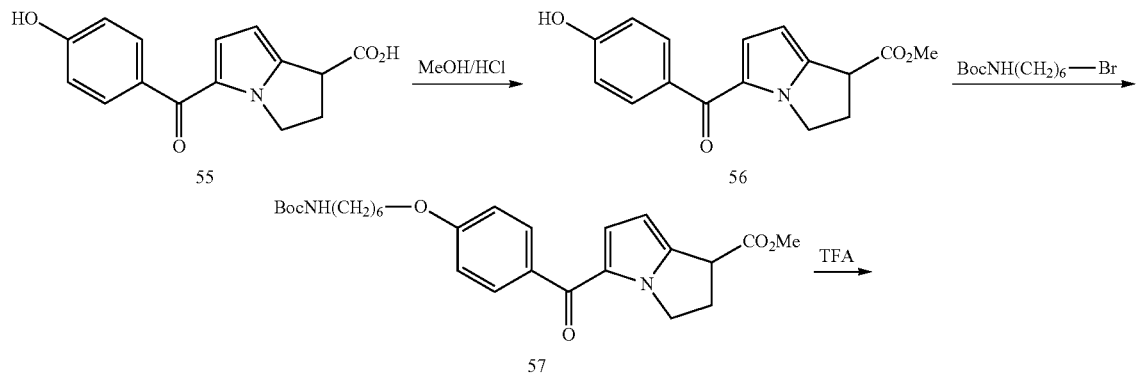

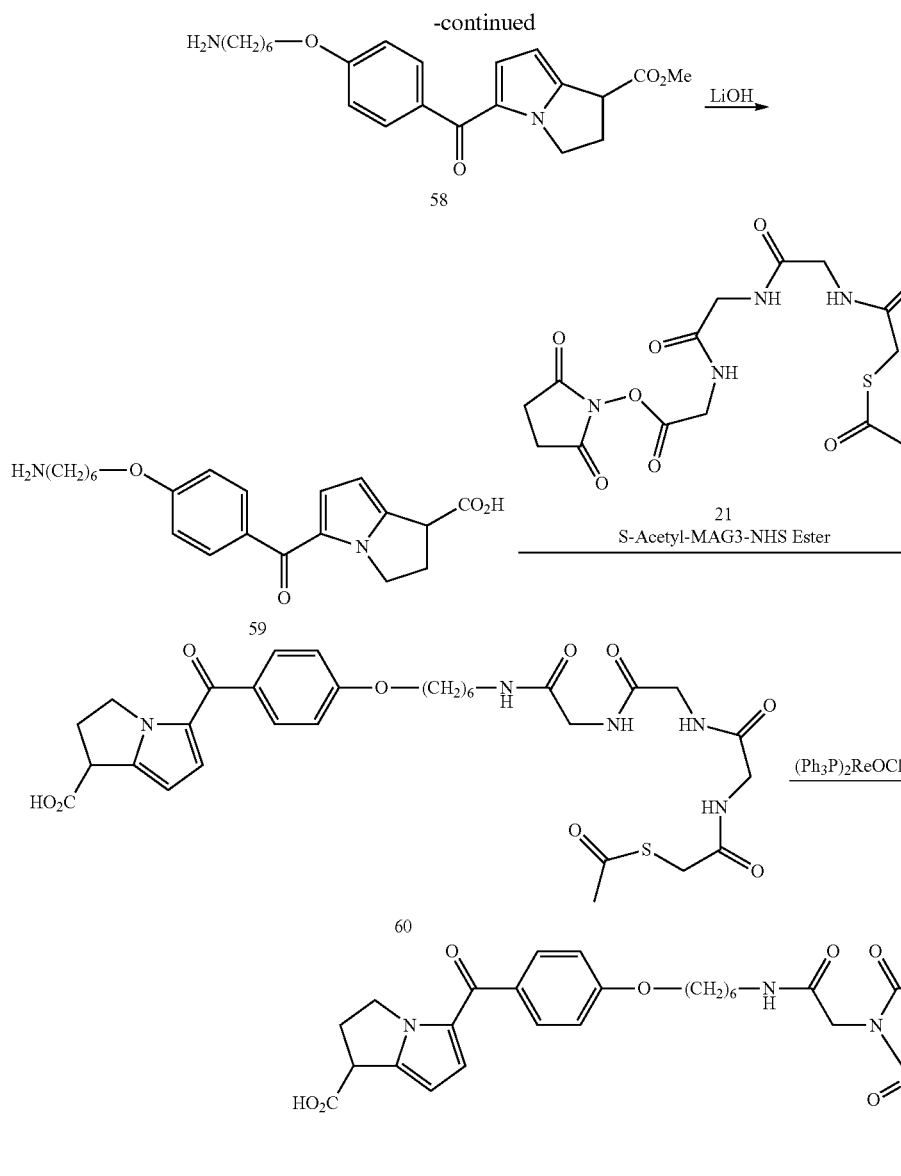
Compound 61 is prepared from compound 55 by first protecting the acid functionality of 55 via acid-catalyzed esterification to give 56, and then using a procedure analogous to that given in Example 7.
Example 15
Synthesis of Ketorolac Ethylenedicysteine Ligand
Part 1
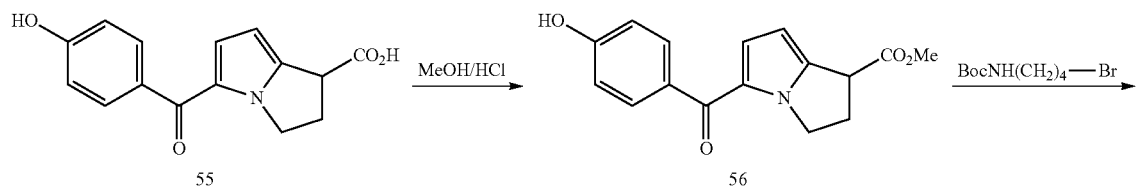

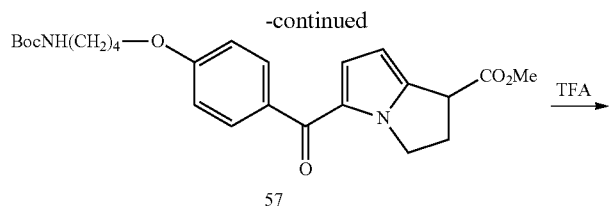
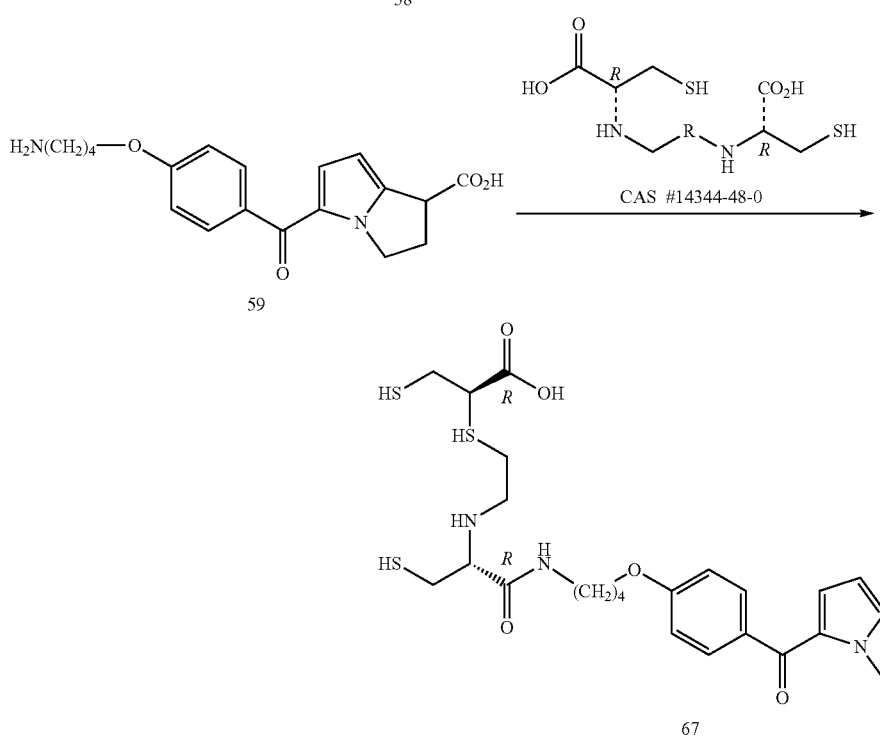
Compound 67 is prepared from compound 55 by preparation of 57 via a procedure analogous to that given in Example 7 using N-Boc-protected 1-amino-4-bromobutane, and then by following the deprotection and coupling steps given in Example 8.
Part 2
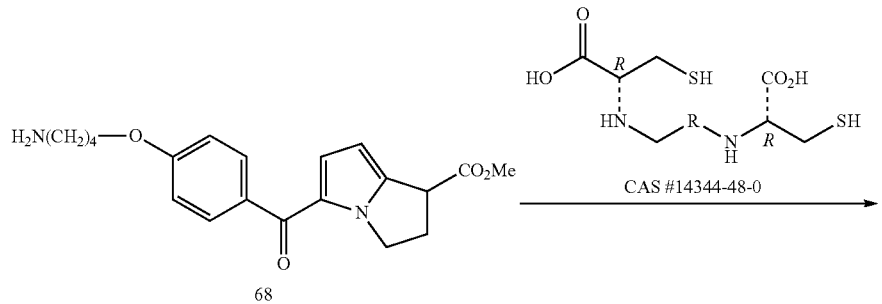

-continued
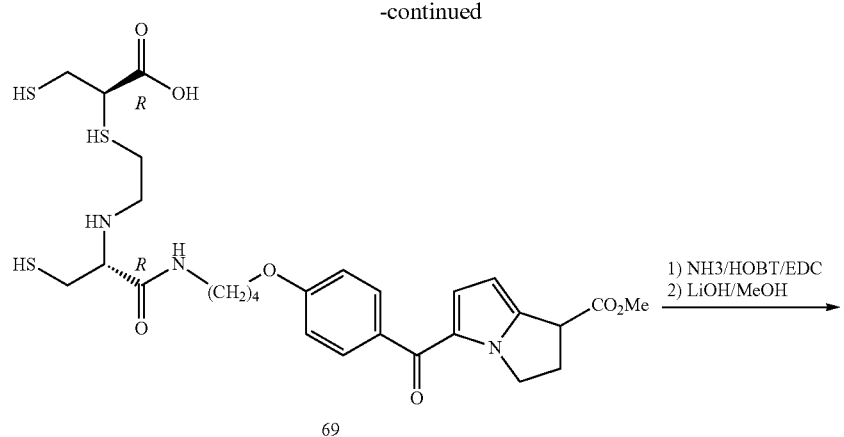
69
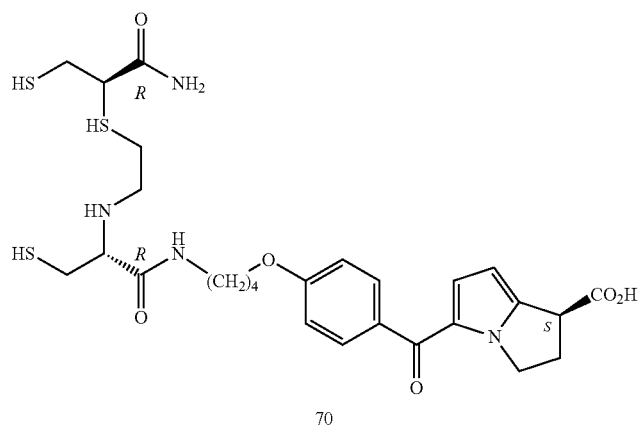
70
Compound 70 is prepared from compound 68 in a similar manner to Part 1 of this Example.
Part 3
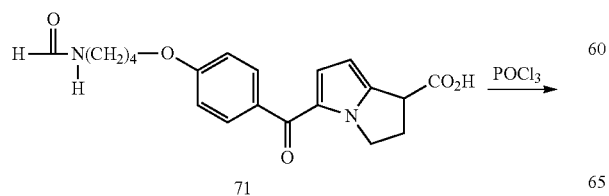
-continued
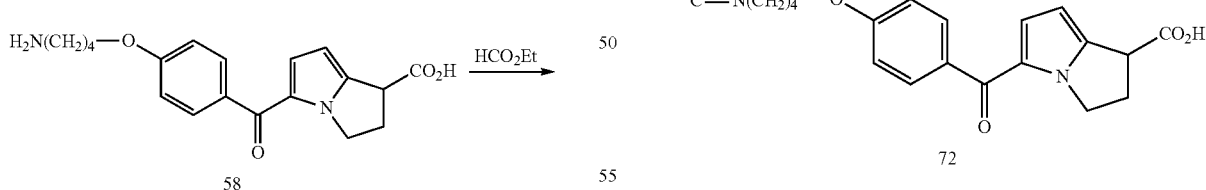
Compound 72 is prepared from compound 58 in a manner similar to Example 8, Part 2.

Example 16
Synthesis of Ketorolac $^{99m}$Tc Complex
Part 1
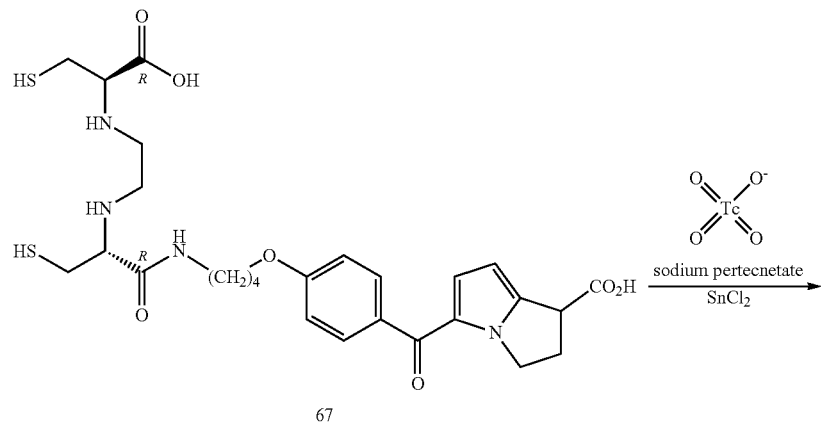
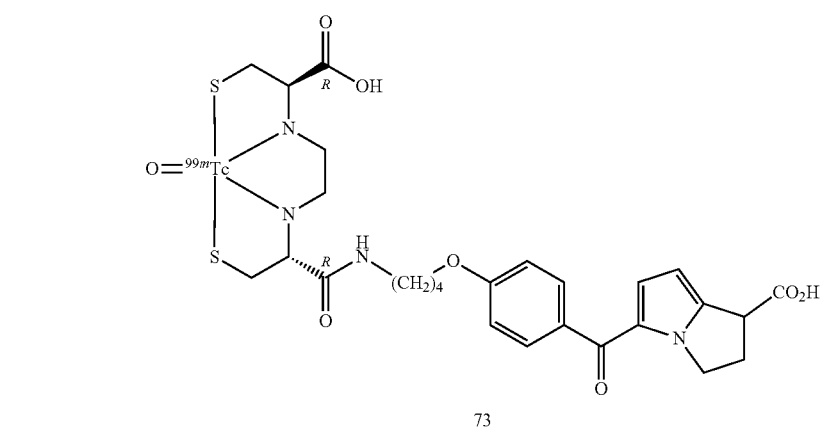
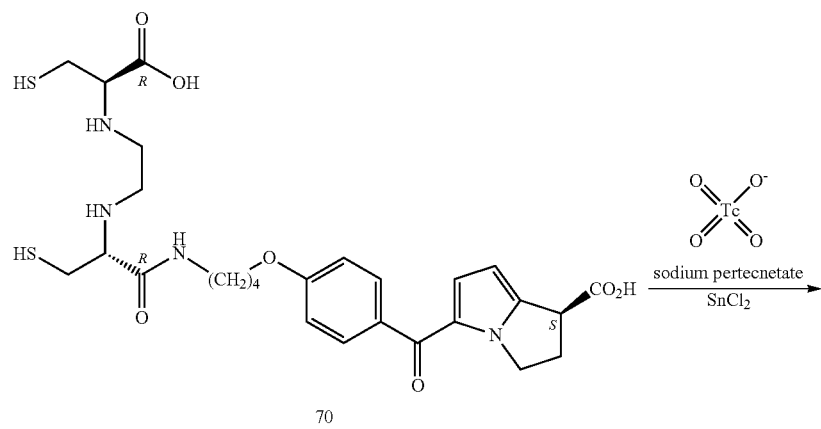

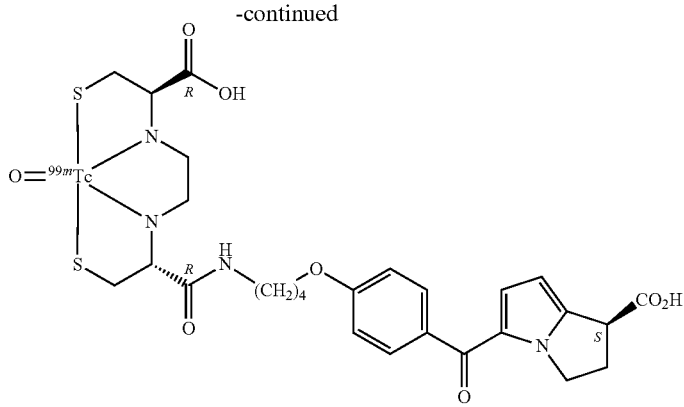
74
Compounds 73 and 74 are prepared from compounds 67 and 70, respectively, by treating with sodium pertechnetate as described in Example 3, substituting 67 and 70, respectively, for compound 2.
Part 2
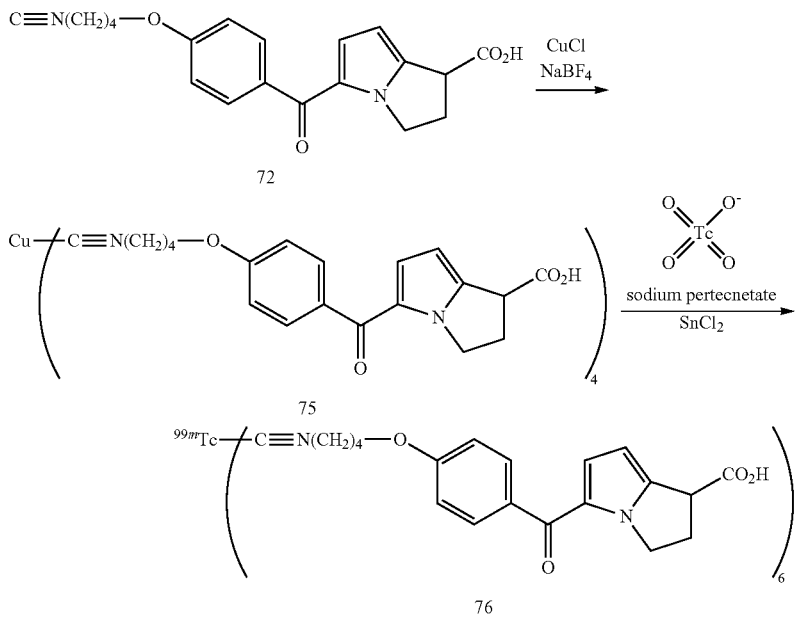
Compound 76 is prepared from compound 72 using procedures analogous to those of Example 2 and Example 3.
Example 17
Synthesis of $^{99m}$Tc Ketorolac MAG3 Analog (77)
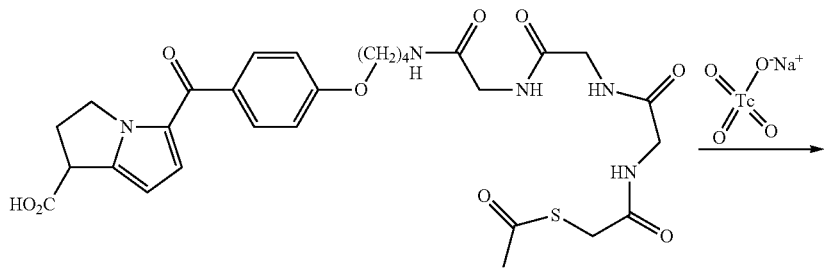

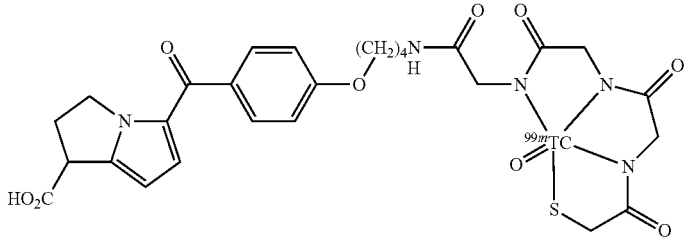
77
Compound 77 is prepared from compound 60 using the procedure of Example 10.
Example 18
Synthesis of $^{99m}$Tc Ketorolac MAG3 Analog (78)
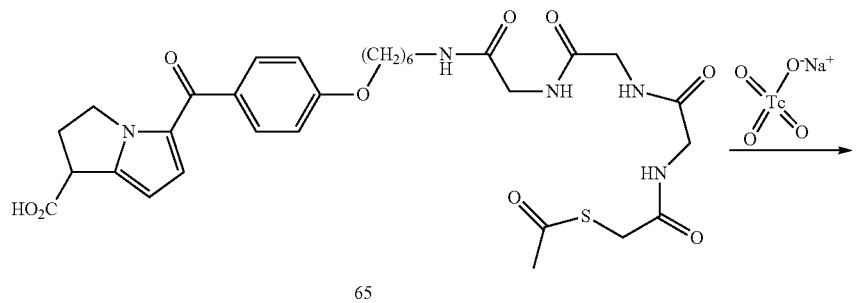
65
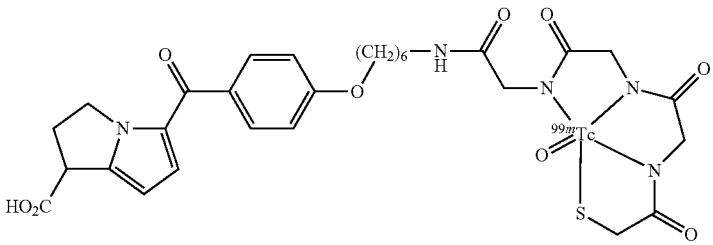
78
Compound 78 is prepared from compound 65 using the procedure of Example 10.
Example 19
Synthesis of Naproxen Butanyl MAG3 Ligand
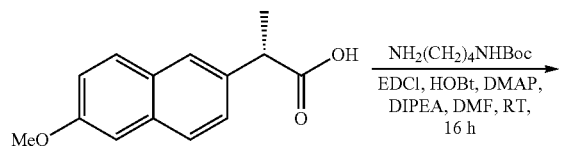

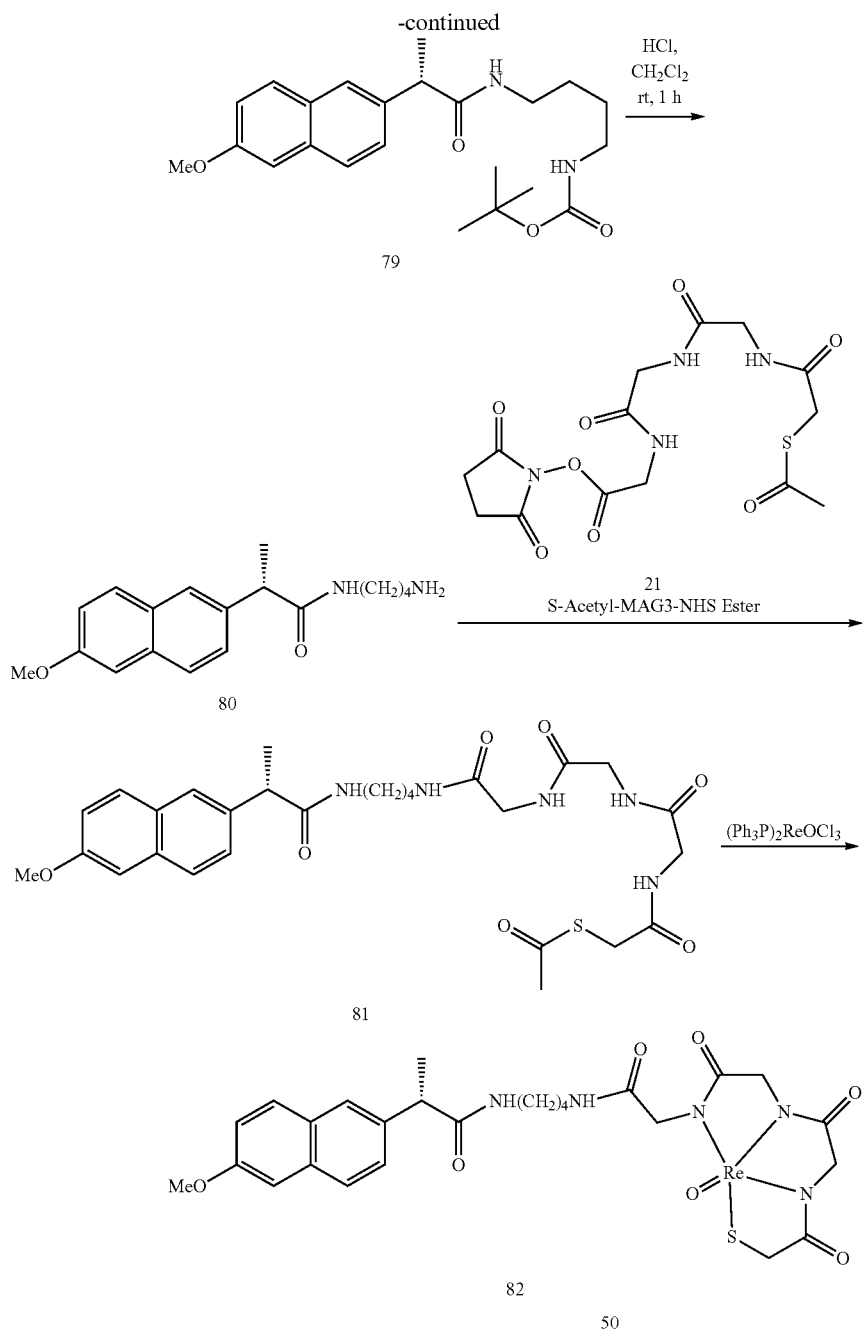
Compound 79 is prepared from compound 3 using N¹-Boc-1,4-diaminobutane. Compound 82 is prepared from compound 79 by using a procedure analogous to the corresponding steps of Example 7.
Example 20
Synthesis of Naproxen Hexanyl Ligand
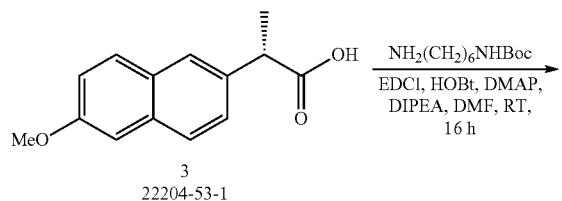

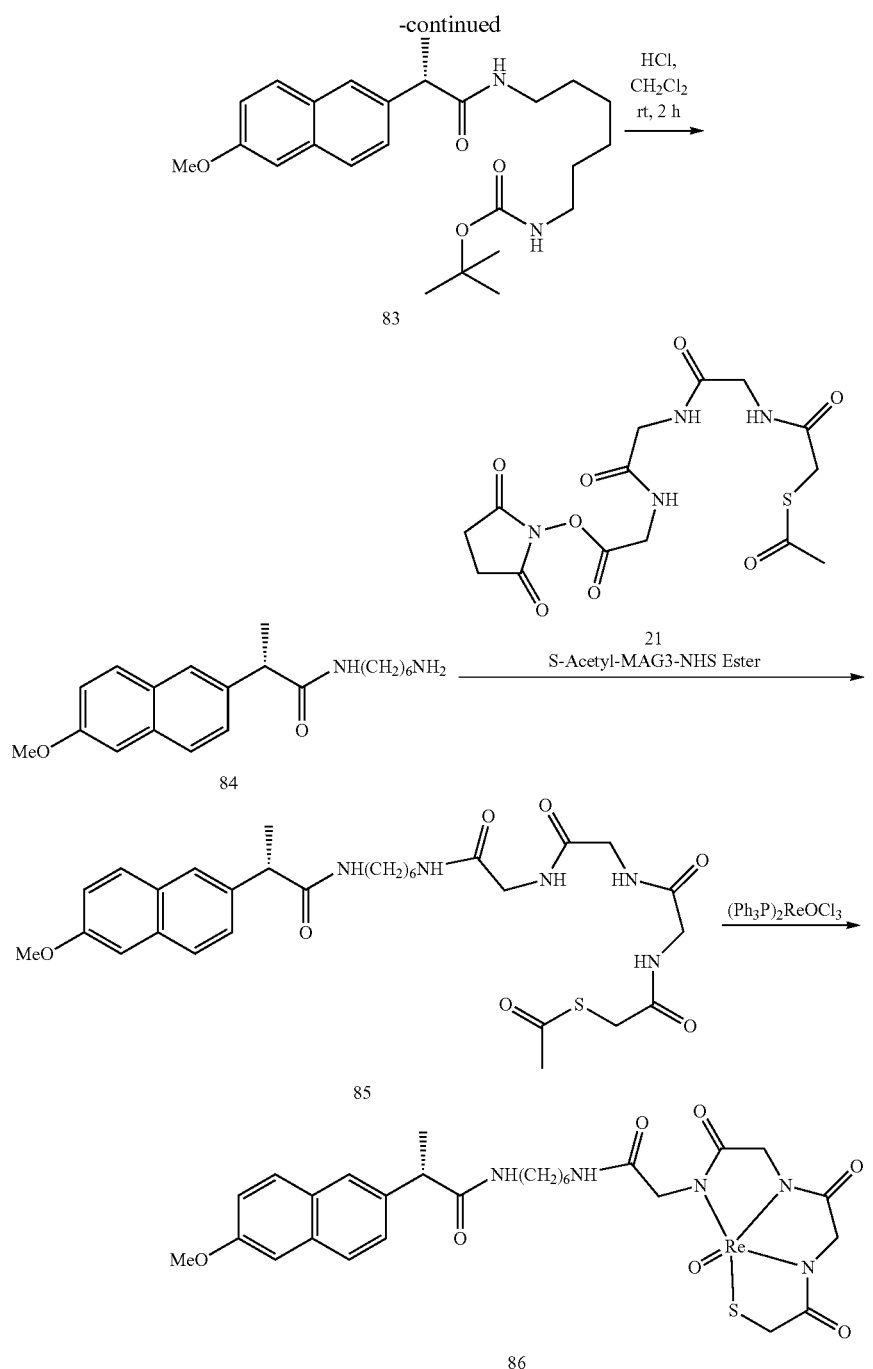
Compound 86 is prepared from compound 3 using the procedure of Example 19.
Example 21
Synthesis of Naproxen Derivatives
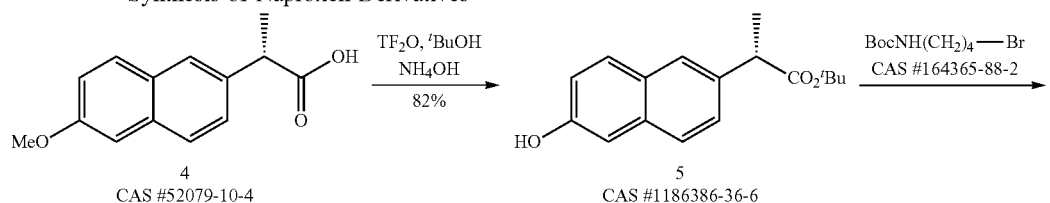

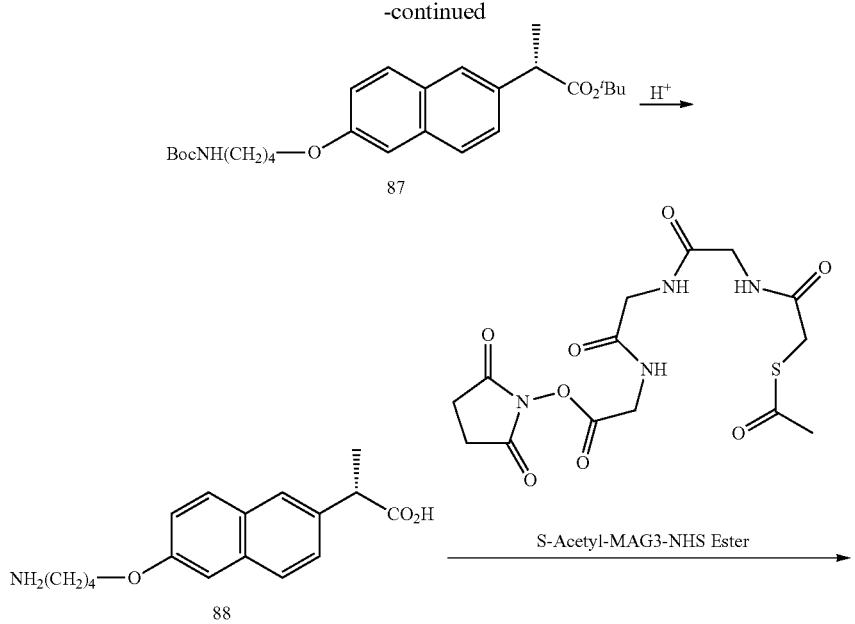

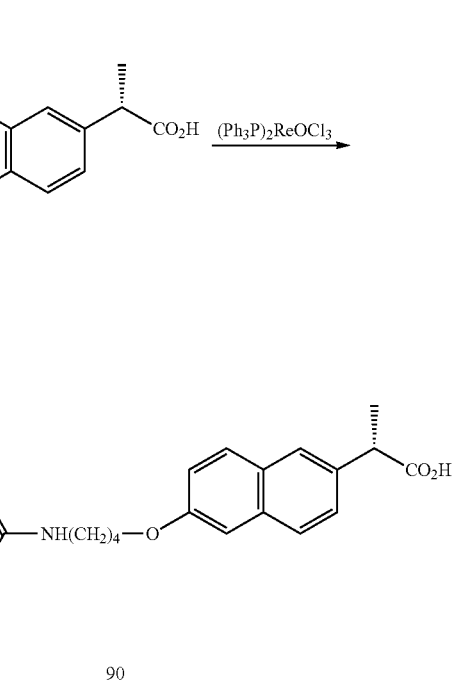

Compound 5 is obtained from the commercial starting material 4 in 82% yield as reported in WO 2013/025790 A2. Alkylation of 5 with $^t$BocNH(CH$_2$)$_4$Br and deprotection of the $^t$BOC amine and the $^t$Bu-ester provides amino acid 88 which can be reacted with NHS—S-Acetyl-MAG3 following the procedure in: Wang Y, et al. Nat Protoc. 2007; 2(4), 972-8 to afford 89. The reagent S-Acetyl-MAG3-NHS ester is available commercially (KeraFAST Inc., Boston, Mass., USA; catalog no. ES1001; see the supplier web site: www.kerafast.com/p-1447-s-acetyl-mag3-nhs-ester.aspx?gclid=Cj0KEQjwur2eBRDtvMS0gIuS-dYBEiQANBPMR3SKY-ABw0HCC08Gud53dB29wsldYYUl3UeQFvVxc_gaAiIA8P8HAQ; see also Winnard P. et al., Nucl Med Biol. 1997 July; 24(5):425-32; Wang Y. et al., Nat. Protoc. 2007; 2(4):972-8; Rusckowski M. et al., Cancer Biotherapy & Radiopharmaceuticals 2007; 22(4): 564-72; and Wang Y. et al., European J Nucl Med Mol Imag 2009; 36(12): 1977-86).

The rhenium-indomethacin derivative 90 is made following a procedure similar to the one described by Ono, et al. Bioorg. Med. Chem. Lett. (2010), 20, 5743-5748. The reagent Trichlorooxobis(triphenylphosphine)rhenium(V) is commercially available (Sigma-Aldrich, Saint Louis, Mo., USA; catalog no. 370193).

Example 22
Synthesis of $^{99m}$Tc Naproxen Butanyl MAG3 Analog (91)
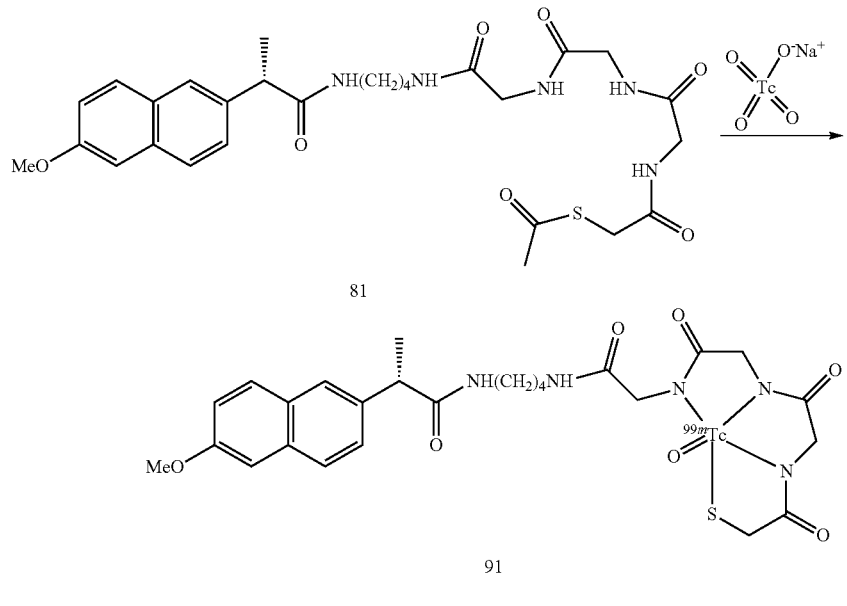
Compound 91 is prepared from compound 81 using the procedure of Example 10.
Example 23
Synthesis of $^{99m}$Tc Naproxen Hexanyl MAG3 Analog (92)
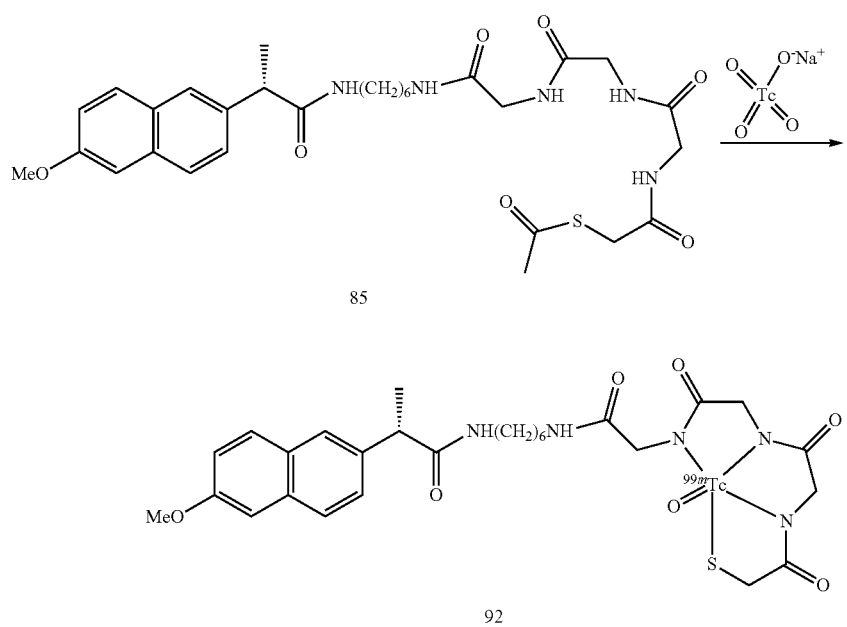
Compound 92 is prepared from compound 85 using the procedure of Example 10.

Example 24
Synthesis of $^{99m}$Tc Naproxen MAG3 Analog (93)
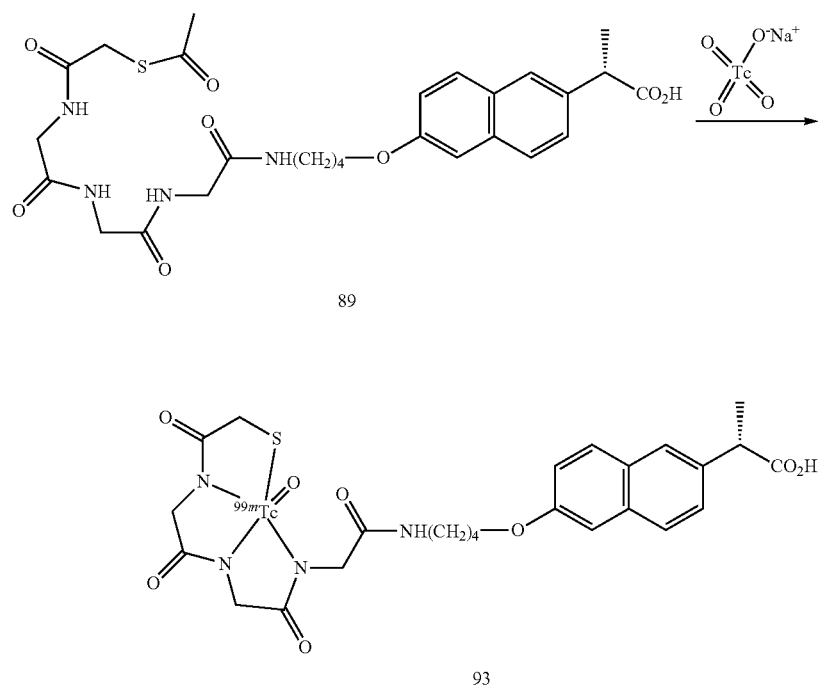
Compound 93 is prepared from compound 89 using the procedure of Example 10.
Example 25
Synthesis of Celecoxib Hexanyl MAG3 Ligand
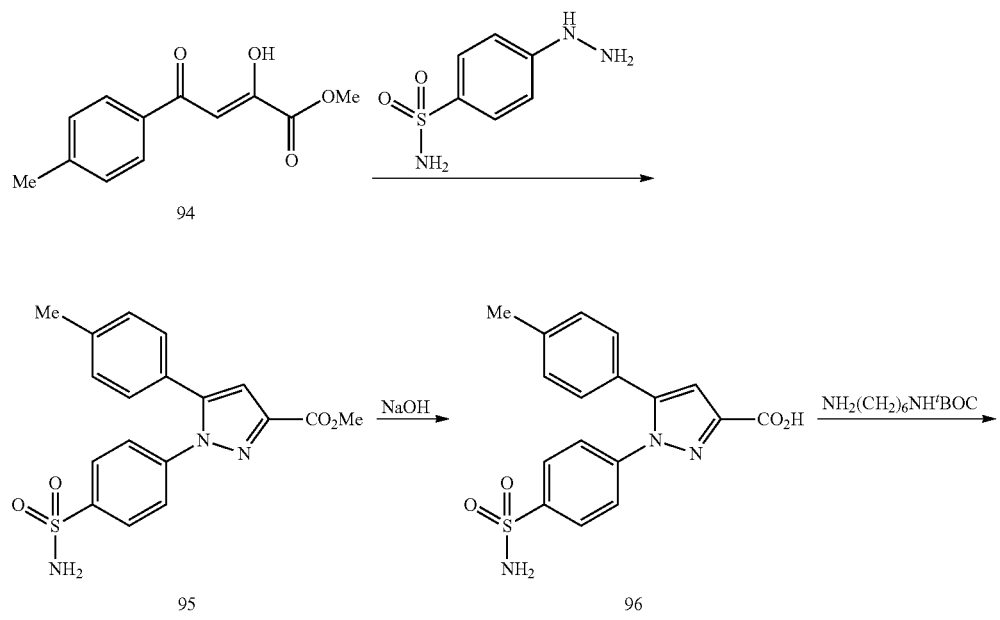

-continued
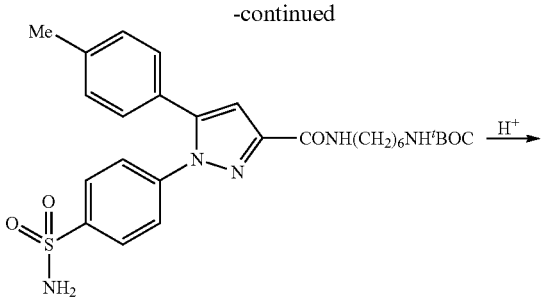
97
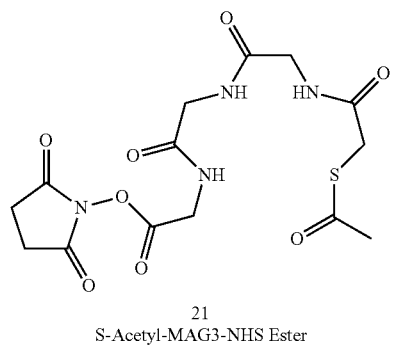
21
S-Acetyl-MAG3-NHS Ester
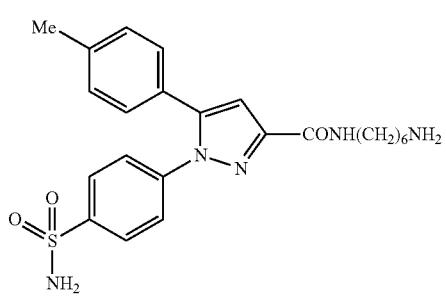
98
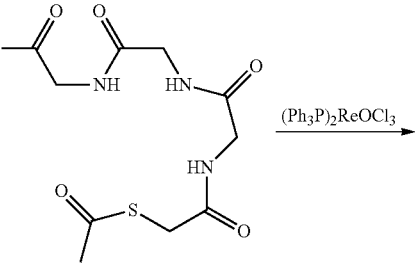
99
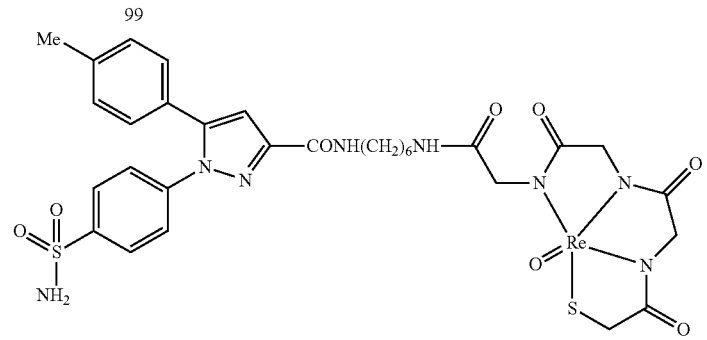
100
The celecoxib analog 95, in which a methyl ester replaces the trifluoromethyl group of celecoxib, is synthesized from 94 using the procedure described in Lill et al., Tetrahedron Letters 54, 6682-6686, (2013). The ester is hydrolyzed to give 96, and coupled with $N^1$-Boc-1,6-diaminohexane to yield 97. The corresponding steps of Example 7 are then followed to yield 100.

Example 26
Synthesis of Celecoxib Butanyl MAG3 Ligand
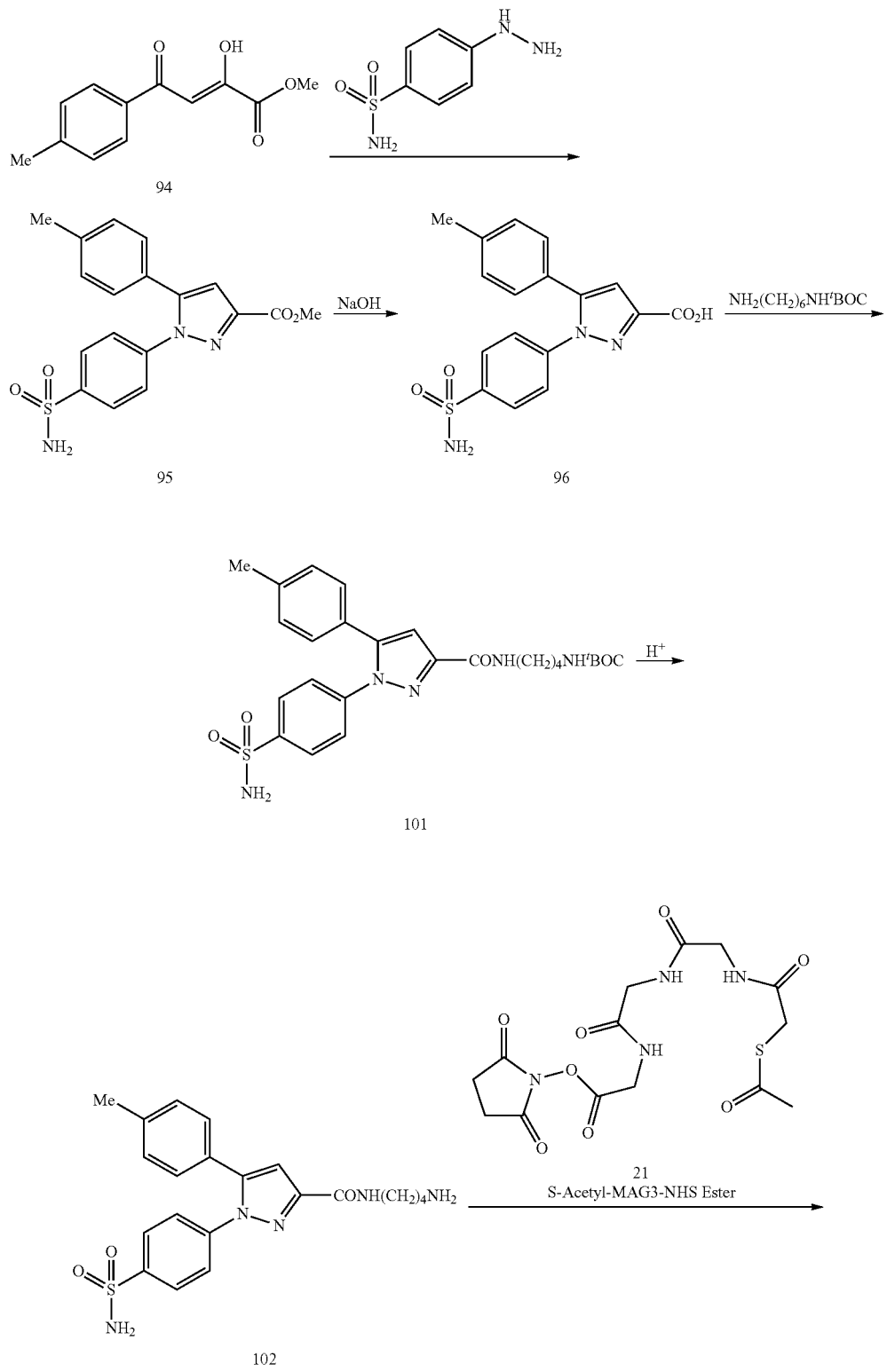

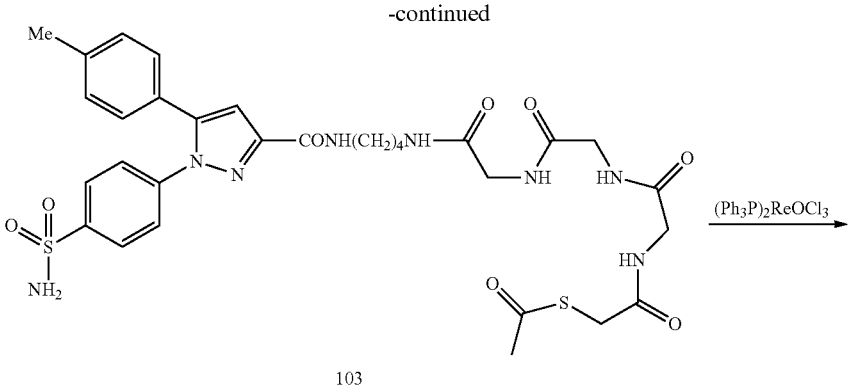
103
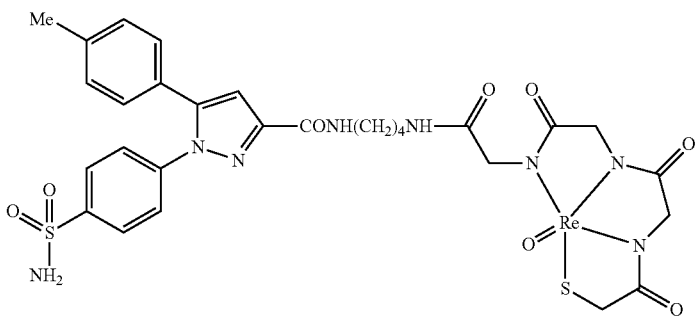
104
Compound 104 is produced as in Example 25, using $N^1$-Boc-1,4-diaminobutane in place of $N^1$-Boc-1,6-diaminohexane.
Example 27
Synthesis of Celecoxib Decanyl MAG3 Ligand
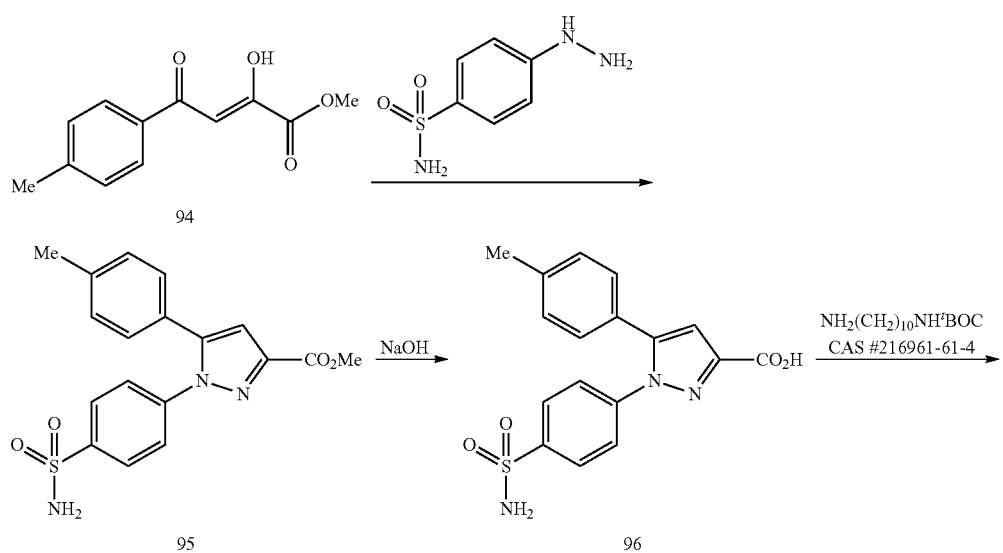

-continued
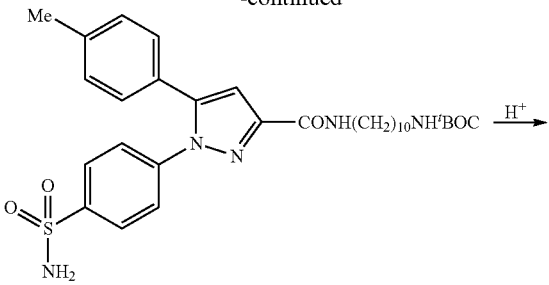
105
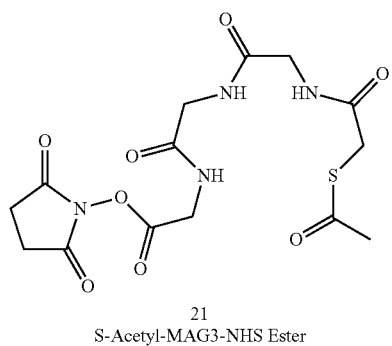
21
S-Acetyl-MAG3-NHS Ester
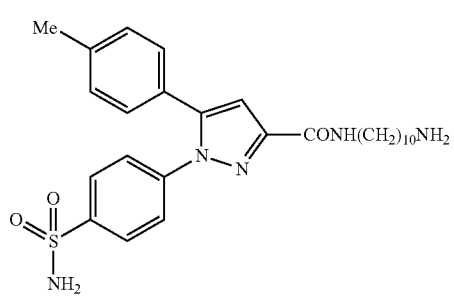
106
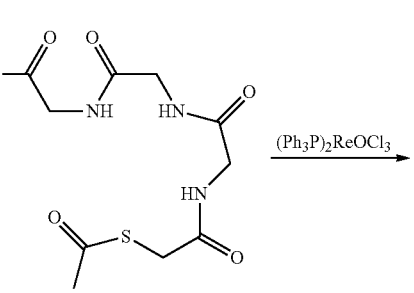
107
(Ph₃P)₂ReOCl₃
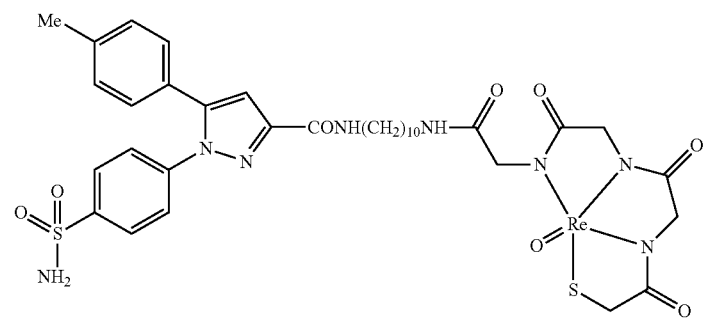
108
Compound 108 is produced as in Example 25, using $N^1$-Boc-1,10-diaminodecane in place of $N^1$-Boc-1,6-diaminohexane.

Example 28
Synthesis of $^{99m}$Tc Celecoxib MAG3 Analog (109)
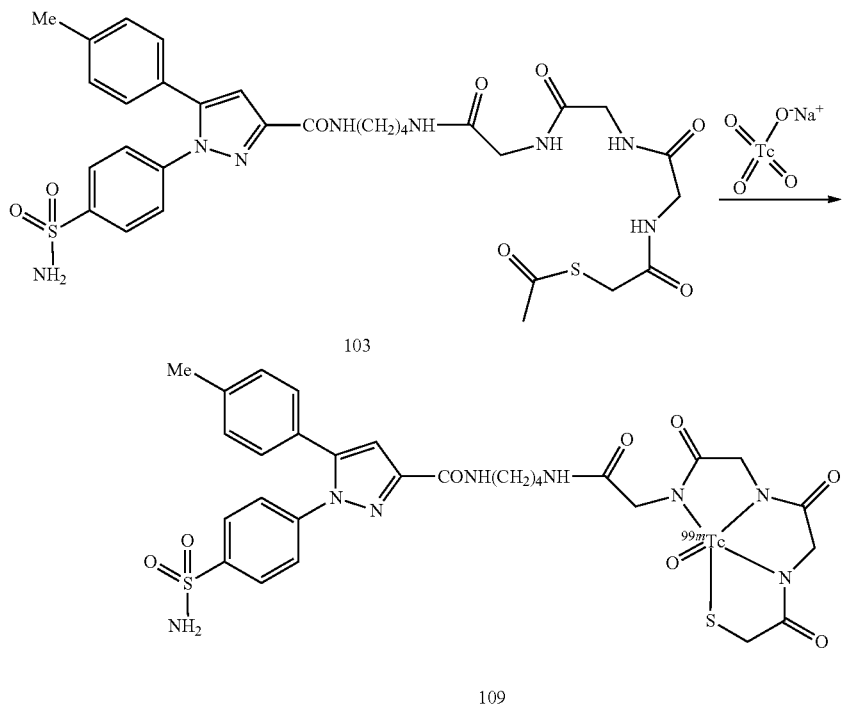
Compound 109 is prepared from compound 103 using the procedure of Example 10.
Example 29
Synthesis of $^{99m}$Tc Celecoxib MAG3 Analog (110)
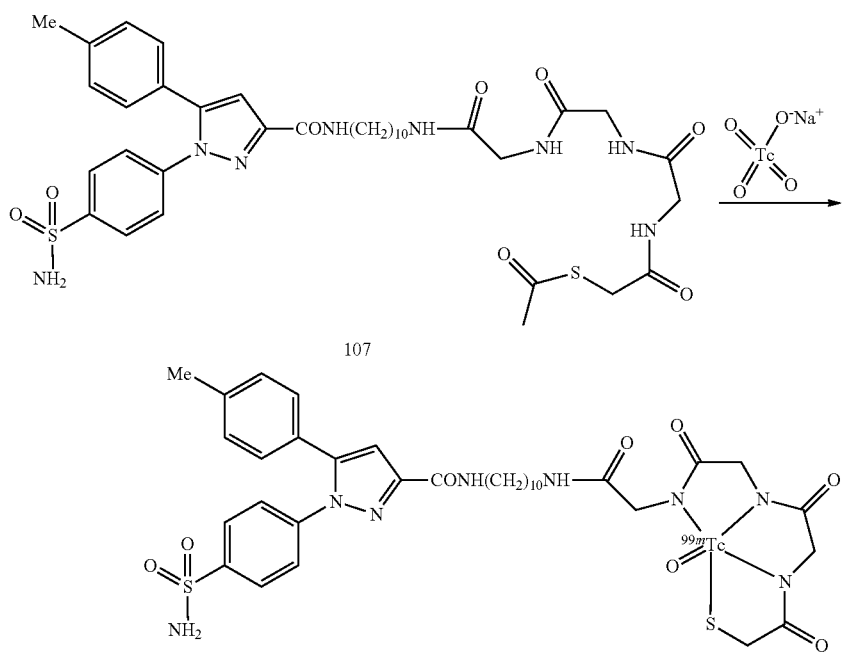

Compound 110 is prepared from compound 107 using the procedure of Example 10.
Example 30
Synthesis of $^{99m}$Tc Celecoxib MAG3 Analog (111)
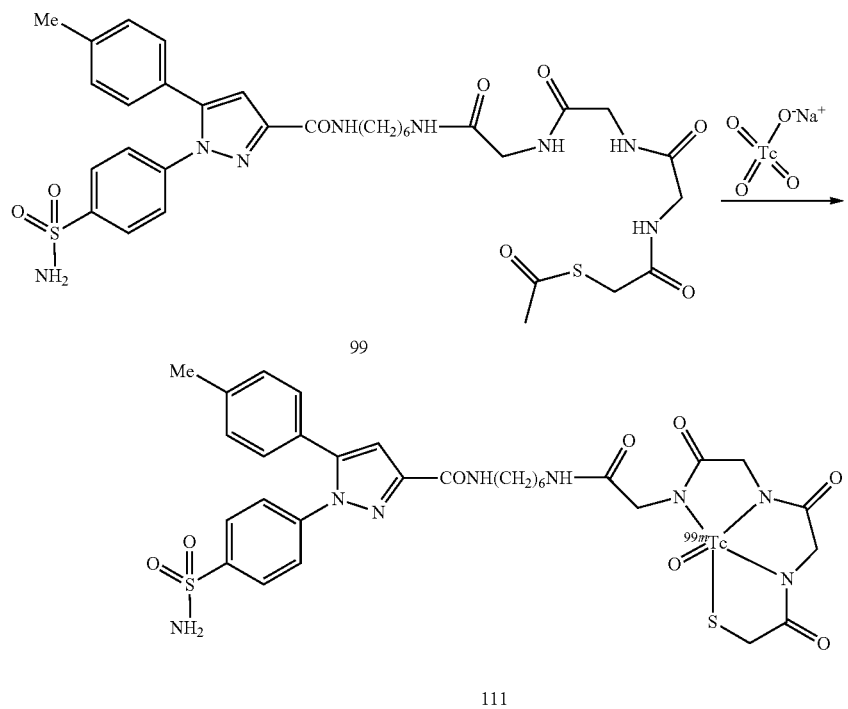
Compound 111 is prepared from compound 99 using the procedure of Example 10.
Example 31
Synthesis of Compound 178
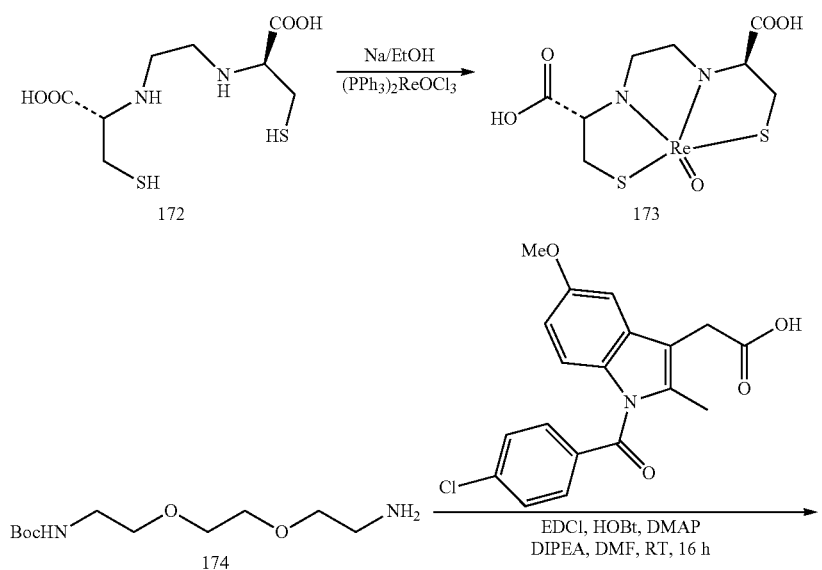

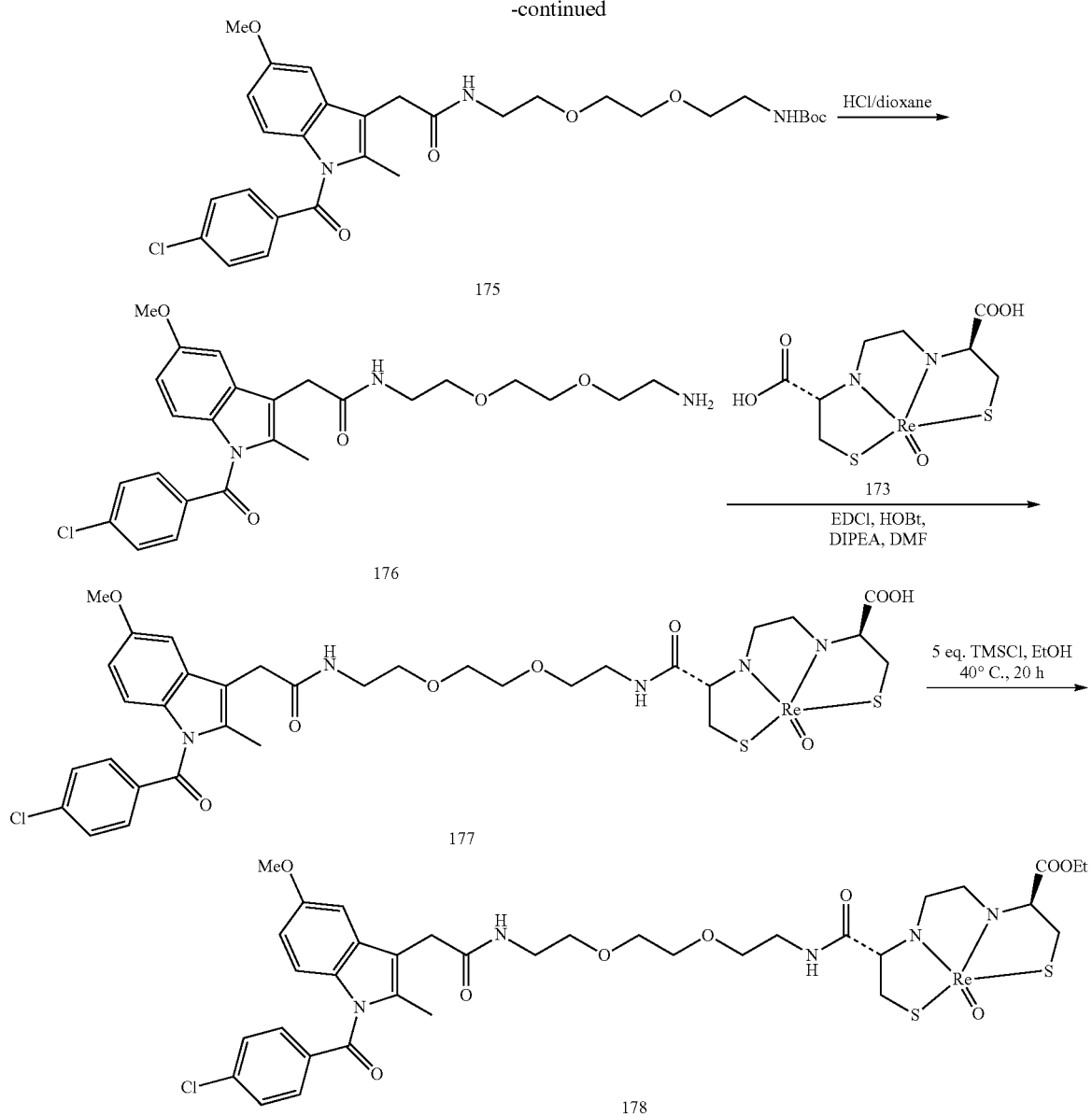

Compound 178 was prepared by the following procedure: S,S-ethylenedicysteine 172 (CAS#14344-48-0) was prepared according to the procedures described in the literature, see e.g. Blondeau, Berse, Gravel, Can. J. Chem. 45, 49-52, (1967); Ratner, Clarke, J. Am. Chem. Soc. 59, 200-206, (1937). Compound 176 was prepared by a procedure similar to the one described for compounds 20 and 25 in examples 5 and 6. 176 is coupled with acid 173 to give the amide 177 as described in example 5. Compound 177 is dissolved in ethanol and treated with 5 eq of TMSCl at 40° C. for 20 h. Solvent is removed and the product is purified by HPLC to give the target compound 178.

$^1$H NMR (400 MHz, CDCl3) δ 7.68 (d, J=8.3 Hz, 2H), 7.49 (d, J=8.3 Hz, 2H), 7.00-6.80 (m, 1H), 6.84-6.47 (m, 2H), 6.16 (s, 1H), 5.90 (s, 1H), 4.67 (d, J=7.1 Hz, 1H), 4.44-4.26 (m, 2H), 3.96-3.76 (m, 5H), 3.65 (s, 2H), 3.61-3.26 (m, 13H), 3.23-3.05 (m, 2H), 3.05-2.83 (m, 2H), 2.38 (s, 3H), 1.34 (t, J=7.1 Hz, 3H). MS (ESI) m/z: 966.1 (M+H$^+$).

The following compounds 179-185 can also be prepared according to the procedure given in Example 31 by replacing tert-butyl 2-(2-(2-aminoethoxy)ethoxy)ethylcarbamate 174 with the appropriate reagent shown in Table 1.

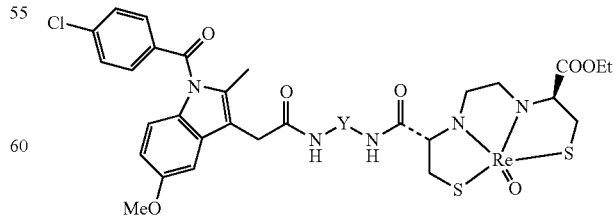

TABLE 1

| Compound | Y = | Reagent used |
|---|---|---|
| 179 | 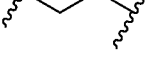 | tert-butyl (2-aminoethyl)carbamate |
| 180 | 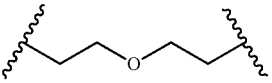 [SMILES: *CCOCC*] | tert-butyl (2-(2-aminoethoxy)ethyl)carbamate |
| 181 |  | tert-butyl (6-aminohexyl)carbamate |
| 182 |  | tert-butyl (7-aminoheptyl)carbamate |
| 183 |  | tert-butyl (8-aminooctanyl)carbamate |
| 184 |  | tert-butyl (2-(2-(2-(2-aminoethoxy)ethoxy)ethoxy)ethyl)carbamate |

Compound 181

$^1$H NMR (400 MHz, CDCl3) δ 7.67 (d, J=7.3 Hz, 2H), 7.49 (d, J=7.1 Hz, 2H), 6.89 (d, J=6.9 Hz, 2H), 6.70 (d, J=8.8 Hz, 1H), 6.48 (s, 1H), 5.72 (s, 1H), 4.67 (s, 1H), 4.36 (s, 2H), 4.08-3.72 (m, 5H), 3.70-3.28 (m, 5H), 3.27-2.87 (m, 5H), 2.78 (s, 1H), 2.37 (s, 3H), 1.51-0.91 (m, 11H). MS (ESI) m/z: 934.1 (M+H$^+$).

Compound 182

$^1$H NMR (400 MHz, CDCl3) δ 7.67 (d, J=8.5 Hz, 2H), 7.50 (t, J=9.2 Hz, 2H), 6.90 (d, J=9.1 Hz, 2H), 6.70 (dd, J=9.0, 2.5 Hz, 1H), 6.57 (s, 1H), 5.69 (d, J=26.8 Hz, 2H), 4.67 (d, J=6.1 Hz, 1H), 4.43-4.26 (m, 2H), 4.03-3.75 (m, 5H), 3.70-3.33 (m, 5H), 3.32-3.10 (m, 4H), 3.03 (dd, J=12.9, 6.4 Hz, 2H), 2.75 (s, 1H), 2.37 (s, 3H), 1.32 (dd, J=41.6, 34.4 Hz, 13H). MS (ESI) m/z: 948.1 (M+H$^+$).

Compound 183

$^1$H NMR (400 MHz, CDCl3) δ 7.67 (d, J=8.4 Hz, 2H), 7.50 (t, J=8.6 Hz, 2H), 7.00-6.83 (m, 2H), 6.70 (dd, J=9.0, 2.4 Hz, 1H), 6.58 (s, 1H), 5.73 (s, 1H), 5.62 (s, 1H), 4.68 (d, J=7.1 Hz, 1H), 4.37 (qd, J=10.7, 3.5 Hz, 2H), 3.99-3.76 (m, 5H), 3.63 (s, 2H), 3.59-3.32 (m, 3H), 3.30-2.86 (m, 6H), 2.84-2.65 (m, 1H), 2.37 (s, 3H), 1.55-0.93 (m, 15H). MS (ESI) m/z: 962.1 (M+H$^+$).

Compound 185

185

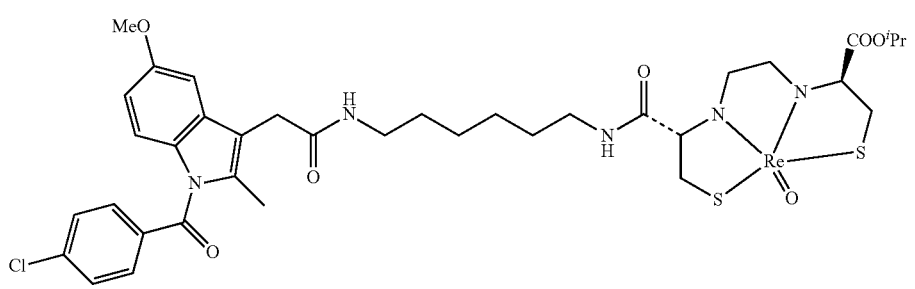

Compound 185 was prepared by a procedure similar to the one described in Example 31 by replacing ethanol in the last step with isopropanol (Propan-2-ol).
$^{1}$H NMR (400 MHz, CDCl3) δ 7.67 (d, J=7.8 Hz, 2H), 7.49 (d, J=8.0 Hz, 2H), 6.89 (d, J=7.1 Hz, 2H), 6.70 (d, J=8.3 Hz, 1H), 6.58 (s, 1H), 5.73 (s, 2H), 5.28 (d, J=57.0 Hz, 2H), 4.68 (s, 1H), 4.01-3.75 (m, 5H), 3.74-3.34 (m, 5H), 3.32- 2.93 (m, 5H), 2.74 (s, 1H), 2.38 (s, 3H), 2.02 (s, 1H), 1.48-1.13 (m, 15H). MS (ESI) m/z: 474.7[(M+2H$^{+}$)/2]
Example 32
Synthesis of Compound 190
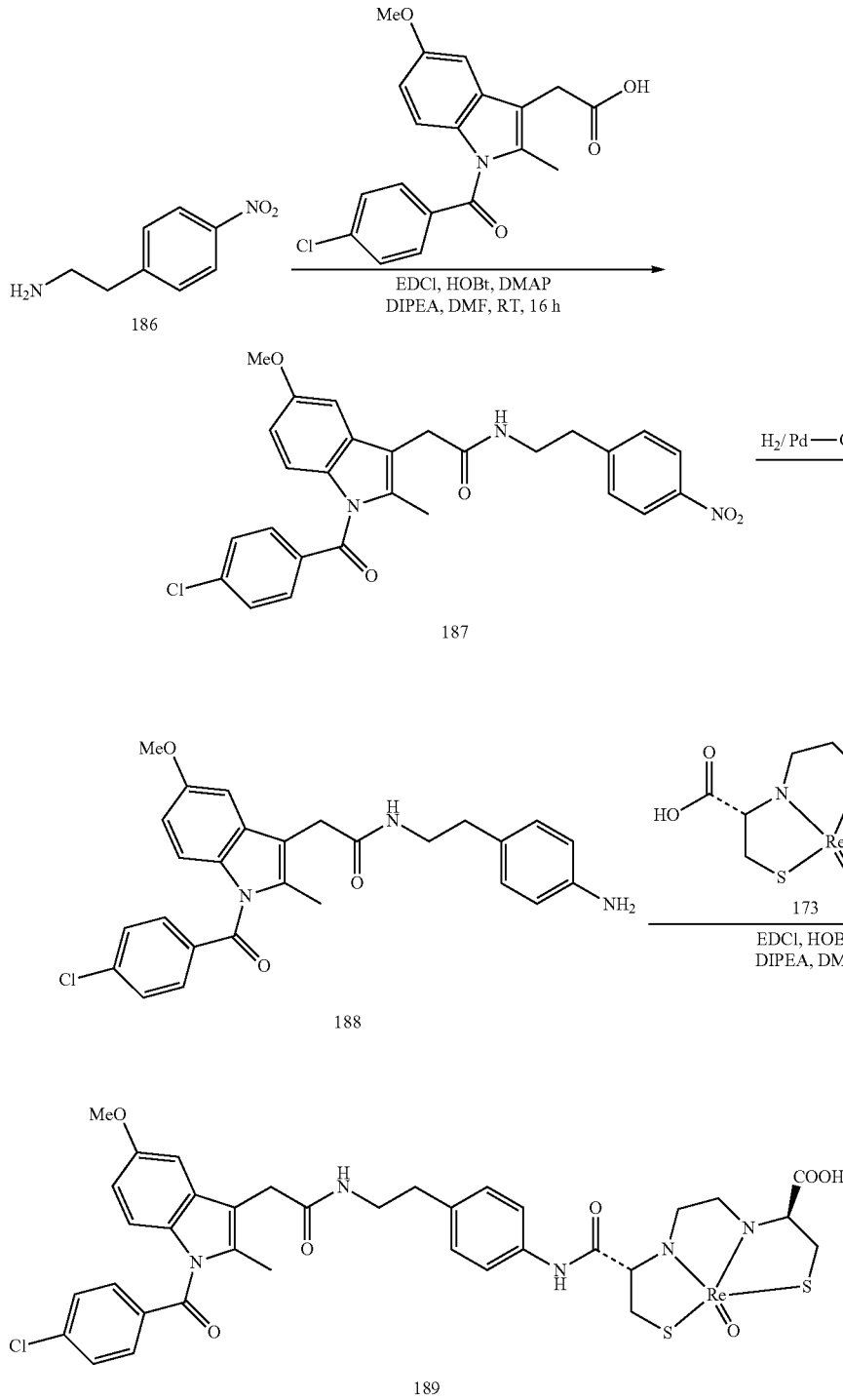

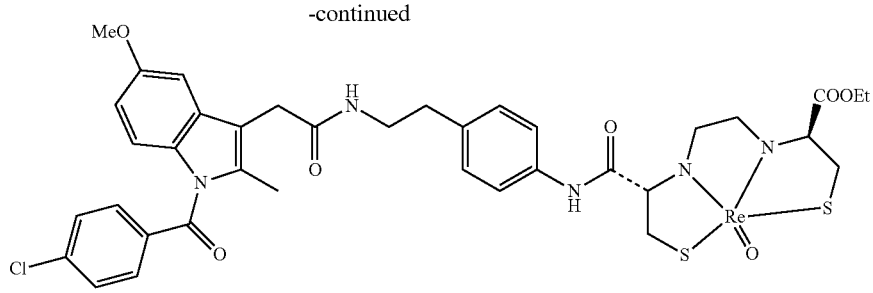
186 is coupled with indomethacin to give the amide 187 as described in example 5. Compound 187 is dissolved in methanol and hydrogenated over Pd/C to give compound 188. Compound 188 is then coupled with acid 173 and esterified to give compound 190 as described in example 31.
Example 33
Synthesis of Compound 193
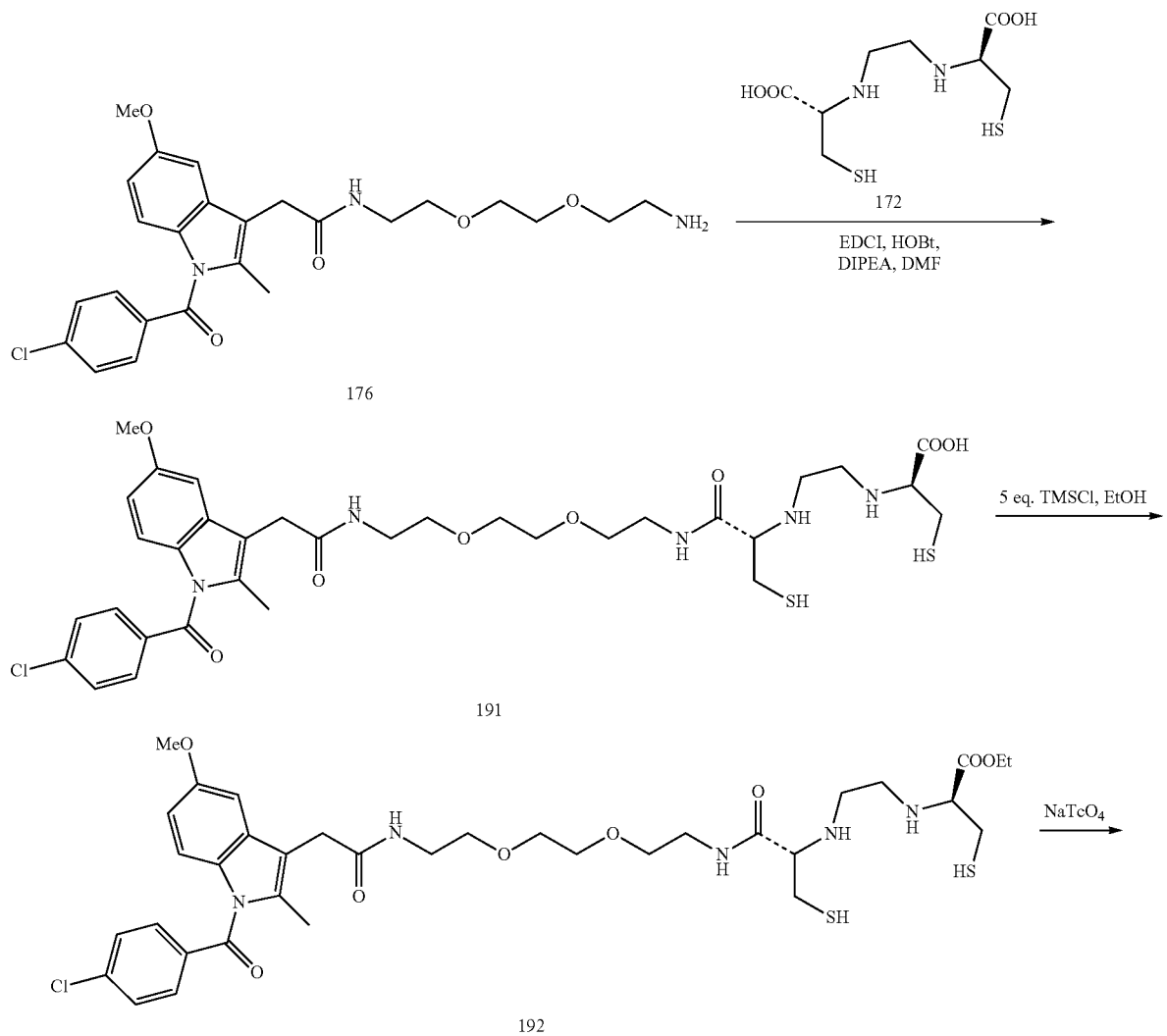

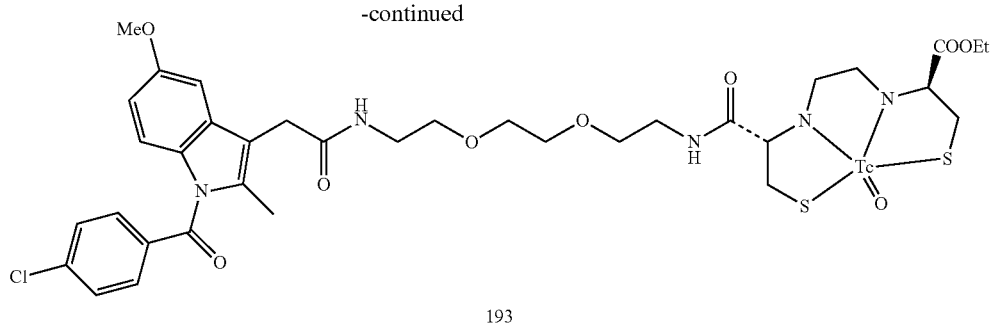

193

Compound 176 is synthesized as described in Example 31. 176 is coupled with S,S-ethylenedicysteine 172 (CAS#14344-48-0) according to literature procedures, see e.g. Yang et al., US 2006/6692724. The ethylester 192 is obtained by treating 191 with EtOH/TMSCl or EtOH/HCl. Compound 193 is prepared from compound 192 by treating with sodium pertechnetate as described in Example 3.

The following compounds 194-201 can also be prepared according to the procedure given in Example 33 by replacing compound 176 with the appropriate intermediate (synthesis described in examples 31-32.

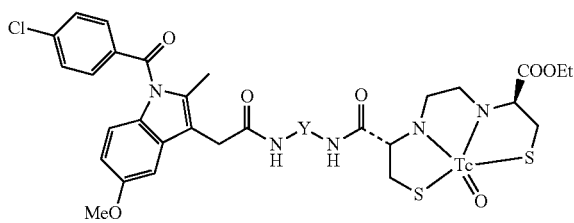

| Example | Y = |
|---|---|
| 194 | 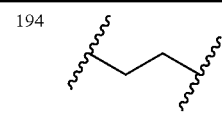 |
| 195 | 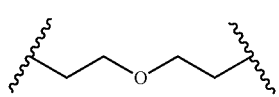 [SMILES: *CCOCC*] |
| 196 | 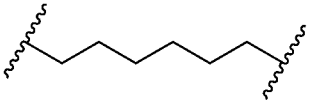 [SMILES: *CCCCCC*] |
| 197 | 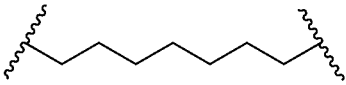 |
| 198 | 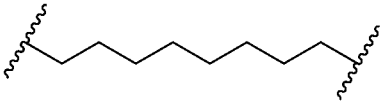 [SMILES: *CCCCCCCC*] |
| 199 | 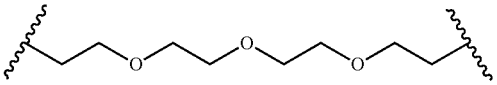 [SMILES: *CCOCCOCCOCC*] |
| 200 |  |
| 201 | 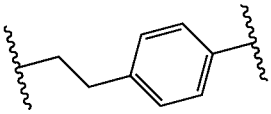 [SMILES: *CCc1ccc(*)cc1] |

Example 34

Synthesis of Compound 204

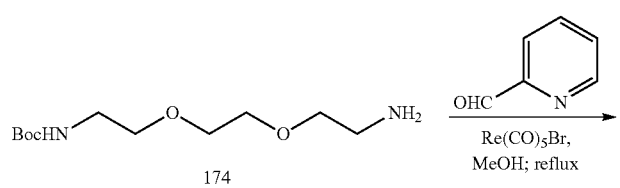

174

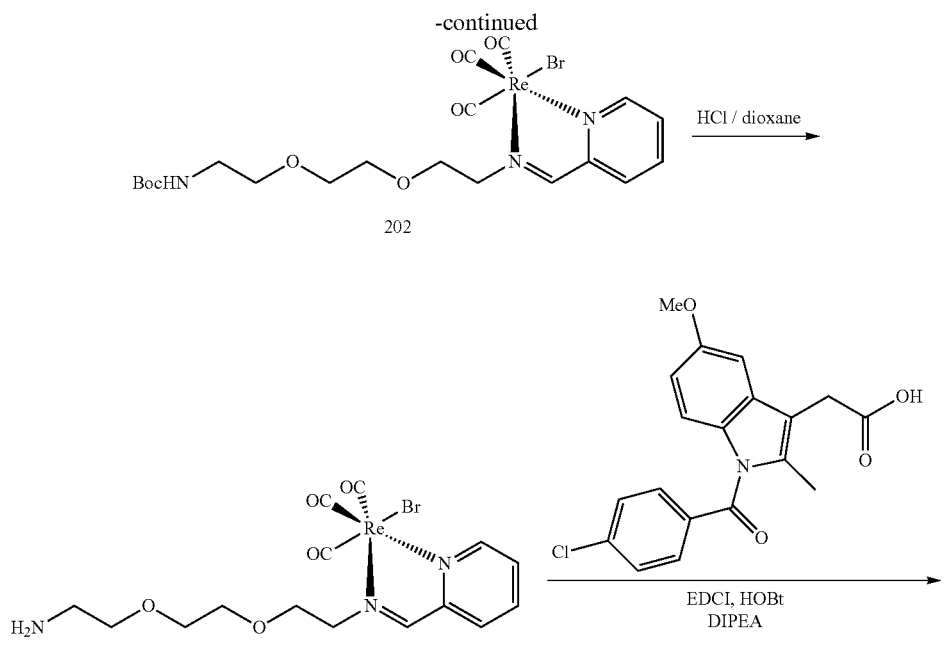

Compound 204 was prepared by the following procedure:

A solution of tert-butyl 2-(2-(2-aminoethoxy)ethylcarbamate 174 (50 mg, 0.2 mmol), Re(CO)$_5$Br (82 mg, 0.2 mmol), and picolinaldehyde (22 mg, 0.2 mmol) in methanol (20 ml) was stirred at 80° C. for 12 h under nitrogen. The reaction mixture was then concentrated and purified by column chromatography to give compound 202 (110 mg, 79%).

A solution of HCl in dioxane (4N, 10 ml) and compound 202 (110 mg, 0.16 mmol) was stirred at rt for 2 h, and then concentrated in vacuo to give crude product 203 (100 mg), which was used directly in the next step.

To a solution of indomethacin (57 mg, 0.16 mmol) in DCM (20 ml) was added HOBt (22 mg, 0.16 mmol), EDCI (31 mg, 0.16 mmol), and DIEA (62 mg, 0.48 mmol). The mixture was stirred at RT for 0.5 h, after which 203 (100 mg, 0.16 mmol) was added. The reaction mixture was stirred at RT overnight. The mixture was then diluted with water (30 ml) and extracted with EtOAc (25 ml×3). The combined organic layers were washed with brine (15 ml×2), dried over Na$_2$SO$_4$, filtered and the filtrate was concentrated and purified by prep-HPLC (Column: Acquity BEH C18, Waters Corp.; solvent A: water, solvent B: MeCN) to give the desired product 204.

$^1$H NMR (400 MHz, CDCl3) δ 9.00 (d, J=5.3 Hz, 1H), 8.66 (s, 1H), 8.09-7.97 (m, 1H), 7.88 (d, J=7.6 Hz, 1H), 7.67 (d, J=8.5 Hz, 2H), 7.60-7.44 (m, 3H), 6.98-6.84 (m, 2H), 6.69 (dd, J=9.0, 2.5 Hz, 1H), 6.00 (s, 1H), 4.32-4.11 (m, 2H), 4.04-3.89 (m, 2H), 3.86-3.76 (m, 3H), 3.61 (s, 2H), 3.57-3.38 (m, 6H), 3.38-3.22 (m, 2H), 2.39 (d, J=7.7 Hz, 3H). MS (ESI) m/z: 927.2 (M+H$^+$).

The following compounds 205-211 can also be prepared according to the procedure given in Example 34 by replacing tert-butyl 2-(2-(2-aminoethoxy)ethoxy)ethylcarbamate 174 with the appropriate reagent given in Table 2.

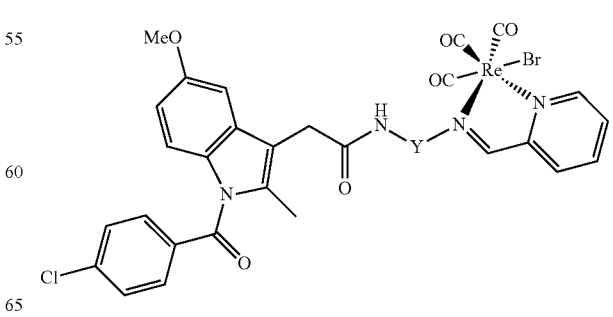

TABLE 2

| Compound | Y = | Reagent used |
|---|---|---|
| 205 | (ethylene linker) | tert-butyl (2-aminoethyl)carbamate |
| 206 | (CH₂CH₂-O-CH₂CH₂) | tert-butyl (2-(2-aminoethoxy)ethyl)carbamate |
| 207 | (hexyl chain) | tert-butyl (6-aminohexyl)carbamate |
| 208 | (heptyl chain) | tert-butyl (7-aminoheptyl)carbamate |
| 209 | (octyl chain) | tert-butyl (8-aminooctanyl)carbamate |
| 210 | (PEG3 chain with three O) | tert-butyl (2-(2-(2-(2-aminoethoxy)ethoxy)ethoxy)ethyl) carbamate |
| 211 | (para-xylylene) | tert-butyl (4-(aminomethyl)benzyl)carbamate |

Compound 207

$^1$H NMR (400 MHz, DMSO-d$_6$) δ 9.19 (s, 1H), 9.03 (d, J=5.0 Hz, 1H), 8.43-8.20 (m, 2H), 8.06 (s, 1H), 7.86-7.73 (m, 1H), 7.66 (dd, J=18.1, 8.4 Hz, 4H), 7.13 (s, 1H), 6.93 (d, J=8.9 Hz, 1H), 6.70 (d, J=9.0 Hz, 1H), 4.29-4.07 (m, 1H), 4.06-3.92 (m, J=6.5 Hz, 2H), 3.75 (s, 3H), 3.48 (s, 2H), 3.17 (d, J=5.2 Hz, 2H), 2.22 (s, 3H), 1.90 (s, 2H), 1.52-1.14 (m, J=36.9 Hz, 6H). MS (ESI) m/z: 851.2 (M+H$^+$).

Compound 208

$^1$H NMR (400 MHz, CDCl3) δ 9.04 (d, J=5.1 Hz, 1H), 8.71 (s, 1H), 8.05 (dd, J=7.7, 6.5 Hz, 1H), 7.92 (d, J=7.6 Hz, 1H), 7.67 (d, J=8.5 Hz, 2H), 7.58-7.53 (m, 1H), 7.50 (t, J=8.0 Hz, 2H), 6.87 (t, J=5.3 Hz, 2H), 6.69 (dd, J=9.0, 2.5 Hz, 1H), 5.59 (s, 1H), 4.37-4.14 (m, 1H), 4.07-3.97 (m, 1H), 3.94-3.71 (m, 3H), 3.62 (s, 2H), 3.20 (dd, J=13.0, 6.7 Hz, 2H), 2.37 (s, 3H), 2.15-1.92 (m, 2H), 1.52-1.14 (m, 8H). MS (ESI) m/z: 910.2 (M+H$^+$).

Compound 209

$^1$H NMR (400 MHz, CDCl3) δ 9.04 (d, J=5.1 Hz, 1H), 8.70 (s, 1H), 8.12-8.00 (m, 1H), 7.90 (d, J=7.7 Hz, 1H), 7.67 (d, J=8.4 Hz, 2H), 7.61-7.53 (m, 1H), 7.49 (d, J=8.4 Hz, 2H), 6.87 (t, J=5.7 Hz, 2H), 6.70 (dd, J=9.0, 2.5 Hz, 1H), 5.59 (t, J=5.8 Hz, 1H), 4.34-4.12 (m, 1H), 4.02 (dt, J=11.8, 7.4 Hz, 1H), 3.82 (s, 3H), 3.62 (s, 2H), 3.34-3.13 (m, 2H), 2.38 (s, 3H), 2.23-1.85 (m, 2H), 1.47-1.11 (m, 10H). MS (ESI) m/z: 923.2 (M+H$^+$).

Compound 210

$^1$H NMR (400 MHz, CDCl3) δ 9.08-8.96 (m, 1H), 8.75 (s, 1H), 8.01 (td, J=7.8, 1.4 Hz, 1H), 7.88 (d, J=7.7 Hz, 1H), 7.67 (d, J=8.5 Hz, 2H), 7.54 (d, J=9.5, 3.8 Hz, 1H), 7.49 (d, J=8.5 Hz, 2H), 7.01-6.81 (m, 2H), 6.68 (dd, J=9.0, 2.5 Hz, 1H), 6.07 (s, 1H), 4.25 (ddd, J=16.8, 16.2, 8.2 Hz, 2H), 4.03 (dt, J=8.7, 6.3 Hz, 2H), 3.83 (d, J=11.1 Hz, 3H), 3.70-3.59 (m, 3H), 3.55-3.34 (m, 8H). MS (ESI) m/z: 971.2 (M+H$^+$).

Compound 211

$^1$H NMR (400 MHz, DMSO-d$_6$) δ 9.37 (s, 1H), 9.01 (d, J=5.2 Hz, 1H), 8.55 (t, J=5.7 Hz, 1H), 8.31 (d, J=3.2 Hz, 2H), 7.77 (dd, J=8.8, 5.2 Hz, 1H), 7.66 (dd, J=24.0, 8.4 Hz, 4H), 7.36 (d, J=7.9 Hz, 2H), 7.27 (d, J=7.9 Hz, 2H), 7.14 (d, J=2.0 Hz, 1H), 6.96 (d, J=9.0 Hz, 1H), 6.71 (dd, J=8.9, 2.1 Hz, 1H), 5.76 (s, 2H), 5.37 (d, J=13.6 Hz, 1H), 5.09 (d, J=13.3 Hz, 1H), 4.31 (d, J=5.6 Hz, 2H), 3.73 (s, 3H), 3.59 (s, 2H), 2.22 (s, 3H). MS (ESI) m/z: 915.2 (M+H$^+$).

The following compounds 212-219 can also be prepared according to the procedure given in Example 34 and for compounds 204-211, by substituting Re(CO)$_5$Br (CAS No. 14220-21-4) in step 1 of example 34 with Re(CO)$_5$Cl (CAS No. 14099-01-5).

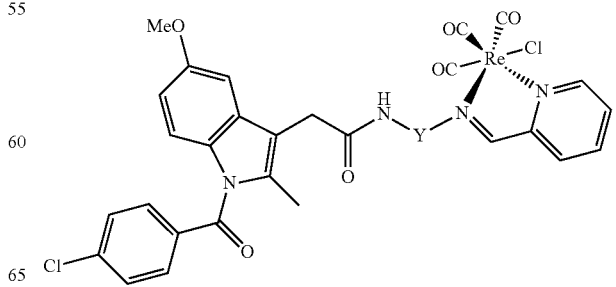

| Compound | Y = |
|---|---|
| 212 | 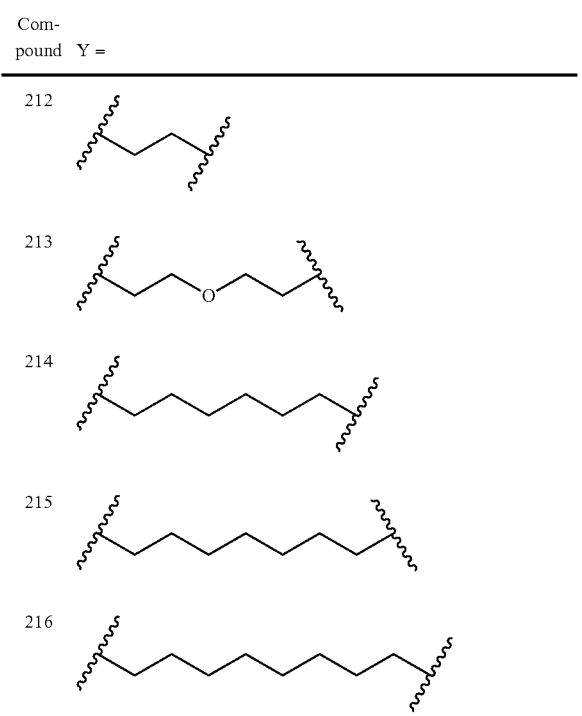 |
| 213 | |
| 214 | |
| 215 | |
| 216 | |
-continued
| Compound | Y = |
|---|---|
| 217 | 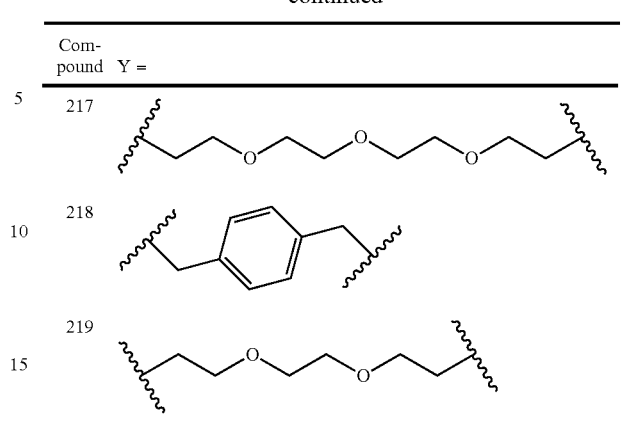 |
| 218 | |
| 219 | |
Compound 219
$^1$H NMR (400 MHz, CDCl3) δ 8.98 (d, J=5.2 Hz, 1H), 8.69 (s, 1H), 8.03 (t, J=7.7 Hz, 1H), 7.87 (d, J=7.7 Hz, 1H), 7.68 (d, J=8.5 Hz, 2H), 7.63-7.52 (m, 1H), 7.49 (d, J=8.4 Hz, 2H), 6.89 (dd, J=11.2, 5.7 Hz, 2H), 6.69 (dd, J=9.0, 2.4 Hz, 1H), 6.05 (s, 1H), 4.33-4.15 (m, 2H), 3.95 (qd, J=10.8, 4.3 Hz, 2H), 3.81 (s, 3H), 3.61 (s, 2H), 3.58-3.23 (m, 8H), 2.38 (s, 3H). MS (ESI) m/z: 883.2 (M+H$^+$).
Example 35
Synthesis of Compound 221
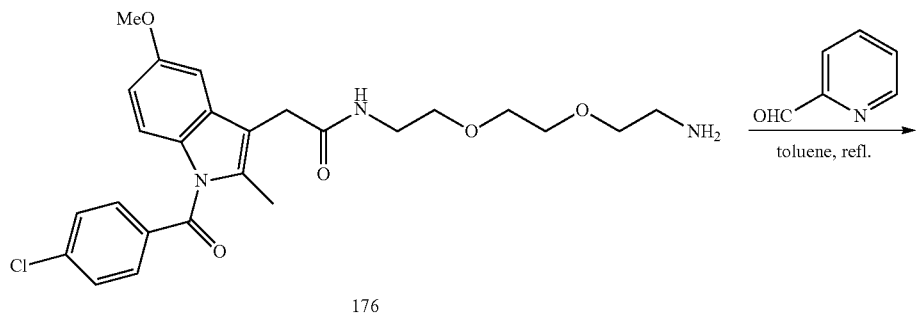
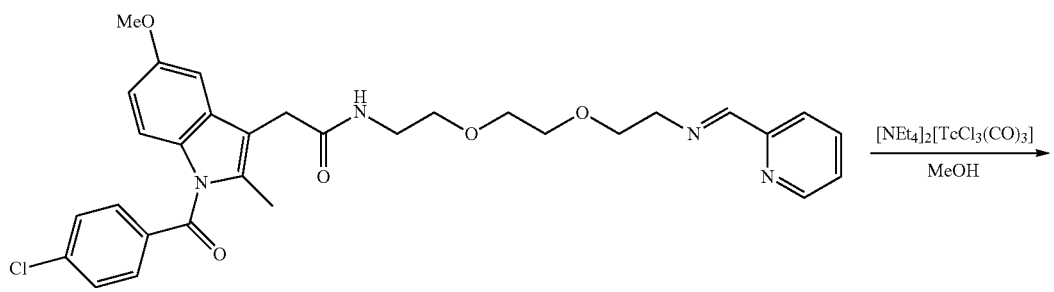

-continued

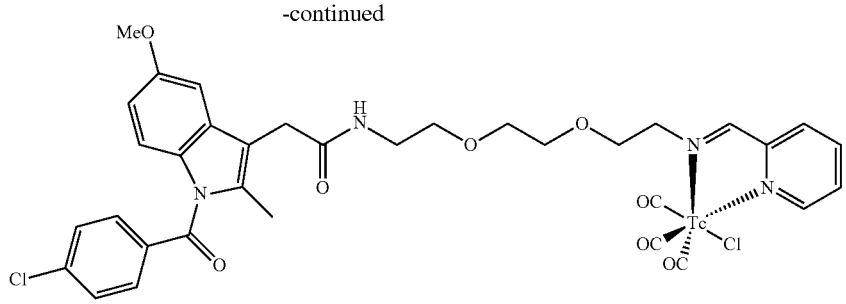

221

Compound 176 is synthesized as described in Example 31. 176 is coupled with picolinaldehyde to give the imine 220 according to literature procedures or methods well known to a person skilled in the art. For example, dissolving equal amounts in toluene and heating to reflux will accomplish such a transformation. Compound 221 is prepared from compound 220 as described by e.g. Alberto, R., Schibli, R., Schubiger, A. P., J. Am. Chem. Soc., 121, 6076-6077, (1999).

The following compounds 222-229 can also be prepared according to the procedure given in Example 35 by replacing compound 176 with the appropriate intermediate (synthesis described in examples 5, 6, 31-32.

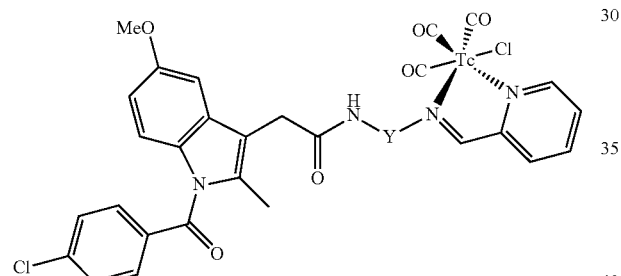

| Compound | Y = |
|---|---|
| 222 | 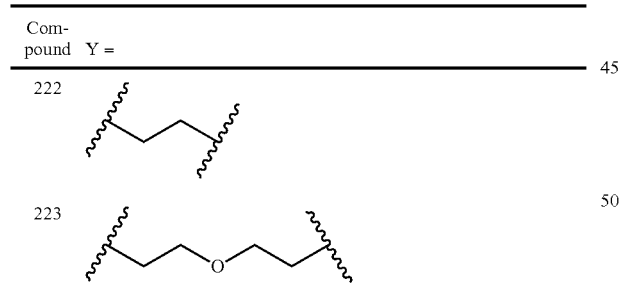 |
| 223 | |

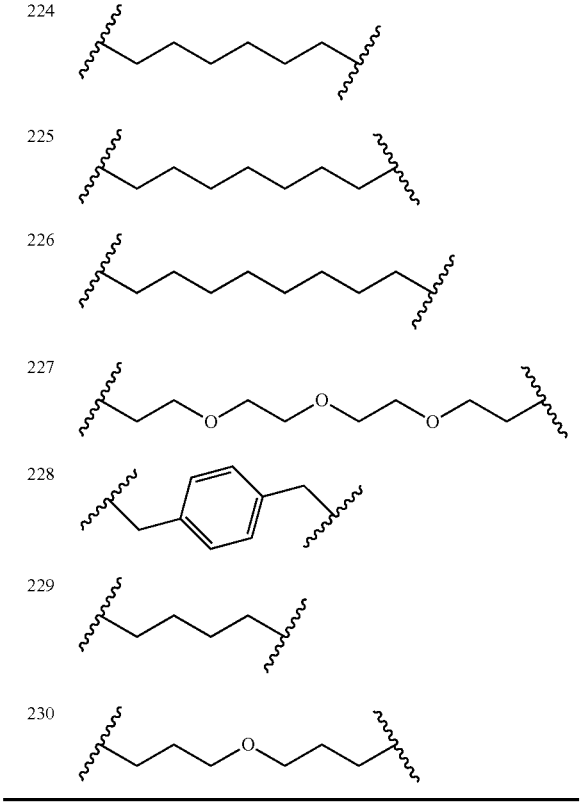

| Compound | Y = |
|---|---|
| 224 | |
| 225 | |
| 226 | |
| 227 | |
| 228 | |
| 229 | |
| 230 | |

Example 36

Synthesis of Compound 234

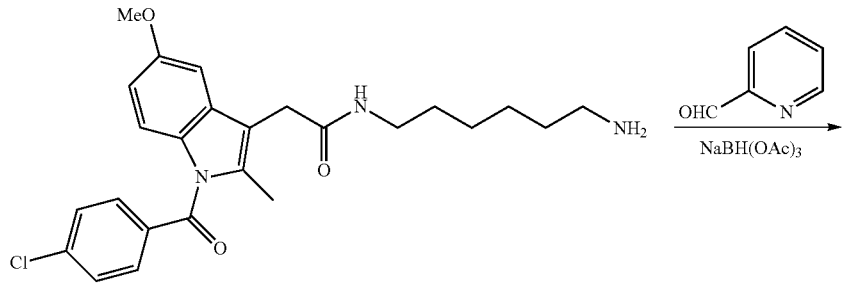

-continued
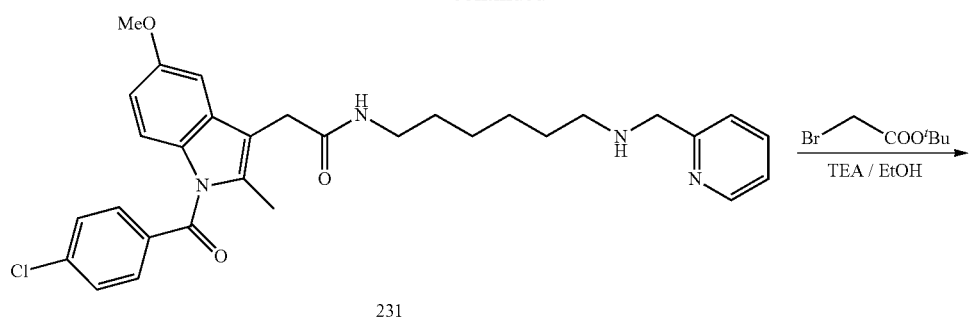
231
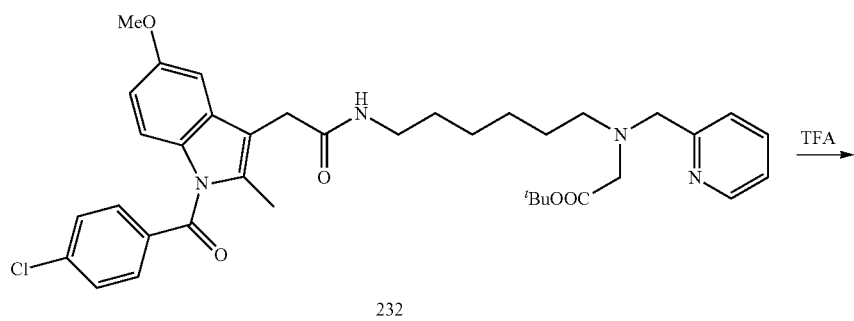
232
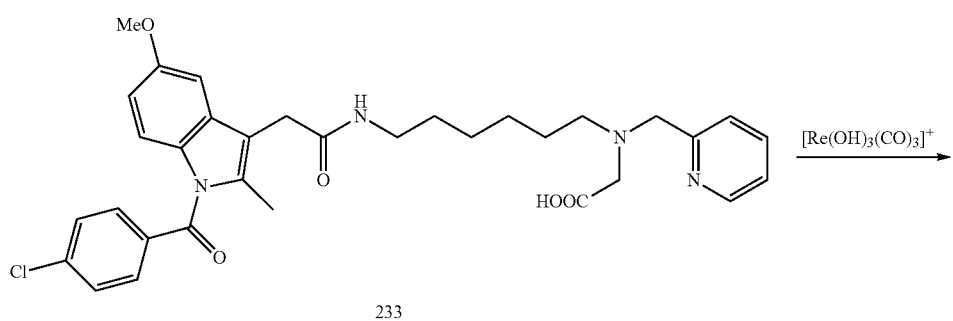
233
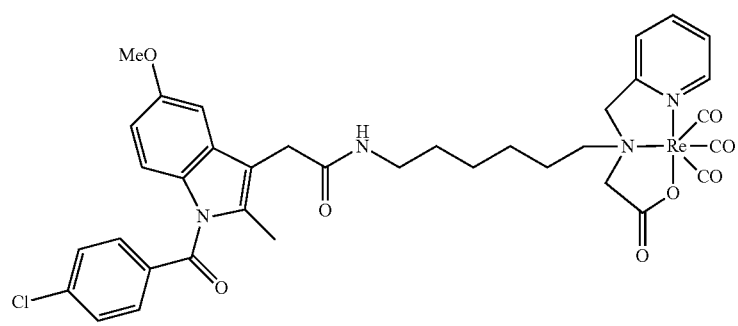
234

The synthesis of compound 25 is described in Example 6.

Intermediate 231:

To a solution of 25 (400 mg, 0.81 mmol) and picolinaldehyde (87 mg, 0.81 mmol, 1 eq) in MeOH (10 ml) was added AcOH (0.3 ml), the mixture was stirred at RT for 30 min, NaBH(OAc)$_3$ (687 mg, 3.24 mmol, 4 eq) was added, the mixture was stirred at RT overnight. Water (20 ml) was added and extracted with ethyl acetate (30 ml×3), the combined organic layers were washed with brine, dried over Na$_2$SO$_4$, filtered and the filtrate was concentrated to give the crude product which was purified by column chromatography (DCM: MeOH=10:1) to get the product (120 mg, 27%) as a yellow solid. LC-MS: m/z=547.3 [M+1]$^+$ Intermediate 232:

To a solution of 231 (120 mg, 0.22 mmol) and TEA (45 mg, 0.44 mmol) in THF (10 mL) was added tert-butyl 2-bromoacetate (64 mg, 0.33 mmol). The mixture was stirred at 60° C. for 2 h. Water (10 ml) was added and extracted with ethyl acetate (3×30 ml), the combined organic layers were washed with brine, dried over Na$_2$SO$_4$, concentrated to get the crude product (130 mg, 90%) as yellow oil, which was used in the next step without further purification. LC-MS: m/z=661.3 [M+1]$^+$ Intermediate 233:

To a solution of 232 (130 mg, 0.20 mmol) in DCM (10 ml) was added TFA (2 ml), the mixture was stirred at RT for 4 h and then evaporated the solvent to give the crude product (110 mg, 92%) as a yellow oil, which was used directly in the next step. LC-MS: m/z=605.3 [M+1]$^+$.

233 (100 mg, 0.16 mmol) was dissolved in MeOH (5 ml), Re(CO)$_5$Cl (90 mg, 0.25 mmol) was added and the mixture was stirred at 80° C. overnight. The solvent was evaporated and the residue was purified by Prep-HPLC (Column: Acquity BEH C18, Waters Corp, A: water/B: MeCN) to get the product 234 (20 mg, 14%) as a white solid. LC-MS: m/z=875.0[M+1]$^+$. $^1$H NMR (400 MHz, MeOD) δ 8.83 (d, J=5.2 Hz, 1H), 8.10 (td, J=7.8, 1.3 Hz, 1H), 7.72 (d, J=8.5 Hz, 3H), 7.56 (dd, J=13.3, 7.5 Hz, 3H), 7.07 (d, J=2.4 Hz, 1H), 6.97 (d, J=9.0 Hz, 1H), 6.71 (dd, J=9.0, 2.5 Hz, 1H), 4.67 (d, J=15.6 Hz, 1H), 4.51 (d, J=15.5 Hz, 1H), 3.89 (d, J=17.3 Hz, 1H), 3.84 (s, 3H), 3.63 (s, 2H), 3.52 (ddd, J=31.5, 18.4, 11.2 Hz, 3H), 3.26 (t, J=6.8 Hz, 2H), 2.35 (s, 3H), 1.91-1.67 (m, 2H), 1.65-1.53 (m, 2H), 1.39 (d, J=3.1 Hz, 4H). $^{13}$C NMR (101 MHz, MeOD) δ 196.76, 195.90, 181.92, 171.87, 168.59, 159.46, 156.23, 152.15, 140.25, 138.81, 135.75, 134.32, 130.98, 130.82, 128.83, 125.57, 123.60, 114.62, 113.52, 111.33, 101.17, 100.15, 69.68, 67.91, 60.58, 54.85, 38.88, 31.11, 28.89, 26.17, 26.05, 24.79, 12.18.

Example 37

Synthesis of Compound 235

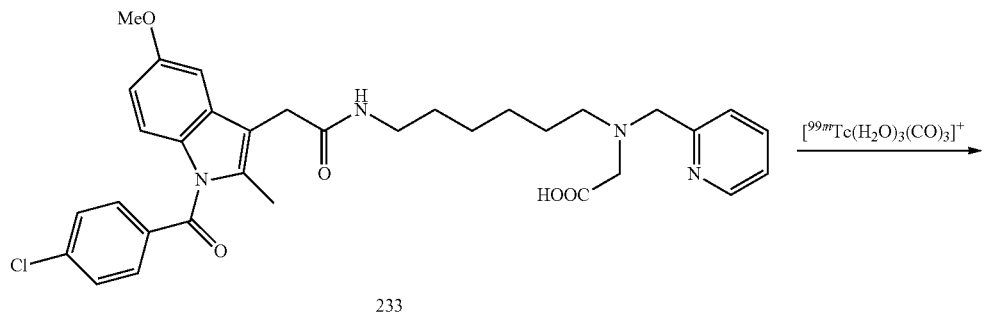

233

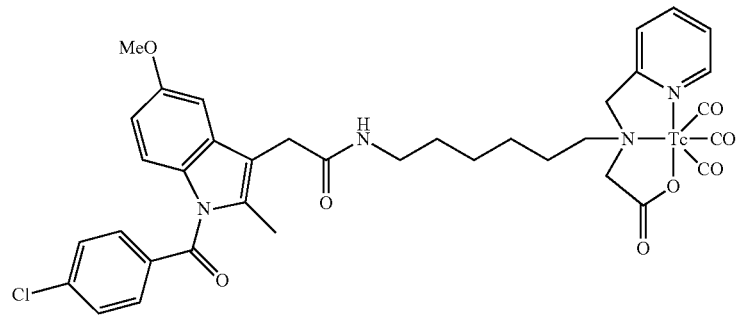

235

Compound 233 is prepared as described in Example 36.

233 is converted to 235 via the addition of [$^{99m}$Tc—(H$_2$O)$_3$(CO)$_3$]+(Isolink® kit; Mallinckrodt, St. Louis, Mo., USA) to a vial containing 100 g of compound 235 dissolved in 100 μl of water. The yield of radiolabeled conjugate is maximized by adjusting the pH to 7 using 0.1 M HCl prior to heating at 80° C. for 1 hour. After incubation, the metallated complexes are purified by RP-HPLC and the peaks collected into either 100 μl of deionized H$_2$O containing 100 g of bovine serum albumin solution (BSA, in vitro analysis) or 100 μl of isotonic saline (in vivo analysis). Residual MeCN is evaporated from the solution using a stream of nitrogen.

Example 38

Synthesis of Compound 237

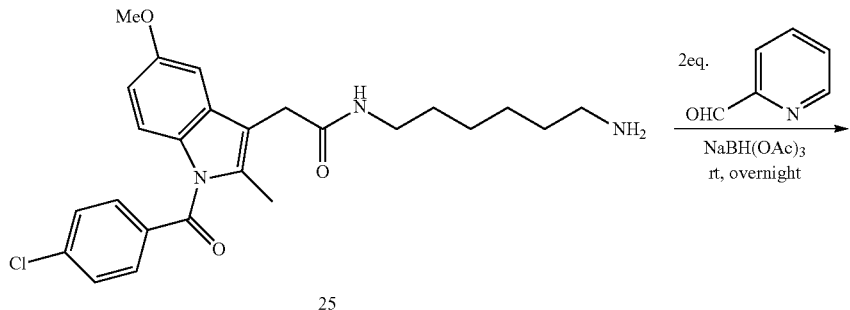

25

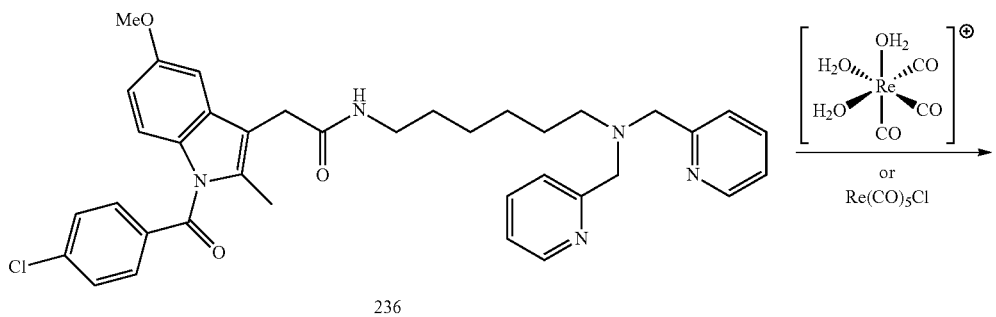

236

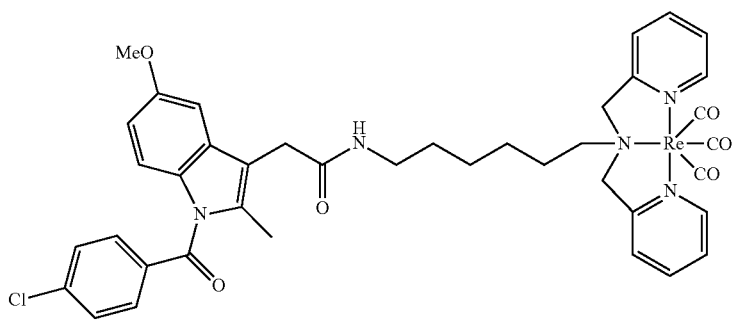

237

Intermediate 236:

To a solution of 25 (400 mg, 0.81 mmol) and picolinaldehyde (520 mg, 4.86 mmol, 6 eq) in MeOH (20 ml) was added AcOH (0.3 ml), the mixture was stirred at RT for 30 min. NaBH(OAc)$_3$ (687 mg, 3.24 mmol, 4 eq) was added and the mixture was stirred at RT overnight. Water (20 ml) was added and the mixture was extracted with ethyl acetate (3×30 ml). The combined organic layers were washed with brine, dried over Na$_2$SO$_4$, filtered and the filtrate was concentrated to give the crude product, which was purified by column chromatography on silica gel (DCM:MeOH=10:1) to get the product (150 mg, 34%) as a yellow solid. LC-MS: m/z=638.0 [M+1]$^+$.

To a solution of 236 (64 mg, 0.1 mmol) in MeOH (5 ml) was added Re(CO)$_5$Cl (54.3 mg, 0.15 mmol, 1.5 eq), the mixture was stirred at 80° C. overnight. The mixture was then concentrated and purified by Prep-HPLC (Column: Acquity BEH C18, Waters Corp, A: water/B: MeCN) to give the product 237 (20 mg, 23%) as a white solid. LC-MS: m/z=908.1 [M+H]$^+$. $^1$H NMR (400 MHz, MeOD): δ 8.77-8.76 (d, J=5.5 Hz, 2H), 7.84-7.81 (m, 2H), 7.60 (d, J=8.6 Hz, 2H), 7.48-7.42 (dd, J=20.2, 8.2 Hz, 4H), 7.32-7.21 (m, 2H), 6.96 (d, J=2.4 Hz, 1H), 6.86 (d, J=9.0 Hz, 1H), 6.60-6.57 (dd, J=9.0, 2.5 Hz, 1H), 4.78-4.63 (m, 4H), 3.73 (s, 3H), 3.69-3.59 (m, 2H), 3.52 (s, 2H), 3.16-3.14 (t, J=6.9 Hz, 2H), 2.23 (s, 3H), 1.76 (s, 2H), 1.56-1.42 (m, 2H), 1.32 (s, 4H).

Example 39
Synthesis of Compound 238
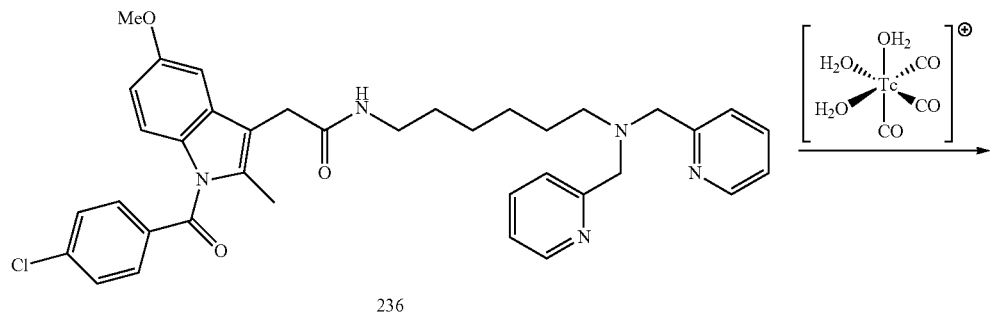
236
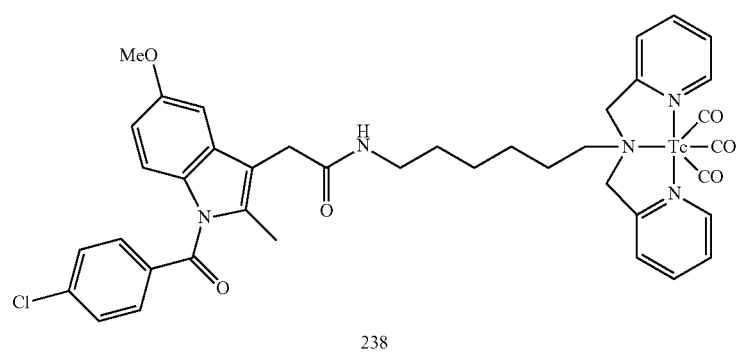
238
Compound 236 is prepared as described in example 38. 236 is converted to 238 by a procedure similar to the one described in example 37.
Example 40
Synthesis of Compound 242
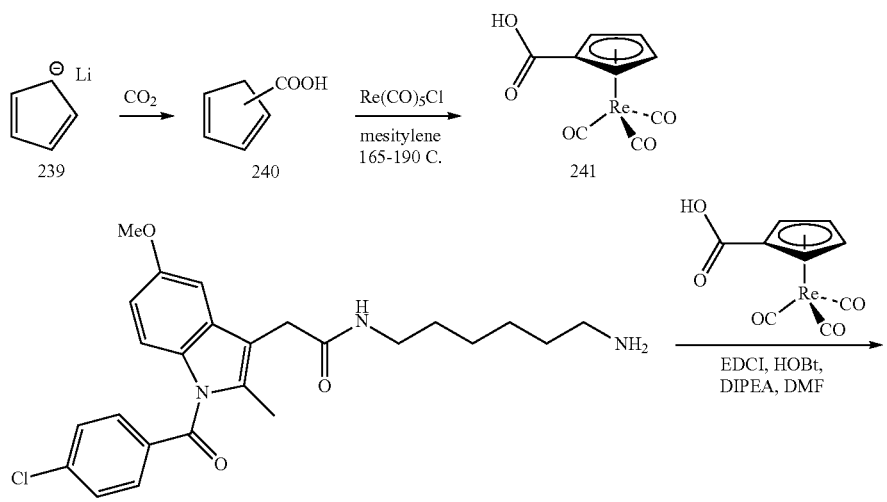

-continued

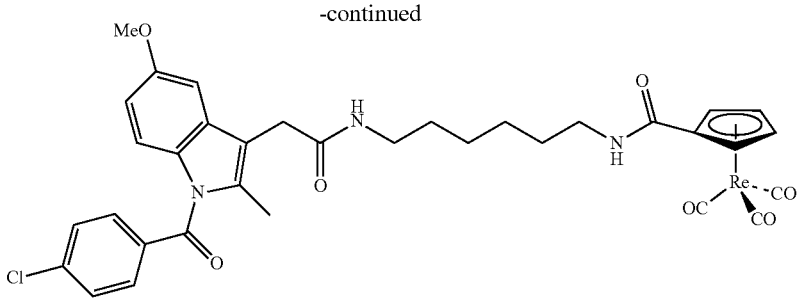

242

Cyclopentadienyltricarbonylrhenium(I) carboxylic acid 241 is synthesized as described by Siden Top, Jean-Sebastien Lehn, Pierre Morel, Gerard Jaouen, J. Organomet. Chem., 583, 63-68, (1999). To a solution of compound 25 (example 6) (0.16 mmol) in DCM (20 ml) was added HOBt (22 mg, 0.16 mmol), EDCI (31 mg, 0.16 mmol), and DIEA (62 mg, 0.48 mmol). The mixture was stirred at RT for 0.5 h, after which 241 (0.16 mmol) was added. The reaction mixture was stirred at RT overnight. The mixture was then diluted with water (30 ml) and extracted with EtOAc (25 ml×3). The combined organic layers were washed with brine, dried over $Na_2SO_4$, filtered and the filtrate was concentrated and purified by prep-HPLC (Column: Acquity BEH C18, Waters Corp, A: water, B: MeCN) to give the desired product 242.

$^1$H NMR (400 MHz, MeOD) δ 8.03 (s, 1H), 7.72 (d, J=8.5 Hz, 2H), 7.58 (d, J=8.5 Hz, 2H), 7.04 (d, J=2.4 Hz, 1H), 6.95 (d, J=9.0 Hz, 1H), 6.69 (dd, J=9.0, 2.4 Hz, 1H), 6.17 (t, J=4.0 Hz, 2H), 5.57 (t, J=4.0 Hz, 2H), 3.82 (s, 3H), 3.63 (s, 2H), 3.24-3.18 (m, 4H), 2.34 (s, 3H), 1.61-1.44 (m, 4H), 1.41-1.27 (m, 4H). MS (ESI) m/z: 818.0[M+H$^+$].

The following compounds 243-251 can also be prepared according to the procedure given in Example 40 by replacing compound 25 with the appropriate intermediate (synthesis described in examples 5, 31, and 32).

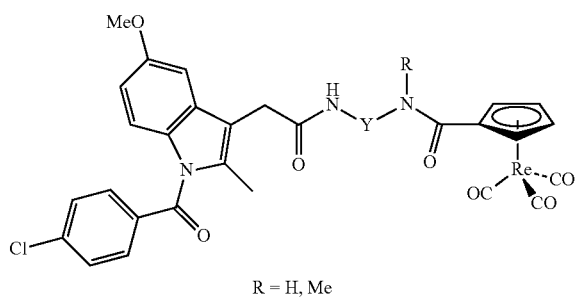

R = H, Me

| Compound | Y = |
|---|---|
| 243 |  |
| 244 | |
| 245 | |
| 246 | |
| 247 | |
| 248 | |
| 249 | |
| 250 | |
| 251 | |

Compound 243
$^1$H NMR (400 MHz, DMSO-d$_6$) δ 8.31 (t, J=5.2 Hz, 1H), 8.07 (t, J=5.2 Hz, 1H), 7.67 (dd, J=22.2, 8.6 Hz, 4H), 7.09 (d, J=2.4 Hz, 1H), 6.94 (d, J=9.0 Hz, 1H), 6.70 (dd, J=9.0, 2.5 Hz, 1H), 6.20 (t, J=2.2 Hz, 2H), 5.76-5.68 (m, 2H), 3.76 (s, 3H), 3.50 (s, 2H), 3.23-3.09 (m, 4H), 2.22 (s, 3H). MS (ESI) m/z: 762.0 [M+H$^+$].

Compound 244
$^1$H NMR (400 MHz, CDCl3) δ 7.68 (d, J=8.5 Hz, 2H), 7.50 (d, J=6.9 Hz, 2H), 6.91 (d, J=2.3 Hz, 1H), 6.88 (d, J=9.0 Hz, 1H), 6.71 (dd, J=9.0, 2.3 Hz, 2H), 6.12 (t, J=2.0 Hz, 2H), 5.95 (s, 1H), 5.34 (t, J=2.0 Hz, 2H), 3.83 (s, 3H), 3.68 (s, 2H), 3.53-3.35 (m, 8H), 2.39 (s, 3H). MS (ESI) m/z: 806.0[M+H$^+$].

Compound 245

$^1$H NMR (400 MHz, CDCl3) δ 7.63 (d, J=8.2 Hz, 3H), 7.50 (d, J=8.3 Hz, 2H), 7.17 (d, J=8.2 Hz, 2H), 7.04 (d, J=8.9 Hz, 1H), 6.84-6.73 (m, 4H), 6.12 (s, 2H), 5.45 (s, 2H), 5.32 (s, 1H), 3.83 (s, 3H), 3.55 (s, 2H), 3.44 (s, 2H), 2.66 (s, 2H), 2.14 (s, 3H). MS (ESI) m/z: 860.0 [M+H$^+$].

Compound 246

$^1$H NMR (400 MHz, CDCl3) δ 7.67 (d, J=8.4 Hz, 2H), 7.50 (d, J=8.4 Hz, 2H), 6.87 (d, J=9.3 Hz, 2H), 6.71 (dd, J=9.0, 2.2 Hz, 1H), 6.01 (s, 1H), 5.96 (s, 2H), 5.61 (s, 1H), 5.34 (s, 2H), 3.82 (s, 3H), 3.64 (s, 2H), 3.31 (d, J=5.7 Hz, 2H), 3.21 (d, J=5.9 Hz, 2H), 2.39 (s, 3H), 1.42 (m, 4H), 1.22 (m, 6H). MS (ESI) m/z: 832.2 [M+H$^+$].

Compound 247

$^1$H NMR (400 MHz, CDCl3) δ 7.67 (d, J=7.9 Hz, 2H), 7.49 (d, J=7.7 Hz, 2H), 6.87 (d, J=9.1 Hz, 2H), 6.70 (d, J=8.0 Hz, 1H), 5.90 (s, 2H), 5.61 (s, 1H), 5.32 (d, J=16.8 Hz, 3H), 3.82 (s, 3H), 3.64 (s, 2H), 3.25 (dd, J=41.8, 5.8 Hz, 4H), 2.39 (s, 3H), 1.59-1.23 (m, 8H). MS (ESI) m/z: 846.2[M+H$^+$].

Compound 248

$^1$H NMR (400 MHz, CDCl3) δ 7.68 (d, J=8.5 Hz, 2H), 7.50 (t, J=7.8 Hz, 2H), 6.93-6.86 (m, 2H), 6.70 (dd, J=9.0, 2.4 Hz, 1H), 6.61 (s, 1H), 6.08 (s, 1H), 5.96 (s, 2H), 5.31 (t, J=4.0 Hz, 2H), 3.82 (s, 3H), 3.65 (s, 2H), 3.59-3.37 (m, 16H), 2.38 (s, 3H). MS (ESI) m/z: 894.2 [M+H$^+$].

Compound 249

$^1$H NMR (400 MHz, CDCl3) δ 7.64 (d, J=8.5 Hz, 2H), 7.47 (d, J=8.5 Hz, 2H), 7.17 (d, J=8.0 Hz, 2H), 7.09 (d, J=8.0 Hz, 2H), 6.84 (dd, J=5.7, 3.2 Hz, 2H), 6.68 (dd, J=9.1, 2.4 Hz, 1H), 6.09 (t, J=4.0 Hz, 1H), 5.96-5.89 (m, 3H), 5.35 (t, J=4.0 Hz, 2H), 4.46 (d, J=5.6 Hz, 2H), 4.35 (d, J=5.9 Hz, 2H), 3.78 (s, 3H), 3.68 (s, 2H), 2.36 (s, 3H). MS (ESI) m/z: 838.0 [M+H$^+$].

Compound 250

$^1$H NMR (400 MHz, CDCl3) δ 7.68 (d, J=8.3 Hz, 2H), 7.50 (d, J=8.3 Hz, 2H), 7.04 (s, 1H), 6.87 (d, J=9.6 Hz, 2H), 6.72 (d, J=9.1 Hz, 1H), 6.10 (s, 2H), 5.83 (s, 1H), 5.34 (s, 2H), 3.83 (s, 3H), 3.67 (s, 2H), 3.39 (s, 2H), 3.26 (s, 2H), 2.39 (s, 3H), 1.51 (s, 3H). MS (ESI) m/z: 790.0 [M+H$^+$].

Compound 251

$^1$H NMR (400 MHz, CDCl3) δ 7.67 (d, J=8.5 Hz, 2H), 7.50 (d, J=8.5 Hz, 2H), 6.91 (d, J=2.3 Hz, 1H), 6.86 (d, J=9.0 Hz, 1H), 6.70 (dd, J=9.0, 2.4 Hz, 1H), 6.60 (s, 1H), 6.00 (m, 3H), 5.33 (t, J=4.0 Hz, 2H), 3.82 (s, 3H), 3.65 (s, 2H), 3.46 (m, 12H), 2.40 (s, 3H). MS (ESI) m/z: 850.1 [M+H$^+$].

Example 41

Synthesis of Compound 254

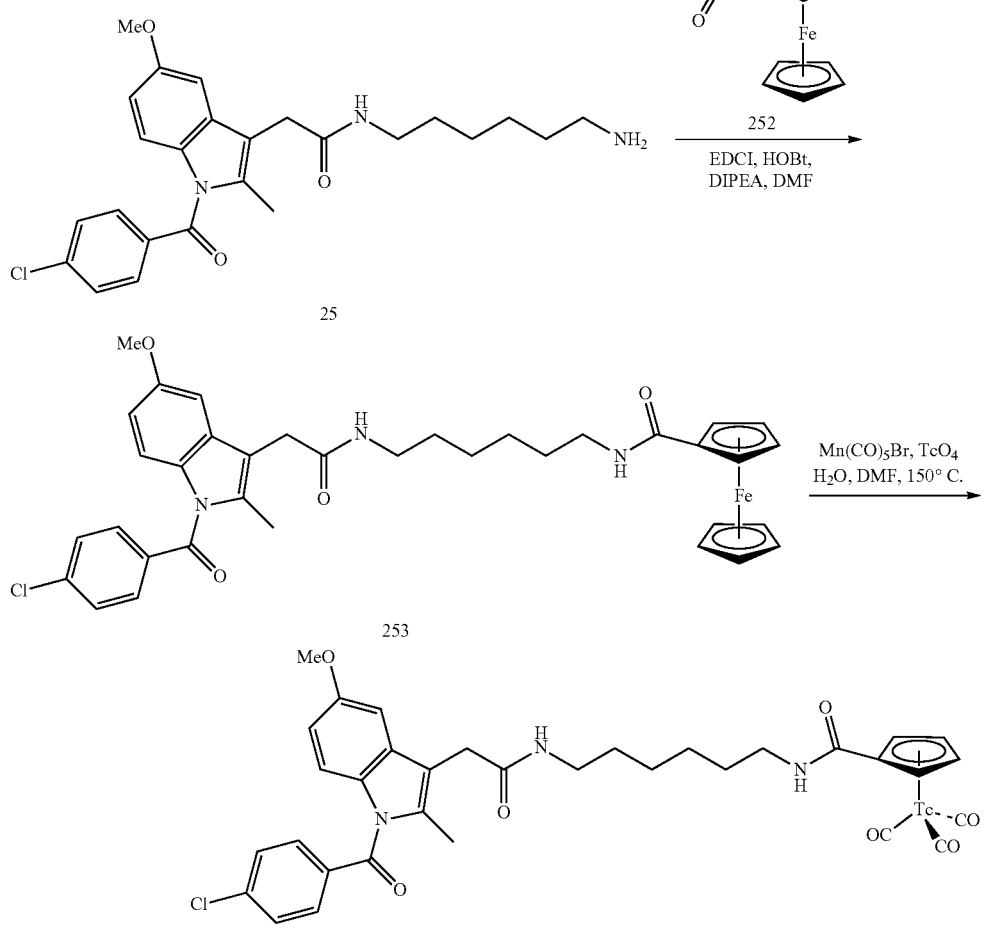

To a solution of compound 25 (example 6) (0.16 mmol) in DCM (20 ml) is added HOBt (22 mg, 0.16 mmol), EDCI (31 mg, 0.16 mmol), and DIEA (62 mg, 0.48 mmol). The mixture was stirred at RT for 0.5 h, after which 252 (CAS No. 1271-42-7, Sigma-Aldrich, Saint Louis, Mo., USA; catalog no. 106887; 0.16 mmol) is added. The reaction mixture is stirred at RT overnight. The mixture is then diluted with water and extracted with EtOAc (25 ml×3). The combined organic layers are washed with brine (15 ml×2), dried over $Na_2SO_4$, filtered and the filtrate is concentrated and purified by prep-HPLC (Column: Acquity BEH C18, Waters Corp, A: water, B: MeCN) to give the desired product 253.

253 can be converted into the Tc complex 254 as described in the literature, see e.g. Bioorg. Med. Chem. Letters 22 (2012) 6352-6357; J. Med. Chem. (2007), 50, 543-549; J. Med. Chem. (2013), 56, 471-482; J. Med. Chem. (2014), 57, 7113-7125.

Example 42

Synthesis of Compound 260

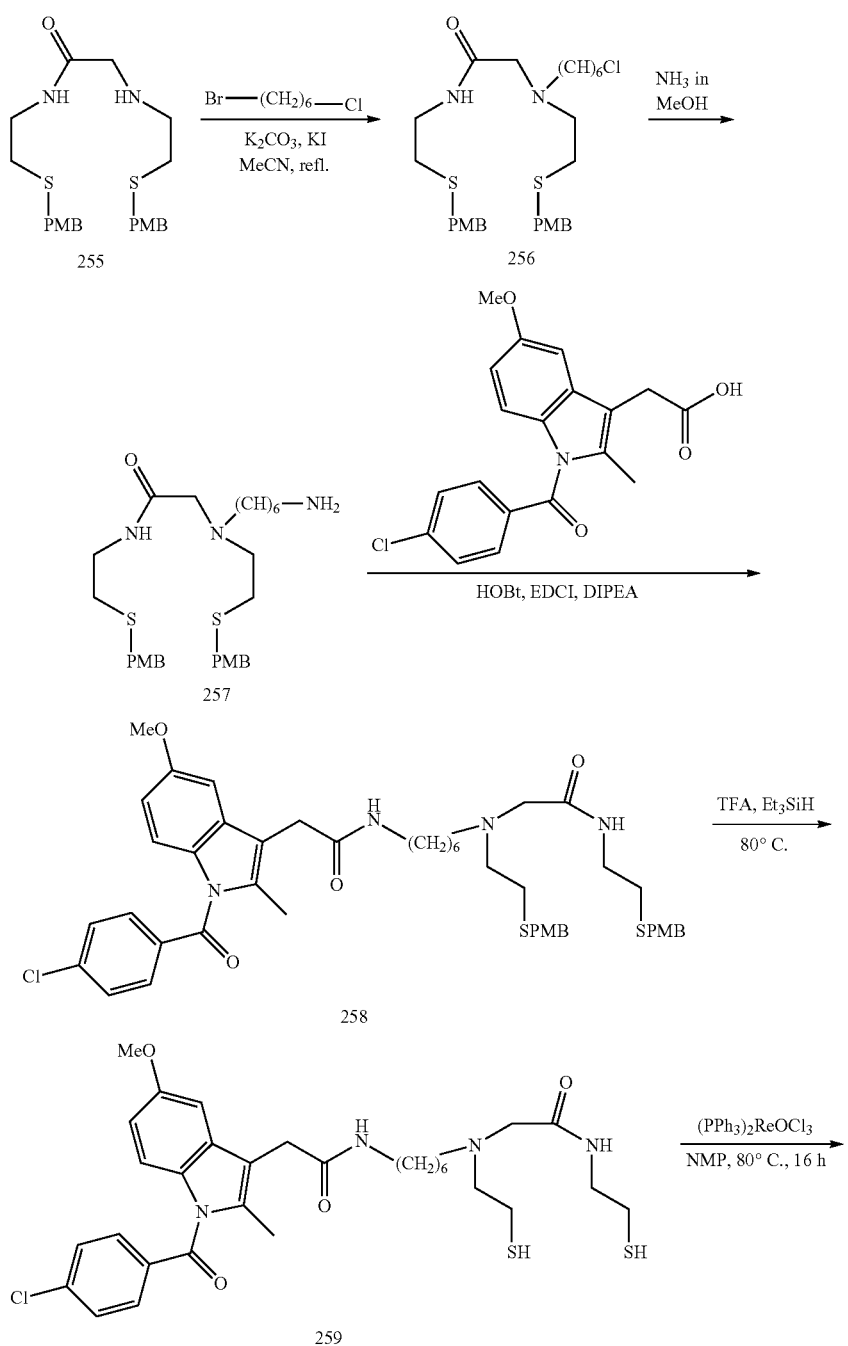

-continued

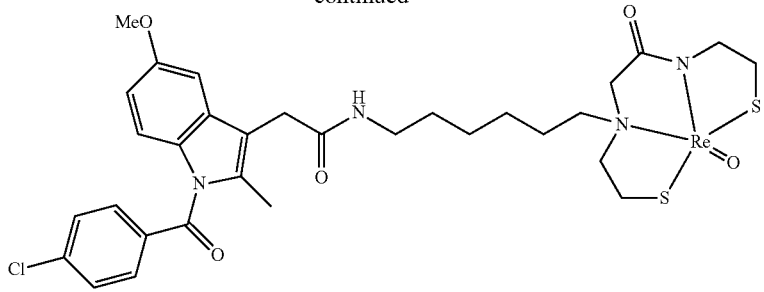

260

Compound 255 is made according to the procedure in: Ziv, Ilan et al., WO 2003/101948 and Mahmood, A., WO 2001/083436. Compound 255 is alkylated with 1-bromo-6-chlorohexane to form 256 as previously described in: Mahmood, A.; et al., "Functionalized tetradentate chelates and their Technetium and Rhenium complexes: synthesis spectroscopy and structural characterization", in Technetium and Rhenium in chemistry and nuclear medicine 5, pp. 253-257 (Nicolini, M. et al.) and also in Mahmood, A., et al., WO 2001/083436. Compound 256 is treated with ammonia in methanol at rt to give amine 257.

To a solution of indomethacin (57 mg, 0.16 mmol) in DCM (20 ml) was added HOBt (22 mg, 0.16 mmol), EDCI (31 mg, 0.16 mmol), and DIEA (62 mg, 0.48 mmol). The mixture was stirred at RT for 0.5 h, after which (257) (85 mg, 0.16 mmol) was added. The reaction mixture was stirred at RT overnight. The mixture was then diluted with water (30 ml) and extracted with EtOAc (25 ml×3). The combined organic layers were washed with brine (15 ml×2), dried over $Na_2SO_4$, filtered and the filtrate was concentrated to give the free dithiol 259.

Compound 259 is dissolved in DCM and treated with TFA in presence of 5 eq. of $Et_3SiH$ at 80° C. for 4 h. The volatiles are removed by lyophilizing overnight. To a stirred solution of the residue (100 mg, 0.14 mmol) in NMP (15 mL), $(PPh_3)_2ReOCl_3$ (Sigma-Aldrich, Order #370193, 106 mg, 0.127 mmol) was added. The mixture was stirred at 80° C. for 16 h. The solution was purified by Prep-HPLC (Column: Acquity BEH C18, Waters Corp, solvent A: Water, $NH_4HCO_3$, solvent B: MeCN) to give compound 260 as a solid.

1H NMR (400 MHz, CDCl3) δ 7.68 (d, J=8.5 Hz, 2H), 7.50 (d, J=8.5 Hz, 2H), 6.91-6.83 (m, 2H), 6.71 (d, J=9.0, 2.4 Hz, 1H), 5.60 (s, 1H), 4.65-4.53 (m, 2H), 4.15-4.03 (m, 2H), 3.94-3.86 (m, 1H), 3.83 (s, 3H), 3.65 (s, 2H), 3.49-3.39 (m, 1H), 3.40-3.11 (m, 6H), 2.85 (dd, J=13.4, 4.2 Hz, 1H), 2.40 (s, 3H), 1.62-1.51 (m, 2H), 1.48-1.38 (m, 2H), 1.37-1.19 (m, 4H). MS (ESI) m/z: 855.0 (M+Na+)

The following compounds 261-269 can also be prepared according to the procedure given in Example 42 by replacing 1-bromo-6-chloro-hexane in Example 42 with the appropriate dihalide.

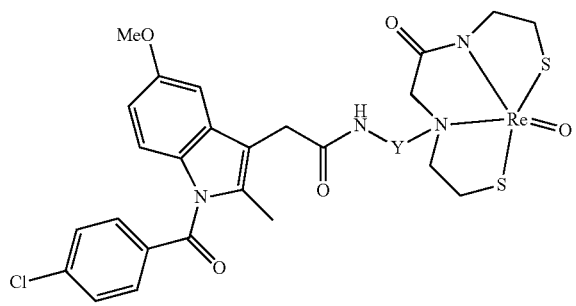

| Compound | Y = |
|---|---|
| 261 | ～(CH2)5～ |
| 262 | ～CH2CH2-O-CH2CH2～ |
| 263 | ～(CH2)6～ |
| 264 | ～(CH2)8～ |
| 265 | ～(CH2)10～ |
| 266 | ～(CH2)3-O-(CH2)3～ |
| 267 | ～(CH2)3-O-(CH2)3～ |

| Compound | Y = |
|---|---|
| 268 | 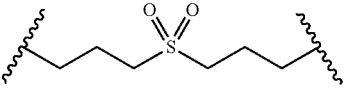 [SMILES: *CCCS(=O)(=O)CCC*] |
| 269 | 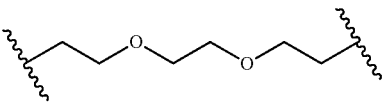 [SMILES: *CCOCCOCC*] |

Compound 261

¹H NMR (400 MHz, CDCl3) δ 7.68 (d, J=8.4 Hz, 2H), 7.50 (d, J=8.3 Hz, 2H), 6.87 (d, J=9.5 Hz, 1H), 6.78-6.64 (m, 1H), 5.77 (s, 1H), 4.70-4.42 (m, 2H), 4.07 (dd, J=10.8, 4.5 Hz, 1H), 3.97 (d, J=16.5 Hz, 1H), 3.83 (s, 3H), 3.67 (s, 2H), 3.56-3.42 (m, 1H), 3.38-2.95 (m, 6H), 2.81 (dd, J=13.6, 4.1 Hz, 1H), 2.40 (s, 3H), 1.85-1.40 (m, 5H). MS (ESI) m/z: 805.0 (M+H⁺)

Compound 262

¹H NMR (400 MHz, CDCl3) δ 7.69 (d, J=8.2 Hz, 2H), 7.50 (d, J=8.3 Hz, 2H), 6.92-6.85 (m, 2H), 6.72 (s, 1H), 6.02 (s, 1H), 4.57-4.55 (m, 1H), 4.46-4.41 (m, 1H), 4.11-4.08 (m, 1H), 3.84-3.80 (m, 5H), 3.68-3.52 (m, 5H), 3.51-3.41 (m, 4H), 3.41-3.09 (m, 4H), 2.66 (d, J=12.8 Hz, 1H), 2.42 (d, J=4.1 Hz, 3H). MS (ESI) m/z: 843.0 (M+Na⁺).

Compound 263

¹H NMR (400 MHz, CDCl3) δ 7.68 (d, J=8.3 Hz, 2H), 7.50 (d, J=8.4 Hz, 2H), 6.90-6.78 (m, 2H), 6.72 (d, J=9.1 Hz, 1H), 5.73 (s, 1H), 4.70-4.49 (m, 2H), 4.19-4.00 (m, 2H), 3.83 (s, 3H), 3.78 (s, 1H), 3.69 (s, 2H), 3.45-3.05 (m, 7H), 2.85 (dd, J=13.2, 4.1 Hz, 1H), 2.41 (s, 3H), 1.87-1.66 (m, 2H), 1.62-1.45 (m, 2H), 1.31-1.15 (m, 2H). MS (ESI) m/z: 840.9 (M+Na⁺).

Compound 264

¹H NMR (400 MHz, CDCl3) δ 7.68 (d, J=8.2 Hz, 2H), 7.50 (d, J=7.8 Hz, 2H), 6.96-6.79 (m, 2H), 6.71 (d, J=8.8 Hz, 2H), 5.58 (s, 1H), 4.70-4.51 (m, 2H), 4.20-4.01 (m, 2H), 3.98-3.88 (m, 1H), 3.82 (s, 1H), 3.64 (s, 1H), 3.52-3.41 (m, 1H), 3.40-3.04 (m, 6H), 2.85 (d, J=9.7 Hz, 1H), 2.40 (s, 3H), 1.85-1.67 (m, 2H), 1.47-1.37 (m, 2H), 1.37-1.12 (m, 6H). MS (ESI) m/z: 847.1 (M+H⁺).

Compound 265

¹H NMR (400 MHz, CDCl3) δ 7.67 (d, J=8.5 Hz, 2H), 7.49 (d, J=8.5 Hz, 2H), 6.87 (dd, J=8.8, 5.7 Hz, 2H), 6.70 (dd, J=9.0, 2.4 Hz, 1H), 5.58 (t, J=5.7 Hz, 1H), 4.71-4.51 (m, 2H), 4.16-4.02 (m, 2H), 4.00-3.88 (m, 1H), 3.82 (s, 3H), 3.64 (s, 2H), 3.55-3.42 (m, 1H), 3.41-3.30 (m, 1H), 3.29-3.08 (m, 5H), 2.85 (dd, J=13.4, 4.3 Hz, 1H), 2.39 (s, 3H), 1.85-1.66 (m, 2H), 1.64-1.56 (m, 2H), 1.46-1.35 (m, 2H), 1.36-1.12 (m, 8H). MS (ESI) m/z: 883.4 (M+Na⁺).

Compound 266

¹H NMR (400 MHz, CDCl3) δ 7.67 (d, J=8.2 Hz, 2H), 7.54-7.44 (m, 2H), 6.99-6.85 (m, 2H), 6.74 (d, J=9.3 Hz, 1H), 6.11 (s, 1H), 4.70-4.49 (m, 2H), 4.22-4.01 (m, 4H), 3.84 (d, J=3.3 Hz, 4H), 3.71 (s, 2H), 3.59-3.12 (m, 10H), 2.87 (d, J=13.5 Hz, 1H), 2.35 (s, 3H), 1.91 (s, 2H), 1.66-1.54 (m, 2H). MS (ESI) m/z: 849.1 (M+H⁺).

Compound 267

¹H NMR (400 MHz, CDCl3) δ 7.67 (d, J=8.5 Hz, 2H), 7.50 (d, J=7.8 Hz, 2H), 6.92-6.81 (m, 2H), 6.71 (dd, J=9.0, 2.5 Hz, 1H), 5.88 (s, 1H), 4.75 (d, J=16.9 Hz, 1H), 4.63-4.51 (m, 1H), 4.20 (d, J=16.8 Hz, 1H), 4.14-4.05 (m, 1H), 4.04-3.94 (m, 1H), 3.84 (s, J=16.4 Hz, 3H), 3.78 (s, 1H), 3.72-3.57 (m, 5H), 3.55-3.06 (m, 8H), 2.97-2.69 (m, 1H), 2.40 (s, 3H), 1.86-1.68 (m, 2H). MS (ESI) m/z: 835.1 (M+H⁺).

Compound 268

¹H NMR (400 MHz, CDCl3) δ 7.68 (d, J=7.5 Hz, 2H), 7.50 (d, J=7.6 Hz, 2H), 7.03-6.93 (m, 1H), 6.90 (s, 1H), 6.73 (d, J=8.6 Hz, 1H), 4.72 (d, J=11.8 Hz, 1H), 4.59 (d, J=6.4 Hz, 1H), 4.22-3.94 (m, 3H), 3.83 (s, 3H), 3.66 (s, 3H), 3.45 (d, J=38.6 Hz, 3H), 3.33-3.06 (m, 3H), 2.88 (s, 3H), 2.37 (s, 5H), 2.01 (s, 2H), 1.66 (s, 2H). MS (ESI) m/z: 897.1 (M+H⁺).

Compound 269

¹H NMR (400 MHz, CDCl3) δ 7.65 (d, J=8.4 Hz, 2H), 7.47 (d, J=8.4 Hz, 2H), 6.95 (s, 2H), 6.89 (d, J=9.0 Hz, 1H), 6.69 (dd, J=8.9, 2.1 Hz, 1H), 4.68 (d, J=17.4 Hz, 1H), 4.43-4.32 (m, 1H), 4.17 (d, J=17.4 Hz, 1H), 4.09-3.98 (m, 1H), 3.95-3.76 (m, 6H), 3.76-3.70 (m, 1H), 3.66 (d, J=6.5 Hz, 2H), 3.62-3.41 (m, 7H), 3.36-3.21 (m, 3H), 3.17-3.05 (m, 2H), 2.80 (dd, J=12.8, 4.0 Hz, 1H), 2.37 (s, 1H). MS (ESI) m/z: 886.9 (M+Na⁺).

Example 43

Synthesis of Compound 270

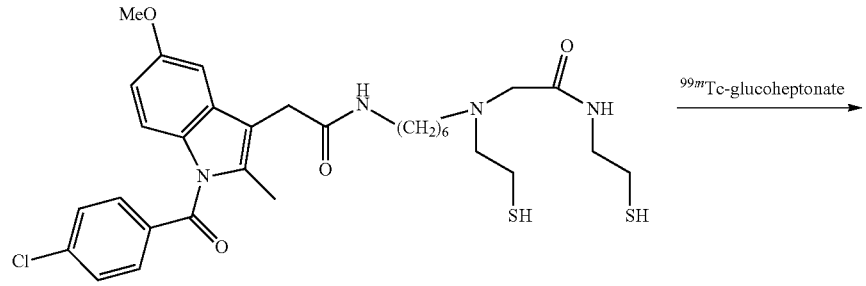

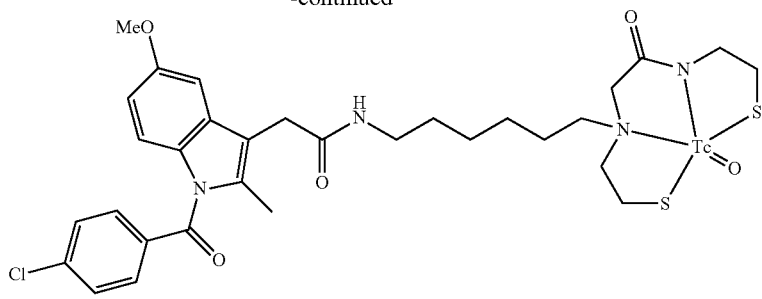
270
Compound 270 is synthesized by reacting 259 (example 42) with $^{99m}$Tc-glucoheptonate as described in: Mahmood, A., et al., WO 2001/083436.
Example 44
Synthesis of Compound 275
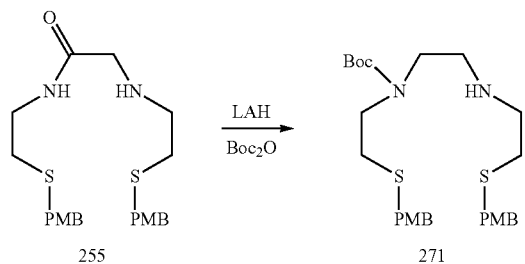
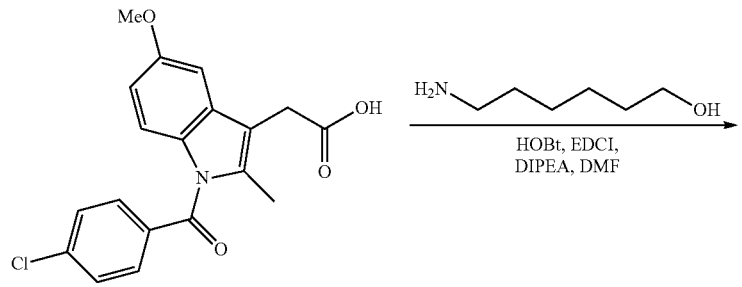
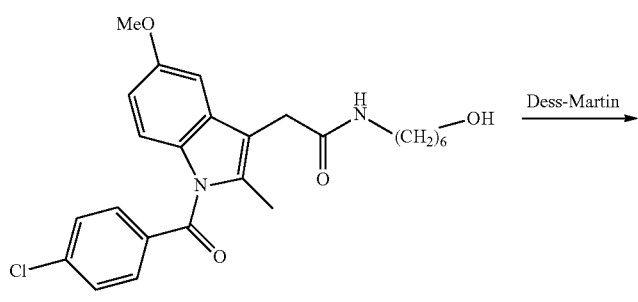
272

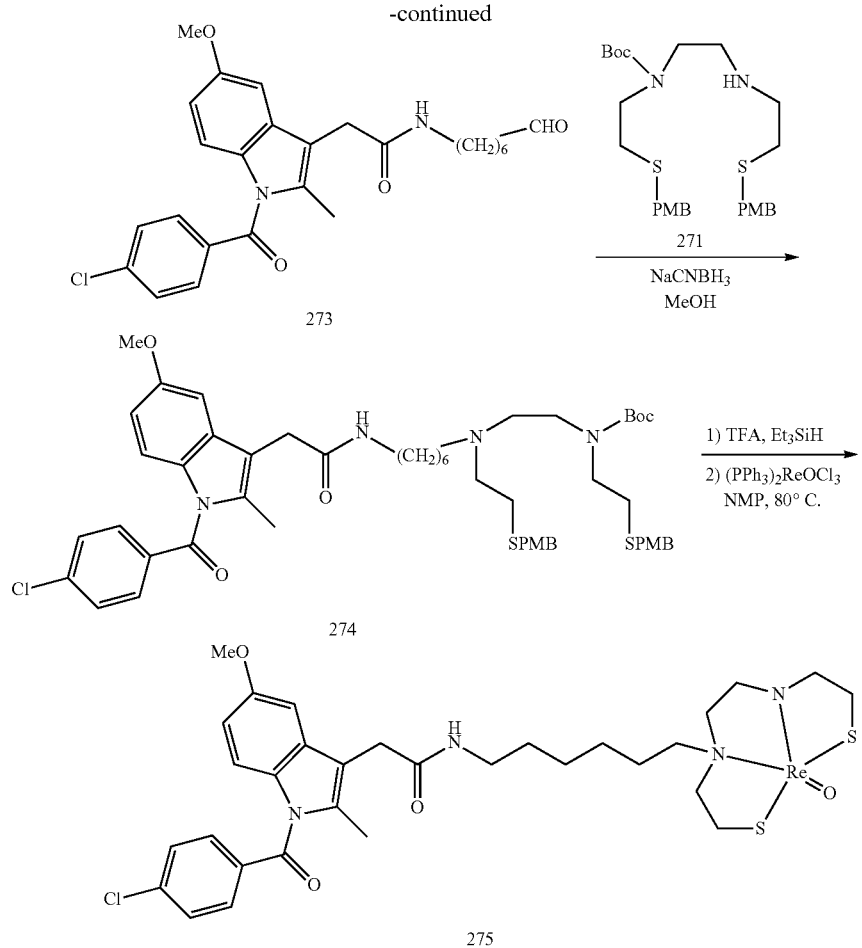

Compound 255 is made according to the procedure in: Ziv, Ilan et al., WO 2003/101948 and Mahmood, A., et al., WO 2001/083436. 255 is reduced with LiAlH₄ and Boc-protected to give compound 271 according to the procedure described in Ono, M., et al., ACS Chem. Neurosci., 1, 598-607, (2010).

Intermediate 272

To a solution of indomethacin (2-(1-(4-chlorobenzoyl)-5-methoxy-2-methyl-1H-indol-3-yl)acetic acid, 1.5 g, 4.2 mmol) in DMF (20 mL) was added 6-aminohexan-1-ol (589 mg, 5.04 mmol), HOBt (1.02 g, 7.56 mmol), EDCI (1.45 g, 7.56 mmol) and DIPEA (2.16 g, 16.8 mmol). The resulting solution was stirred RT overnight by which time LCMS showed completion of the reaction. Then water was added (80 mL), and the mixture was extracted with EtOAc (50 mL×3). The combined organic layers were washed with brine, dried over Na₂SO₄ filtered and the filtrate was concentrated to obtain the product (1.5 g, yield: 78%) as a light yellow solid.

Intermediate 273

To a solution of 272 (1.5 g, 3.28 mmol) in DCM (30 ml) was added Dess-Martin periodinane (1,1,1-tris(acetyloxy)-1,1-dihydro-1,2-benziodoxol-3-(1H)-one, 2.09 g, 4.93 mmol) at 0° C. The resulting solution was stirred RT for 2 h, then a sat'd. aq. solution of Na₂S₂O₃ (10 mL), was added. The mixture was extracted with DCM (20 mL×3). The combined organic layers were washed with brine, dried over Na₂SO₄, filtered and the filtrate was concentrated to get the crude product 273 (1.2 g, yield: 81%) as a yellow solid which was used in the next step without further purification.

Intermediate 274

To a solution of 273 (1.2 g, 2.64 mmol) in MeOH (30 mL) was added compound 271 (1.0 g, 1.98 mmol), and 1 mL of CH₃COOH. The resulting solution was stirred at rt for 0.5 h. Then, NaBH₃CN (332 mg, 5.28 mmol) was added and the mixture was stirred for another 2 h. Then the reaction was quenched with water (20 mL) and extracted with DCM (30 mL×4). The combined organic layers were washed with brine, dried over Na₂SO₄, filtered and the filtrate was concentrated to give the crude product, which was purified by chromatography on silica gel (DCM:MeOH=50:1) to get the product 274 (1.2 g yield: 63%) as a yellow oil.

Compound 275

To a solution of 274 (1.2 g, 1.26 mmol) in TFA (20 mL) was added Et3SiH (220 mg, 1.9 mmol). The resulting mixture was stirred at 80° C. for 2 h. Then volatiles were removed and the residue was dissolved in NMP (10 mL). (PPh₃)₂ReOCl₃ (Sigma-Aldrich, Order #370193, 1.0 eq) was added and the mixture was stirred at 80° C. overnight. The reaction was concentrated and the residue was purified by Prep-HPLC (Column: Acquity BEH C18, Waters Corp, A: water/B: MeCN) to give 275 as a light pink solid (80 mg, 8% yield over both steps).

¹H NMR (400 MHz, CDCl3) δ 7.68 (d, J=8.4 Hz, 2H), 7.50 (d, J=8.4 Hz, 2H), 6.98-6.80 (m, 2H), 6.70 (dd, J=9.0, 2.3 Hz, 1H), 5.61 (s, 1H), 4.12 (dt, J=12.7, 6.3 Hz, 2H), 3.99 (dd, J=18.6, 7.5 Hz, 2H), 3.91-3.73 (m, 5H), 3.64 (s, 2H), 3.51-3.16 (m, 7H), 3.11-2.88 (m, 2H), 2.82-2.61 (m, 1H), 2.40 (s, 3H), 1.69 (dd, J=11.9, 7.1 Hz, 2H), 1.51-1.36 (m, 2H), 1.29 (s, 4H). MS (ESI) m/z: 818.9 [M+H⁺].

Example 45
Synthesis of Compound 276
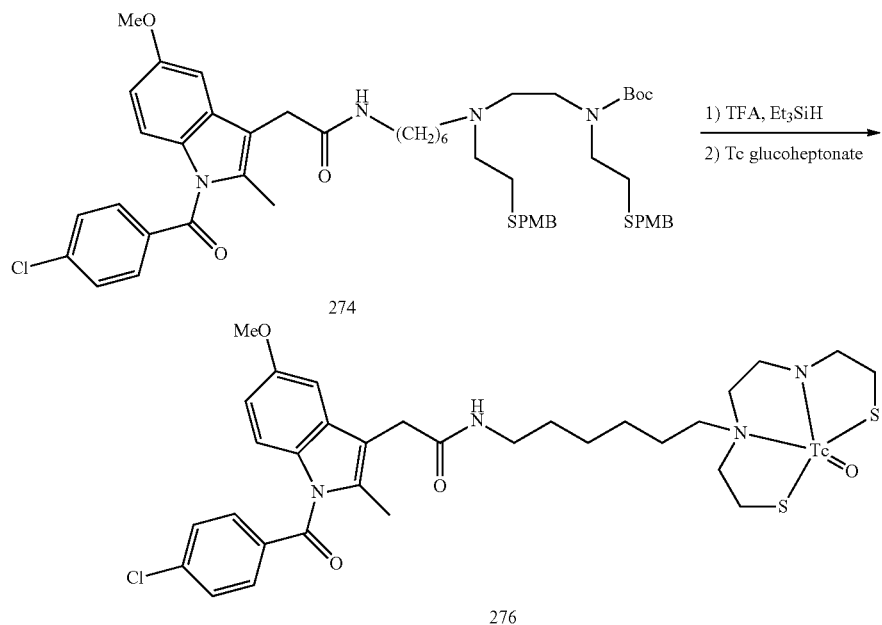
274 is converted into the dithiol by reacting with TFA and Et$_3$SiH as described for compound 275. The $^{99m}$Tc complex 276 is prepared by a ligand exchange reaction employing $^{99m}$Tc-glucoheptonate as described in e.g.: Ono, M., et al., ACS Chem. Neurosci., 1, 598, (2010) and Ono, M., et al., Bioorg. Med. Chem. Lett., 20, 5743-5748, (2010).
Example 46
Synthesis of Compound 283
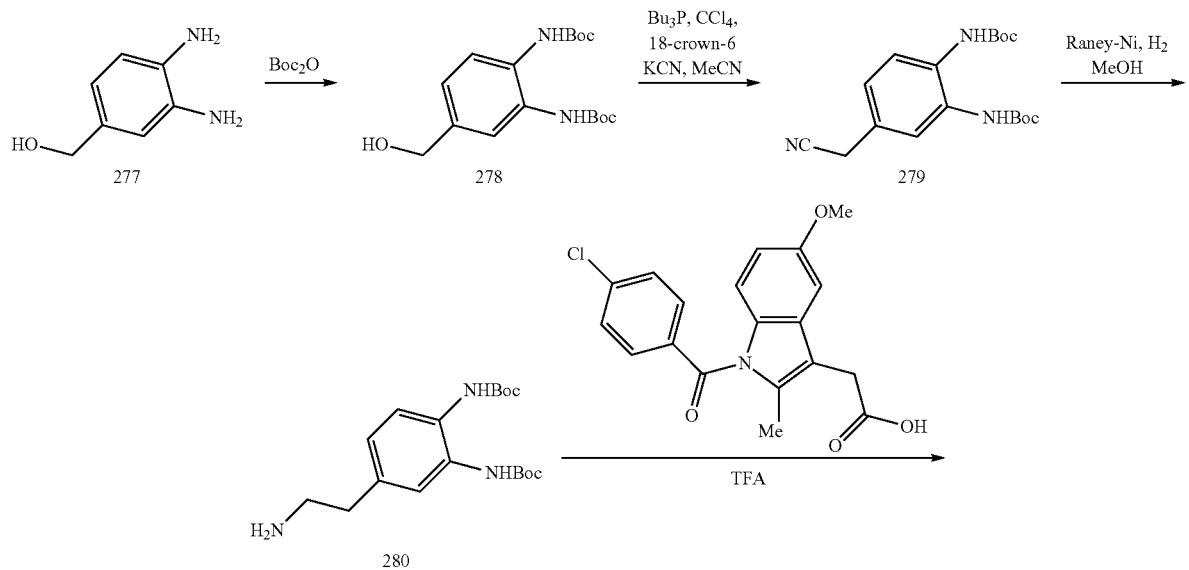

-continued

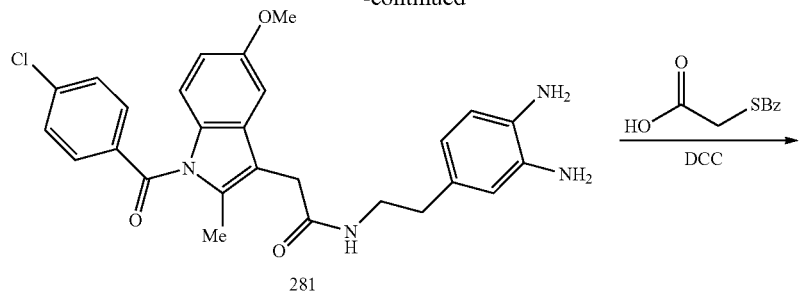
281

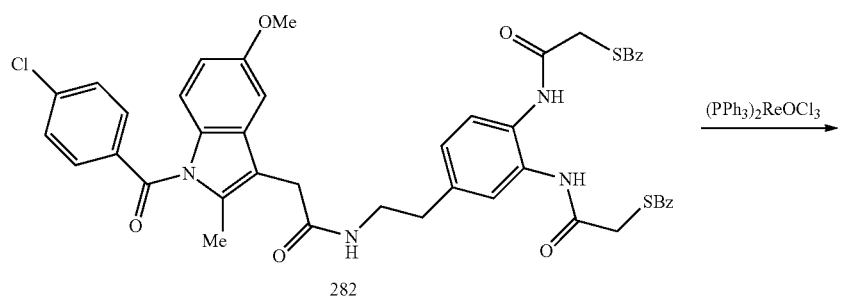
282

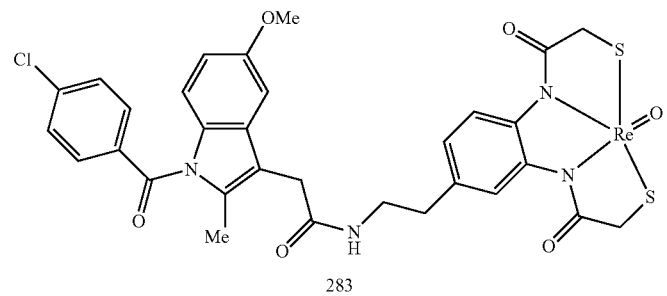
283

Compound 277 can be transformed to 278 by reacting 277 with di-tert-butyldicarbonate in the presence of a base such as NaHCO₃ or aq. NaOH. The nitrile 279 is obtained using a procedure similar to the one described in: Mizuno, A.; Hamada, Y.; Shioiri, T., Synthesis 1007, (1980). The nitrile is reduced with hydrogen in presence of a catalyst, such as Raney®-Nickel (W.R. Grace and Co.) in a solvent such as methanol or tert-butanol to give amine 280. Indomethacin is coupled to compound 280 as described in example 5 and treated with TFA to give the amide 281. 281 is coupled with the S-benzoyl-protected thioglycolic acid using DCC as the coupling agent to afford ligand 282. 283 is made following the procedure in Ono, et al. Bioorg. Med. Chem. Lett. (2010), 20, 5743-5748.

Example 47

Synthesis of Compound 284

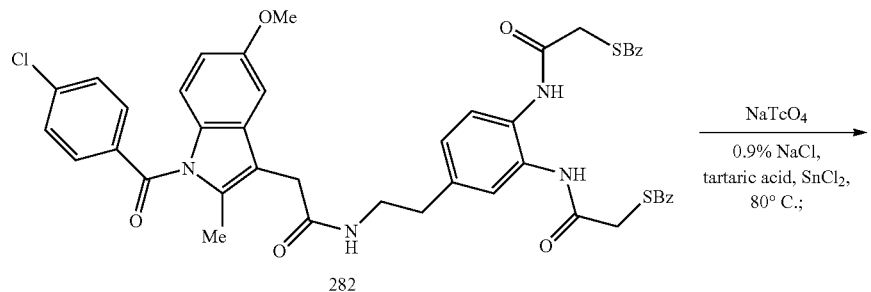
282

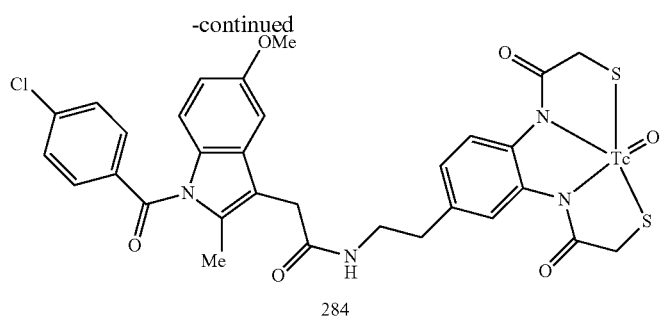
The Technetium complex 284 is prepared from compound 282 (example 46) as described in: Eisenhut, M., et al., J. Med. Chem., 45, 5802-5805, (2002).
Example 48
Synthesis of Compound 286
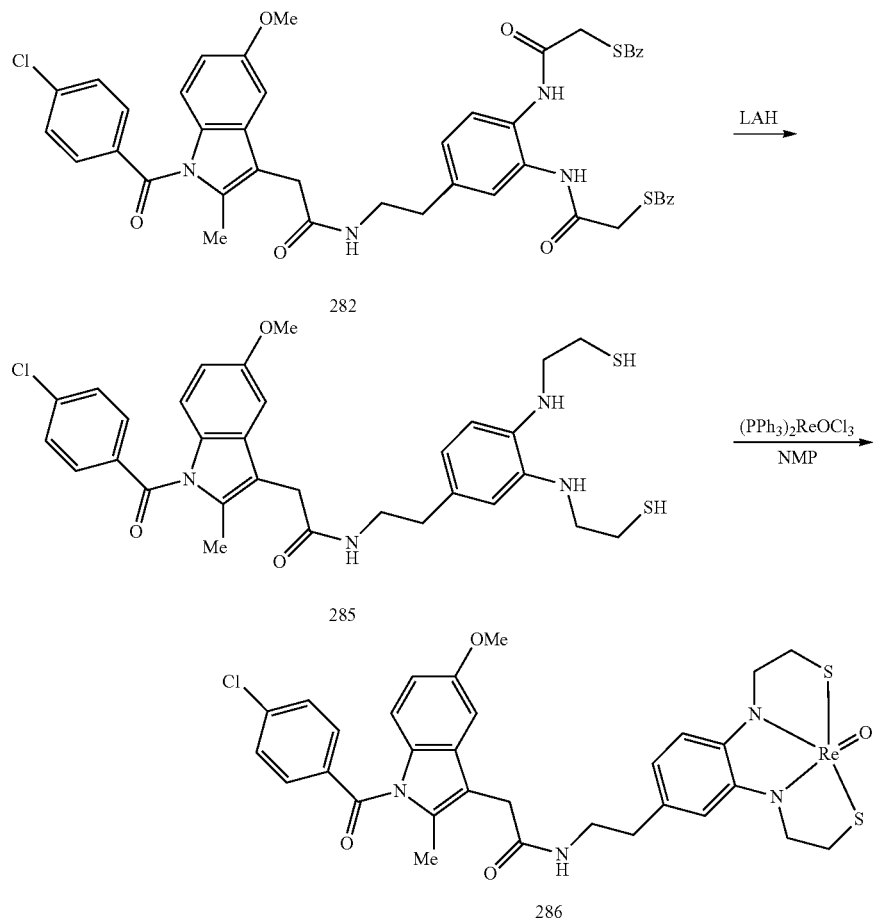
Compound 282 (Example 46) is reduced with LiAlH₄ in a solvent such as THF to give compound 285. 286 is prepared from 285 following the procedure in Ono, et al. Bioorg. Med. Chem. Lett. (2010), 20, 5743-5748.

Example 49
Synthesis of Compound 287
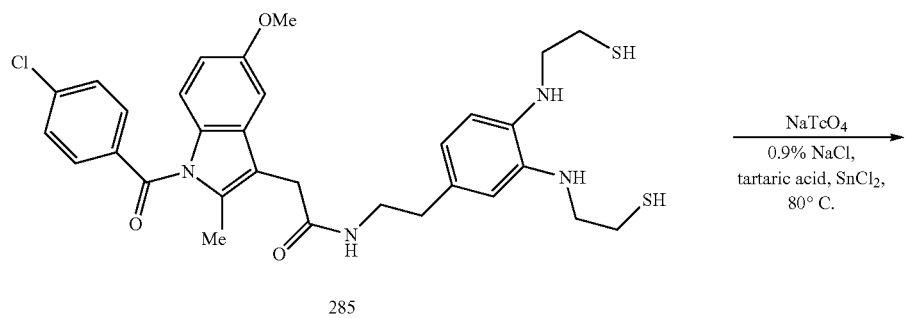
285
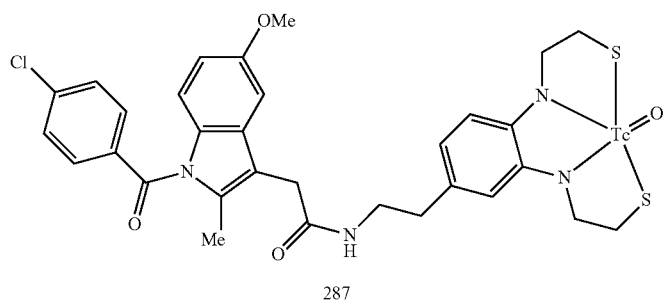
287
The Technetium complex 287 is prepared from compound 285 (example 48) as described in: Eisenhut, M., et al., J. Med. Chem., 45, 5802-5805, (2002).
Example 50
Synthesis of Compounds 290 and 291
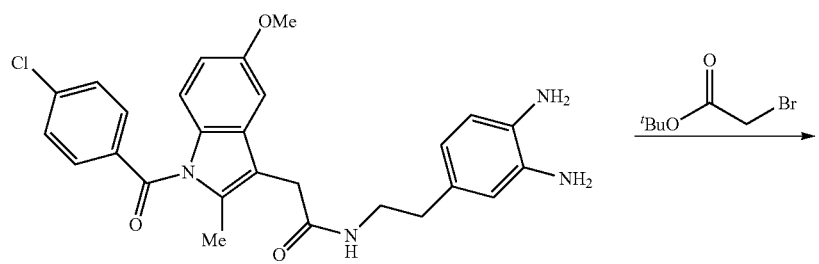
281

-continued
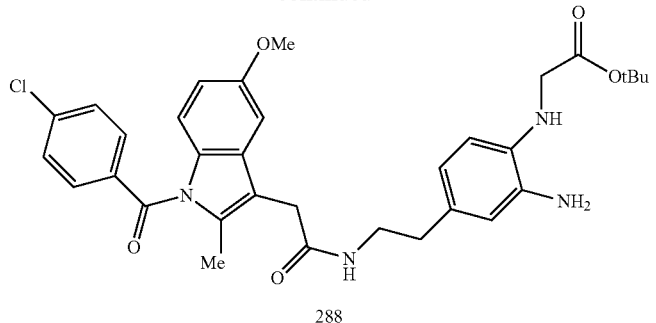
288
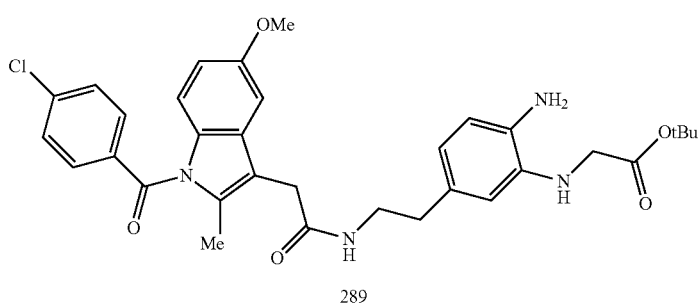
289
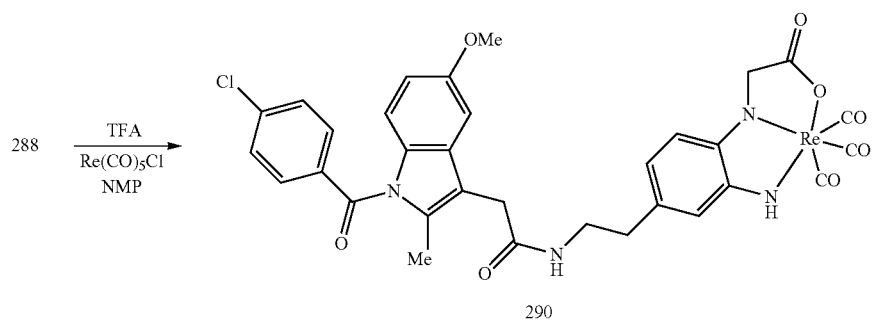
290
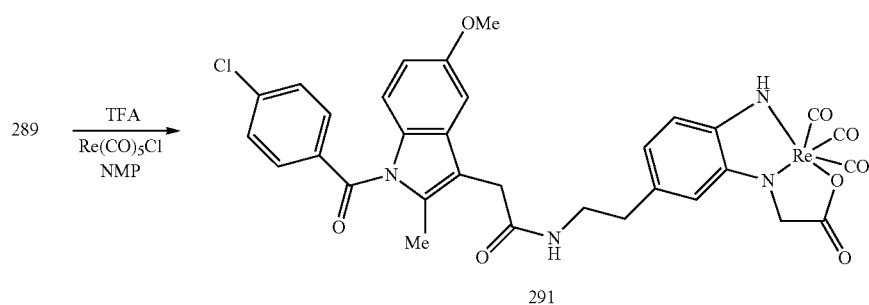
291
Compound 281 (Example 46) is coupled with tert-butyl bromoacetate in presence of a base, such as NaH, to afford compounds 288 and 289, which are separated by column chromatography on silica gel. 288 is transformed to 290 by treating with TFA in DCM followed by reaction with Re(CO)$_5$Cl by a procedure similar to the one described in Example 36. Similarly, 291 can be obtained form 289.

Example 51
Synthesis of Compounds 292 and 293
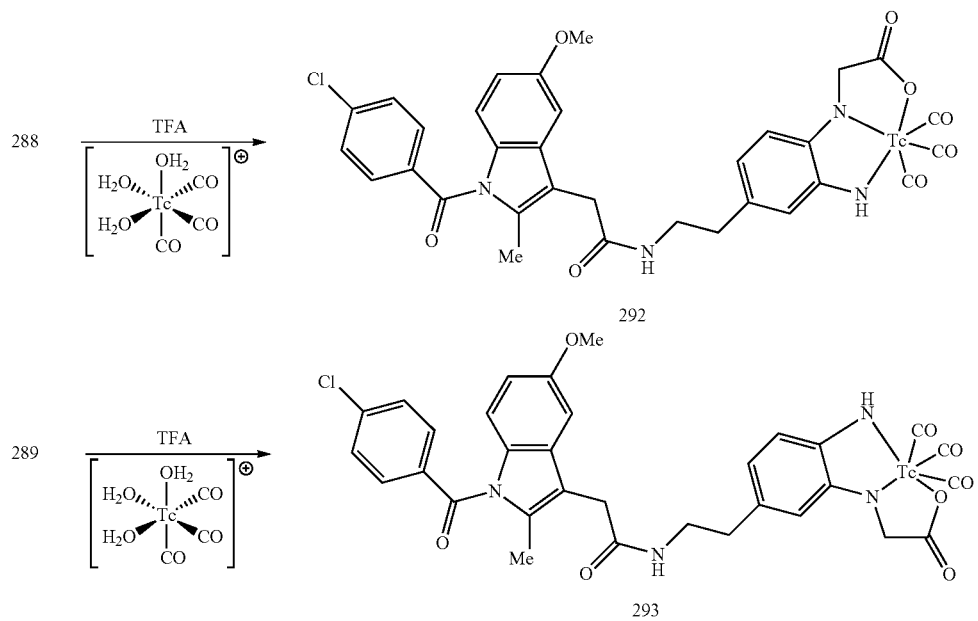
288 and 289 are converted to 292 and 293, respectively, by a procedure similar to the one described in example 37.
Example 52
Synthesis of Compound 297
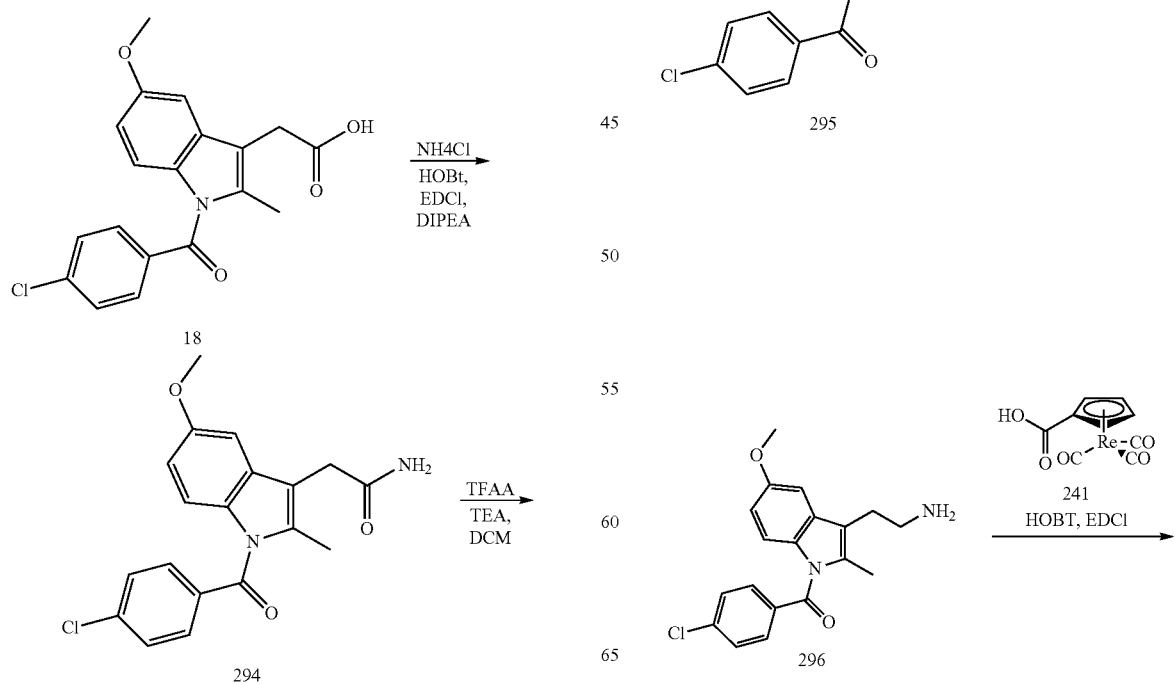

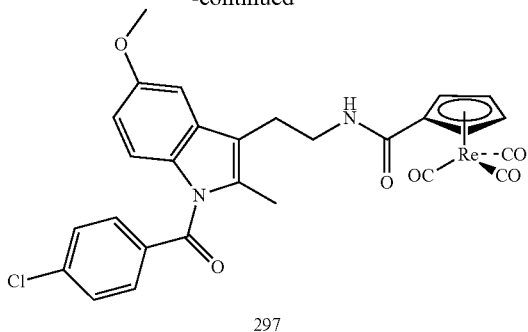

297

Intermediate 294

To the mixture of 18 (1.07 g, 3 mmol) and NH$_4$Cl (318 mg, 6 mmol) in DMF (40 ml) was added HOBt (607 mg, 4.5 mmol), EDCI (864 mg, 4.5 mmol) and DIPEA (1.6 ml, 9 mmol). The resulting mixture was stirred at room temperature overnight. Water (100 ml) was added and the product was extracted with EtOAc (2×100 ml). The combined organic layers were dried over Na$_2$SO$_4$, and the solvent was removed under reduced pressure to give the product without further purification as a yellow oil (1 g, 93.6%). LC-MS: m/z=357.1 [M+H]$^+$ Intermediate 295

To the solution of compound 294 (1 g, 2.8 mmol) in DCM (20 ml) was added TEA (606 mg, 6 mmol) and TFAA (2.1 g, 10 mmol) at 0° C. The resulting solution was stirred at RT for 1 h.

The reaction solution was concentrated under reduced pressure to give a yellow solid. The crude solid was washed with hexane (50 ml) to give the product 295 as a yellow solid (700 mg, 74%). LC-MS: m/z=339.2 [M+H]$^+$ Intermediate 296

The mixture of compound 295 (700 mg, 2.07 mmol) and Raney®-Nickel (W.R. Grace and Co., 100 mg) in THF/MeOH (5 ml/20 ml) was stirred under a hydrogen atmosphere overnight. The catalyst was removed by filtering through a column of Celite® (J.T. Baker, Phillipsberg, N.J., diatomaceous earth) and the filtrate was concentrated under reduced pressure to give the crude product, which was purified by prep-HPLC (Column: Acquity BEH C18, Waters Corp, solvent A: water/solvent B: MeCN) to give the product as light yellow solid (500 mg, 70%). LC-MS: m/z=343.1 [M+H]$^+$.

To a solution of compound 296 (171 mg, 0.5 mmol) and compound 241 (191 mg, 0.5 mmol) in DMF (15 ml) was added HOBt (135 mg, 1 mmol), EDCI (192 mg, 1 mmol) and DIPEA (258 mg, 2 mmol). The resulting solution was stirred at rt overnight. The reaction was quenched with saturated NaHCO$_3$ solution (30 ml) and extracted with ethyl acetate (2×50 ml). The combined organic extracts were washed with brine (30 ml), dried over Na$_2$SO$_4$, concentrated, and purified by prep-HPLC (Column: Acquity BEH C18, Waters Corp, solvent A: water/solvent B: MeCN) to give the compound 297 as a light yellow solid (20 mg, 6%). LC-MS: m/z=343.2 [M+H]$^+$; $^1$H NMR (400 MHz, DMSO-d6) δ 8.42 (t, J=5.8 Hz, 1H), 7.65 (q, J=8.6 Hz, 3H), 7.10 (d, J=2.3 Hz, 1H), 7.01 (d, J=9.0 Hz, 1H), 6.72 (dd, J=9.0, 2.4 Hz, 1H), 6.23 (t, J=2.1 Hz, 2H), 5.93-5.55 (m, 2H), 3.78 (s, 3H), 3.46-3.33 (m, 2H), 2.82 (t, J=6.8 Hz, 2H), 2.15 (s, 3H).

Example 53

Synthesis of Compound 299

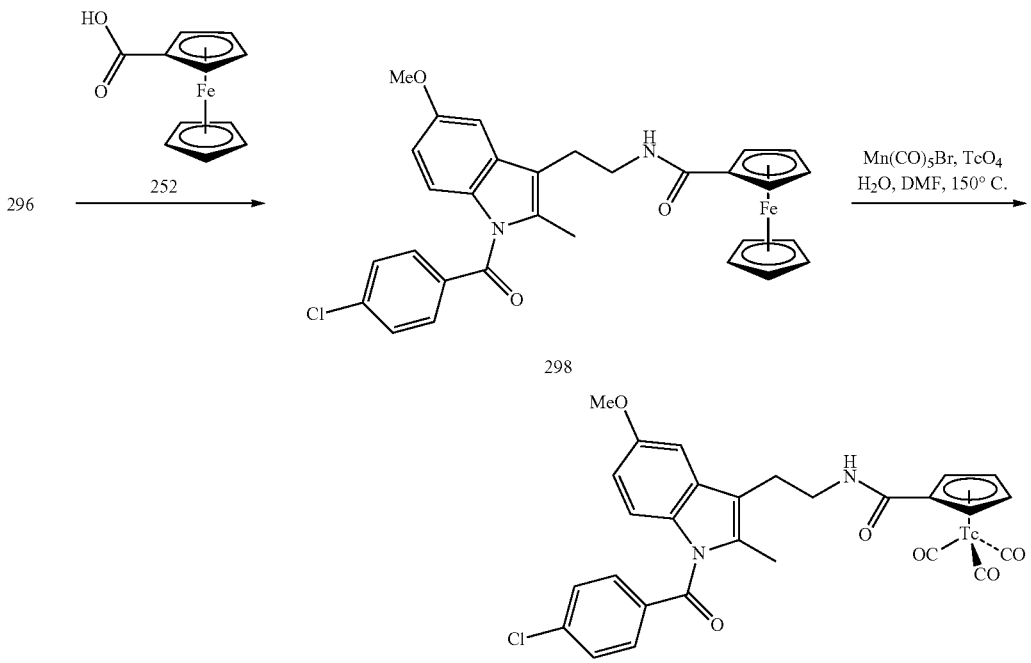

Compound 299 is prepared from compound 296 (example 52) by a procedure similar to the one described in Example 41.

Example 54

Synthesis of Compound 301

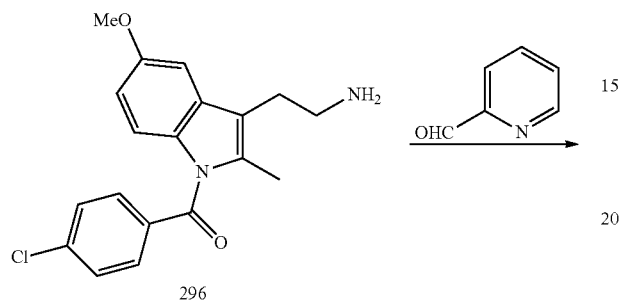

296

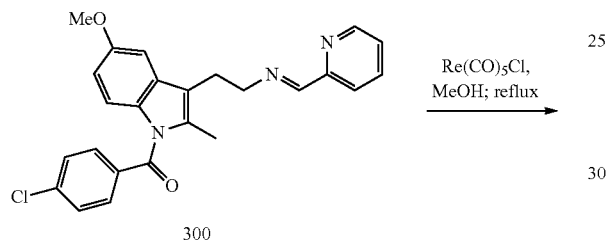

300

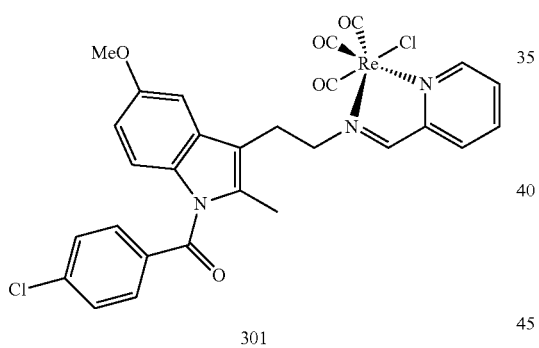

301

Compound 296 is transformed into the imine 300 by a procedure similar to the one described for compound 220 in example 35. 300 is converted into the Rhenium complex 301 as described in example 36.

Alternatively, compound 301 can be prepared as follows: A mixture of 296 (100 mg, 0.29 mmol), picolinaldehyde (31 mg, 0.29 mmol) and Re(CO)$_5$Cl (105 mg, 0.29 mmol) in MeOH (10 mL) was stirred at 75° C. for 3 h, then cooled to rt. The precipitate was filtered and washed with MeOH (2×20 ml), and dried to give compound 301 as a yellow solid (51 mg, 23%). LC-MS: m/z=759.9 [M+H]$^+$; $^1$H NMR (400 MHz, DMSO-d$_6$) δ 9.32 (s, 1H), 9.06 (d, J=5.2 Hz, 1H), 8.36 (t, J=7.7 Hz, 1H), 8.27 (d, J=7.5 Hz, 1H), 7.92-7.76 (m, 1H), 7.68 (dd, J=28.7, 8.4 Hz, 4H), 7.23 (d, J=2.1 Hz, 1H), 7.03 (d, J=9.0 Hz, 1H), 6.76 (dd, J=9.0, 2.2 Hz, 1H), 4.21 (t, J=7.9 Hz, 2H), 3.77 (s, 3H), 3.43-3.02 (m, 2H), 2.27 (s, 3H).

Example 55

Synthesis of Compound 302

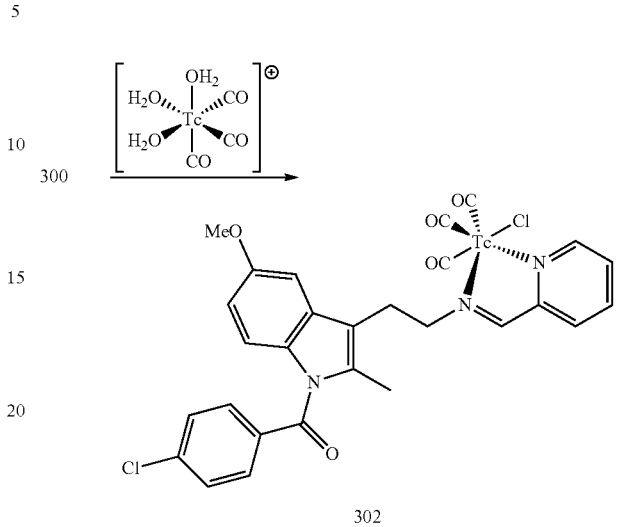

302

Compound 300 (example 54) is converted to 302 by a procedure similar to the one described in example 37.

The following compounds 303-307 can be prepared according to the procedure given in Example 44 by replacing 6-aminohexan-1-ol with the appropriate aminoalcohol.

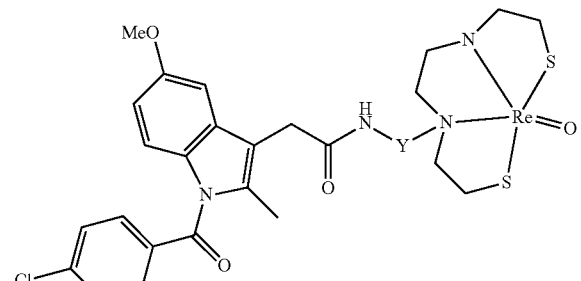

| Compound | Y = |
|---|---|
| 303 | 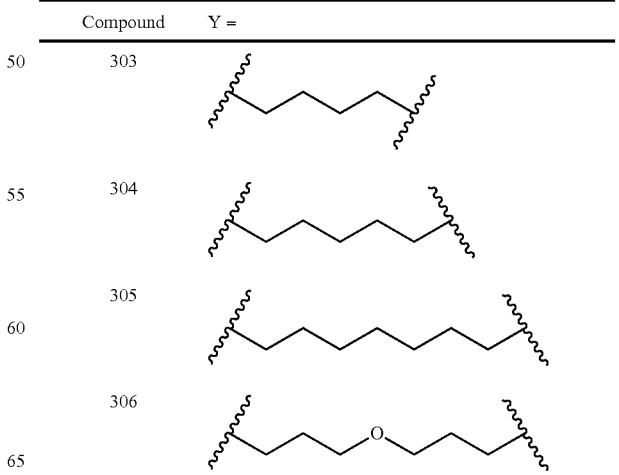 |
| 304 | |
| 305 | |
| 306 | |

| Compound | Y = |
|---|---|
| 307 | ![structure] -CH2-CH2-C(CH3)2-CH2-CH2- |

Compound 303
¹H NMR (400 MHz, CDCl3) δ 7.67 (d, J=8.2 Hz, 2H), 7.50 (d, J=8.3 Hz, 2H), 7.01-6.83 (m, 2H), 6.77-6.63 (m, 1H), 5.78 (s, 1H), 4.22-4.00 (m, 2H), 3.98-3.58 (m, 8H), 3.59-3.06 (m, 8H), 2.96 (td, J=11.7, 6.5 Hz, 1H), 2.81 (d, J=11.4 Hz, 1H), 2.74-2.52 (m, 1H), 2.39 (s, 3H), 1.78-1.64 (m, 2H), 1.46 (d, J=22.8 Hz, 2H). MS (ESI) m/z: 791.0 [M+H⁺].

Compound 304
¹H NMR (400 MHz, CDCl3) δ 7.67 (d, J=8.3 Hz, 2H), 7.49 (d, J=8.2 Hz, 2H), 6.99-6.77 (m, 2H), 6.71 (dd, J=9.0, 1.9 Hz, 1H), 5.71 (d, J=5.5 Hz, 1H), 4.26-4.07 (m, 2H), 4.02-3.89 (m, 1H), 3.85-3.71 (m, 5H), 3.64 (s, 2H), 3.51-3.13 (m, 8H), 3.09-2.87 (m, 2H), 2.71 (dd, J=13.1, 3.2 Hz, 1H), 2.40 (s, 3H), 1.89-1.70 (m, 2H), 1.59-1.46 (m, 2H), 1.32-1.19 (m, 2H). MS (ESI) m/z: 805.0 [M+H⁺].

Compound 305
¹H NMR (400 MHz, CDCl3) δ 7.67 (d, J=8.5 Hz, 2H), 7.49 (d, J=8.5 Hz, 2H), 6.99-6.78 (m, 2H), 6.70 (dd, J=9.1, 2.3 Hz, 1H), 5.59 (s, 1H), 4.27-3.92 (m, 4H), 3.90-3.71 (m, 5H), 3.64 (s, 2H), 3.55-3.14 (m, 7H), 3.06-2.88 (m, 2H), 2.79-2.65 (m, 1H), 2.39 (s, 3H), 1.81-1.68 (m, 2H), 1.41 (dt, J=14.5, 7.3 Hz, 2H), 1.35-1.13 (m, 6H). MS (ESI) m/z: 833.2 [M+H⁺].

Compound 306
1H NMR (400 MHz, CDCl3) δ 7.68 (d, J=8.4 Hz, 2H), 7.49 (d, J=8.4 Hz, 2H), 7.10-6.79 (m, 2H), 6.71 (dd, 1H), 5.89 (s, 1H), 4.22-3.97 (m, 3H), 3.97-3.74 (m, 5H), 3.63 (s, 2H), 3.58-3.07 (m, 11H), 3.05-2.94 (m, 1H), 2.89 (d, J=11.6 Hz, 1H), 2.71 (d, J=9.5 Hz, 2H), 2.36 (s, 3H), 1.98-1.83 (m, 2H), 1.78-1.66 (m, 2H). MS (ESI) m/z: 835.1 [M+H⁺].

Compound 307
¹H NMR (400 MHz, CDCl3) δ 7.68 (d, J=8.3 Hz, 2H), 7.50 (d, J=8.3 Hz, 2H), 7.05-6.78 (m, 2H), 6.71 (d, J=8.9 Hz, 1H), 5.60 (s, 1H), 4.36-3.94 (m, 3H), 3.94-3.71 (m, 5H), 3.64 (s, 2H), 3.58-3.43 (m, 1H), 3.40-3.08 (m, 6H), 3.09-2.89 (m, 2H), 2.84-2.65 (m, 1H), 2.40 (s, 3H), 2.13-1.88 (m, 1H), 1.85-1.60 (m, 2H), 1.44-1.34 (m, 2H), 1.14-0.90 (m, 6H). MS (ESI) m/z: 833.1 [M+H⁺].

The following compounds 308-313 can also be prepared according to the procedure given in Example 40 by replacing compound 25 with the appropriate intermediate (synthesis described in examples 5, 31, and 32).

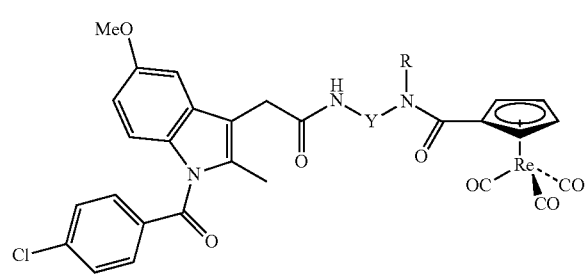

R = H, Me

| Compound | Y = |
|---|---|
| 308 | -(CH2)6- |
| 309 | -CH2-CH2-C(CH3)2-CH2-CH2- (with gem-dimethyl) |
| 310 | -CH2-CH2-CH2-O-CH2-CH2-CH2- |
| 311 | -C(CH3)2-CH2- |
| 312 | -CH2-CH2-CH2-C(CH3)2-CH2- |
| 313 | -(CH2)4-C(CH3)2-(CH2)4- |

Compound 308
¹H NMR (400 MHz, CDCl3) δ 7.66 (d, J=8.1 Hz, 2H), 7.49 (d, J=8.1 Hz, 2H), 6.88 (d, J=8.8 Hz, 2H), 6.71 (d, J=8.8 Hz, 1H), 6.48 (s, 1H), 6.09 (s, 2H), 5.81 (s, 1H), 5.33 (s, 2H), 3.82 (s, 3H), 3.65 (s, 2H), 3.33-3.19 (m, 4H), 2.38 (s, 3H), 1.61-1.51 (m, 2H), 1.48-1.40 (m, 2H), 1.36-1.23 (m, 2H). MS (ESI) m/z: 804.0 [M+H⁺].

Compound 309
¹H NMR (400 MHz, CDCl3) δ 7.68 (d, J=8.1 Hz, 2H), 7.49 (d, J=8.1 Hz, 2H), 6.87 (d, J=9.4 Hz, 2H), 6.71 (d, J=8.1 Hz, 2H), 6.00 (s, 2H), 5.85 (s, 1H), 5.31 (s, 2H), 3.83 (s, 3H), 3.64 (s, 2H), 3.32 (s, 2H), 3.19 (s, 2H), 2.39 (s, 3H), 1.50 (s, 2H), 1.44-1.37 (m, 2H), 0.87 (s, 6H). MS (ESI) m/z: 832.2 [M+H⁺].

Compound 310
¹H NMR (400 MHz, CDCl3) δ 7.67 (d, J=8.2 Hz, 2H), 7.49 (d, J=8.3 Hz, 2H), 7.41 (s, 1H), 6.91 (d, J=9.2 Hz, 2H), 6.72 (d, J=8.9 Hz, 1H), 6.20 (s, 2H), 5.99 (s, 1H), 5.30 (s, 2H), 3.82 (s, 3H), 3.67 (s, 2H), 3.48-3.33 (m, 8H), 2.38 (s, 3H), 1.66 (d, J=23.4 Hz, 4H). MS (ESI) m/z: 834.2 [M+H⁺].

Compound 311
¹H NMR (400 MHz, CDCl3) δ 7.71 (d, J=8.5 Hz, 2H), 7.50 (d, J=8.5 Hz, 2H), 6.93-6.89 (m, 2H), 6.72 (dd, J=9.0, 2.4 Hz, 1H), 5.84 (t, J=2.2 Hz, 2H), 5.77 (s, 1H), 5.57 (s, 1H), 5.34 (t, J=2.2 Hz, 2H), 3.84 (s, 3H), 3.66 (s, 2H), 3.23 (dd, J=12.8, 6.7 Hz, 2H), 2.41 (s, 3H), 1.46-1.24 (m, 10H). MS (ESI) m/z: 818.1 [M+H⁺].

Compound 312
¹H NMR (400 MHz, CDCl3) δ 7.68 (d, J=8.5 Hz, 2H), 7.49 (d, J=8.5 Hz, 2H), 6.88 (t, J=5.5 Hz, 2H), 6.70 (dd, J=9.0, 2.4 Hz, 1H), 6.10 (s, 2H), 5.92 (s, 1H), 5.76 (s, 1H), 5.34 (d, J=1.9 Hz, 2H), 3.82 (s, 3H), 3.65 (s, 2H), 3.24 (d, J=6.1 Hz, 2H), 2.39 (s, 3H), 1.71-1.63 (m, 2H), 1.58 (s, 2H), 1.46-1.38 (m, 1H), 1.36-1.23 (m, 8H). MS (ESI) m/z: 832.1 [M+H⁺].

Compound 313
¹H NMR (400 MHz, CDCl3) δ 7.67 (d, J=7.6 Hz, 2H), 7.49 (d, J=7.6 Hz, 2H), 6.87 (d, J=9.0 Hz, 2H), 6.70 (d, J=8.9 Hz, 1H), 5.87 (s, 2H), 5.71 (s, 1H), 5.44 (s, 1H), 5.32 (s, 2H), 3.83 (s, 3H), 3.65 (s, 2H), 3.32 (s, 2H), 2.40 (s, 3H), 1.40 (m, 14H). MS (ESI) m/z: 846.1 [M+H⁺].

Example 56
Synthesis of Compound 320
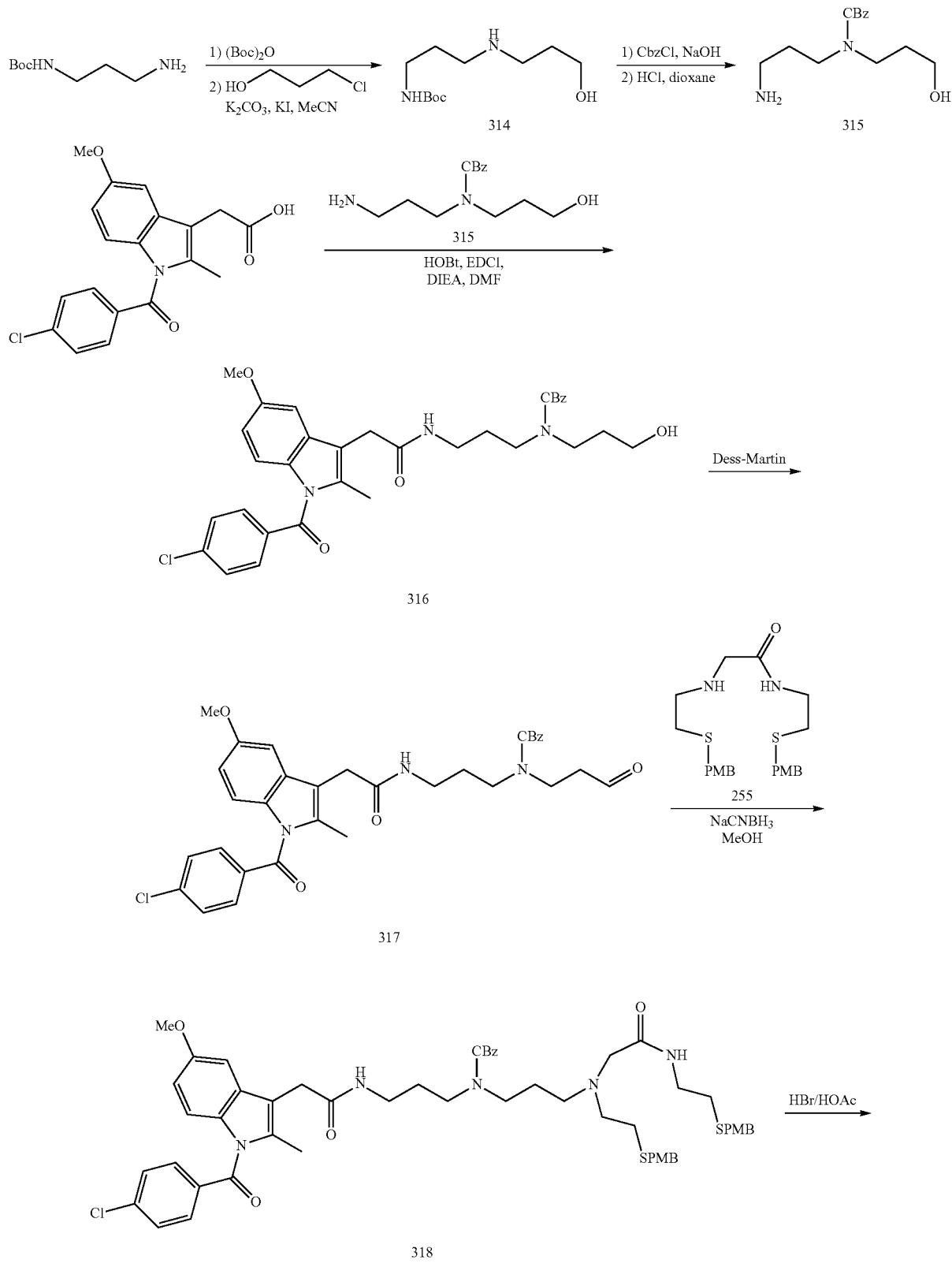

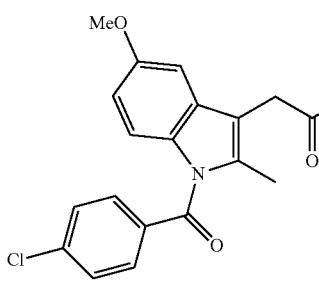
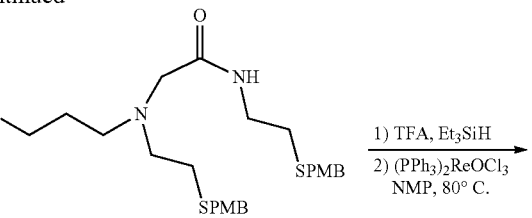

319

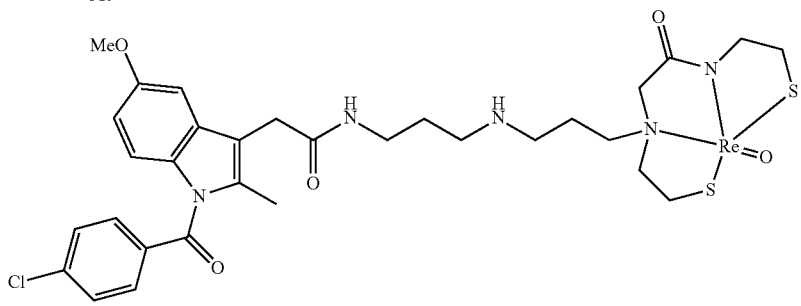

320

Intermediate 314

To a solution of propane-1,3-diamine (5.0 g, 67.5 mmol) in 100 mL of MeOH: THF (2:1) was slowly added a solution of Boc$_2$O (7.4 g, 33.8 mmol) in THF (20 mL) at 0° C. The reaction mixture was allowed to stir at room temperature overnight. LCMS showed the reaction was completed, the solvent was evaporated, water (100 mL) was added, and the mixture was extracted with DCM (100 mL×3). The combined organic layers were washed with brine, dried over Na$_2$SO$_4$, filtered and the filtrate was concentrated in vacuum to give tert-butyl(3-aminopropyl)carbamate as a colorless oil (1.8 g, yield: 32%). A mixture of tert-butyl(3-aminopropyl)carbamate (5.22 g, 30 mmol), 3-chloropropan-1-ol (11.28 g, 120 mmol), K$_2$CO$_3$ (24.84 g, 180 mmol) and KI (996 mg, 6 mmol) in MeCN (300 mL) was stirred at 80° C. overnight. The solvent was evaporated and the residue was washed with water (300 mL) and extracted with EtOAc (200 mL×3). The combined organic layers were washed with brine, dried over Na$_2$SO$_4$, filtered and the filtrate was concentrated to give compound 314 (6.5 g, 93%) as a yellow oil.

Intermediate 315

To a solution of compound 314 (6.5 g, 28 mmol) in dioxane (100 mL) was added NaOH (4 M, 21 mL) followed by CbzCl (4.76 g, 28 mmol) at 0° C. The resulting mixture was stirred at rt overnight. The pH was adjusted to pH=6 with HCl (1 N), and the mixture was extracted with EtOAc (100 mL×3). The combined organic layers were washed with brine, dried over Na$_2$SO$_4$, filtered and the filtrate was concentrated. The residue was purified by column chromatography on silica gel (eluent: PE/EtOAc: 8/1) to give tert-butyl(3-((3-hydroxypropyl) (2-oxo-2-phenyl-1$\lambda^2$-ethyl) amino)propyl) carbamate as a colorless oil (7 g, 74%). This was dissolved in a solution of HCl in Dioxane (4M, 5 ml) and stirred at rt for 2 h. The volatiles were removed to yield compound 315 (2-((3-aminopropyl) (3-hydroxypropyl) amino)-1-phenyl-2$\lambda^2$-ethan-1-one) which was used in subsequent reactions without further purification.

Intermediate 316

To a solution of indomethacin (366 mg, 0.93 mmol) in DMF (5 mL) was added compound 315 (300 mg, 1.12 mmol), HOBt (228 mg, 1.69 mmol), EDCI (323 mg, 1.69 mmol) and DIPEA (479 mg, 3.72 mmol) at 0° C. The resulting solution was stirred at room temperature for 3.0 h. Then water was added (20 mL) and the mixture was extracted with EtOAc (30 mL×3). The combined organic layers were washed with brine, dried over Na$_2$SO$_4$, filtered and the filtrate was concentrated to get the intermediate 316 (500 mg, yield: 89%) as a light yellow solid.

Intermediate 317

To a solution of 316 (500 mg, 0.83 mmol) in DCM (20 ml) at 0° C. was added Dess-Martin periodinane (385 mg, 0.91 mmol). The resulting solution was stirred rt for 1.5 h, saturated Na$_2$S$_2$O$_3$ (10 mL) was added and the mixture was stirred for 10 min, then washed with aqueous Na$_2$CO$_3$ solution, extracted with DCM (30 mL×3). The combined organic layers were washed with brine, dried over Na$_2$SO$_4$, filtered and the filtrate was concentrated to give compound 317 (490 mg, yield: 95%) as a yellow solid.

Intermediate 318

To a solution of compound 317 (490 mg, 0.81 mmol) in MeOH (10 mL) was added 255 (352 mg, 0.81 mmol), and 0.5 mL of acetic acid. The resulting solution was stirred at room temperature for 0.5 h. Then NaBH$_3$CN (256 mg, 4.06 mmol) was added to the reaction mixture, which was stirred for 2. h. Then water (20 mL) was added and the mixture was extracted with DCM (30 mL×3). The combined organic layers were washed with brine, dried over Na$_2$SO$_4$, filtered and the filtrate was concentrated to give the crude product 318, which was purified by chromatography on silica gel (DCM/MeOH: 50/1) to give the product (360 mg, yield: 45%) as yellow oil.

Intermediate 319

318 (360 mg, 0.35 mmol) was dissolved in a solution of HBr in AcOH (40%, 5 mL) and was stirred at room temperature for 2 h. The reaction was concentrated to give 319, which was used in the next step without purification (290 mg, crude).

Compound 320

To a solution of 319 (290 mg, 0.32 mmol) in TFA (8 mL) was added Et₃SiH (68 mg, 0.59 mmol). The resulting mixture was stirred at 80° C. for 1.5 h. The volatiles were removed and the residue was dissolved in NMP and (PPh₃)₂ReOCl₃ (Sigma-Aldrich, Order #370193, 1.0 eq) was added. The mixture was stirred at 80° C. overnight. The reaction was concentrated and the residue was purified by Prep-HPLC (Column: Acquity BEH C18, Waters Corp, A: water/B: MeCN) to give compound 320 as a light pink solid (16 mg, yield: 6%)

¹H NMR (400 MHz, CDCl3) δ 8.29 (s, 1H), 7.67 (d, J=8.5 Hz, 2H), 7.49 (d, J=8.6 Hz, 2H), 6.97-6.82 (m, 2H), 6.74-6.57 (m, 2H), 4.76 (d, J=16.3 Hz, 1H), 4.60-4.48 (m, 1H), 4.16-4.03 (m, 2H), 4.01-3.89 (m, 2H), 3.82 (s, 3H), 3.75-3.61 (m, 3H), 3.56-3.43 (m, 1H), 3.38-3.05 (m, 5H), 2.98-2.65 (m, 5H), 2.42-2.11 (m, 5H), 1.75-1.50 (m, 2H). MS (ESI) m/z: 848.1 (M+H⁺).

Example 57

Synthesis of Compounds 328 and 329

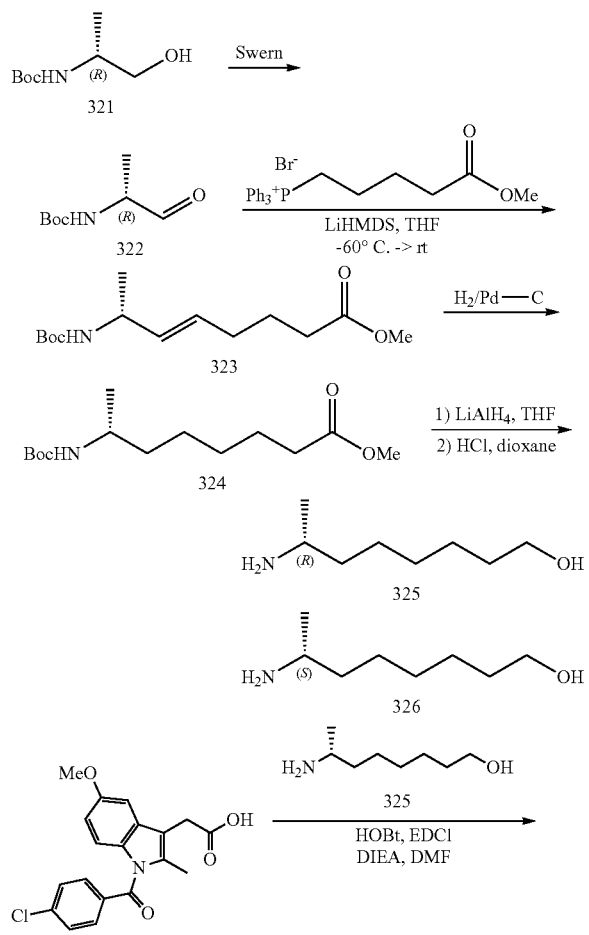

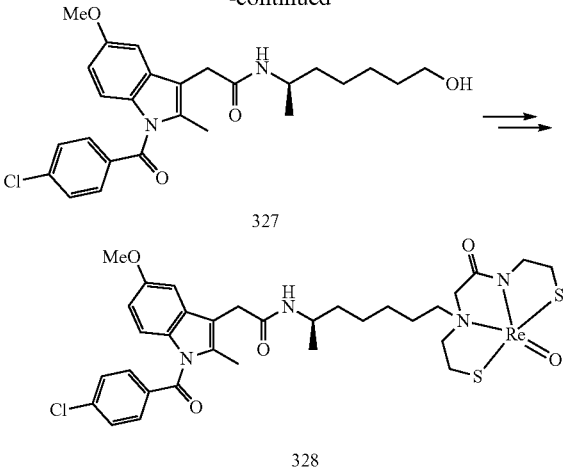

Intermediate 322

To a solution of oxalyl chloride (3.1 g, 24.5 mmol) in dry DCM (200 mL) was added DMSO (2.9 mL, 40.8 mmol) at −60° C. The mixture was stirred for 30 min. Then a solution of tert-butyl(R)-(1-hydroxypropan-2-yl)carbamate (3.5 g, 20 mmol) in DCM (20 mL) was added at −60° C. The resulting solution was stirred for another 30 min. Triethylamine (11.1 mL, 80 mmol) was added at −60° C., and the mixture was stirred for 2 h at room temperature. Water (100 mL) was added and the mixture was extracted with DCM (3×50 mL). The combined organic layers were washed with brine, dried over Na₂SO₄, filtered and the filtrate was concentrated to give the aldehyde 322 as a light yellow oil (3.2 g, 94%), which was used in the next step without further purification.

Intermediate 323

To a solution of (4-methoxy-4-oxobutyl)triphenylphosphonium bromide (8.2 g, 18.5 mmol) in dry THF (150 mL) was added LiHMDS (1 M in THF, 20 mL) dropwise. The resulting reaction was stirred at 0° C. for 30 min. Then the reaction was recooled to −60° C. A solution of compound 322 (3.2 g, 18.5 mmol) in dry THF (50 mL) was added to the reaction. The solution was slowly warmed to RT and stirred overnight. The reaction was quenched with NH₄Cl (aq.), extracted with EtOAc (100 mL×3). The combined organic layers were washed with brine, dried over Na₂SO₄, filtered and the filtrate was concentrated in vacuo. The residue was purified by chromatography on silica gel (eluent: PE/EtOAc=10/1) to give the compound 323 as a colorless oil (1.9 g, yield: 40%).

Intermediate 324

A mixture of compound 323 (1.9 g, 7.4 mmol) and Pd/C (200 mg) in MeOH (50 mL) was stirred under an atmosphere of H₂ overnight. The catalyst was filtered off, the filtrate was washed with MeOH (30 mL×3), and concentrated to give 324 as a light yellow oil (1.9 g, yield: 99%) which was used without further purification.

Intermediate 325

To a solution of compound 324 (518 mg, 2 mmol) in dry THF (15 mL) was added LiAlH₄ (114 mg, 3 mmol) slowly at 0° C. The resulting reaction was stirred at room temperature for another 2 h. The reaction was quenched with H₂O (15 ml), extracted with EtOAc (20 mL×3).

The combined organic layers were washed with brine, dried over Na₂SO₄, filtered and the filtrate was concentrated. The residue was purified by chromatography on silica gel (eluent: PE/EtOAc=4/1) to give the Boc-protected product as a colorless oil (270 mg, yield: 58%). This was dissolved in HCl (4M in dioxane, 5 mL) and stirred at rt for 2 h, after which time LCMS showed the reaction was completed. The reaction was concentrated to give 325, which was used without further purification (150 mg, yield: 99%).

Intermediate 326

326 was obtained by a sequence similar to the one described for intermediate 325, starting with (S)-(1-hydroxypropan-2-yl)carbamate.

Intermediate 327

To a solution of indomethacin (341 mg, 0.95 mmol) in DMF (5 mL) was added 325 (150 mg, 1.14 mmol), HOBt (230 mg, 1.71 mmol), EDCI (327 mg, 1.71 mmol) and DIPEA (490 mg, 3.8 mmol) at 0° C. The resulting solution was stirred room temperature for 3.0 h. Then water was added (20 mL) and the mixture was extracted with EtOAc (20 mL×3). The combined organic layers were washed with brine, dried over $Na_2SO_4$, filtered and the filtrate was concentrated to give 327 (300 g, yield: 67%) as a light yellow solid.

Compound 328

Compound 328 was obtained from compound 327 by applying procedures similar to the ones described in Example 56 (compound 316 to compound 320). The compound was purified by Prep-HPLC (Column: Acquity BEH C18, Waters Corp, A: water/B: MeCN) to give a light pink solid.

$^1$H NMR (400 MHz, $CDCl_3$) δ 7.68 (d, J=7.4 Hz, 2H), 7.50 (d, J=5.4 Hz, 2H), 6.93-6.81 (m, 2H), 6.75-6.67 (m, 1H), 5.29 (d, J=8.4 Hz, 1H), 4.69-4.52 (m, 2H), 4.14-3.95 (m, 3H), 3.94-3.85 (m, 1H), 3.83 (s, 3H), 3.63 (s, 2H), 3.55-3.06 (m, 6H), 2.91-2.78 (m, 1H), 2.40 (d, J=1.8 Hz, 3H), 1.60-1.52 (m, 1H), 1.38-1.15 (m, 7H), 1.05 (d, J=6.6 Hz, 3H). MS (ESI) m/z: 847.1 (M+H$^+$).

Compound 329

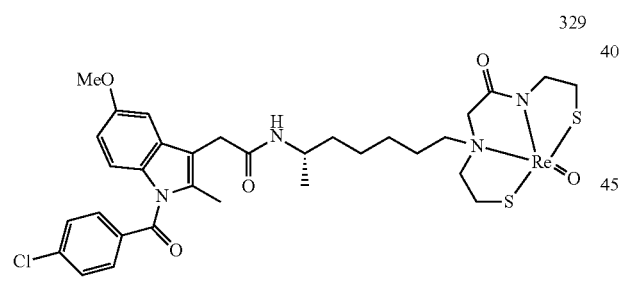

329

Compound 329 was obtained by procedures similar to the ones described for compound 328, using intermediate 326.

$^1$H NMR (400 MHz, $CDCl_3$) δ 7.67 (d, J=8.5, 1.0 Hz, 2H), 7.50 (d, J=8.6 Hz, 2H), 6.92-6.82 (m, 2H), 6.74-6.67 (m, 1H), 5.30 (d, J=8.5 Hz, 1H), 4.67-4.52 (m, 2H), 4.14-3.95 (m, 3H), 3.95-3.75 (m, 4H), 3.63 (s, 2H), 3.54-3.02 (m, 6H), 2.89-2.78 (m, 1H), 2.40 (d, J=1.8 Hz, 3H), 1.61-1.55 (m, 1H), 1.48-1.13 (m, 7H), 1.05 (d, J=6.6 Hz, 3H). MS (ESI) m/z: 847.1 (M+H$^+$).

The following compounds 330-333 can also be prepared according to the procedure given in Example 57 by replacing intermediates 325/326 with the appropriate aminoalcohol.

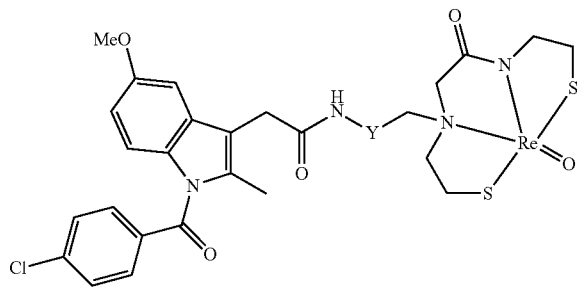

| Compound | Y = |
|---|---|
| 330 | ![gem-dimethyl linker] |
| 331 | ![cyclopropane linker] |
| 332 | ![gem-difluoro linker] |
| 333 | ![trans-cyclopropane linker] |

Example 58

Synthesis of Compound 341

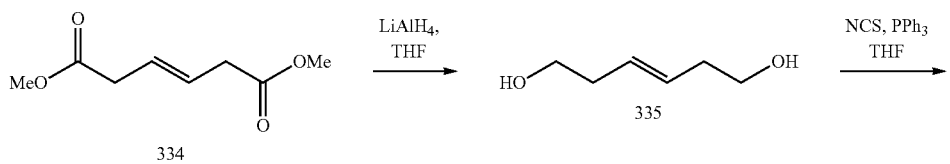

-continued
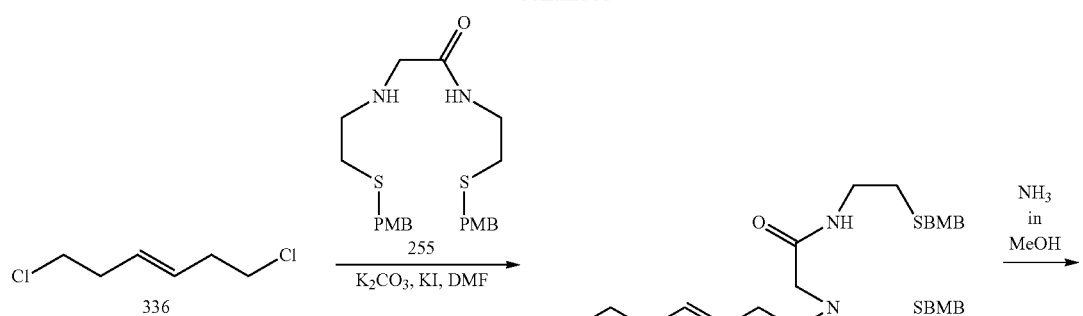
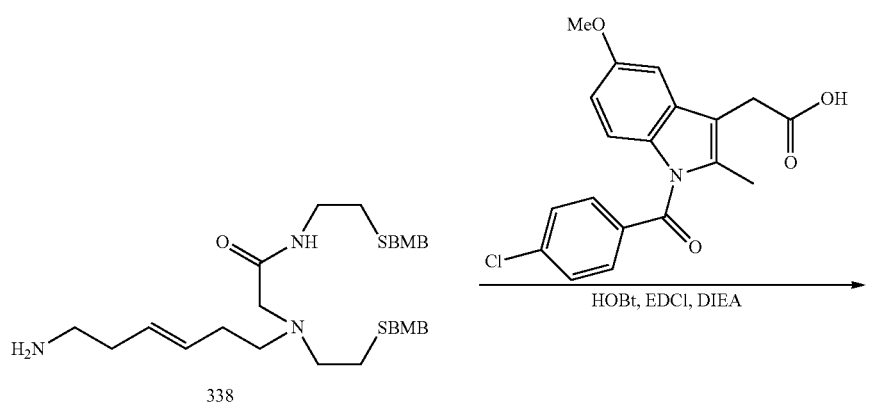
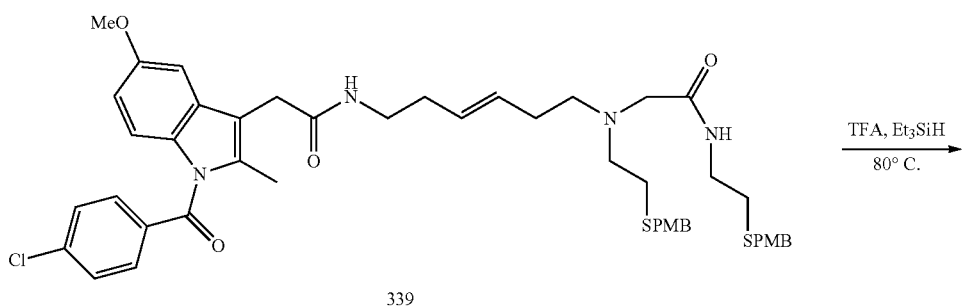
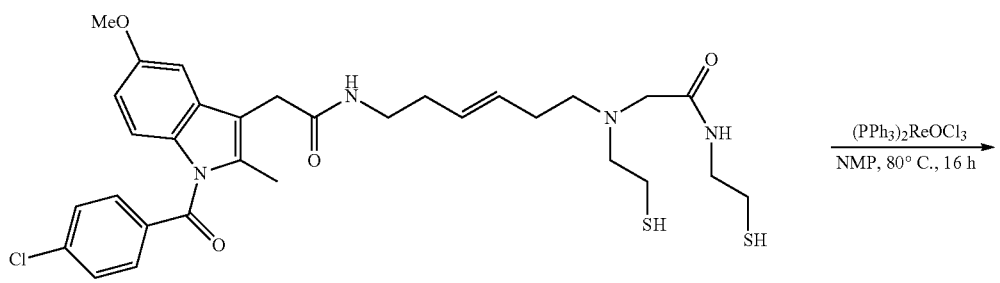

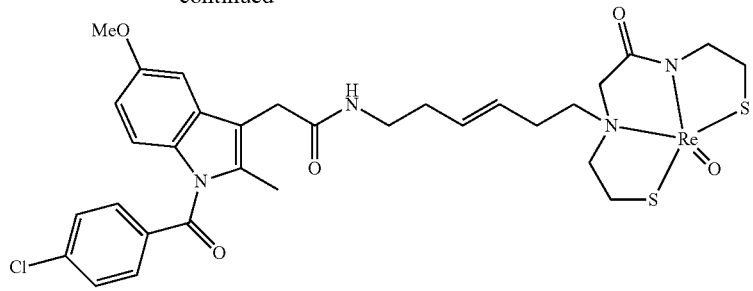

341

Intermediate 335

To a solution of 334 (CAS No.: 25126-93-6, 3.45 g, 20.08 mmol) in THF (100 ml) was added lithium aluminum hydride (2.27 g, 60 mmol) at −78° C. After an hour the mixture was warmed to room temperature and stirred under nitrogen for 4 h. The reaction was then quenched by the slow addition of cold ethyl acetate. The white precipitate that formed was then filtered off and washed with cold ether to give the diol 335 3.2 g (100%) as a colorless oil.

Intermediate 336

To a solution of triphenylphosphine (2.0 g, 7.50 mmol) in THF (10 mL) was added N-chlorosuccinimide (1.0 g, 7.50 mmol). The reaction mixture was allowed to stir at room temperature for 10 min, then 331 (400 mg, 3.4 mmol) was added. The mixture was stirred overnight. Then water (20 mL) was added. The mixture was extracted with EtOAc (30 mL×3), the combined organic layers were washed with brine, dried over $Na_2SO_4$, filtered and the filtrate was concentrated to give the crude product, which was purified by chromatography on silica gel (EtOAc/hexanes) to give the dichloride 336 (260 mg yield: 50%) as a colorless oil.

Intermediate 337

To a solution of 336 (900 mg, 5.92 mmol) in DMF (15 mL) compound 255 (850 mg, 1.97 mmol), $K_2CO_3$ (543 mg, 3.94 mmol) and KI (327 mg, 1.97 mmol) were added. The mixture was heated to 80° C. overnight. Then water (50 mL) was added. The mixture was extracted with EtOAc (40 mL×3), the combined organic layers were washed with brine, dried over $Na_2SO_4$, filtered and the filtrate was concentrated to give the crude product which was purified by chromatography on silica gel (DCM/MeOH=50/1) to give 337 (400 mg, yield: 37%) as yellow oil.

Intermediate 338

Compound 337 (400 mg, 0.72 mmol) was dissolved in a solution of $NH_3$ in MeOH (7M, 15 mL) and was heated to 110° C. in an autoclave overnight. The volatiles were removed and the crude product was purified by chromatography on silica gel (DCM/MeOH/$H_2O$=100:5:1) to give the intermediate 338 (240 mg, yield: 63%) as yellow oil.

Intermediate 339

To the solution of 338 (240 mg, 0.45 mmol) in DMF (10 mL) was added indomethacin (2-(1-(4-chlorobenzoyl)-5-methoxy-2-methyl-1H-indol-3-yl)acetic acid, 134 mg, 0.37 mmol), HOBt (92 mg, 0.68 mmol), EDCI (130 mg, 0.68 mmol) and DIPEA (190 mg, 1.48 mmol) at) 0° C. The resulting solution was stirred at rt for 3 h. Water (20 mL) was added and the mixture was extracted with EtOAc (20 mL×4). The combined organic layers were washed with brine, dried over $Na_2SO_4$, filtered and the filtrate was concentrated. Chromatography on silica gel (DCM: MeOH=50:1) afforded the product 339 (300 mg, yield: 93%) as a white solid.

Intermediate 340

To a solution of 339 (300 mg, 0.34 mmol) in TFA (2.0 mL) was added $Et_3SiH$ (75 mg, 0.68 mmol). The resulting mixture was stirred at 80° C. for 1.5 h. The reaction was concentrated to give 340 which was used without further purification.

Compound 341

To a solution of 340 in NMP was added $(PPh_3)_2ReOCl_3$ (Sigma-Aldrich, Order #370193, 1.0 eq) and the mixture was stirred at 80° C. overnight. The reaction was concentrated and the residue was purified by Prep-HPLC (Column: Acquity BEH C18, Waters Corp, A: water/B: MeCN) to give compound 341 as a light pink solid (35 mg, yield: 10%).

$^1$H NMR (400 MHz, CDCl3) δ 7.67 (d, J=8.5 Hz, 2H), 7.50 (d, J=8.5 Hz, 2H), 6.95-6.85 (m, 2H), 6.73 (dd, J=9.0, 2.5 Hz, 1H), 5.63 (t, J=5.5 Hz, 1H), 5.49-5.36 (m, 1H), 5.18-5.08 (m, 1H), 4.70-4.53 (m, 2H), 4.13-4.03 (m, 2H), 3.84 (s, 3H), 3.83-3.74 (m, 1H), 3.64 (s, 2H), 3.51-3.04 (m, 8H), 2.86 (dd, J=13.5, 4.3 Hz, 1H), 2.36 (s, 3H), 2.34-2.21 (m, 2H), 2.17-2.06 (m, 2H). MS (ESI) m/z: 831.1 (M+H$^+$).

Example 59

Synthesis of Compound 346

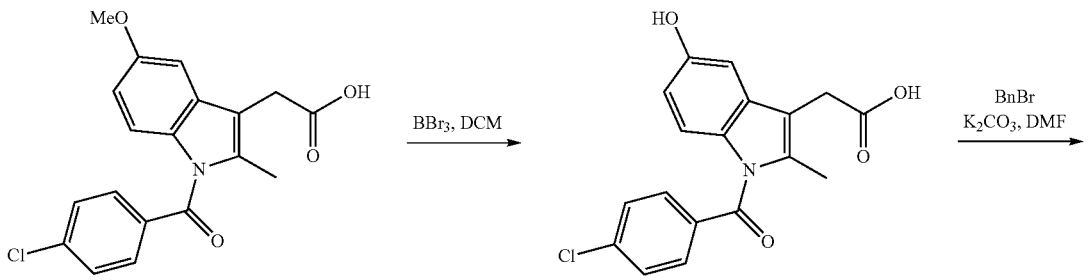

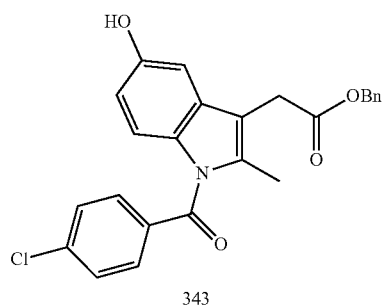

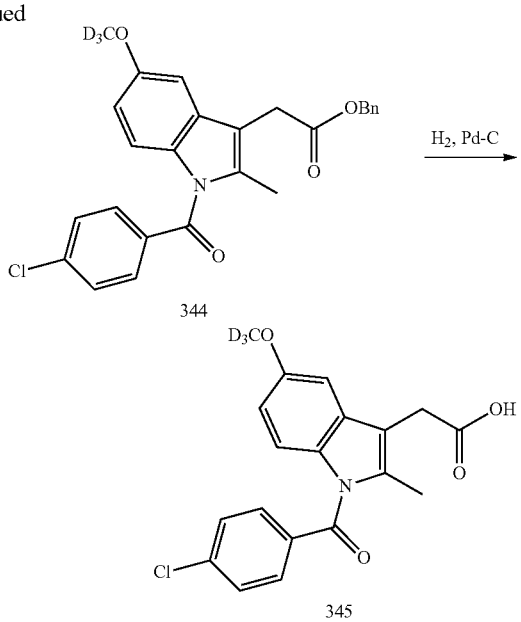

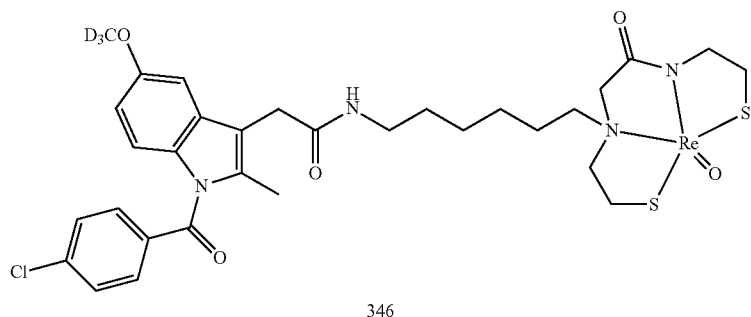

Intermediate 342

To a solution of indomethacin (2-(1-(4-chlorobenzoyl)-5-methoxy-2-methyl-1H-indol-3-yl)acetic acid, 3.57 g, 10 mmol) in dry DCM (50 mL) was added a solution of BBr$_3$ in DCM (1M, 13 mL) dropwise at −78° C. The resulting solution was stirred at room temperature for another 1 h. LCMS showed the reaction was completed. Water (100 mL) was added to the reaction slowly, and the mixture was extracted with DCM (70 mL×3). The combined organic layers were washed with brine, dried over Na$_2$SO$_4$, filtered and the filtrate was concentrated to give the product (2.4 g, yield: 70%) as light yellow solid.

Intermediate 343

To a solution of 342 (2.4 g, 4.86 mmol) and K$_2$CO$_3$ (520 mg, 4.86 mmol) in DMF (30 mL) was added BnBr (0.3 mL) dropwise. The mixture was stirred at room temperature for 1.0 h, then water (50 mL) was added and the mixture was extracted with EtOAc (50 mL×3). The combined organic layers were washed with brine, dried over Na$_2$SO$_4$, filtered and the filtrate was concentrated. The residue was purified by chromatography on silica gel (PE/EA=2/1) to give the benzyl ester 343 (2.5 g yield: 83%) as a white solid.

Intermediate 344

To a solution of 343 (800 mg, 2.54 mmol) and PPh$_3$ (1.45 g, 7.62 mmol) in THF (30 ml) was added CD$_3$OD (135 mg, 5.08 mmol) under N$_2$ at 0° C. The mixture was stirred for 20 min, and then DEAD (964 mg, 7.62 mmol) was added dropwise at 0° C. The mixture was stirred at room temperature overnight. Then water (30 mL) was added and the mixture was extracted with EtOAc (40 mL×3). The combined organic layers were washed with brine, dried over Na$_2$SO$_4$, filtered and the filtrate was concentrated. The residue was purified by chromatography on silica gel (PE/EA=10/1) to get the product 344 (450 mg, yield: 40%) as a white solid.

Intermediate 345

A mixture of compound 344 (300 mg, 0.66 mmol) and Pd/C (60 mg) in THF (20 mL) was stirred under H$_2$ for 3 h. The catalyst was filtered off, the filtrate was washed with THF (O$_1$ mL×3), and concentrated to give 2-(1-(4-chlorobenzoyl)-5-(methoxy-d$_3$)-2-methyl-1H-indol-3-yl)acetic acid 345 (240 mg, 98%) which was used without further purification.

Compound 346 was synthesized from 2-(1-(4-chlorobenzoyl)-5-(methoxy-d$_3$)-2-methyl-1H-indol-3-yl)acetic acid 345 by a procedure similar to the one described in Example 57, using 6-aminohexan-1-ol instead of intermediate 315.

$^1$H NMR (400 MHz, CDCl3) δ 7.68 (d, J=8.5 Hz, 2H), 7.50 (d, J=8.5 Hz, 2H), 6.93-6.79 (m, 2H), 6.71 (dd, J=9.0, 2.5 Hz, 1H), 5.60 (t, J=5.7 Hz, 1H), 4.67-4.51 (m, 2H), 4.17-4.01 (m, 2H), 3.97-3.81 (m, 1H), 3.65 (s, 2H), 3.53-3.41 (m, 1H), 3.39-3.07 (m, 6H), 2.85 (dd, J=13.4, 4.2 Hz, 1H), 2.40 (s, 3H), 1.80-1.63 (m, 2H), 1.50-1.38 (m, 2H), 1.36-1.20 (m, 4H). MS (ESI) m/z: 836.0 (M+H$^+$).

Example 60

Synthesis of Compound 351

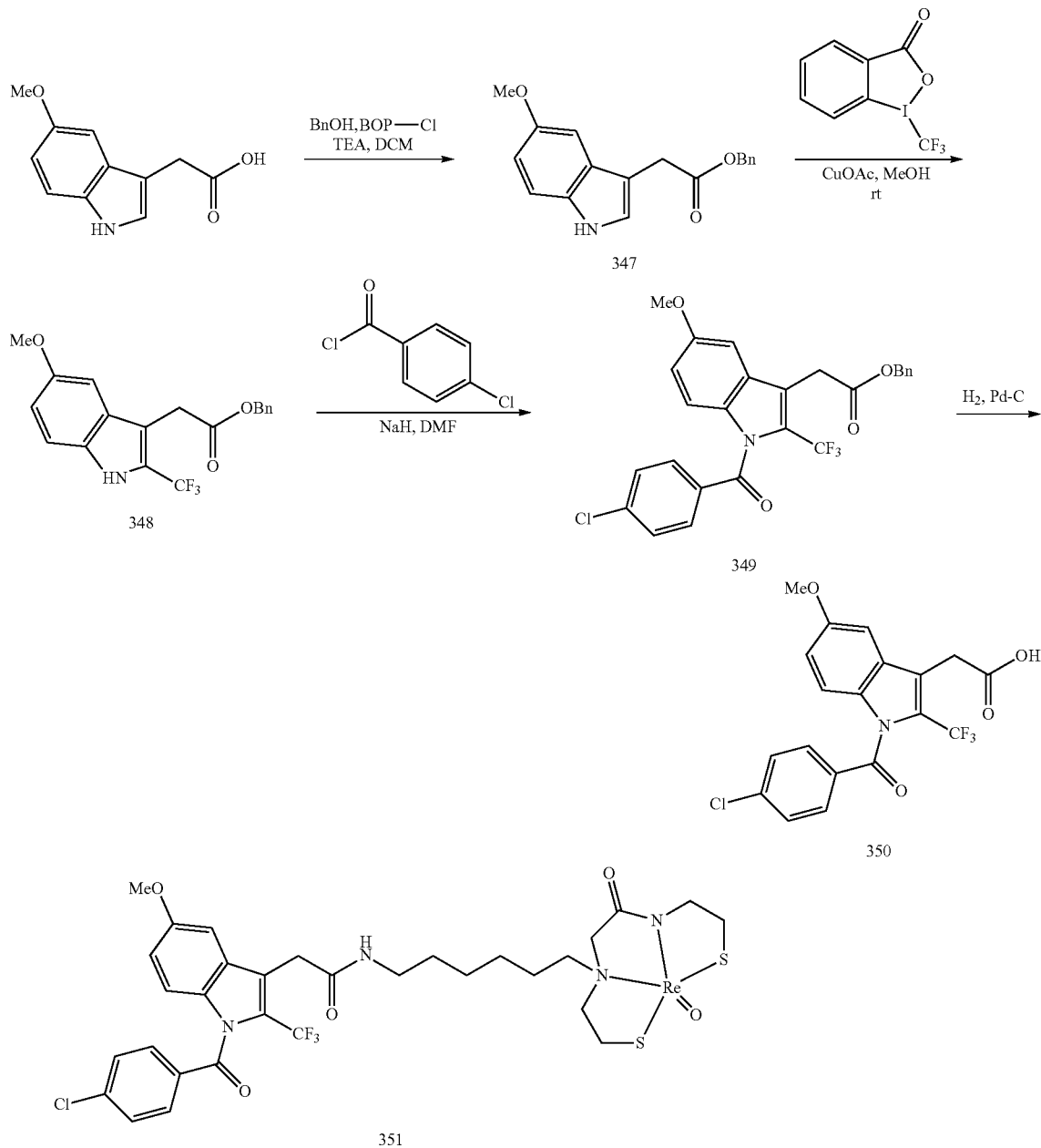

2-(1-(4-Chlorobenzoyl)-5-methoxy-2-(trifluoromethyl)-1H-indol-3-yl)acetic acid, 350, can be synthesized as described by Anna L. Blobaum, Md. Jashim Uddin, Andrew S. Felts, Brenda C. Crews, Carol A. Rouzer, and Lawrence J. Marnett, ACS Med. Chem. Lett., 4, 486-490, (2013). Alternatively, 350 can be synthesized as outlined below.

Intermediate 347

2-(5-methoxy-1H-indol-3-yl)acetic acid (5 g, 24.4 mmol) and BOP-Cl (7.4 g, 29 mmol) were suspended in DCM (100 mL), and $Et_3N$ (5.4 g, 53.7 mmol) was slowly added. The resulting solution was stirred for 30 min. Benzyl alcohol (2.9 g, 26.8 mmol) was added and the mixture was stirred for 12 h. DCM (100 mL) was added, the layers were separated and the organic layer was washed with water (200 mL) and brine. The organic layer was concentrated and purified by chromatography on silica gel (eluent: PE/EtOAc=2/1) to give 347 as a white solid (6.1 g, 85%).

Intermediate 348

A mixture of compound 347 (4.7 g, 15.82 mmol) and Togni's reagent (1-Trifluoromethyl-1,2-benziodoxol-3-(1H)-one, 6.5 g, 20.56 mmol) in MeOH (100 mL) was degassed for 15 min, then CuOAc (1.4 g, 11 mmol) was added. The resulting mixture was stirred at rt overnight. The solvent was removed; water (100 mL) was added, extracted with EtOAc (100 mL×2). The combined organic layers were washed with brine, dried over $Na_2SO_4$, filtered and the filtrate was concentrated. The residue was purified by chromatography on silica gel (eluent: PE/EtOAc=5/1) to give the product as a white solid (4 g, 70%).

Intermediate 349

To a solution of compound 348 (4 g, 11 mmol) in dry DMF (50 mL) was added NaH (750 mg, 18.7 mmol). The reaction was stirred for another 30 min, and then 4-chlorobenzoyl chloride (2.9 g, 16.5 mmol) was added. The resulting mixture was stirred at room temperature overnight. The reaction was quenched by addition of sat'd aq, $NH_4Cl$ solution (100 mL), extracted with EtOAc (100 mL×3). The combined organic layers were washed brine, dried over $Na_2SO_4$, filtered and the filtrate was concentrated. The residue was purified by chromatography on silica gel (eluent: PE/EtOAc=2/1) to give the product as a yellow solid (3.3 g, 50%).

Intermediate 350

A mixture of compound 349 (3.3 g, 6.5 mmol) and Pd/C (1 g) in THF (30 mL) was stirred at 40° C. for 1 h under $H_2$ atmosphere. The catalyst was filtered off and washed with MeOH (30 mL×3). The filtrate was concentrated in vacuo to give the crude product which was purified by chromatography on silica gel (eluent: DCM/MeOH=40/1) to give 2-(1-(4-chlorobenzoyl)-5-methoxy-2-(trifluoromethyl)-1H-indol-3-yl) acetic acid, 350, as a solid (1.6 g, yield: 60%).

Compound 351 was synthesized from 2-(1-(4-chlorobenzoyl)-5-methoxy-2-(trifluoromethyl)-1H-indol-3-yl) acetic acid, 350, by a procedure similar to the one described in Example 42.

$^1$H NMR (400 MHz, CDCl3) δ 7.83 (d, J=8.7 Hz, 2H), 7.56 (d, J=7.7 Hz, 2H), 7.15 (s, 1H), 6.91 (d, J=9.0 Hz, 1H), 6.73 (d, J=9.2 Hz, 1H), 5.60 (s, 1H), 4.74-4.54 (m, 2H), 4.23-4.04 (m, 2H), 4.00-3.74 (m, 6H), 3.49 (s, 1H), 3.42-3.06 (m, 6H), 2.89 (s, 1H), 1.69-1.44 (m, 4H), 1.42-1.25 (m, 4H). MS (ESI) m/z: 887.1 (M+H$^+$).

The following compound 352 can also be prepared according to the procedure given in Example 60.

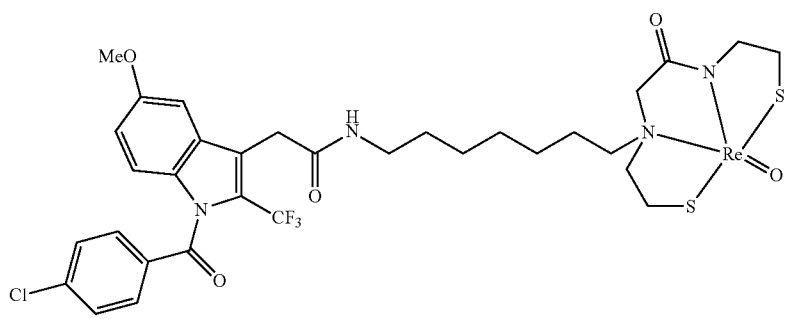

$^1$H NMR (400 MHz, CDCl3) δ 7.80 (d, J=8.5 Hz, 2H), 7.53 (d, J=8.4 Hz, 2H), 7.11 (d, J=2.2 Hz, 1H), 6.88 (dd, J=9.2, 2.3 Hz, 1H), 6.71 (d, J=9.2 Hz, 1H), 5.62 (s, 1H), 4.76-4.51 (m, 1H), 4.20-4.02 (m, 2H), 4.02-3.79 (m, 6H), 3.60-3.42 (m, 1H), 3.41-3.09 (m, 7H), 2.86 (dd, J=13.4, 4.2 Hz, 1H), 1.60-1.38 (m, 2H), 1.41-1.09 (m, 8H). MS (ESI) m/z: 901.1 (M+H$^+$).

Example 61

Synthesis of Compound 356

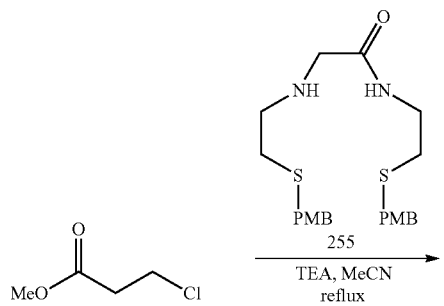

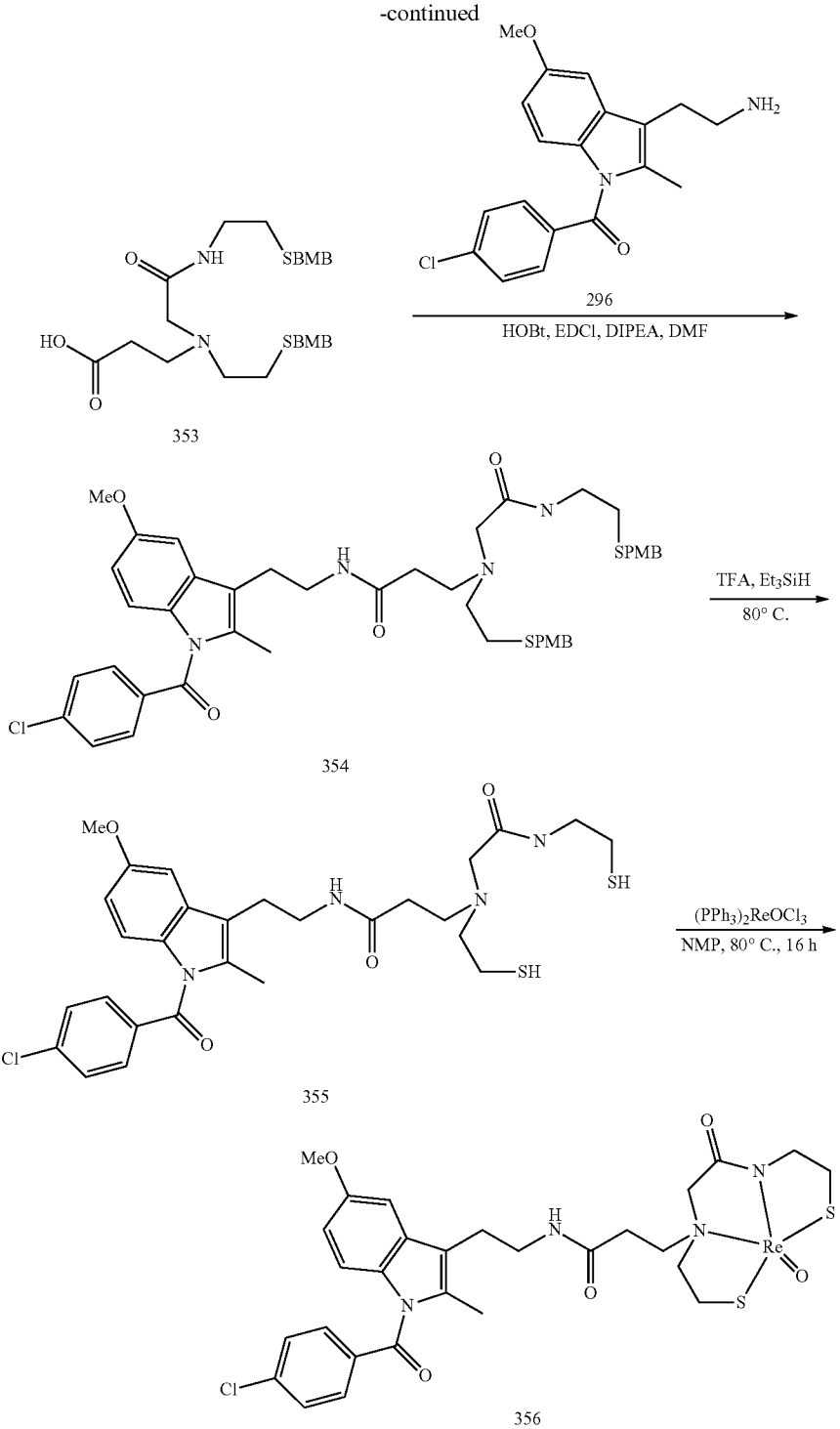

Synthesis of Intermediate 353

A mixture of compound 255 (1.3 g, 3 mmol), 3-chloro-propanoic acid (1.3 g, 12 mmol) and TEA (1.52 g, 15 mmol) in MeCN (30 mL) was stirred at 80° C. overnight. LCMS showed the reaction was completed. The reaction was concentrated in vacuo, washed with water (50 mL) and extracted with EtOAc (50 mL×3). The combined organic layers were washed brine, dried over Na₂SO₄, filtered and the filtrate was concentrated to give 353 as a yellow oil (1.4 g, 92%).

Synthesis of Intermediate 354

To a solution of 353 (1.4 g, 2.77 mmol) in DMF (20 mL) were added compound 296 (Example 52, 950 mg, 2.77 mmol), HOBt (560 mg, 4.15 mmol), EDCI (792 mg, 4.15 mmol) and DIPEA (1.8 g, 13.8 mmol) at 0° C. The resulting solution was stirred rt overnight. Then water (40 mL) was added and the mixture was extracted with EtOAc (50 mL×4). The combined organic layers were washed with brine, dried over Na₂SO₄, filtered and the filtrate was concentrated. The residue was purified by chromatography on silica gel (eluent: DCM/MeOH=40/1) to give the product (1 g, 43%) as light yellow solid.

Synthesis of Intermediate 355

At 0° C., to a solution of compound 3 (300 mg, 0.36 mmol) in TFA (2 mL) was added anisole (0.1 mL). MeSO₃H (1 mL) was added dropwise. The resulting reaction was stirred at room temperature for another 1 h. When LCMS showed completion of the reaction, the mixture was concentrated to give the crude product 355 (310 mg) which was used without further purification.

A solution of 355 (310 mg) and (PPh₃)₂ReOCl₃ (Sigma-Aldrich, Order #370193, 300 mg, 0.36 mmol) was stirred at 80° C. for 16 h. The reaction was concentrated and purified by Prep-HPLC (Column: Acquity BEH C18, Waters Corp, A: water/B: MeCN) to give 356 as a light pink solid (30 mg, yield: 10%).

$^1$H NMR (400 MHz, CDCl3) δ 7.71-7.59 (m, 2H), 7.55-7.43 (m, 2H), 6.94 (s, 1H), 6.86 (d, J=9.0 Hz, 1H), 6.67 (d, J=9.0 Hz, 1H), 5.90 (s, 1H), 4.61 (d, J=16.5 Hz, 1H), 4.51 (dd, J=11.6, 5.1 Hz, 1H), 4.07 (dd, J=10.5, 3.9 Hz, 1H), 4.03-3.74 (m, 6H), 3.63-3.36 (m, 3H), 3.29-3.04 (m, 3H), 2.98-2.78 (m, 3H), 2.65 (t, J=6.6 Hz, 2H), 2.36 (s, 3H). MS (ESI) m/z: 790.8 (M+H+)

Example 62

Synthesis of Compound 359

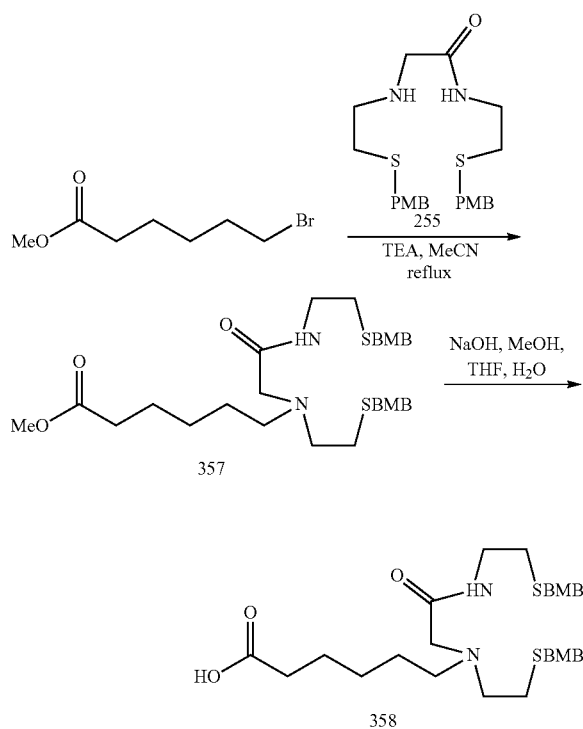

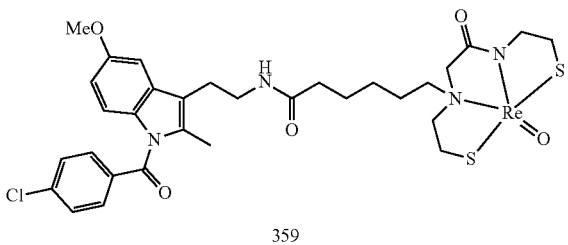

Synthesis of Intermediate 357

A mixture of 255 (868 mg, 2 mmol), methyl 6-bromohexanoate (1.3 g, 6 mmol), K₂CO₃ (1.3 g, 10 mmol) and KI (500 mg, 3 mmol) in MeCN (50 mL) was stirred at 80° C. overnight. Then water (40 mL) was added and the mixture was extracted with EtOAc (50 mL×4). The combined organic layers were washed brine, dried over Na₂SO₄, filtered and the filtrate was concentrated to give 357 as a white solid (1.1 g, yield: 92%).

Synthesis of Intermediate 358

A mixture of 357 (1.1 g, 1.95 mmol) and NaOH (156 mg, 3.9 mmol) in THF/MeOH/H₂O (10 mL/10 mL/4 mL) was stirred at rt. Once LCMS showed the reaction to be completed, the pH was adjusted to 4 and the mixture was extracted with EtOAc (30 mL×3). The combined organic layers were washed with brine, dried over Na₂SO₄, filtered and the filtrate was concentrated to give 358 as light yellow solid (850 mg, 79%).

Compound 359 was synthesized from intermediate 358 by a procedure similar to the one described in Example 61.

$^1$H NMR (400 MHz, CDCl3) δ 7.66 (d, J=8.4 Hz, 2H), 7.48 (d, J=8.3 Hz, 2H), 6.98 (d, J=16.3 Hz, 1H), 6.86 (d, J=9.0 Hz, 1H), 6.68 (d, J=9.0 Hz, 1H), 5.53 (s, 1H), 4.82-4.33 (m, 2H), 4.07 (dd, J=21.9, 13.1 Hz, 2H), 3.98-3.72 (m, 4H), 3.58-3.05 (m, 7H), 2.88 (dt, J=13.7, 5.4 Hz, 3H), 2.45 (d, J=63.8 Hz, 3H), 2.16 (dd, J=17.8, 10.6 Hz, 2H), 1.95-1.56 (m, 4H), 1.38 (dd, J=15.1, 7.5 Hz, 2H). MS (ESI) m/z: 833.1 (M+H⁺).

Example 63

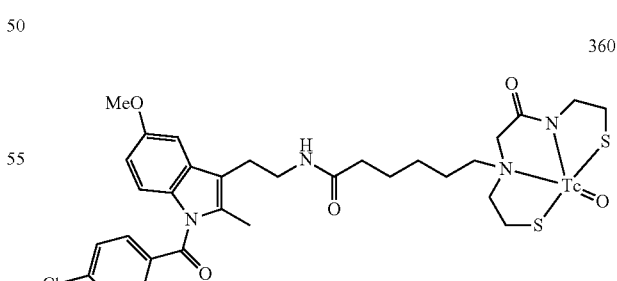

The $^{99m}$Tc complex 360 is prepared as described in Example 62 using as the last step a ligand exchange reaction employing $^{99m}$Tc-glucoheptonate as described in e.g.: Ono, M., et al., ACS Chem. Neurosci. 1, 598, (2010) and Ono, M., et al., Bioorg. Med. Chem. Lett., 20, 5743-5748, (2010).

Example 64
Synthesis of Compound 365
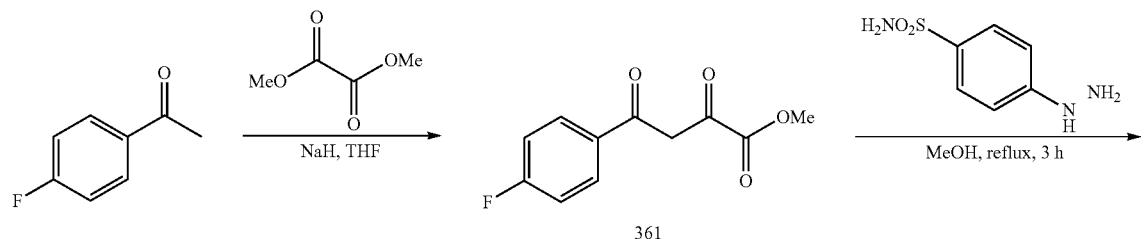
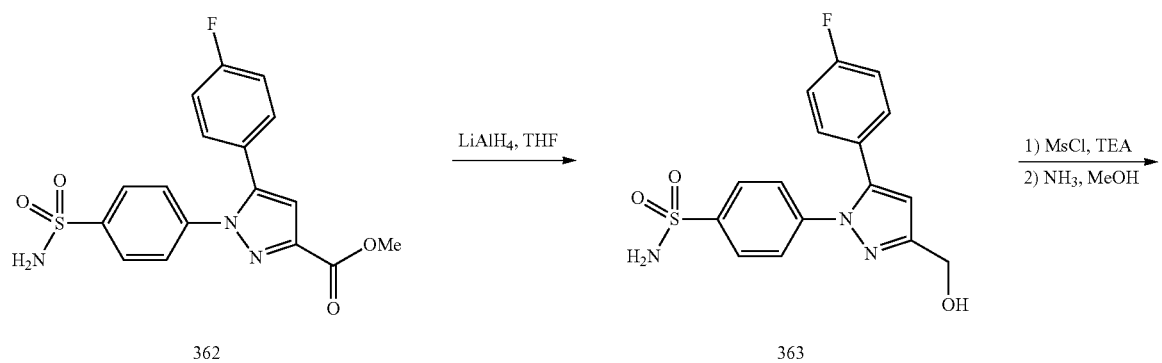
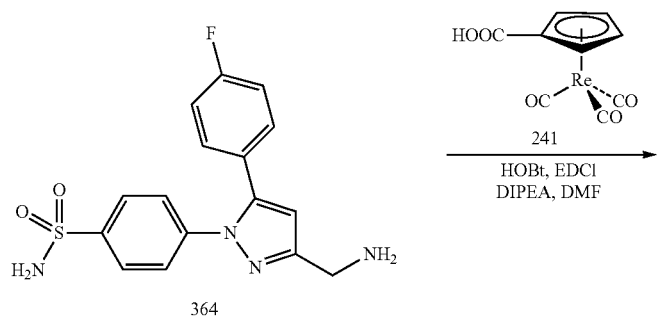
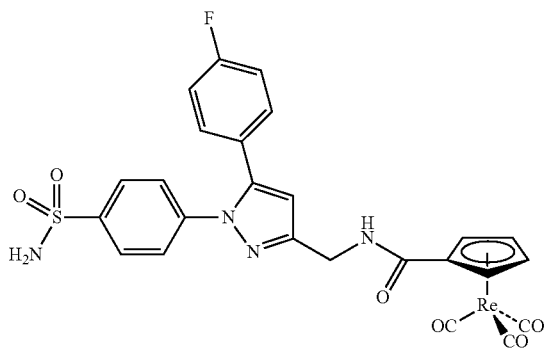

Intermediate 361

To a solution of 4-fluorophenyl methyl ketone (8.28 g, 60 mmol) in dry THF (200 mL) was added NaH (3.12 g, 78 mmol), followed by dimethyl oxalate (7.8 g, 66 mmol). The resulting solution was stirred at 70° C. overnight. LCMS showed the reaction was completed. The reaction was quenched by addition of sat'd aq. $NH_4Cl$ solution and extracted with EtOAc (200 mL×3). The combined organic layers washed with brine, dried over $Na_2SO_4$, filtered and the filtrate was concentrated to give the crude product which was purified by chromatography on silica gel (eluent: PE/EtOAc=8/1) to give 361 (10 g, yield: 75%) as a colorless oil.

Intermediate 362

A solution of 361 (10 g, 44.6 mmol) and 4-hydrazinyl-benzenesulfonamide (8.34 g, 44.6 mmol) in MeOH (150 mL) was stirred at 70° C. overnight. LCMS showed the reaction was completed. The reaction was concentrated, washed with water (150 mL) and extracted with EtOAc (150 mL×3). The combined organic layers were washed with brine, dried over $Na_2SO_4$, filtered and the filtrate was concentrated to give 362 (15 g, 90%) as a white solid.

Intermediate 363

To a solution of 362 (15 g, 40 mmol) in dry THF (200 mL) at 0° C. was slowly added $LiAlH_4$ (1.82 g, 48 mmol). The resulting reaction was stirred at room temperature for 1 h. LCMS showed the reaction was completed. The reaction was quenched with 2 mL of water at 0° C., then 150 mL water was added thereto. The mixture was extracted with EtOAc (150 mL×3) and the combined organic layers were washed with brine, dried over $Na_2SO_4$, filtered and the filtrate was concentrated to give the crude product, which was purified by chromatography on silica gel (eluent: DCM/MeOH=40/1) to give 363 (9.5 g, yield: 68%).

Intermediate 364

To a solution of compound 4 (500 mg, 1.44 mmol) in dry THF (20 mL) at 0° C. was added MsCl (248 mg, 2.16 mmol), followed by TEA (363 mg, 3.6 mmol). The resulting mixture was stirred at room temperature for another 1 h. The reaction was judged complete by TLC and $H_2O$ (20 mL) was added. The mixture was extracted with EtOAc (30 mL×3). The combined organic layers were washed with brine, dried over $Na_2SO_4$, filtered and the filtrate was concentrated to give a colorless oil. This was dissolved in a solution of $NH_3$ in MeOH (7 M, 5 mL) and stirred at room temperature for 1 h. LCMS showed the reaction was completed. The reaction was concentrated in vacuo to give 364 (450 mg, yield: 93%).

To a solution of 364 (450 mg, 1.3 mmol) in DMF (10 mL) acid 241 (580 mg, 1.5 mmol), HOBt (350 mg, 2.6 mmol), EDCI (497 mg, 2.6 mmol) and DIPEA (671 mg, 5.2 mmol) were added at 0° C. The resulting solution was stirred room temperature overnight. The reaction was quenched with saturated $NaHCO_3$ solution (30 ml) and extracted with ethyl acetate (2×50 ml). The combined organic extracts were washed with brine (30 ml), dried over $Na_2SO_4$, concentrated, and purified by prep-HPLC (Column: Acquity BEH C18, Waters Corp, solvent A: water/solvent B: MeCN) to give the compound 365 (90 mg, yield: 10%).

$^1$H NMR (400 MHz, CDCl3) δ 7.65 (d, J=8.0 Hz, 2H), 7.21-6.89 (m, 7H), 6.55 (s, 1H), 6.07 (d, J=39.8 Hz, 4H), 5.36 (s, 2H), 4.62 (d, J=4.9 Hz, 2H). MS (ESI) m/z: 709.0 (M+H$^+$)

Example 65

Synthesis of Compound 366

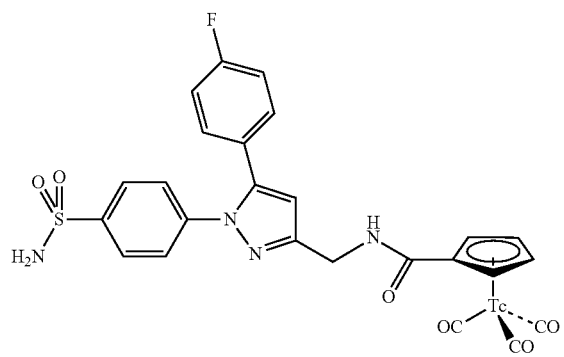

366

Compound 366 is prepared from compound 364 (Example 64) by a procedure similar to the one described in Example 41.

Example 66

Synthesis of Compound 367

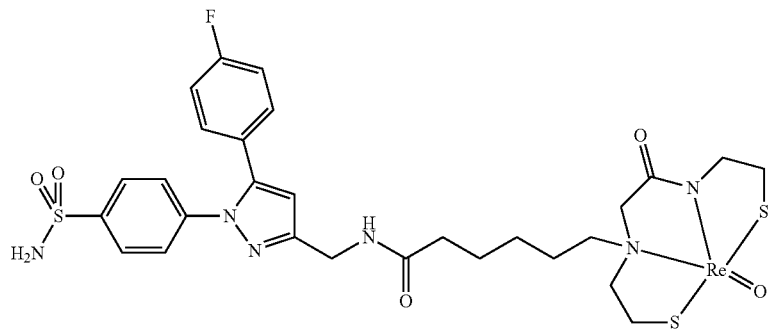

367

Compound 367 is prepared from compound 364 (Example 64) and compound 358 (Example 62) using a procedure similar to the one described in Example 61.

Example 67

Synthesis of Compound 368

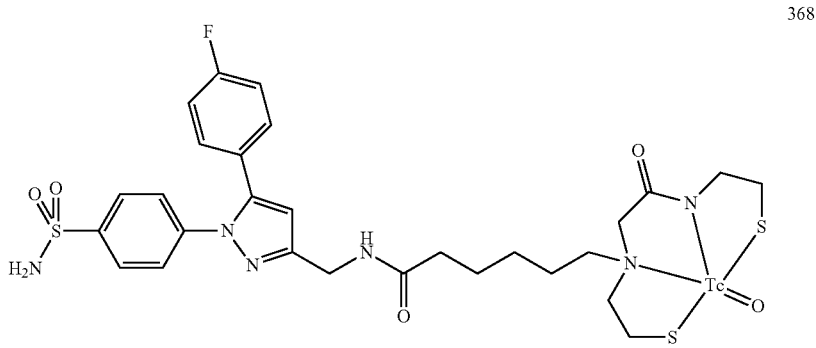

368

The $^{99m}$Tc complex 368 is prepared as described in Example 66 using as the last step a ligand exchange reaction employing $^{99m}$Tc-glucoheptonate as described in e.g.: Ono, M., et al., ACS Chem. Neurosci. 1, 598, (2010) and Ono, M., et al., Bioorg. Med. Chem. Lett., 20, 5743-5748, Example 68

Synthesis of Compound 371

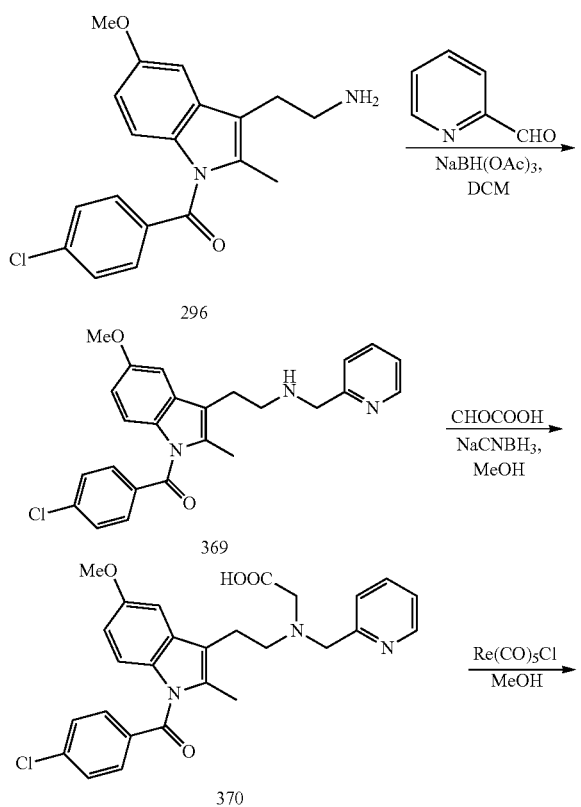

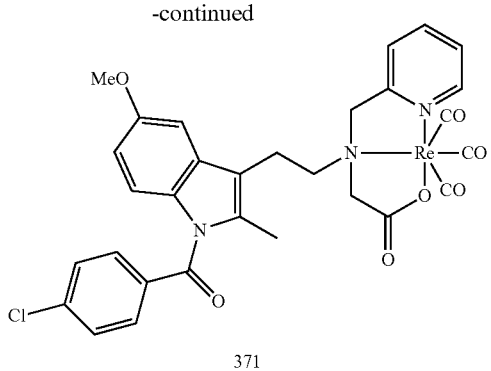

371

Intermediate 369

To a solution of 296 (170 mg, 0.5 mmol) and picolinaldehyde (54 mg, 0.5 mmol) in DCM (15 ml) was added AcOH (0.2 ml). The mixture was stirred at room temperature for 30 min, NaBH(OAc)$_3$ (422 mg, 2.0 mmol) was added, the mixture was stirred at room temperature overnight, then water (20 mL) was added and the mixture was extracted with EtOAc (20 mL×3). The combined organic layers were washed with brine, dried over Na$_2$SO$_4$, filtered and the filtrate was concentrated. The residue was purified by chromatography on silica gel (DCM/MeOH=10/1) to give 369 (60 mg yield: 28%).

Intermediate 370

To a solution of 369 (120 mg, 0.3 mmol) and 2-oxoacetic acid (50% in water, 133 mg. 0.9 mmol) in MeOH (10 mL) was added AcOH (0.1 mL). The mixture was stirred at room temperature for 30 min, then NaCNBH$_3$ (93 mg, 1.5 mmol) was added and the mixture was stirred at room temperature overnight. Water (20 mL) was added and the mixture was extracted with EtOAc (20 mL×3). The combined organic layers were washed with brine, dried over Na$_2$SO$_4$, filtered and the filtrate was concentrated. The residue was purified by chromatography on silica gel (DCM/MeOH=3/1) to give 370 (30 mg yield: 20%).

To a solution of compound 370 (30 mg, 0.065 mmol) in MeOH (3 mL) was added Re(CO)$_5$Cl (36 mg, 0.1 mmol).

The resulting mixture was refluxed overnight. LCMS showed the reaction to be complete. The reaction mixture was concentrated in vacuo to give the crude product, which was purified by Prep-HPLC (Column: Acquity BEH C18, Waters Corp.) to give 371 (10 mg yield: 20%) as a white solid.

$^1$H NMR (400 MHz, DMSO-d$_6$) δ 8.80 (d, J=5.3 Hz, 1H), 8.20 (t, J=7.6 Hz, 1H), 7.79 (d, J=7.9 Hz, 1H), 7.72 (d, J=8.4 Hz, 2H), 7.63 (dd, J=18.1, 7.5 Hz, 3H), 7.25 (d, J=2.1 Hz, 1H), 6.91 (d, J=9.0 Hz, 1H), 6.74 (dd, J=9.0, 2.1 Hz, 1H), 4.94 (dd, J=35.8, 15.8 Hz, 2H), 4.14 (d, J=16.7 Hz, 1H), 3.79 (s, 3H), 3.72-3.48 (m, 3H), 3.25-3.09 (m, 2H), 2.33 (s, 3H). MS (ESI) m/z: 762.0 [M+H$^+$].

CLINICAL AND SCREENING EXAMPLES

Example A

"Pain Scans" to Localize Site(s) of Inflammation

A patient with an undiagnosed cause of pain, or a cause of pain which cannot be localized to a site of pathology, is scheduled for a "pain scan." The patient refrains from drinking or eating for at least eight hours prior to the pain scan. A compound of the invention is administered to the patient either orally or parenterally. After an appropriate period of time determined by the pharmacokinetics of the compound of the invention, during which the compound of the invention binds to cyclooxygenase, the patient is scanned with the appropriate modality to determine the locus or loci of the greatest concentration of the compound. The loci are imaged and viewed or photographed as appropriate. Scans of the patient can be repeated at various intervals after ingestion or injection of the compound of the invention, for example, at two hours, three hours, and four hours after ingestion or injection. The scan findings are correlated with the patient's medical history, physical examination and other information to assist in diagnosis of the etiology of the pain and determine appropriate treatment.

Example B

"Tumor Scans" to Localize Site(s) of Tumor(s)

A patient to be screened for presence of a tumor is scheduled for a "COX scan." The patient refrains from drinking or eating for at least eight hours prior to the COX scan. A compound of the invention is administered to the patient either orally or parenterally. After an appropriate period of time determined by the pharmacokinetics of the compound of the invention, during which the compound of the invention binds to cyclooxygenase, the patient is scanned with the appropriate modality to determine the locus or loci of the greatest concentration of the compound. The loci are imaged and viewed or photographed as appropriate. Scans of the patient can be repeated at various intervals after ingestion or injection of the compound of the invention, for example, at two hours, three hours, and four hours after ingestion or injection. The scan findings are correlated with the patient's medical history, physical examination and other information to assist in diagnosis of the presence and/or location of the tumor and determine appropriate treatment.

Example C

Scans to Screen for Asymptomatic Infections or Localized Infections

A patient to be screened for an asymptomatic infection, or to have the site of a localized infection identified, is scheduled for a "COX scan." The patient refrains from drinking or eating for at least eight hours prior to the COX scan. A compound of the invention is administered to the patient either orally or parenterally. After an appropriate period of time determined by the pharmacokinetics of the compound of the invention, during which the compound of the invention binds to cyclooxygenase, the patient is scanned with the appropriate modality to determine the locus or loci of the greatest concentration of the compound. The loci are imaged and viewed or photographed as appropriate. Scans of the patient can be repeated at various intervals after ingestion or injection of the compound of the invention, for example, at two hours, three hours, and four hours after ingestion or injection. The scan findings are correlated with the patient's medical history, physical examination and other information to assist in diagnosis of the presence and/or location of an infection, and to determine appropriate treatment.

Example D

Scans to Screen Candidate Compounds for Imaging

Animal models can be used to test the conjugates and compounds of the invention for their suitability for clinical use. Animal models of pain (and inflammation related to pain), of infection, and of cancer are well known. See, for example, *Handbook of Laboratory Animal Sciense, Second Edition: Animal Models, Volume* 2 (Jann Hau, Gerald L. Van Hoosier Jr., editors), Boca Raton: CRC Press, 2003; *Animal Models for the Study of Human Disease* (P. Michael Conn, editor), San Diego: Academic Press, 2013.

A suitable animal model (for pain, for cancer, or for infection) is selected and the appropriate pathology is induced. The site of the induced pain, inflammation, infection, or tumor is recorded by the investigator. One or more candidate conjugates or compounds of the invention is administered to the animal, either by oral gavage or parenterally. After an appropriate period of time determined by the pharmacokinetics of the compound of the invention, during which the compound of the invention binds to cyclooxygenase, the animal is scanned with the appropriate modality to determine the locus or loci of the greatest concentration of the compound. The location(s) indicated by the scan are compared with the known site or sites at which the pathology was induced, for evaluation of the effectiveness of the conjugate for accumulating at the site of pathology.

The carrageenan induced rat paw edema assay can be used as an exemplary model for inflammation; see Shalini, V. et al., *Molecular Immunology* 66:229-239 (2015); see also Winter, C. et al., *Proc. Soc. Exp. Biol. Med.* 111:544-547 (1962). Briefly, acute inflammation is induced by aponeurosis injection of 0.1 ml of 1% carrageenan in 0.9% saline. Additional information regarding model assays is described in Guay et al., *J. Biol. Chem.* 279:24866-24872 (2004); Nantel et al., *British Journal of Pharmacology* 128:853-859 (1999); Siebert et al., *Proc. Natl. Acad. Sci. USA* 91:12013-12017 (1994); de Vries et al., *J Nucl. Med.* 44:1700-1706 (2003); and Uddin et al., *Cancer Prev. Res.* 4:1536-1545 (2011).

The animal is then imaged using the appropriate modality, for example, scintigraphic imaging or SPECT imaging. Exemplary imaging methods that can be used are described in Pacelli et al., *J. Label. Compd. Radiopharm.* 57:317-322 (2014); de Vries et al., *J Nucl. Med.* 44:1700-1706 (2003); and Tietz et al., *Current Medicinal Chemistry,* 20, 4350-4369 (2013).

Example E

COX Inhibition Assay

A variety of assays can be used to evaluate inhibition of compounds to cyclooxygenase (COX). Compounds in the present invention display inhibition of cyclooxygenase in the following assays.

Cell Culture:

RAW264.7 murine macrophages were obtained from the Cell Bank of Shanghai Institute of Biochemistry and Cell Biology, Chinese Academy of Sciences (Shanghai, China) and cultured in Dulbecco's modified Eagle's medium containing 100 U/ml penicillin and 100 μg/ml streptomycin at 37° C. in 5% $CO_2$.

Cell-Based COX-2 Assay:

RAW264.7 cells were plated at a density of 2.5×105/ml cells in a 96-well plate with 0.1 ml of culture medium per well and cultured overnight. The cells were pre-incubated for 30 min with various doses of compounds and stimulated for 7 h with 1 μg/ml LPS and 10 U/ml IFN-g. The cell culture supernatants were collected immediately following treatment and centrifuged at 1,000 rpm for 5 min to remove the particulate matter. PGE2 was determined using a Prostaglandin E2 assay kit (catalog no. 62P2APEB; Cisbio Co.,). 10 μL of cell supernatant was transferred to a 384-well low volume plate (e.g. Corning® 3544), 5 μL of PGE2-d2 was added, followed by 5 μL anti-PGE2 Cryptate as a negative control. Replace the standard by 10 μL of diluent and PGE2-d2 by 5 μL of reconstitution buffer, Cal0 (for positive control), replace the standard by 10 μL of diluent. Incubate at 4° C. overnight. After centrifuging at 1,000 rpm for 1 min, the dual fluorescence emissions of 615 and 665 nm with a 320 nm excitation were measured using an Envision plate reader (Perkin Elmer, Shelton, Conn.). The results are expressed as the ratio of 665 nm/615 nm emissions.

COX-1/-2 Enzyme Assay:

The ability of compounds to inhibit ovine COX-1 and human COX-2 was determined using a commercially available enzyme immunoassay (EIA) kit (catalog no. 701090 (COX-1); 701080 (COX-2) Cayman Chemical Co., Ann Arbor, Mich., USA) according to the manufacturer's protocol. COX catalyzes the first step in the biosynthesis of AA to PGH2. PGF2α, produced from PGH2 by reduction with stannous chloride, was measured by EIA (ACE™ competitive EIA, Cayman Chemical, Ann Arbor, Mich., USA). Briefly, to a series of supplied reaction buffer solutions [960 μl 0.1 M Tris-HCl (pH 8.0) containing 5 mM EDTA and 2 mM phenol] with either COX-1 or COX-2 (10 μl) enzyme in the presence of heme (10 μl), 10 μl of various concentrations of test drug solutions were added. These solutions were incubated for 15 min at 37° C. and subsequently 10 μl AA solution (100 μM) was added. The COX reaction was stopped by the addition of 30 μl stannus chloride after 2 min, mixed immediately, supernatants were 2000 fold diluted. The produced PGF2α was measured by EIA. This assay is based on the competition between PGs and a PG-acetylcholinesterase conjugate (PG tracer) for a limited amount of PG antiserum. The amount of PG tracer that is able to bind to the PG antiserum is inversely proportional to the concentration of PGs in the wells since the concentration of the PG tracer is held at a constant while the concentration of PGs varies. The specific antiserum-PG complex bound to a mouse anti-rabbit IgG that had been previously attached to the well. The plate was washed to remove any unbound reagents and 200 μl Ellman's reagent (5,5'-dithiobis-(2-nitrobenzoic acid), which contains the substrate to acetylcholine esterase, was added to the well. The product of this enzymatic reaction generates a distinct yellow color that absorbs at 406 nm. The intensity of this color, determined by spectrophotometry, is proportional to the amount of PG tracer bound to the well, which is inversely proportional to the amount of PGs present in the well during the incubation. Percent inhibition was calculated by the comparison of the compounds treated to the various control incubations.

Dose-response curves were generated using XLFit (IDBS, Surrey, UK) or Prism (GraphPad Software, La Jolla, Calif., US) to calculate $IC_{50}$ values for each compound tested.

Representative results for COX-2 inhibition are provided in Table 3 below. $IC_{50}$ values are given in micromolar units.

TABLE 3

| Compound | COX-2 $IC_{50}$ (μM) | |
|---|---|---|
| | enzyme | cell |
| 23 | 12.0 | — |
| 27 | 0.6 | 12.7 |
| 35 | 1.6 | — |
| 39 | 1.1 | — |
| 178 | 0.2 | 1.8 |
| 181 | 1.0 | 1.5 |
| 182 | 0.8 | 0.6 |
| 183 | 0.4 | 0.7 |
| 185 | 1.2 | 0.5 |
| 204 | 0.2 | 0.9 |
| 207 | 0.6 | 0.8 |
| 208 | 0.3 | 0.6 |
| 209 | 2.4 | 0.7 |
| 210 | 0.3 | 0.6 |
| 211 | 2.2 | 1.6 |
| 219 | 4.0 | 2.1 |
| 234 | 1.7 | 3.7 |
| 237 | 4.5 | >1 |
| 242 | 0.3 | 0.4 |
| 243 | 0.5 | 0.7 |
| 244 | >30 | 1.5 |
| 245 | >30 | 0.3 |
| 246 | 0.1 | 0.2 |
| 247 | 0.2 | 2.6 |
| 248 | 0.2 | >30 |
| 249 | 1.1 | 4.4 |
| 250 | 0.2 | 0.3 |
| 251 | 0.3 | >30 |
| 260 | 0.3 | 0.2 |
| 261 | 0.8 | 1.8 |
| 262 | 0.9 | 1.7 |
| 263 | 0.3 | 0.3 |
| 264 | 0.3 | 0.1 |
| 265 | 2.1 | 0.1 |
| 266 | 0.6 | 0.2 |
| 267 | >30 | 0.3 |
| 268 | >30 | >10 |
| 269 | 0.5 | 0.9 |
| 275 | 0.7 | 0.2 |
| 297 | 0.5 | 0.8 |
| 301 | >30 | >1 |
| 303 | >30 | 0.9 |
| 304 | >30 | 0.9 |
| 305 | 0.3 | 0.1 |
| 306 | 0.7 | 0.2 |
| 307 | >30 | 0.5 |
| 308 | 0.9 | 0.2 |
| 309 | 0.5 | 0.3 |
| 310 | >30 | 0.2 |
| 311 | — | 0.4 |
| 312 | 0.1 | 0.4 |
| 313 | — | 0.2 |
| 320 | — | 5.0 |
| 328 | 0.6 | 0.1 |
| 329 | 0.6 | 0.1 |
| 341 | 0.8 | 0.3 |
| 346 | 0.3 | 0.2 |
| 351 | >30 | 0.4 |

TABLE 3-continued

| | COX-2 IC$_{50}$ (µM) | |
| Compound | enzyme | cell |
| --- | --- | --- |
| 352 | >30 | 0.3 |
| 356 | — | 1.6 |
| 359 | 0.6 | 0.2 |
| 365 | 7.9 | 1.1 |
| 367 | 4.5 | >10 |
| 371 | 0.1 | 2.1 |

Representative results for COX-1 inhibition are provided in Table 4 below. IC$_{50}$ values are given in micromolar units.

TABLE 4

| Compound | COX-1 IC$_{50}$ (µm) enzyme |
| --- | --- |
| 242 | >30 |
| 246 | >30 |
| 260 | >30 |
| 264 | >30 |
| 275 | >30 |
| 305 | >30 |
| 306 | >30 |
| 275 | >30 |
| 369 | >30 |

Example F

Pharmacokinetic Data

In vitro data of metabolic stability and protein binding as well as in vivo pharmacokinetic data for the conjugates of the invention can be generated using the techniques disclosed in Silber, B. M. et al., Pharm. Res. 30(4):932-950 (2013), which is hereby incorporated by reference in its entirety. Various biological, pharmacokinetic and other properties of the conjugates, including hepatic microsomal stability, determination of metabolites, binding to proteins such as plasma protein binding, and in vivo studies, including single-dose and multi-dose pharmacokinetic studies, are determined using the protocols described in that publication and the publications cited therein.

EXEMPLARY EMBODIMENTS

The invention is further described by the following exemplary embodiments. The features of each of the embodiments are combinable with any of the other embodiments where appropriate and practical.

Embodiment 1

A conjugate comprising: a non-steroidal anti-inflammatory drug (NSAID) or a residue of a NSAID bonded or complexed to an imaging moiety which is a radioactive agent, wherein the radioactive agent is selected from the group consisting of a gamma-ray emitter and an X-ray emitter; or a pharmaceutically acceptable salt thereof.

Embodiment 2

The conjugate of embodiment 1, wherein said radioactive agent is $^{99m}$Tc.

Embodiment 3

The conjugate of embodiment 1, wherein the NSAID or the residue of a NSAID and imaging moiety are bonded or complexed via a linker selected from the group consisting of an optionally substituted C$_1$-C$_{30}$ hydrocarbylene group and an optionally substituted C$_3$-C$_{30}$ heterohydrocarbylene group.

Embodiment 4

The conjugate of any of embodiments 1-3, wherein the NSAID or the residue of a NSAID is selected from the group consisting of acetylsalicylic acid, diflunisal, salsalate, choline magnesium trisalicylate, ibuprofen, dexibuprofen, naproxen, fenoprofen, ketoprofen, dexketoprofen, flurbiprofen, oxaprozin, loxoprofen, indomethacin, tolmetin, sulindac, etodolac, ketorolac, diclofenac, aceclofenac, nabumetone, piroxicam, meloxicam, tenoxicam, droxicam, lornoxicam, isoxicam, mefenamic acid, meclofenamic acid, flufenamic acid, tolfenamic acid, celecoxib, rofecoxib, valdecoxib, parecoxib, lumiracoxib, etoricoxib, firocoxib, nimesulide, and licofelone, and a residue of any of the foregoing compounds.

Embodiment 5

The conjugate of any of embodiments 1-3, wherein the optionally substituted C$_3$-C$_{30}$ heterohydrocarbylene group is

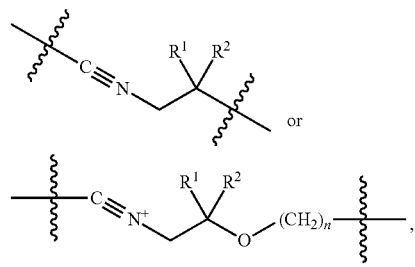

where R$^1$ and R$^2$ are independently selected from hydrogen, C$_1$-C$_4$ alkyl, C$_1$-C$_4$ alkyl substituted with hydroxy, —O—C$_1$-C$_4$ alkyl, or C$_3$-C$_6$ cycloalkyl; or R$^1$ and R$^2$ together with the carbon to which they are attached form a C$_3$-C$_8$ cycloalkyl ring; and n is an integer selected from 0 to 4, inclusive.

Embodiment 6

The conjugate of embodiment 5, wherein R$^1$ and R$^2$ are methyl.

Embodiment 7

The conjugate of embodiment 5, wherein the linking group is

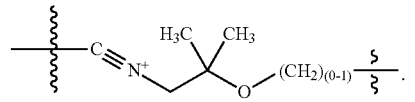

Embodiment 8

The conjugate of any of embodiments 1-3, wherein the non-steroidal anti-inflammatory drug (NSAID) or a residue of a NSAID is selected from the group consisting of naproxen, ketorolac, a residue of naproxen, and a residue of ketorolac.

Embodiment 9

The conjugate of embodiment 1, wherein the non-steroidal anti-inflammatory drug (NSAID) or a residue of a NSAID bonded or complexed to an imaging moiety which is a radioactive agent is:

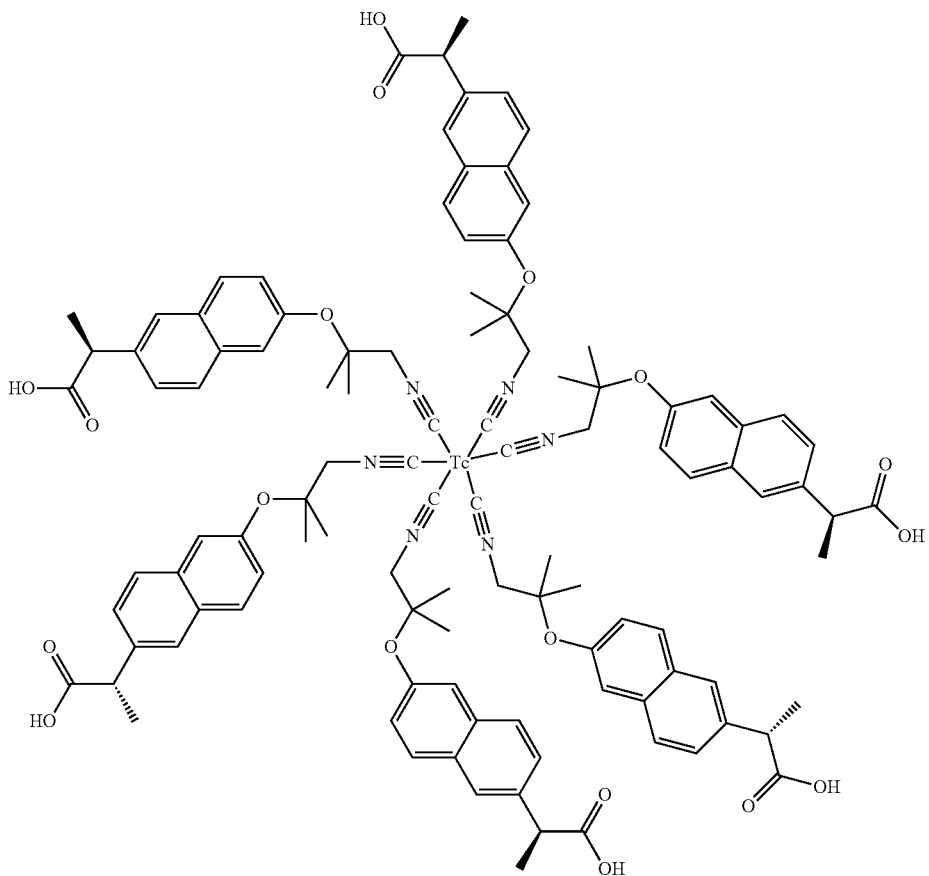

wherein Tc is $^{99m}$Tc; or a pharmaceutically acceptable salt thereof.

Embodiment 10

The conjugate of embodiment 1, wherein the non-steroidal anti-inflammatory drug (NSAID) or a residue of a NSAID bonded or complexed to an imaging moiety which is a radioactive agent is:

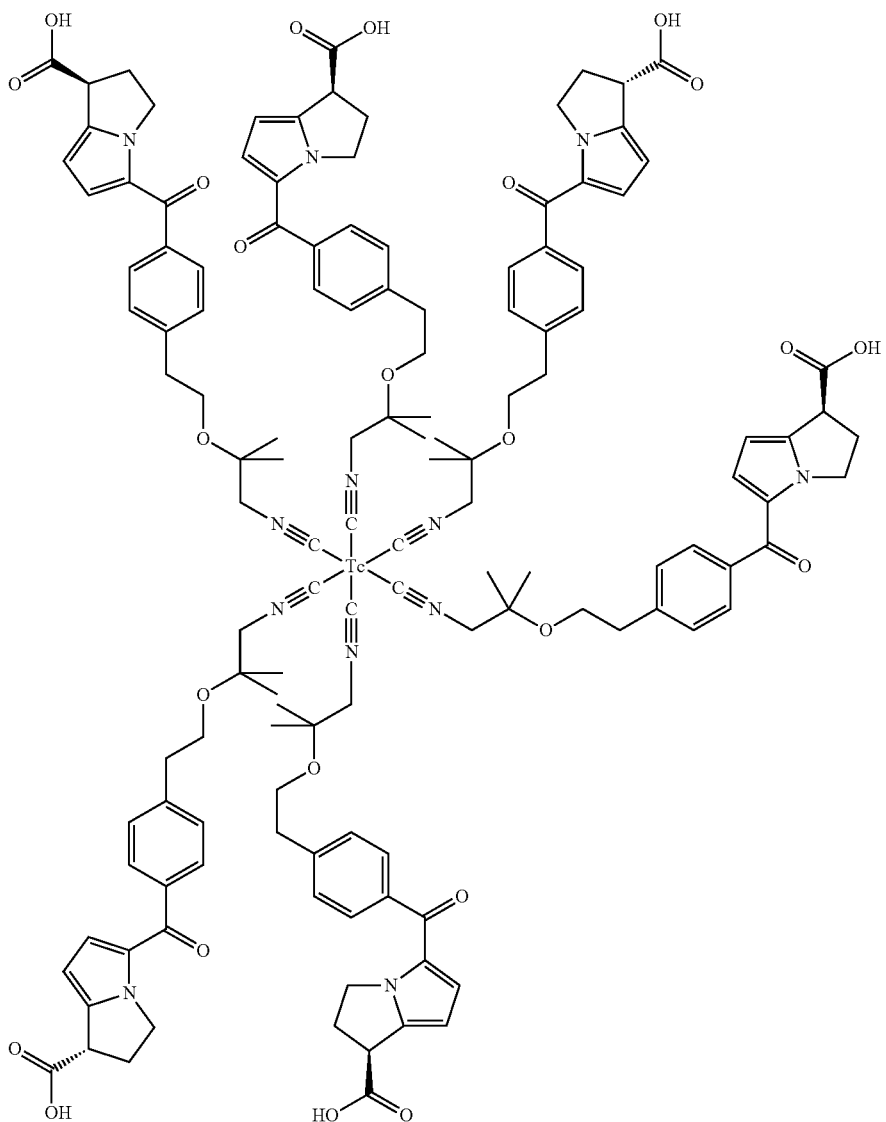

wherein Tc is $^{99m}$Tc; or a pharmaceutically acceptable salt thereof.

Embodiment 11

A pharmaceutical composition comprising the conjugate of any of embodiments 1-3, 9, or 10, and a pharmaceutically acceptable excipient.

Embodiment 12

A method of imaging a site of pathology in a subject, comprising: a) administering a conjugate comprising a non-steroidal anti-inflammatory drug (NSAID) or a residue of a NSAID bonded or complexed to an imaging moiety which is a radioactive agent, wherein the radioactive agent is selected from the group consisting of a gamma-ray emitter and an X-ray emitter; or a pharmaceutically acceptable salt of said conjugate; or a pharmaceutical composition comprising said conjugate or a pharmaceutically acceptable salt of said conjugate and a pharmaceutically acceptable excipient; and b) generating an image of the subject or an image of a portion of the subject.

Embodiment 13

The method of embodiment 12, wherein said radioactive agent is $^{99m}$Tc.

Embodiment 14

The method of embodiment 12, wherein the NSAID or the residue of a NSAID and imaging moiety are bonded or complexed via an optionally substituted $C_1$-$C_{30}$ hydrocarbylene group or an optionally substituted $C_3$-$C_{30}$ heterohydrocarbylene group.

Embodiment 15

The method of any of embodiments 12-14, wherein the NSAID or the residue of a NSAID is selected from the group consisting of acetylsalicylic acid, diflunisal, salsalate, choline magnesium trisalicylate, ibuprofen, dexibuprofen, naproxen, fenoprofen, ketoprofen, dexketoprofen, flurbiprofen, oxaprozin, loxoprofen, indomethacin, tolmetin, sulindac, etodolac, ketorolac, diclofenac, aceclofenac, nabumetone, piroxicam, meloxicam, tenoxicam, droxicam, lornoxicam, isoxicam, mefenamic acid, meclofenamic acid, flufenamic acid, tolfenamic acid, celecoxib, rofecoxib, valdecoxib, parecoxib, lumiracoxib, etoricoxib, firocoxib, nimesulide, and licofelone, and a residue of any of the foregoing compounds.

Embodiment 16

The method of any of embodiments 12-14, wherein the optionally substituted $C_3$-$C_{30}$ heterohydrocarbylene group is

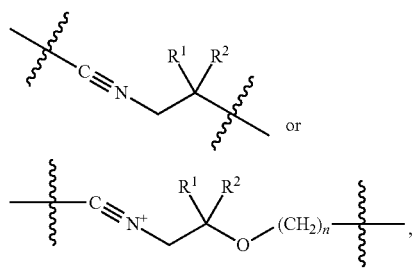

where $R^1$ and $R^2$ are independently selected from hydrogen, $C_1$-$C_4$ alkyl, $C_1$-$C_4$ alkyl substituted with hydroxy, —O—$C_1$-$C_4$ alkyl, or $C_3$-$C_6$ cycloalkyl; or $R^1$ and $R^2$ together with the carbon to which they are attached form a $C_3$-$C_8$ cycloalkyl ring; and n is an integer selected from 0 to 4, inclusive.

Embodiment 17

The method of embodiment 16, wherein $R^1$ and $R^2$ are methyl.

Embodiment 18

The method of embodiment 16, wherein the linking group is

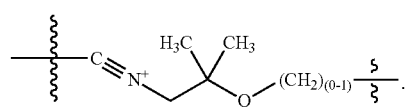

Embodiment 19

The method of any of embodiments 12-14, wherein the non-steroidal anti-inflammatory drug (NSAID) or a residue of a NSAID is selected from the group consisting of naproxen, ketorolac, a residue of naproxen, and a residue of ketorolac.

Embodiment 20

The method of embodiment 12, wherein the conjugate is:

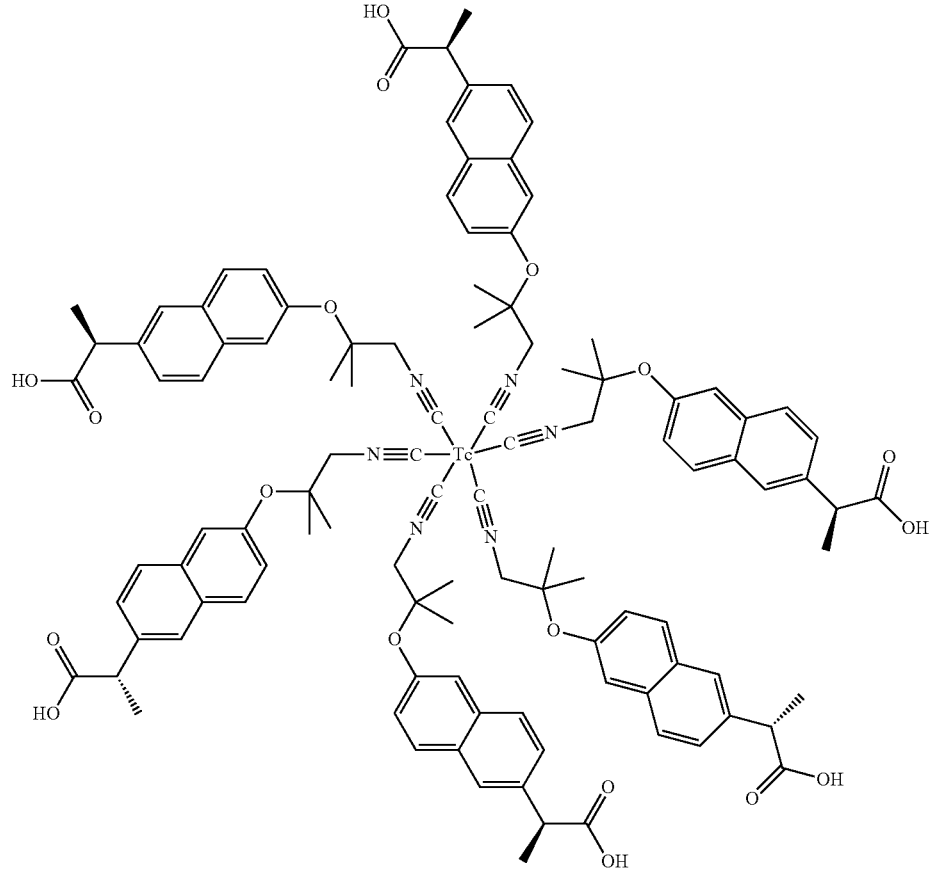

wherein Tc is $^{99m}$Tc; or a pharmaceutically acceptable salt thereof.

Embodiment 21

The method of embodiment 12, wherein the conjugate is:

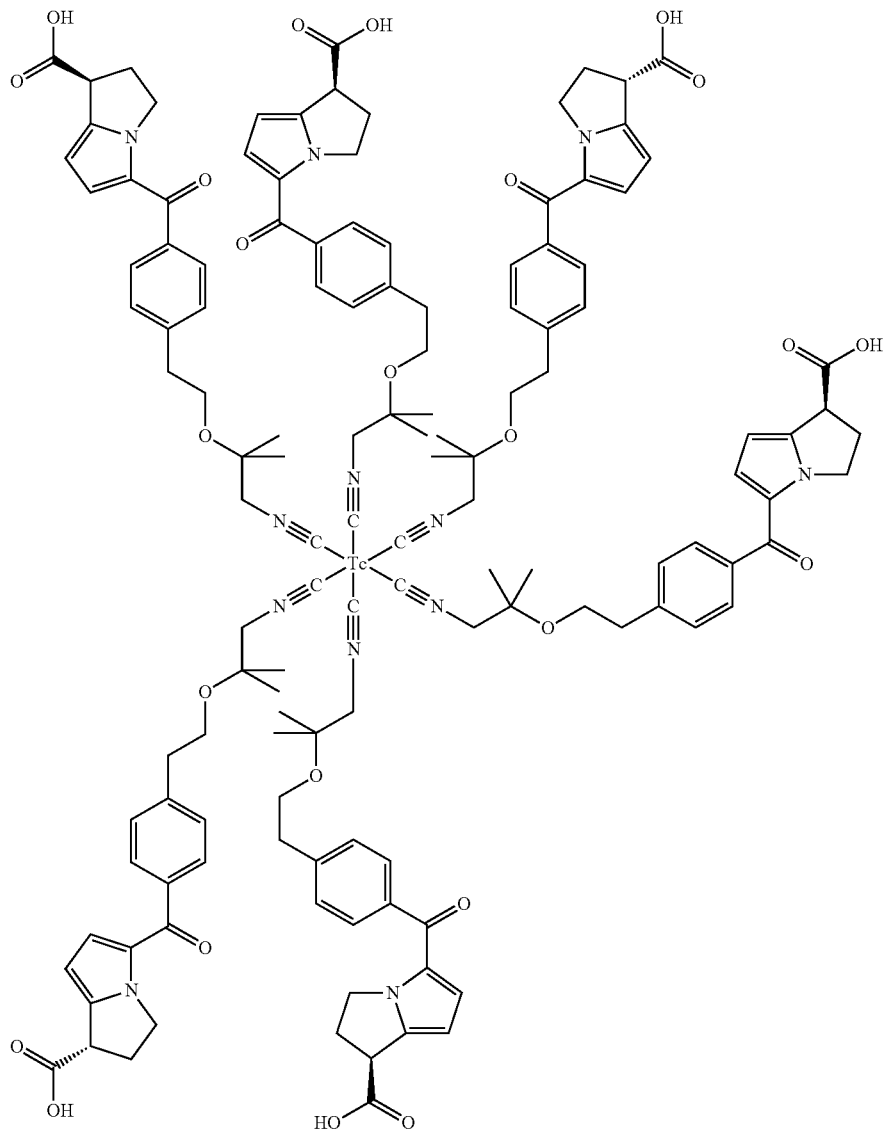

wherein Tc is $^{99m}$Tc; or a pharmaceutically acceptable salt thereof.

Embodiment 22

The method of any of embodiments 12-14, 20, or 21, wherein the conjugate is administered as a composition additionally comprising a pharmaceutically acceptable excipient.

Embodiment 23

A conjugate comprising: a non-steroidal anti-inflammatory drug (NSAID) or a residue of a NSAID bonded or complexed to an imaging moiety which comprises a radioactive agent, wherein the radioactive agent is selected from the group consisting of a gamma-ray emitter and an X-ray emitter; or a pharmaceutically acceptable salt thereof.

Embodiment 24

The conjugate of embodiment 23, wherein said radioactive agent is $^{99m}$Tc, 52Mn, $^{186}$Re or $^{188}$Re.

Embodiment 25

The conjugate of embodiment 23, of the form:

(NSAID or NSAID residue)-(linker)-(chelating group)-M-(terminal ligand)$_z$ where z is an integer between 0 and 5 inclusive; and each "terminal ligand" is independently selected from a ligand that bonds or complexes to M, but which does not have a NSAID or NSAID residue attached to it.

Embodiment 26

The conjugate of embodiment 23, wherein the NSAID or the residue of a NSAID and the imaging moiety are bonded or complexed via a linker, wherein the linker is selected from the group consisting of:
an optionally substituted $C_1$-$C_{40}$ hydrocarbylene group;
an optionally substituted $C_2$-$C_{40}$ heterohydrocarbylene group; and
a linker of the form -$L_E$-$R^4$-$L_F$-,
where $L_E$ is absent or is selected from the group consisting of —NH— and —N($R^8$)—, and $R^8$ is optionally substituted $C_1$-$C_4$ alkyl,
$R^4$ is selected from the group consisting of optionally substituted $C_1$-$C_{40}$ hydrocarbylene, optionally substituted $C_2$-$C_{40}$ heterohydrocarbylene, $C_3$-$C_8$ cycloalkyl, $C_1$-$C_6$ alkyl-$C_3$-$C_8$ cycloalkyl, $C_3$-$C_8$ cycloalkyl-$C_1$-$C_6$ alkyl, $C_1$-$C_6$ alkyl-$C_3$-$C_8$ cycloalkyl-$C_1$-$C_6$ alkyl, $C_6$-$C_{10}$ aryl, $C_1$-$C_6$ alkyl-$C_6$-$C_{10}$ aryl, $C_6$-$C_{10}$ aryl-$C_1$-$C_6$ alkyl, and $C_1$-$C_6$ alkyl-$C_6$-$C_{10}$ aryl-$C_1$-$C_6$ alkyl,
and $L_F$ is absent or is a functional group selected from the group consisting of —(C=O)—, —O—, —N($R^9$)—, —(C=O)N($R^9$)—, —N($R^9$)—(C=O)—, —($SO_2$)N($R^9$)—, —N($R^9$)—($SO_2$)—, —N($R^9$)(C=O)N($R^9$)—, —N($R^9$)—(C=O)—O—, —O—(C=O)N($R^9$)—, —(CH=CH)—, or a divalent cycloalkyl or heterocyclic group, where $R^9$ is selected from the group consisting of H and optionally substituted $C_1$-$C_4$ alkyl.

Embodiment 27

The conjugate of embodiment 26, wherein the linker is selected from the group consisting of:
(—$CH_2CH_2$—O—)$_n$ and (—$CH_2CH(CH_3)$—O—)$_n$, where n is an integer from 1 to 12 inclusive.

Embodiment 28

The conjugate of embodiment 26, wherein the linker is selected from the group consisting of: —(NR$_a$)—($CH_2$)$_n$—(NR$_a$)—, —(NH)—($CH_2$)$_n$—(NH)—, —(NR$_a$)—($CH_2CH_2$)—($OCH_2CH_2$)$_n$—(NR$_a$)—, —(NH)—($CH_2CH_2$)—($OCH_2CH_2$)$_n$—(NH)—, where R$_a$ is ($C_1$-$C_4$ alkyl) and n is an integer from 1 to 12 inclusive,

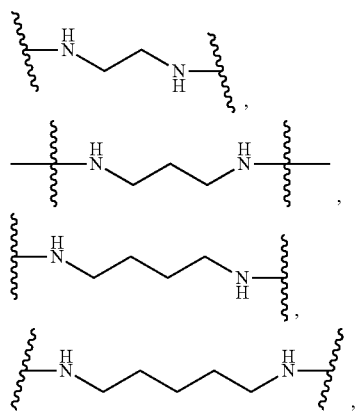

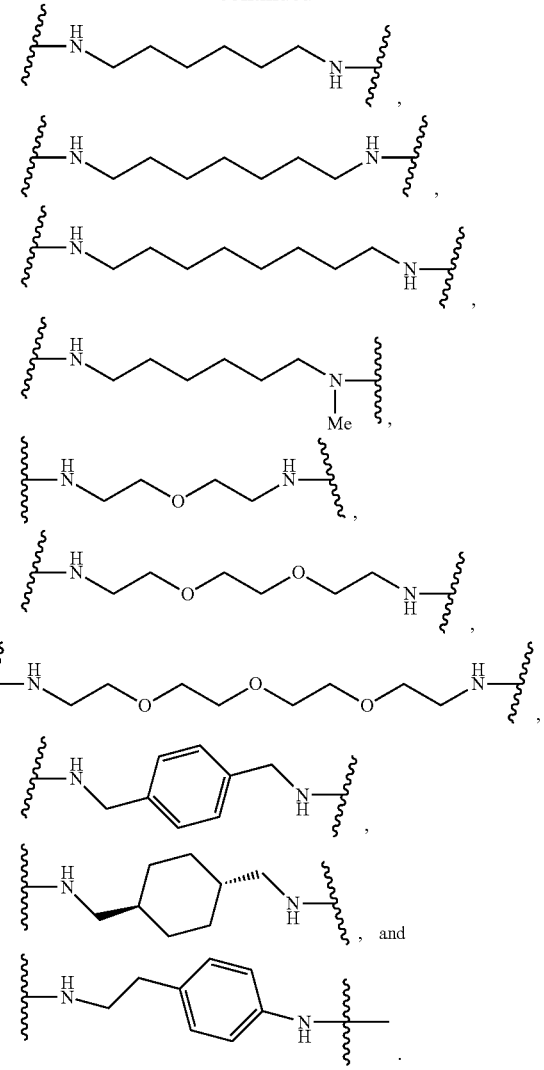

Embodiment 29

The conjugate of embodiment 23 or embodiment 24, wherein the imaging moiety further comprises a group which bonds or complexes to the radioactive agent.

Embodiment 30

The conjugate of embodiment 29, wherein the group which bonds or complexes to the radioactive agent is a chelating group.

Embodiment 31

The conjugate of embodiment 30, wherein the chelating group is of the form:

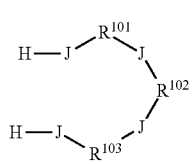

wherein each J is independently selected from the group consisting of NH and S,
$R^{101}$, $R^{102}$, and $R^{103}$ are independently selected from the group consisting of optionally substituted $C_2$-$C_4$ alkyl, and the NSAID or NSAID residue is attached to the H-J-$R^{101}$-J-$R^{102}$-J-$R^{103}$-J-H, either directly or through a linker, at any J, $R^{101}$, $R^{102}$, or $R^{103}$ atom where a hydrogen atom can be replaced with a bond to the NSAID or NSAID residue, or to the linker.

Embodiment 32

The conjugate of embodiment 30, wherein the chelating group is selected from the group consisting of:

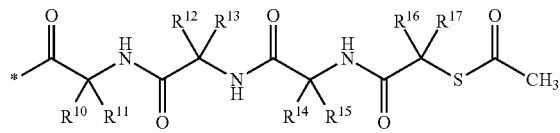

where $R^{10}$, $R^{11}$, $R^{12}$, $R^{13}$, $R^{14}$, $R^{15}$, $R^{16}$, and $R^{17}$ are independently selected from the group consisting of hydrogen, $C_1$-$C_4$ alkyl, $C_1$-$C_4$ alkyl substituted with fluoro, hydroxy, —O—$C_1$-$C_4$ alkyl, or $C_3$-$C_6$ cycloalkyl; or, independently of the other substituents, ($R^{10}$ and $R^{11}$) together with the carbon to which they are attached independently form a $C_3$-$C_8$ cycloalkyl ring or heterocycloalkyl ring, ($R^{12}$ and $R^{13}$) together with the carbon to which they are attached independently form a $C_3$-$C_8$ cycloalkyl ring or heterocycloalkyl ring, or ($R^{14}$ and $R^{15}$) together with the carbon to which they are attached independently form a $C_3$-$C_8$ cycloalkyl ring or heterocycloalkyl ring, or ($R^{16}$ and $R^{17}$) together with the carbon to which they are attached independently form a $C_3$-$C_8$ cycloalkyl ring or heterocycloalkyl ring, with the proviso that only one of ($R^{10}$ and $R^{11}$), ($R^{12}$ and $R^{13}$), ($R^{14}$ and $R^{15}$), and ($R^{16}$ and $R^{17}$) together with the carbon to which they are attached independently form a $C_3$-$C_8$ cycloalkyl ring or heterocycloalkyl ring; and wherein the bond marked with an asterisk * indicates the attachment of the chelating group to the remainder of the conjugate; and

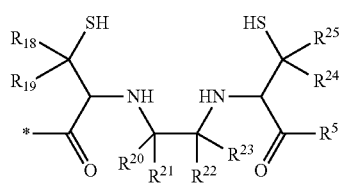

$R^{18}$, $R^{19}$, $R^{20}$, $R^{21}$, $R^{22}$, $R^{23}$, $R^{24}$, and $R^{25}$ are independently selected from the group consisting of hydrogen, $C_1$-$C_4$ alkyl, $C_1$-$C_4$ alkyl substituted with fluoro, hydroxy, —O—$C_1$-$C_4$ alkyl, or $C_3$-$C_6$ cycloalkyl; or, independently of the other substituents, ($R^{18}$ and $R^{19}$) together with the carbon to which they are attached form a $C_3$-$C_8$ cycloalkyl ring or heterocycloalkyl ring, ($R^{20}$ and $R^{21}$) together with the carbon to which they are attached form a $C_3$-$C_8$ cycloalkyl ring or heterocycloalkyl ring, or ($R^{22}$ and $R^{23}$) together with the carbon to which they are attached independently form a $C_3$-$C_8$ cycloalkyl ring or heterocycloalkyl ring, or ($R^{24}$ and $R^{25}$) together with the carbon to which they are attached independently form a $C_3$-$C_8$ cycloalkyl ring or heterocy-cloalkyl ring, with the proviso that only one of ($R^{18}$ and $R^{19}$), ($R^{20}$ and $R^{21}$), or ($R^{22}$ and $R^{23}$), or ($R^{24}$ and $R^{25}$) together with the carbon to which they are attached independently form a $C_3$-$C_8$ cycloalkyl ring or heterocycloalkyl ring; and wherein the bond marked with an asterisk * indicates the attachment of the chelating group to the remainder of the conjugate.

Embodiment 33

A conjugate of the formula:

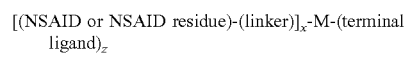

where "NSAID or NSAID residue" refers to a NSAID or a residue of a NSAID; M is selected from the group consisting of $^{99m}$Tc, $^{52}$Mn, and Re;
x is an integer between 1 and 6 inclusive, z is an integer between 0 and 5 inclusive, and the sum of x and z is less than or equal to 6; and
"terminal ligand" is a ligand that coordinates to M, but which does not have a NSAID attached to it; or a pharmaceutically acceptable salt thereof.

Embodiment 34

The conjugate of embodiment 33, wherein said conjugate is of the formula:

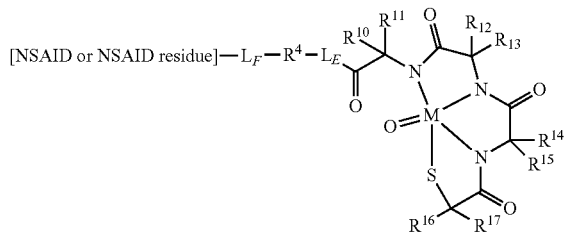

where $L_E$ is absent or is selected from the group consisting of —NH— and —N($R^8$)—,
where $R^8$ is optionally substituted $C_1$-$C_4$ alkyl;
$R^4$ is selected from the group consisting of optionally substituted $C_1$-$C_{40}$ hydrocarbylene, optionally substituted $C_2$-$C_{40}$ heterohydrocarbylene, $C_3$-$C_8$ cycloalkyl, $C_1$-$C_6$ alkyl-$C_3$-$C_8$ cycloalkyl, $C_3$-$C_8$ cycloalkyl-$C_1$-$C_6$ alkyl, $C_1$-$C_6$ alkyl-$C_3$-$C_8$ cycloalkyl-$C_1$-$C_6$ alkyl, $C_6$-$C_{10}$ aryl, $C_1$-$C_6$ alkyl-$C_6$-$C_{10}$ aryl, $C_6$-$C_{10}$ aryl-$C_1$-$C_6$ alkyl, and $C_1$-$C_6$ alkyl-$C_6$-$C_{10}$ aryl-$C_1$-$C_6$ alkyl;
$L_F$ is absent or is a functional group selected from the group consisting of —(C=O)—, —O—, —N($R^9$)—, —(C=O)N($R^9$)—, —N($R^9$)—(C=O)—, —(SO$_2$)N($R^9$)—, —N($R^9$)—(SO$_2$)—, —N($R^9$)(C=O)N($R^9$)—, —N($R^9$)—(C=O)—O—, —O—(C=O)N($R^9$)—, —(CH=CH)—, or a divalent cycloalkyl or heterocyclic group, where $R^9$ is selected from the group consisting of H and optionally substituted $C_1$-$C_4$ alkyl;
where $R^{10}$, $R^{11}$, $R^{12}$, $R^{13}$, $R^{14}$, $R^{15}$, $R^{16}$, and $R^{17}$ are independently selected from the group consisting of hydrogen, $C_1$-$C_4$ alkyl, $C_1$-$C_4$ alkyl substituted with fluoro, hydroxy, —O—$C_1$-$C_4$ alkyl, or $C_3$-$C_6$ cycloalkyl; or, independently of the other substituents, ($R^{10}$ and $R^{11}$) together with the carbon to which they are attached independently form a $C_3$-$C_8$ cycloalkyl ring or heterocycloalkyl ring, ($R^{12}$ and $R^{13}$) together with the carbon to which they are attached independently form a $C_3$-$C_8$ cycloalkyl ring or heterocycloalkyl ring, or ($R^{14}$ and $R^{15}$) together with the carbon to which they are attached independently form a $C_3$-$C_8$ cycloalkyl ring or heterocycloalkyl ring, or ($R^{16}$ and $R^{17}$) together with the carbon to which they are attached independently form a $C_3$-$C_8$ cycloalkyl ring or heterocycloalkyl ring, with the proviso that only one of ($R^{10}$ and $R^{11}$), ($R^{12}$ and $R^{13}$), ($R^{14}$ and $R^{15}$), and ($R^{16}$ and $R^{17}$) together with the carbon to which they are attached independently form a $C_3$-$C_8$ cycloalkyl ring or heterocycloalkyl ring; and M is selected from the group consisting of $^{99m}$Tc and Re;

or a pharmaceutically acceptable salt thereof.

Embodiment 35

The conjugate of embodiment 33, wherein said conjugate is of the formula:

(NSAID or NSAID residue)-(linker)-M-(terminal ligand)$_z$ and -(linker)-M-(terminal ligand)$_z$ is selected from the group consisting of:

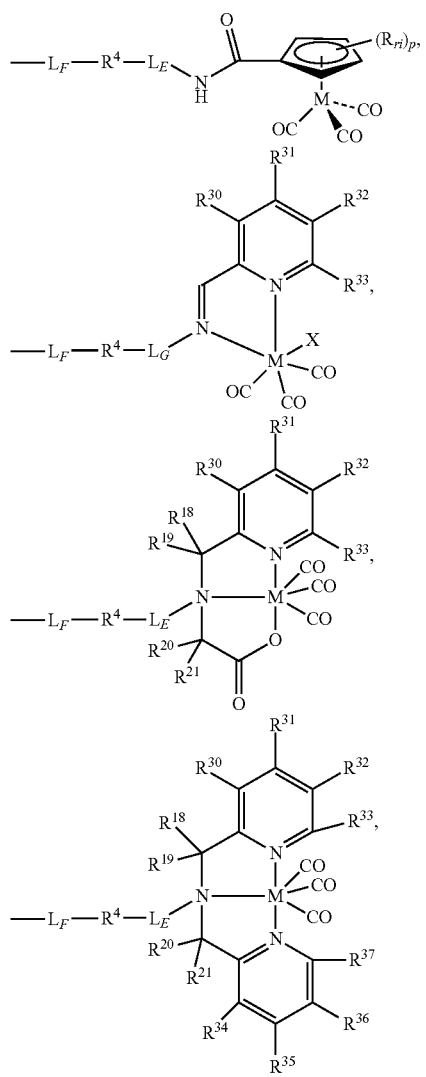

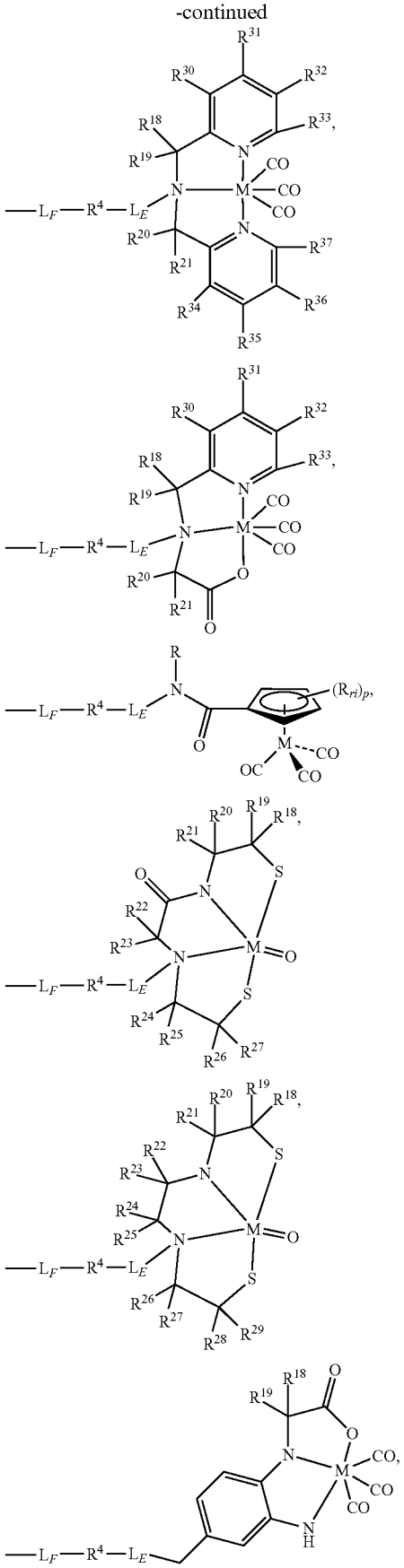

-continued

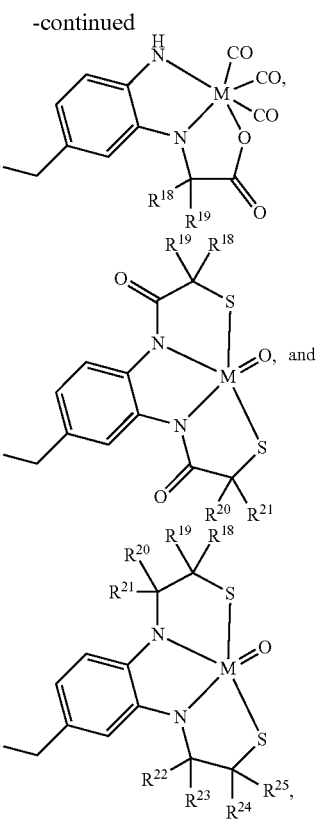

where $L_E$ is absent or is selected from the group consisting of —NH— and —N($R^8$)—, and $R^8$ is optionally substituted $C_1$-$C_4$ alkyl, with the proviso that if the $L_E$ moiety of the group -$L_F$-$R^4$-$L_E$- would be attached to a nitrogen atom, then $L_E$ is absent;

where $L_G$ is absent or is selected from the group consisting of —NH— and —N($R^8$)—, and $R^8$ is optionally substituted $C_1$-$C_4$ alkyl;

$R^4$ is selected from the group consisting of optionally substituted $C_1$-$C_{40}$ hydrocarbylene, optionally substituted $C_2$-$C_{40}$ heterohydrocarbylene, $C_3$-$C_8$ cycloalkyl, $C_1$-$C_6$ alkyl-$C_3$-$C_8$ cycloalkyl, $C_3$-$C_8$ cycloalkyl-$C_1$-$C_6$ alkyl, $C_1$-$C_6$ alkyl-$C_3$-$C_8$ cycloalkyl-$C_1$-$C_6$ alkyl, $C_6$-$C_{10}$ aryl, $C_1$-$C_6$ alkyl-$C_6$-$C_{10}$ aryl, $C_6$-$C_{10}$ aryl-$C_1$-$C_6$ alkyl, and $C_1$-$C_6$ alkyl-$C_6$-$C_{10}$ aryl-$C_1$-$C_6$ alkyl;

$L_F$ is absent or is a functional group selected from the group consisting of —(C=O)—, —O—, —N($R^9$)—, —(C=O)N($R^9$)—, —N($R^9$)—(C=O)—, —(SO$_2$)N($R^9$)—, —N($R^9$)—(SO$_2$)—, —N($R^9$)(C=O)N($R^9$)—, —N($R^9$)—(C=O)—O—, —O—(C=O)N($R^9$)—, —(CH=CH)—, or a divalent cycloalkyl or heterocyclic group, where $R^9$ is selected from the group consisting of H and optionally substituted $C_1$-$C_4$ alkyl; and $R^{18}$, $R^{19}$, $R^{20}$, $R^{21}$, $R^{22}$, $R^{23}$, $R^{24}$, $R^{25}$, $R^{26}$, $R^{27}$, $R^{28}$, and $R^{29}$ are independently selected from the group consisting of hydrogen, $C_1$-$C_4$ alkyl, $C_1$-$C_4$ alkyl substituted with fluoro, hydroxy, —O—$C_1$-$C_4$ alkyl, or $C_3$-$C_6$ cycloalkyl; or, independently of the other substituents, ($R^{18}$ and $R^{19}$) together with the carbon to which they are attached form a $C_3$-$C_8$ cycloalkyl ring or heterocycloalkyl ring, ($R^{20}$ and $R^{21}$) together with the carbon to which they are attached form a $C_3$-$C_8$ cycloalkyl ring or heterocycloalkyl ring, or ($R^{22}$ and $R^{23}$) together with the carbon to which they are attached independently form a $C_3$-$C_8$ cycloalkyl ring or heterocycloalkyl ring, or ($R^{24}$ and $R^{25}$) together with the carbon to which they are attached independently form a $C_3$-$C_8$ cycloalkyl ring or heterocycloalkyl ring, or ($R^{26}$ and $R^{27}$) together with the carbon to which they are attached independently form a $C_3$-$C_8$ cycloalkyl ring or heterocycloalkyl ring, or ($R^{28}$ and $R^{29}$) together with the carbon to which they are attached independently form a $C_3$-$C_8$ cycloalkyl ring or heterocycloalkyl ring, with the proviso that only one of ($R^{18}$ and $R^{19}$), ($R^{20}$ and $R^{21}$), or ($R^{22}$ and $R^{23}$), or ($R^{24}$ and $R^{25}$), or ($R^{26}$ and $R^{27}$), or ($R^{28}$ and $R^{29}$) together with the carbon to which they are attached independently form a $C_3$-$C_8$ cycloalkyl ring or heterocycloalkyl ring;

$R^{30}$, $R^{31}$, $R^{32}$, and $R^{33}$ are independently selected from hydrogen and $C_1$-$C_4$ alkyl, or one pair of ($R^{30}$ and $R^{31}$), ($R^{31}$ and $R^{32}$), or ($R^{32}$ and $R^{33}$), together with the atoms to which they are attached, form a six-membered aryl ring or a five-to-six membered heteroaryl ring;

$R^{34}$, $R^{35}$, $R^{36}$, and $R^{37}$ are independently selected from hydrogen and $C_1$-$C_4$ alkyl, or one pair of ($R^{34}$ and $R^{35}$), ($R^{35}$ and $R^{36}$), or ($R^{36}$ and $R^{37}$), together with the atoms to which they are attached, form a six-membered aryl ring or a five-to-six membered heteroaryl ring;

$R_{(n)}$ is —CH$_3$ or —CH$_2$CH$_3$ and p is an integer between 0 and 4 inclusive;

and

X is Cl or Br;

or a pharmaceutically acceptable salt thereof.

Embodiment 36

The conjugate of embodiment 33, wherein said conjugate is of the formula:

(NSAID or NSAID residue)-(linker)-M-(terminal ligand)$_z$ and -(linker)-M-(terminal ligand)$_z$ is selected from the group consisting of:

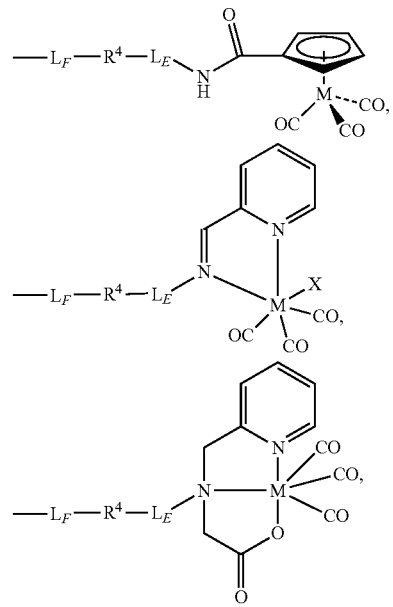

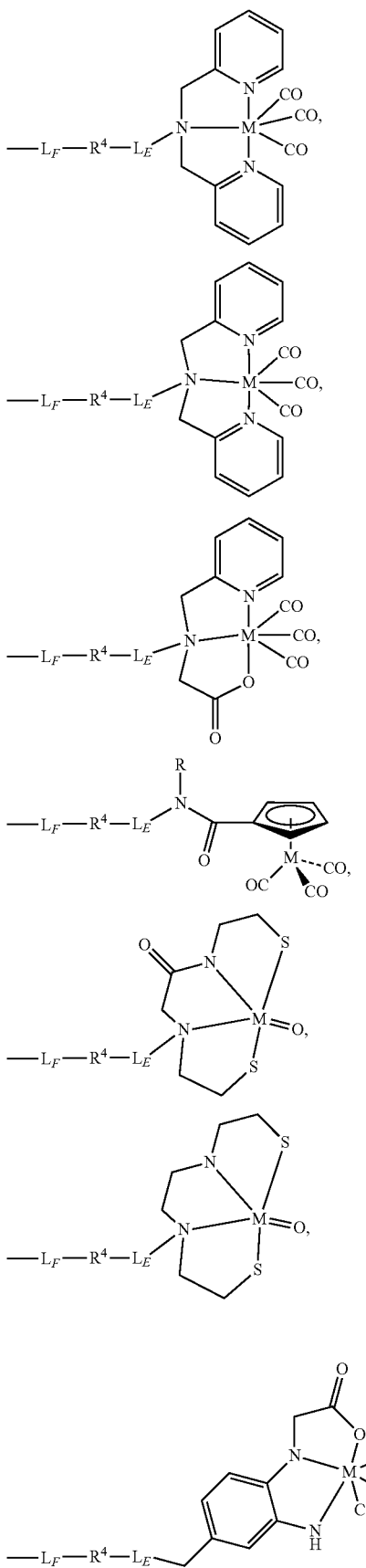

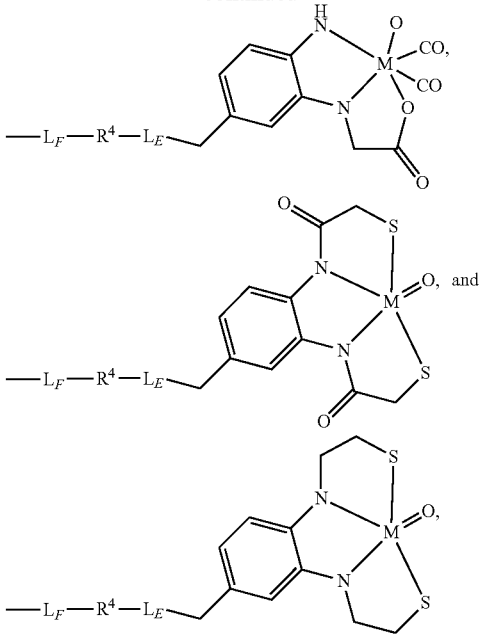

where $L_E$ is absent or is selected from the group consisting of —NH— and —N(R$^8$)—, and R$^8$ is optionally substituted C$_1$-C$_4$ alkyl, with the proviso that if the $L_E$ moiety of the group -$L_F$-R$^4$-$L_E$- would be attached to a nitrogen atom, then $L_E$ is absent;

R$^4$ is selected from the group consisting of optionally substituted C$_1$-C$_{40}$ hydrocarbylene, optionally substituted C$_2$-C$_{40}$ heterohydrocarbylene, C$_3$-C$_8$ cycloalkyl, C$_1$-C$_6$ alkyl-C$_3$-C$_8$ cycloalkyl, C$_3$-C$_8$ cycloalkyl-C$_1$-C$_6$ alkyl, C$_1$-C$_6$ alkyl-C$_3$-C$_8$ cycloalkyl-C$_1$-C$_6$ alkyl, C$_6$-C$_{10}$ aryl, C$_1$-C$_6$ alkyl-C$_6$-C$_{10}$ aryl, C$_6$-C$_{10}$ aryl-C$_1$-C$_6$ alkyl, and C$_1$-C$_6$ alkyl-C$_6$-C$_{10}$ aryl-C$_1$-C$_6$ alkyl;

$L_F$ is absent or is a functional group selected from the group consisting of —(C═O)—, —O—, —N(R$^9$)—, —(C═O)N(R$^9$)—, —N(R$^9$)—(C═O)—, —(SO$_2$)N(R$^9$)—, —N(R$^9$)—(SO$_2$)—, —N(R$^9$)(C═O)N(R$^9$)—, —N(R$^9$)—(C═O)—O—, —O—(C═O) N(R$^9$)—, —(CH═CH)—, or a divalent cycloalkyl or heterocyclic group, where R$^9$ is selected from the group consisting of H and optionally substituted C$_1$-C$_4$ alkyl; and X is Cl or Br;

or a pharmaceutically acceptable salt thereof.

Embodiment 37

The conjugate of embodiment 33, wherein said conjugate is of the formula:

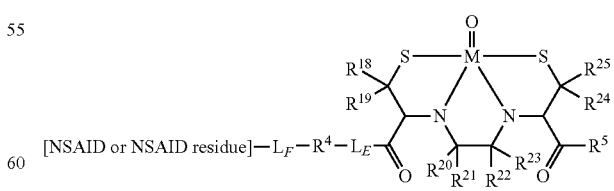

where $L_E$ is absent or is selected from the group consisting of —NH— and —N(R$^8$)—, where R$^8$ is optionally substituted C$_1$-C$_4$ alkyl, R$^4$ is selected from the group consisting of optionally substituted C$_1$-C$_{40}$ hydrocarbylene, optionally substituted $C_2$-$C_{40}$ heterohydrocarbylene, $C_3$-$C_8$ cycloalkyl, $C_1$-$C_6$ alkyl-$C_3$-$C_8$ cycloalkyl, $C_3$-$C_8$ cycloalkyl-$C_1$-$C_6$ alkyl, $C_1$-$C_6$ alkyl-$C_3$-$C_8$ cycloalkyl-$C_1$-$C_6$ alkyl, $C_6$-$C_{10}$ aryl, $C_1$-$C_6$ alkyl-$C_6$-$C_{10}$ aryl, $C_6$-$C_{10}$ aryl-$C_1$-$C_6$ alkyl, and $C_1$-$C_6$ alkyl-$C_6$-$C_{10}$ aryl-$C_1$-$C_6$ alkyl;

$R^5$ is selected from the group consisting of —OH, —$NH_2$, —NH($C_1$-$C_4$ alkyl), and —N($C_1$-$C_4$ alkyl)($C_1$-$C_4$ alkyl);

$L_F$ is absent or is a functional group selected from the group consisting of —(C=O)—, —O—, —N($R^9$)—, —(C=O)N($R^9$)—, —N($R^9$)—(C=O)—, —($SO_2$)N($R^9$)—, —N($R^9$)—($SO_2$)—, —N($R^9$)(C=O)N($R^9$)—, —N($R^9$)—(C=O)—O—, —O—(C=O)N($R^9$)—, —(CH=CH)—, or a divalent cycloalkyl or heterocyclic group, where $R^9$ is selected from the group consisting of H and optionally substituted $C_1$-$C_4$ alkyl;

M is selected from the group consisting of $^{99m}$Tc and Re; and $R^{18}$, $R^{19}$, $R^{20}$, $R^{21}$, $R^{22}$, $R^{23}$, $R^{24}$, and $R^{25}$ are independently selected from the group consisting of hydrogen, $C_1$-$C_4$ alkyl, $C_1$-$C_4$ alkyl substituted with fluoro, hydroxy, —O—$C_1$-$C_4$ alkyl, or $C_3$-$C_6$ cycloalkyl; or, independently of the other substituents, ($R^{18}$ and $R^{19}$) together with the carbon to which they are attached form a $C_3$-$C_8$ cycloalkyl ring or heterocycloalkyl ring, ($R^{20}$ and $R^{21}$) together with the carbon to which they are attached form a $C_3$-$C_8$ cycloalkyl ring or heterocycloalkyl ring, or ($R^{22}$ and $R^{23}$) together with the carbon to which they are attached independently form a $C_3$-$C_8$ cycloalkyl ring or heterocycloalkyl ring, or ($R^{24}$ and $R^{25}$) together with the carbon to which they are attached independently form a $C_3$-$C_8$ cycloalkyl ring or heterocycloalkyl ring, with the proviso that only one of ($R^{18}$ and $R^{19}$), ($R^{20}$ and $R^{21}$), or ($R^{22}$ and $R^{23}$), or ($R^{24}$ and $R^{25}$) together with the carbon to which they are attached independently form a $C_3$-$C_8$ cycloalkyl ring or heterocycloalkyl ring;

or a pharmaceutically acceptable salt thereof.

Embodiment 38

The conjugate of any one of embodiments 23-26, wherein the linker is selected from the group consisting of:

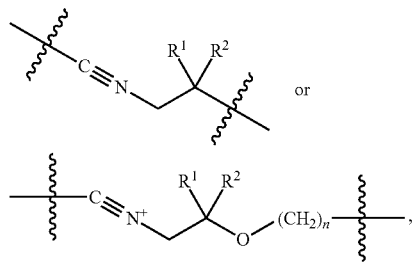

where $R^1$, $R^2$, and $R^3$ can be independently selected from the group consisting of hydrogen, $C_1$-$C_4$ alkyl, $C_1$-$C_4$ alkyl substituted with hydroxy, fluoro, —O—$C_1$-$C_4$ alkyl, or $C_3$-$C_6$ cycloalkyl;

or $R^1$ and $R^2$ together with the carbon to which they are attached form a $C_3$-$C_8$ cycloalkyl ring or heterocycloalkyl ring; and n is an integer selected from 0 to 4, inclusive.

Embodiment 39

The conjugate of any one of embodiments 23-38, wherein the NSAID or the residue of a NSAID is selected from the group consisting of acetylsalicylic acid, diflunisal, salsalate, choline magnesium trisalicylate, ibuprofen, dexibuprofen, naproxen, fenoprofen, ketoprofen, dexketoprofen, flurbiprofen, oxaprozin, loxoprofen, indomethacin, tolmetin, sulindac, etodolac, ketorolac, diclofenac, aceclofenac, nabumetone, piroxicam, meloxicam, tenoxicam, droxicam, lornoxicam, isoxicam, mefenamic acid, meclofenamic acid, flufenamic acid, tolfenamic acid, celecoxib, rofecoxib, valdecoxib, parecoxib, lumiracoxib, etoricoxib, firocoxib, nimesulide, and licofelone, and a residue of any of the foregoing compounds.

Embodiment 40

The conjugate of any one of embodiments 23-38, wherein the non-steroidal anti-inflammatory drug (NSAID) or a residue of a NSAID is selected from the group consisting of indomethacin, naproxen, ketorolac, celecoxib, rofecoxib, a residue of indomethacin, a residue of naproxen, a residue of ketorolac, a residue of celecoxib, and a residue of rofecoxib.

Embodiment 41

The conjugate of embodiment 40, wherein the non-steroidal anti-inflammatory drug (NSAID) or a residue of a NSAID is a residue of a NSAID selected from the group consisting of:

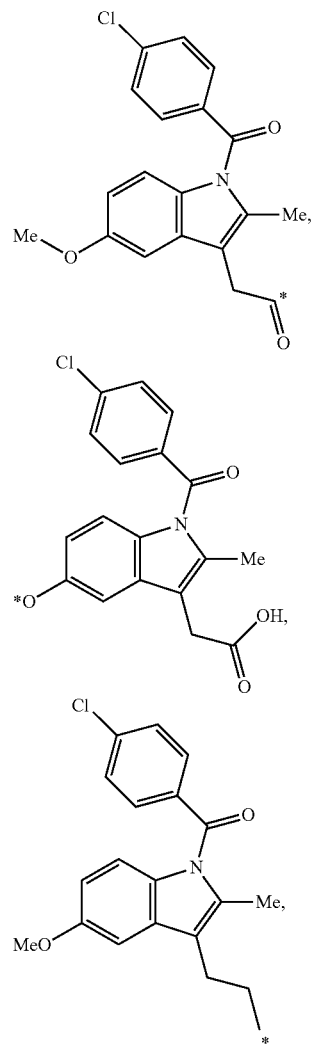

-continued

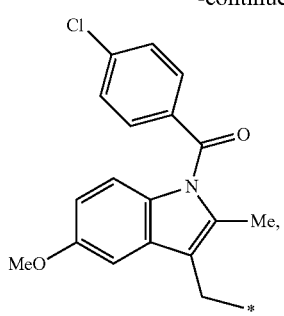

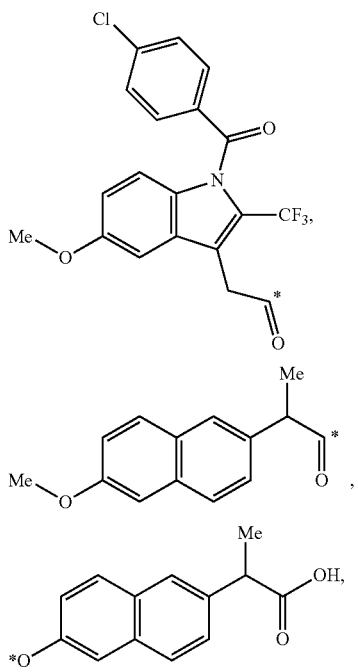

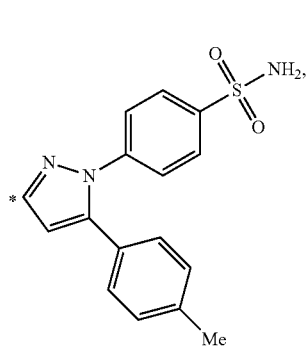

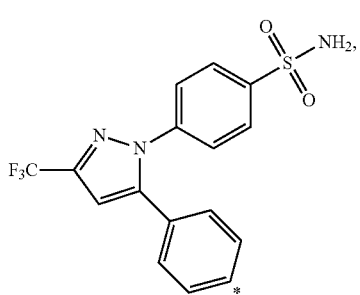

-continued

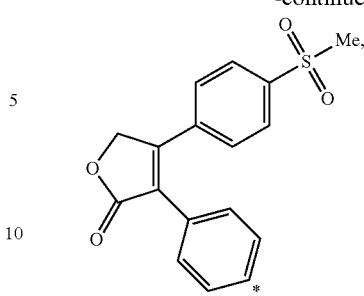

where the carbon atom or oxygen atom marked with an asterisk * indicates an open valence at that atom at which the residue of the NSAID is attached to the remainder of the conjugate.

Embodiment 42

The conjugate of embodiment 40, wherein the non-steroidal anti-inflammatory drug (NSAID) or a residue of a NSAID is selected from the group consisting of indomethacin and a residue of indomethacin.

Embodiment 43

The conjugate of embodiment 40, wherein the non-steroidal anti-inflammatory drug (NSAID) or a residue of a NSAID is a residue of a NSAID selected from the group consisting of:

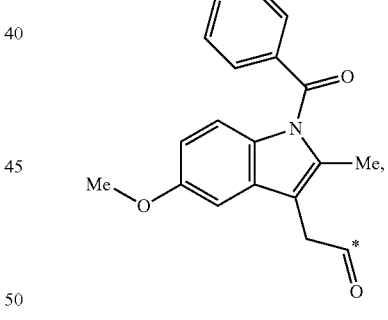

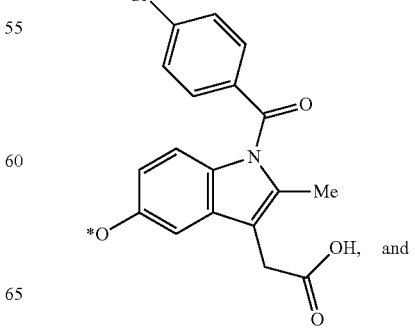

-continued

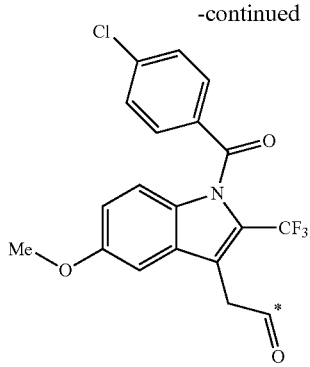

where the carbon atom or oxygen atom marked with an asterisk * indicates an open valence at that atom at which the residue of the NSAID is attached to the remainder of the conjugate.

Embodiment 44

The conjugate of embodiment 23, wherein the non-steroidal anti-inflammatory drug (NSAID) or a residue of a NSAID bonded or complexed to an imaging moiety which comprises a radioactive agent is selected from the group consisting of:

52

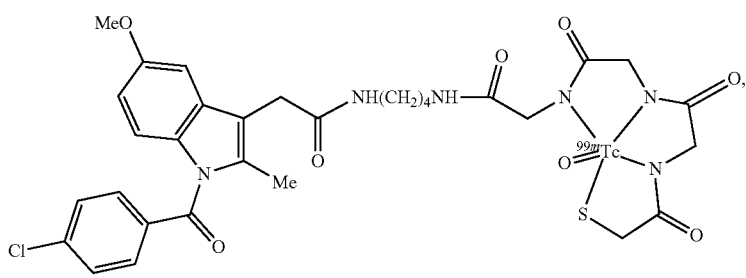

54

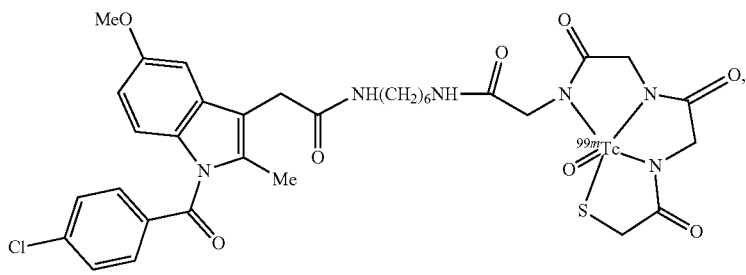

47

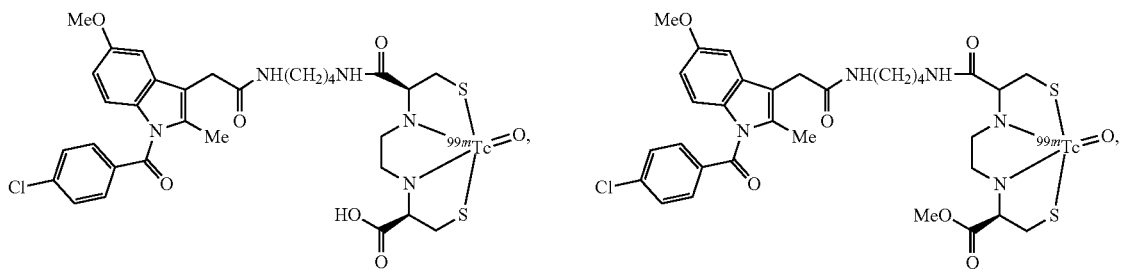

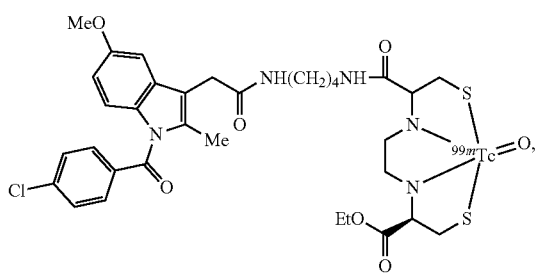

-continued
53
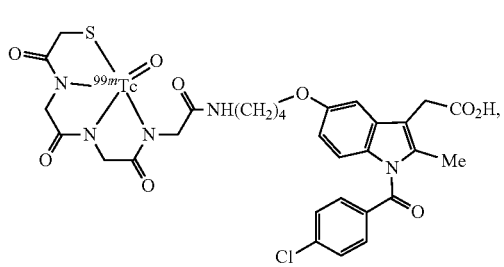
73
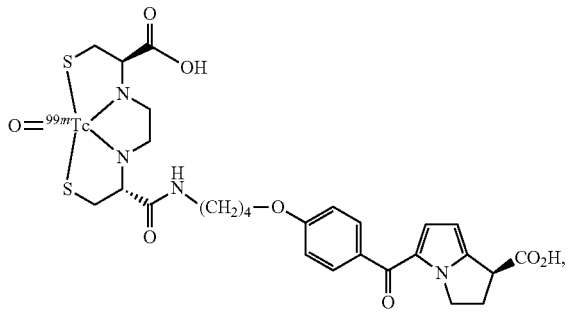
149
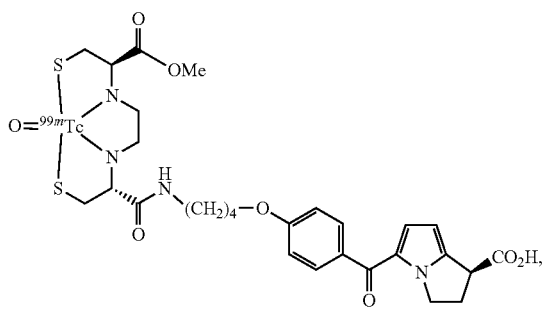
150
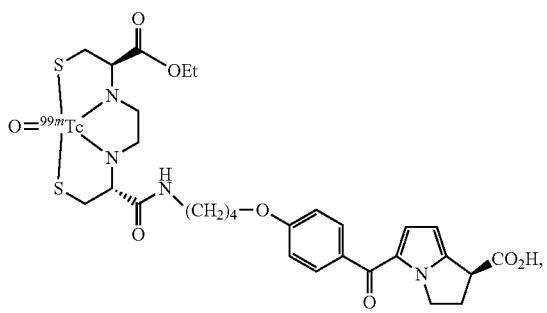
74
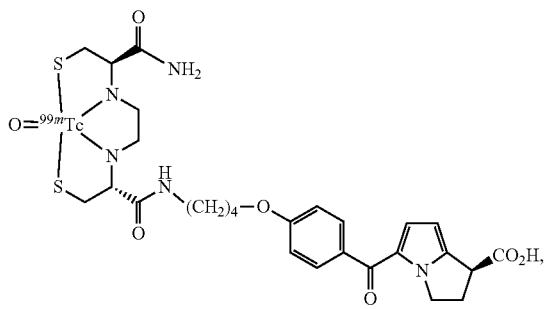
76
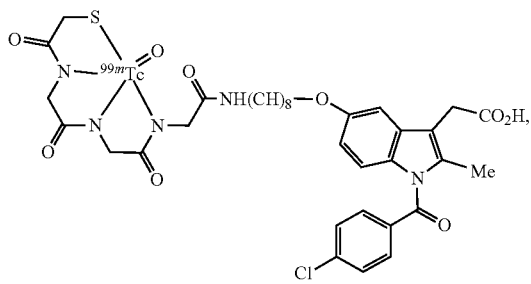
77
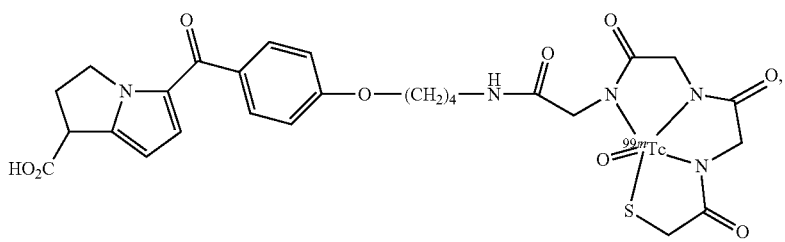
78
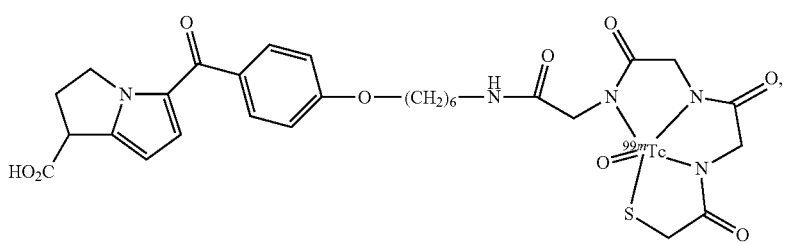

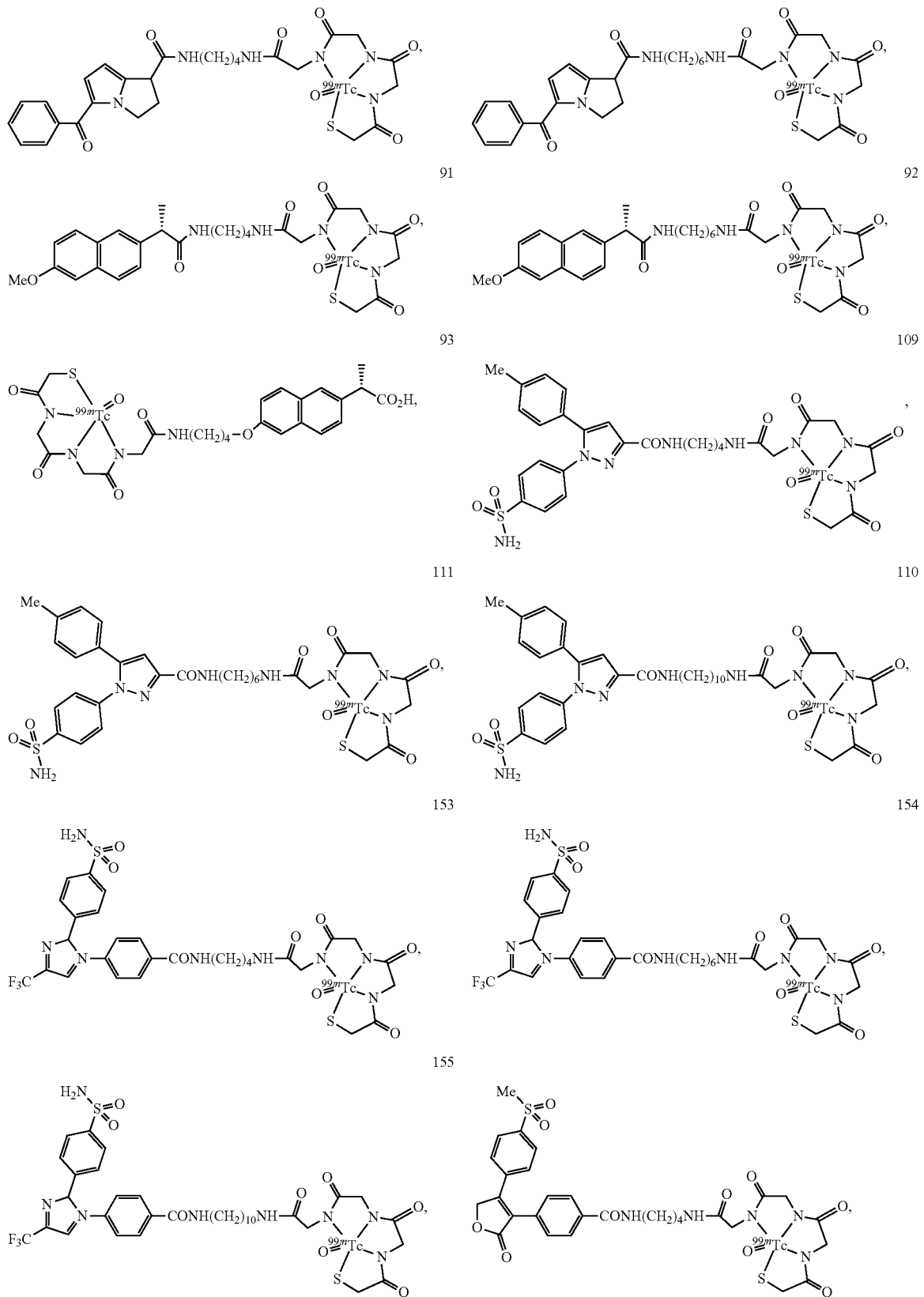

-continued
157
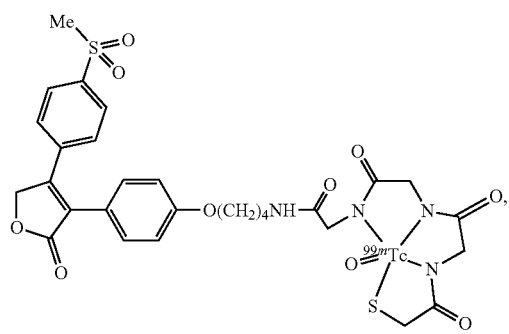
158
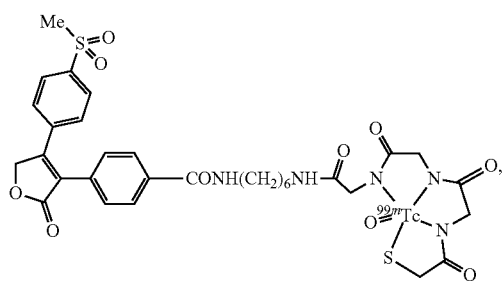
159
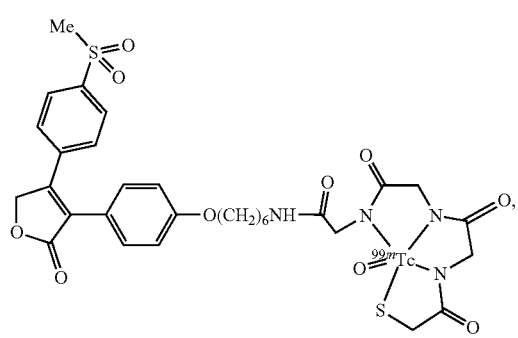
160
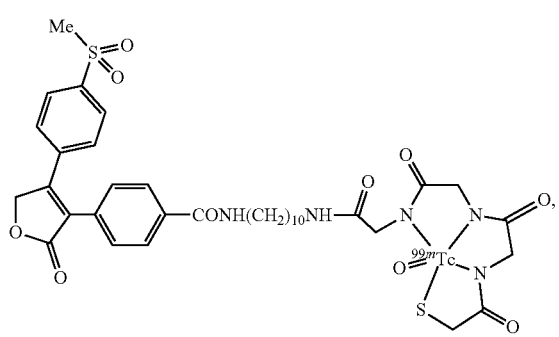
161
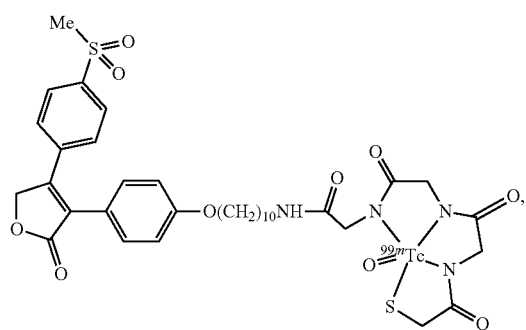
162
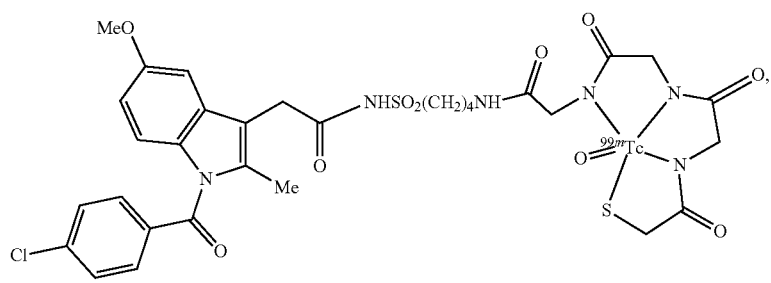
163
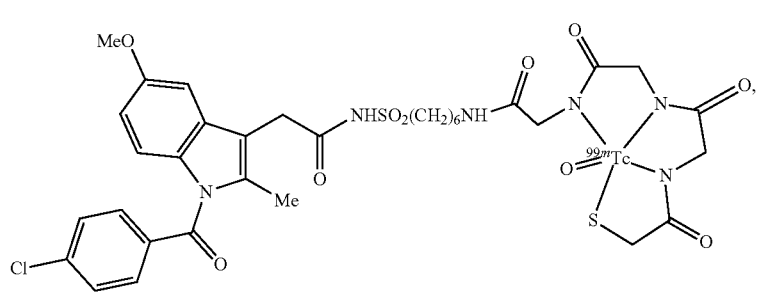

-continued
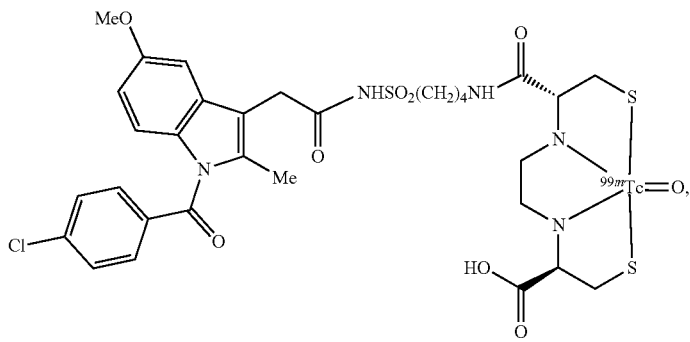
164
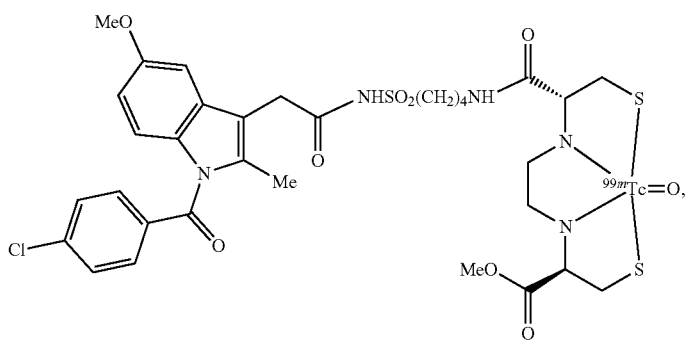
166
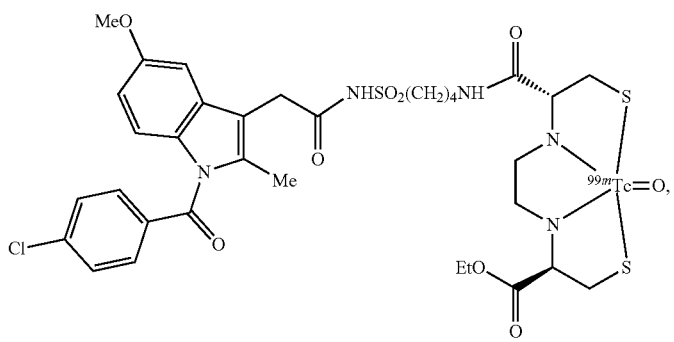
167
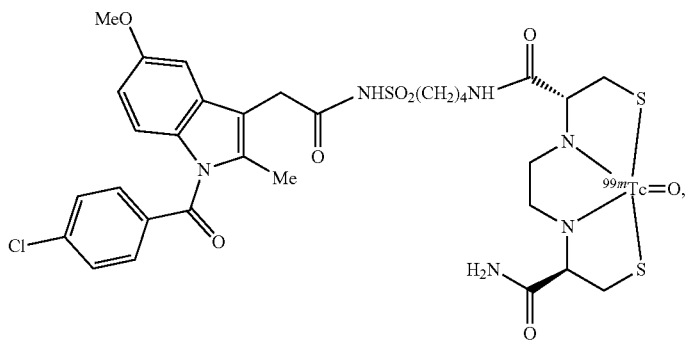
168
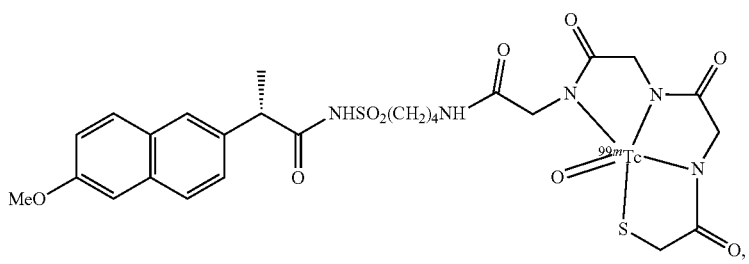

-continued
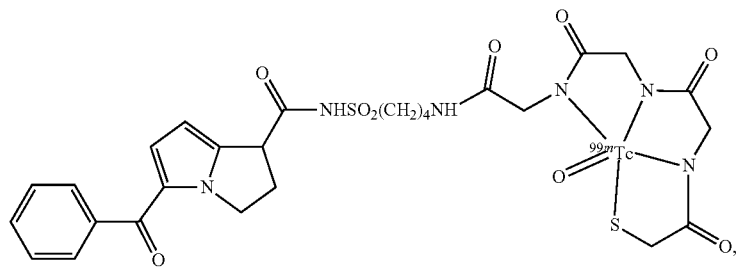
169
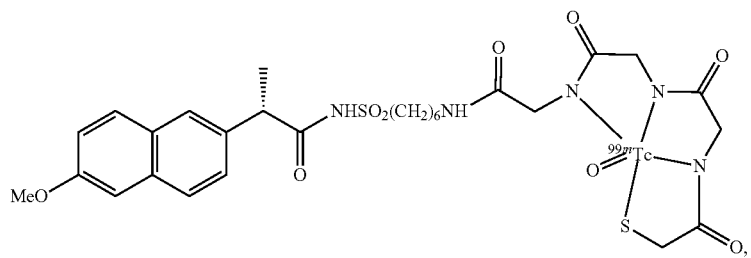
170
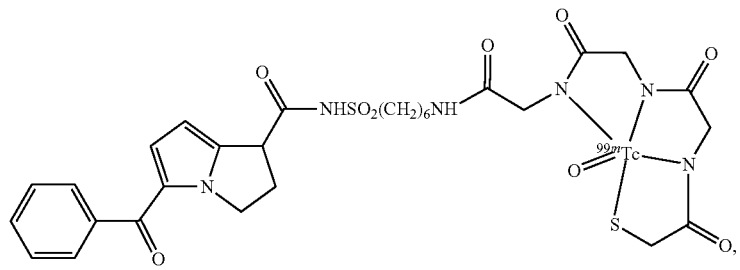
171
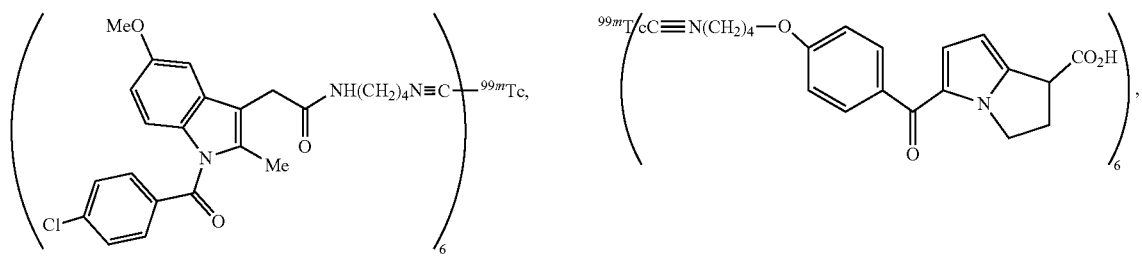
51        76

-continued
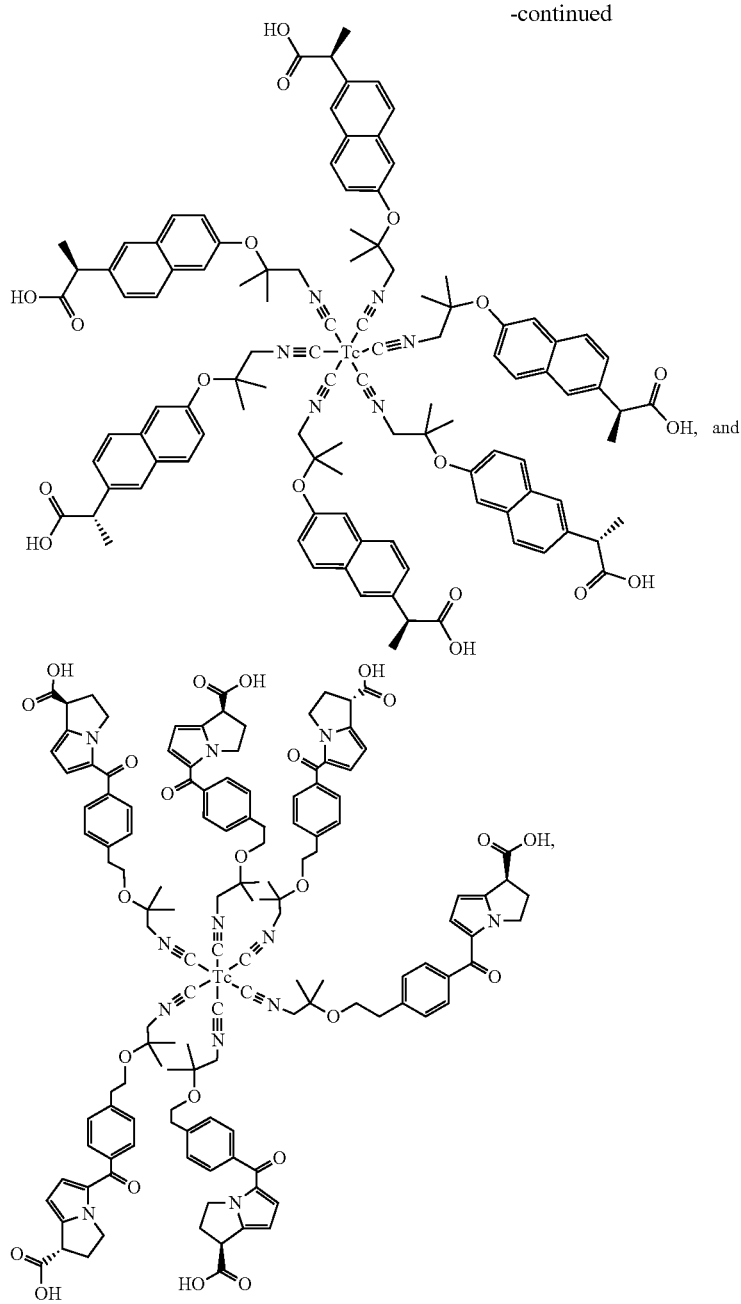
wherein Tc is $^{99m}$Tc;
and pharmaceutically acceptable salts thereof.
Embodiment 45
The conjugate of embodiment 23, wherein the non-steroidal anti-inflammatory drug (NSAID) or a residue of a NSAID bonded or complexed to an imaging moiety which comprises a radioactive agent is selected from the group consisting of:

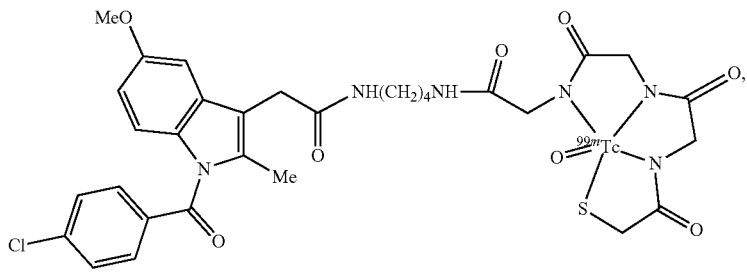
52
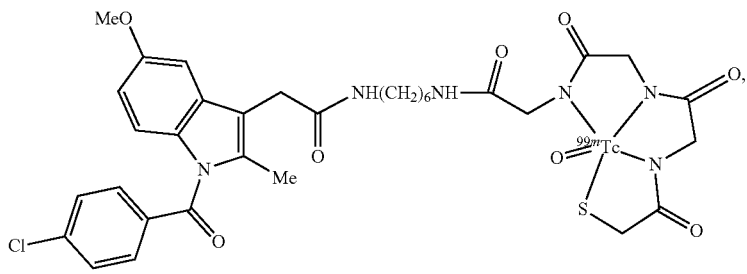
54
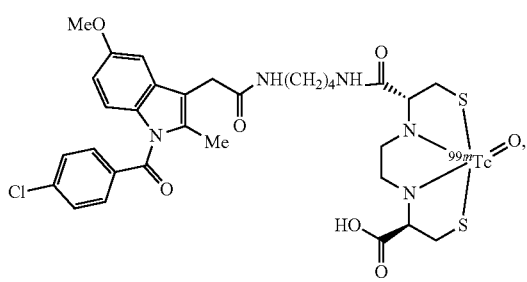
46
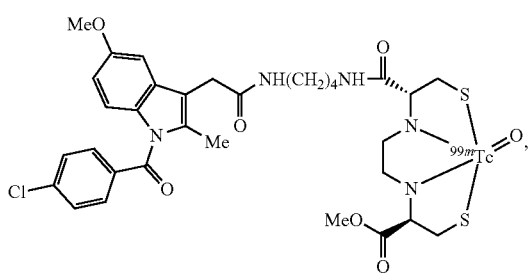
47
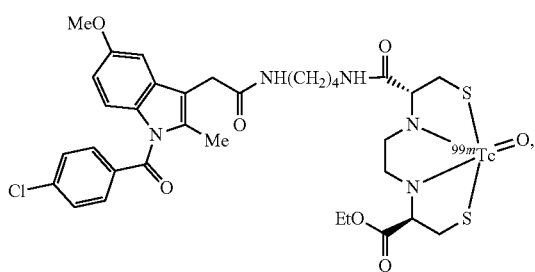
48
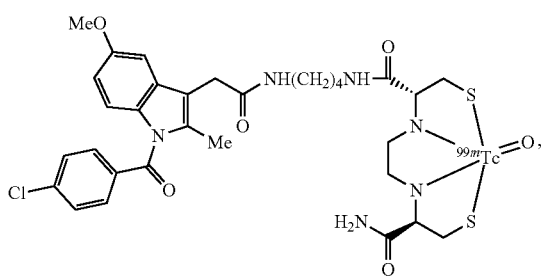
49
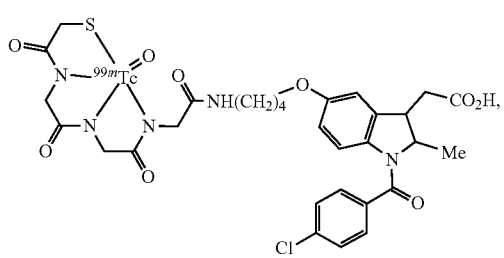
53
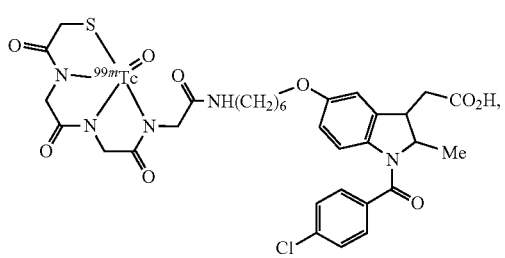

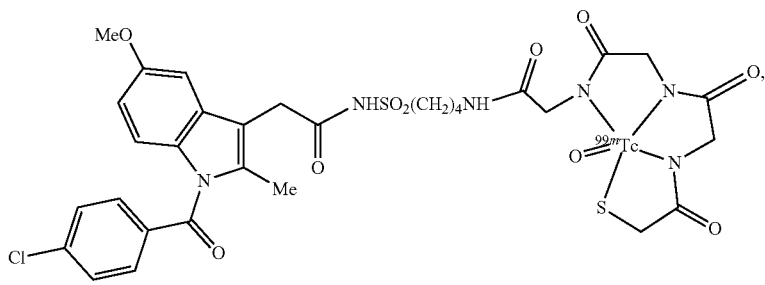
162
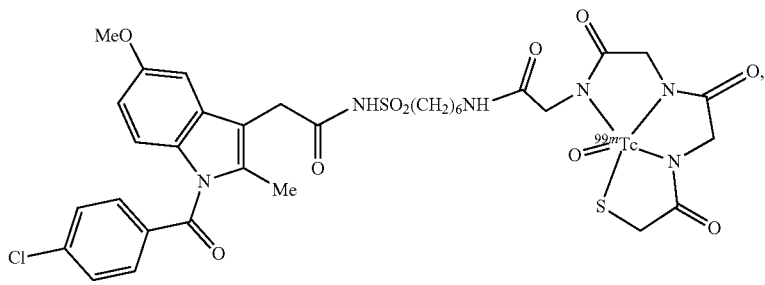
163
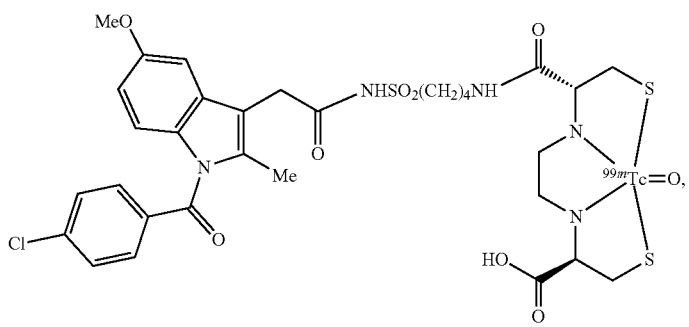
164
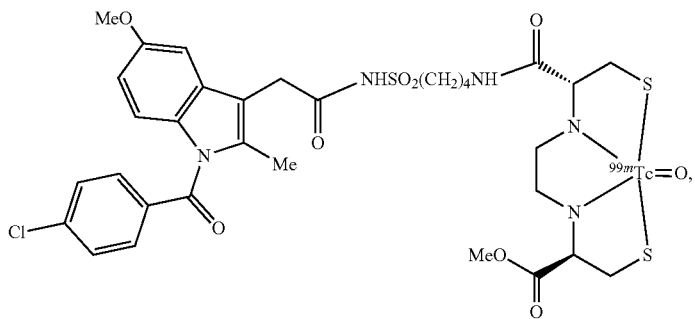
165
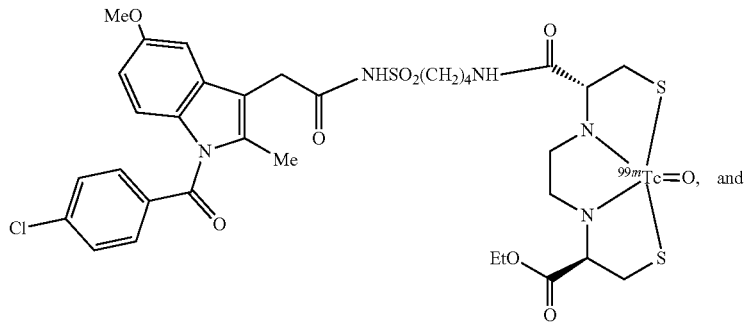
166

-continued wherein Tc is $^{99m}$Tc;
and pharmaceutically acceptable salts thereof.

Embodiment 46

A pharmaceutical composition comprising one or more conjugates of any one of embodiments 23-45, and a pharmaceutically acceptable excipient.

Embodiment 47

A method of imaging a site of pathology or suspected pathology in a subject, comprising:
a) administering one or more conjugates of any one of embodiments 23-45 or the composition of embodiment 46 to the subject, wherein the radioactive agent of the conjugate comprises $^{99m}$Tc, $^{52}$Mn, $^{186}$Re or $^{188}$Re; and
b) generating an image of the subject or an image of a portion of the subject.

Embodiment 48

The method of embodiment 47, wherein the pathology or suspected pathology in the subject is a tumor or a suspected tumor.

Embodiment 49

The method of embodiment 47, wherein the subject is suffering from pain.

Embodiment 50

The method of embodiment 47, wherein the pathology or suspected pathology in the subject is an infection or a suspected infection.

The disclosures of all publications, patents, patent applications and published patent applications referred to herein by an identifying citation are hereby incorporated herein by reference in their entirety.

The present invention has been described in terms of specific embodiments incorporating details to facilitate the understanding of principles of construction and operation of the invention. Such reference herein to specific embodiments and details thereof is not intended to limit the scope of the claims appended hereto. It will be readily apparent to one skilled in the art that other various modifications can be made in the embodiments chosen for illustration without departing from the spirit and scope of the invention. Therefore, the description and examples should not be construed as limiting the scope of the invention.

What is claimed is:

1. A conjugate of the formula:

wherein $R^{38}$ is O—($C_1$-$C_4$) alkyl;
wherein $R^{39}$ is selected from the group consisting of H, F, Cl, Br, I, $CH_3$, and $CF_3$;
wherein $R^{40}$ is selected from the group consisting of H, $CH_3$, and $CF_3$;
wherein $R^{41}$ and $R^{42}$ are both H, or $R^{41}$ is H and $R^{42}$ is OH, or $R^{41}$ and $R^{42}$ together form an oxo group;
wherein $R^{43}$ is selected from the group consisting of —($CH_2$)$_5$—, —($CH_2$)$_6$—, and —($CH_2$)$_7$—;
wherein M is selected from the group consisting of $^{99m}$Tc, $^{52}$Mn, $^{186}$Re and $^{188}$Re;
or a pharmaceutically acceptable salt thereof.

2. The conjugate of claim 1 of the formula:

wherein Re is $^{186}$Re or $^{188}$Re;
or a pharmaceutically acceptable salt thereof.

3. The conjugate of claim 1 of the formula:

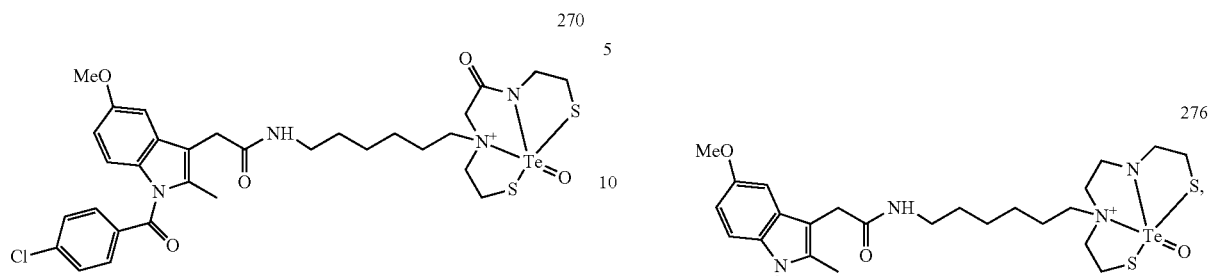

270 wherein Tc is $^{99m}$Tc;
or a pharmaceutically acceptable salt thereof.

4. The conjugate of claim 1, wherein said conjugate is selected from the group consisting of:

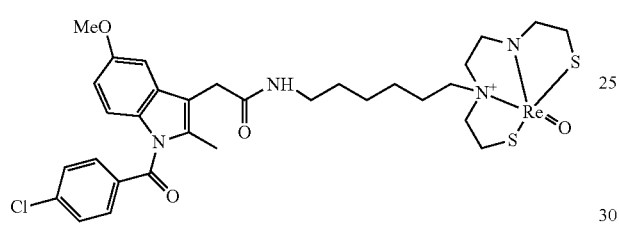

275 and

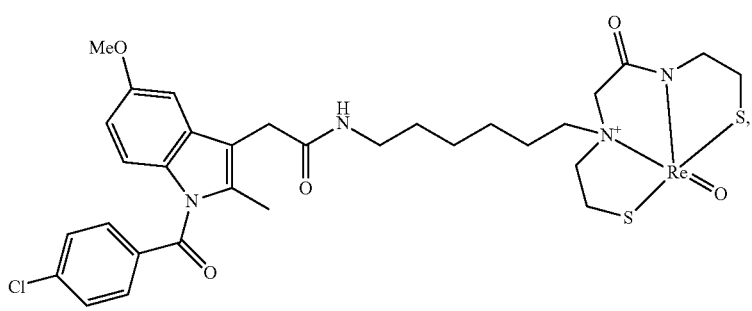

276 wherein Re is $^{186}$Re or $^{188}$Re;

wherein Tc is $^{99m}$Tc;

and pharmaceutically acceptable salts thereof.

5. The conjugate of claim 1, which is selected from the group consisting of:

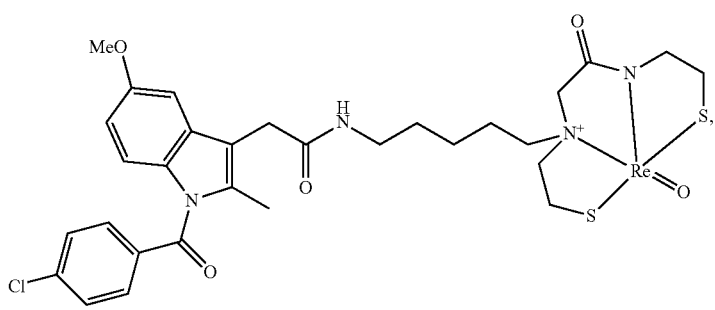

260

263

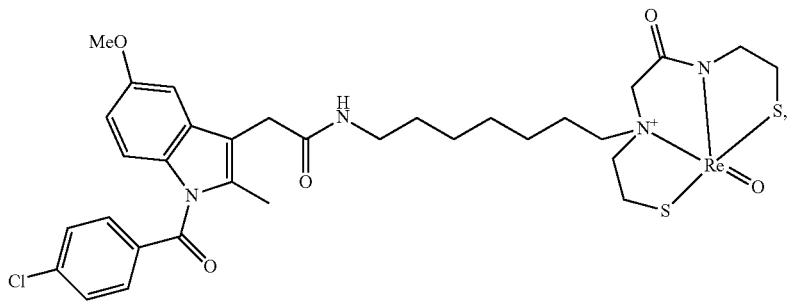
264
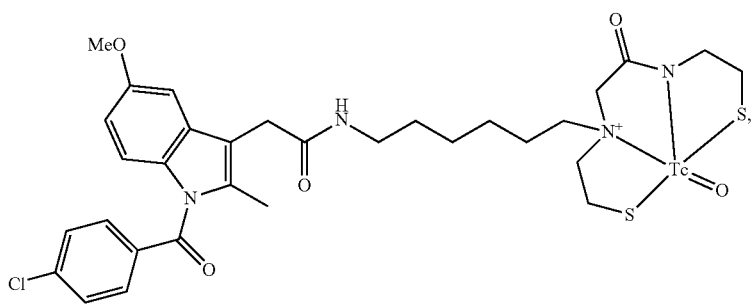
270
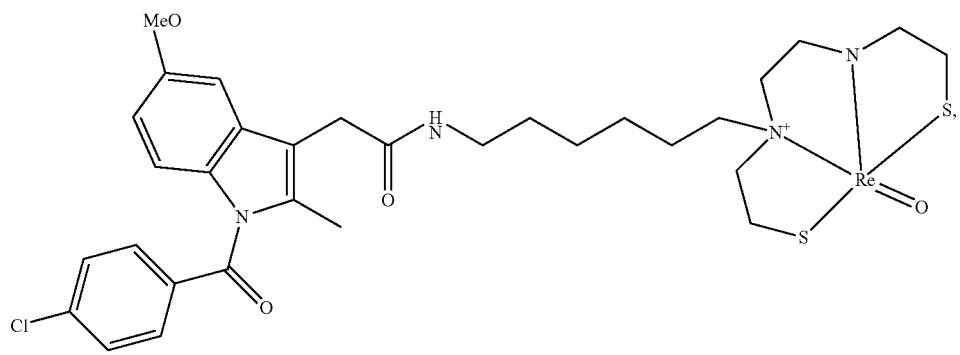

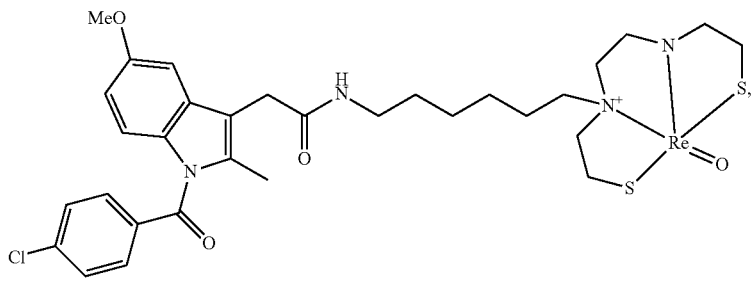

275 and

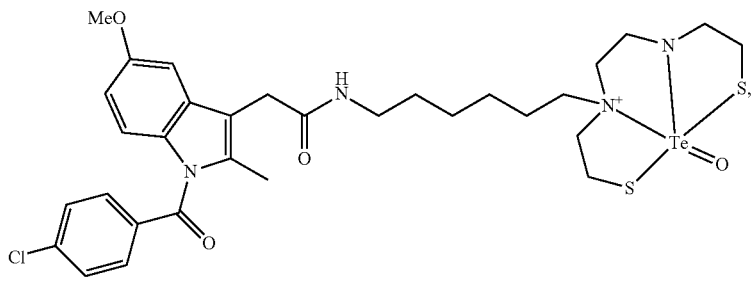

276 where Tc is 99mTc, Re is $^{186}$Re or $^{188}$Re;

and pharmaceutically acceptable salts thereof.

6. A pharmaceutical composition comprising one or more conjugates of claim 1, and a pharmaceutically acceptable excipient.

7. A method of imaging a site of pathology or suspected pathology in a subject, comprising:
   a) administering one or more conjugates of claim 1 to the subject, wherein the radioactive agent of the conjugate comprises $^{99m}$Tc, $^{52}$Mn, $^{186}$Re or $^{188}$Re; and
   b) generating an image of the subject or an image of a portion of the subject.

8. The method of claim 7, wherein the pathology or suspected pathology in the subject is a tumor or a suspected tumor.

9. The method of claim 7, wherein the subject is suffering from pain.

10. The method of claim 7, wherein the pathology or suspected pathology in the subject is an infection or a suspected infection.

11. The conjugate of claim 3, wherein said conjugate has an IC$_{50}$ for cyclooxygenase inhibition of less than about 0.5 micromolar.

12. The conjugate of claim 11, wherein the cyclooxygenase is COX-2.

\* \* \* \* \*